(12) United States Patent  (10) Patent No.: US 8,410,069 B2
Feinstein  (45) Date of Patent: Apr. 2, 2013

(54) OLIGORIBONUCLEOTIDE INHIBITORS OF NRF2 AND METHODS OF USE THEREOF FOR TREATMENT OF CANCER

(75) Inventor: Elena Feinstein, Rehovot (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

(21) Appl. No.: 12/901,207

(22) Filed: Oct. 8, 2010

(65) Prior Publication Data

US 2011/0230543 A1    Sep. 22, 2011

Related U.S. Application Data

(62) Division of application No. 12/077,414, filed on Mar. 19, 2008, now Pat. No. 7,812, 002.

(60) Provisional application No. 60/937,135, filed on Jun. 26, 2007, provisional application No. 60/919,413, filed on Mar. 22, 2007.

(51) Int. Cl.
 *C12N 15/11* (2006.01)
 *C07H 21/02* (2006.01)
 *C97H 21/04* (2006.01)

(52) U.S. Cl. .................... 514/44 A; 536/24.5

(58) Field of Classification Search ............. 514/44; 536/24.1, 24.5
See application file for complete search history.

(56) References Cited

U.S. PATENT DOCUMENTS

| | | | |
|---|---|---|---|
| 5,898,031 | A | 4/1999 | Crooke |
| 6,107,094 | A | 8/2000 | Crooke |
| 6,506,559 | B1 | 1/2003 | Fire et al. |
| 7,056,704 | B2 | 6/2006 | Tuschl et al. |
| 7,078,196 | B2 | 7/2006 | Tuschl et al. |
| 7,452,987 | B2 | 11/2008 | Giese et al. |
| 7,626,015 | B2 | 12/2009 | Feinstein et al. |
| 7,741,299 | B2 | 6/2010 | Feinstein |
| 7,749,977 | B2 | 7/2010 | Yehiely et al. |
| 7,812,002 | B2 | 10/2010 | Feinstein |
| 7,893,245 | B2 | 2/2011 | Giese et al. |
| 8,090,542 | B2 | 1/2012 | Khvorova et al. |
| 8,097,710 | B2 | 1/2012 | Baulcombe et al. |
| 2002/0164576 | A1 | 11/2002 | Pedersen et al. |
| 2004/0005579 | A1 | 1/2004 | Birse et al. |

(Continued)

FOREIGN PATENT DOCUMENTS

| | | |
|---|---|---|
| WO | WO 00/44895 | 8/2000 |
| WO | WO 01/36646 | 5/2001 |

(Continued)

OTHER PUBLICATIONS

Extended European search report and European search opinion issued on Mar. 11, 2011, in connection with European Application No. EP 08720016.8.

European Office Action issued on Oct. 31, 2011, in connection with European Application No. EP 08720016.8.

Knorr-Whitmann et al., 2005, Characterization of Nrf2 activation and heme oxygenase-1 expression in NIH3T3 cells exposed to aqueous extracts of cigarette smoke; Free Radic Biol Med. 39(11):1438-48.

(Continued)

*Primary Examiner* — Terra Cotta Gibbs
(74) *Attorney, Agent, or Firm* — John P. White; Cooper & Dunham LLP

(57) ABSTRACT

The invention provides novel double stranded oligoribonucleotides that inhibit the Nrf2 gene. The invention also provides a pharmaceutical composition comprising one or more such oligoribonucleotides, and a vector capable of expressing the oligoribonucleotide. The present invention also relates to methods and compositions for treating or preventing the incidence or severity of a cancerous disease, particularly various lung cancers.

26 Claims, 1 Drawing Sheet

U.S. PATENT DOCUMENTS

| | | |
|---|---|---|
| 2004/0219569 A1 | 11/2004 | Yehiely et al. |
| 2005/0080246 A1 | 4/2005 | Allerson et al. |
| 2005/0255487 A1 | 11/2005 | Khvorova et al. |
| 2006/0069056 A1 | 3/2006 | Feinstein et al. |
| 2006/0217329 A1 | 9/2006 | Feinstein |
| 2006/0217331 A1 | 9/2006 | Vargeese et al. |
| 2006/0292586 A1 | 12/2006 | Schroth et al. |
| 2006/0293551 A1 | 12/2006 | Dellinger et al. |
| 2007/0031844 A1 | 2/2007 | Khvorova et al. |
| 2007/0032441 A1 | 2/2007 | McSwiggen et al. |
| 2007/0042418 A1 | 2/2007 | Yehiely et al. |
| 2007/0098728 A1 | 5/2007 | Pedersen et al. |
| 2007/0185047 A1 | 8/2007 | Bhat et al. |
| 2008/0064650 A1 | 3/2008 | Feinstein et al. |
| 2008/0108583 A1 | 5/2008 | Feinstein |
| 2009/0162365 A1 | 6/2009 | Feinstein et al. |
| 2009/0215864 A1 | 8/2009 | Feinstein |
| 2012/0004184 A1 | 1/2012 | Collard et al. |

FOREIGN PATENT DOCUMENTS

| | | |
|---|---|---|
| WO | WO 01/75164 | 10/2001 |
| WO | WO 01/94629 | 12/2001 |
| WO | WO 02/44321 | 6/2002 |
| WO | WO 02/055693 | 7/2002 |
| WO | WO 03/070918 | 9/2003 |
| WO | WO 03/074654 | 9/2003 |
| WO | WO 2004/015107 | 2/2004 |
| WO | WO 2006/128041 | 11/2006 |
| WO | WO 2006/129881 | 12/2006 |
| WO | WO 2008/124660 | 10/2008 |

OTHER PUBLICATIONS

Singh, et al., 2006, Glutathione peroxidase 2, the major cigarette smoke-inducible isoform of GPX in lungs, is regulated by Nrf2; Am J Respir Cell Mol Biol. 35(6):639-50.
Barik S. Mol. Med 2005, 83: 764-773.
Bartel DP. Cell. Jan. 23, 2004; 116(2): 281-97 MicroRNAs: genomics, biogenesis.
Bitko V, et al., Nat. Med. 2005, 11(1):50-55.
Caplen NJ, et al., Proc. Natl. Acad. Sci. 2001, 98:9742-9747.
Chakraborty C. Current Drug Targets 2007 8(3):469-82.
Chalk AM, Wahlestedt C, Sonnhammer EL. 2004 Improved and automated prediction of effective siRNA Biochem. Biophys. Res, Commun. Jun. 18; 319(1): 264-74.
Elbashir SM, et al., 2001, Genes Dev., 15, 188.
Elbashir SM, et al., Nature 2001, 411:494-498.
Fire A, et al., Nature 1998, 391, 806.
Lee Y, et al., Nature 2003, 425:415-9.
Levenkova N, Gu Q, Rux JJ. 2004, Gene specific siRNA selector Bioinformatics. I 12; 20(3):430-2.
McManus MT, & Sharp PA. Nature Rev Genet, 2002, v.3, 737-47.
Singh A, et al., Cancer Res. 2008:68(19) RNAi-Mediated Silencing of Nuclear Factor Erythroid-2-Related Factor 2 Gene Expression in Non-Small Cell Lung Cancer Inhibits Tumor Growth and Increases Efficacy of Chemotherapy.
Sioud M, & Leirdal M. 2004, Potential design rules and enzymatic synthesis of siRNAs, Methods Mol. Biol., 252:457-69.
Ui-Tei K, Naito Y, Takahashi F, Haraguchi T, Ohki-Hamazaki H, Juni A, Ueda R, Saigo K., Guidelines for the selection of highly effective siRNA sequences for mammalian and chik RNA interference Nucleic Acids Res. 2004 I 9; 32(3); 936-48.
International Search Report issued by the International Searching Authority (ISA/US) on Jan. 8, 2009 in connection with International Application No. PCT/IL08/00391.
Written Opinion issued by the International Searching Authority (ISA/US) on Jan. 8, 2009 in connection with International Application No. PCT/IL08/00391.
Yehiely et al., U.S. Appl. No. 09/499,553, and claims pending at time of abandonment.
Kotlo et al., (2003). "Nrf2 is an inhibitor of the Fas pathway as identified by Achilles' Heel Method, a new function-based approach to gene identification in human cells," Oncogene, 22: pp. 797-806.
Nov. 30, 2008 Office Action in connection with U.S. Appl. No. 11/586,021.
Jan. 2, 2009 Office Action in connection with U.S. Appl. No. 11/586,021.
Jul. 14, 2009 Office Action in connection with U.S. Appl. No. 11/586,021.
International Preliminary Report on Patentability issued by the International Searching Authority (ISA/US) on Jan. 28, 2010 in connection with International Application No. PCT/IL08/00391.
Gong et al. (2006), "Nrf2 is increased by CYP2E1 in Rodent Liver and HepG2 Cells and Protects Against Oxidative Stress Caused by CYP2E1". Hepatology, 43:144-153.
AB162435, Bos taurus nrf2 mRNA for NF-E2-related factore-2, complete cds. Dec. 21, 2004 [retrieved from the Internet May 6, 2010; http://www.ncbi.nlm.nih.gov/nuccore/56744173].
International Search Report issued by the International Searching Authority (ISA/US) on Apr. 2, 2010 in connection with International Application No. PCT/IL09/00387.
Written Opinion issued by the International Searching Authority (ISA/US) on Apr. 2, 2010 in connection with International Application No. PCT/IL09/00387.
Feb. 26, 2010 Notice of Allowance in connection with U.S. Appl. No. 11/586,021.
Sep. 10, 2009 Office Action in connection with U.S. Appl. No. 12/077,414.
Jan. 7, 2010 Office Action in connection with U.S. Appl. No. 12/077,414.
Feb. 26, 2010 Notice of Allowance in connection with U.S. Appl. No. 12/077,414.
Amarzguioui at al., (2003) "Tolerance for Mutations and Chemical Modifications in a siRNA". Nucleic Acids Res., 31(2):589-95.
Braasch et al., (2003) "RNA Interference in Mammalian Cells by Chemically-Modified RNA". Biochemistry, 42:7967-7975.
Chiu and Rana, (2002) "RNAi in Human Cells: basic Structural and Function Features of Small Interfering RNA" Molecular Cell, 10:549-561.
Chiu and Rana, (2003) "siRNA function in RNAi: a chemical modification analysis". RNA, 9(9):1034-48.
Czauderna at al., (2003) "Structural Variations and Stabilising Modifications of Synthetic siRNAs in Mammalian Cells". Nucleic Acids Research, 31(11):2705-16.
Elbashir et al., (2001) "Functional Anatomy of siRNAs for Mediating Efficient RNAi in Drosophila Melanogaster Embryo Lysate". EMBO Journal, 20(23):6877-88.
Holen et al., (2002) "Positional effects of short interfering RNAs targeting the human coagulation trigger Tissue Factor". Nucleic Acids Res. 30(8):1757-66.
Mahato at al., (2005) "Modulation of Gene Expression by Antisense and Antigen Oligodeoxynucleotides and Small Interfering RNA". Expert Opinion on Drug Delivery 2(1):3-28.
Prakash at al., (2005) "Positional effect of chemical modifications on short interference RNA activity in mammalian cells". J. Med Chem. :48(13)4247-53.
Scherer and Rossi, (2004) "Therapeutic Applications of RNA Interferences: Recent Advances in siRNA Design". Advances in Genetics 52:1-21.
Ui-Tei et al., (2006) "Essential notes regarding the design of functional siRNAs for efficient mammalian RNAi". J Biomed Biotechnol, 2006:65052.
Ui-Tei et al., (2008) "DNA-modified siRNA-dependent gene silencing with reduced off-target effect is induced through a pathway parallel to that for siRNA-mediated RNA interference." Proc 2008 Micro-NanoMechatronics and Human Science (MHS2008), 339-345.
Ui-Tei at al., (2008) "Functional dissection of siRNA sequence by systematic DNA substitution: modified siRNA with a DNA seed arm is a powerful tool for mammalian gene silencing with significantly reduced off-target effect". Nucleic Acids Res. 36(7):2136-51.
Zamore et al., (2000) "RNAi: Double-Stranded RNA Directs the ATP-Dependent Cleavage of mRNA at 21 to 23 Nucleotide Intervals". Cell, 101:25-33.

Imaging after
3 weeks of tumor
growth (24 h
before siRNA
inhalation)

Imaging after
4 weeks of tumor
growth (following
two siRNA
inhalations)

SEQUENCE LISTING

```
<160> NUMBER OF SEQ ID NOS: 2008

<210> SEQ ID NO 1
<211> LENGTH: 19
<212> TYPE: RNA
<213> ORGANISM: artificial
<220> FEATURE:
<223> OTHER INFORMATION: RNA Oligomer

<400> SEQUENCE: 1
gggguaagaa uaaaguggc                                              19

<210> SEQ ID NO 2
<211> LENGTH: 19
<212> TYPE: RNA
<213> ORGANISM: artificial
<220> FEATURE:
<223> OTHER INFORMATION: RNA Oligomer

<400> SEQUENCE: 2
ggagggguaa gaauaaagu                                              19

<210> SEQ ID NO 3
<211> LENGTH: 19
<212> TYPE: RNA
<213> ORGANISM: artificial
<220> FEATURE:
<223> OTHER INFORMATION: RNA Oligomer

<400> SEQUENCE: 3
gcaaaacuaa ccacuaugu                                              19

<210> SEQ ID NO 4
<211> LENGTH: 19
<212> TYPE: RNA
<213> ORGANISM: artificial
<220> FEATURE:
<223> OTHER INFORMATION: RNA Oligomer

<400> SEQUENCE: 4
aaggagaaaa ugacaaaag                                              19

<210> SEQ ID NO 5
<211> LENGTH: 19
<212> TYPE: RNA
<213> ORGANISM: artificial
<220> FEATURE:
<223> OTHER INFORMATION: RNA Oligomer

<400> SEQUENCE: 5
cagaauugca gaaaaagaa                                              19
```

```
<210> SEQ ID NO 6
<211> LENGTH: 19
<212> TYPE: RNA
<213> ORGANISM: artificial
<220> FEATURE:
<223> OTHER INFORMATION: RNA Oligomer

<400> SEQUENCE: 6
ggguaagaau aaaguggcu                                              19

<210> SEQ ID NO 7
<211> LENGTH: 19
<212> TYPE: RNA
<213> ORGANISM: artificial
<220> FEATURE:
<223> OTHER INFORMATION: RNA Oligomer

<400> SEQUENCE: 7
gcccucaccu gcuacuuua                                              19

<210> SEQ ID NO 8
<211> LENGTH: 19
<212> TYPE: RNA
<213> ORGANISM: artificial
<220> FEATURE:
<223> OTHER INFORMATION: RNA Oligomer

<400> SEQUENCE: 8 aggguaaga auaaagugg                                               19

<210> SEQ ID NO 9
<211> LENGTH: 19
<212> TYPE: RNA
<213> ORGANISM: artificial
<220> FEATURE:
<223> OTHER INFORMATION: RNA Oligomer

<400> SEQUENCE: 9
aggaggggua agaauaaag                                              19

<210> SEQ ID NO 10
<211> LENGTH: 19
<212> TYPE: RNA
<213> ORGANISM: artificial
<220> FEATURE:
<223> OTHER INFORMATION: RNA Oligomer

<400> SEQUENCE: 10
ucccguuugu agaugacaa                                              19

<210> SEQ ID NO 11
<211> LENGTH: 19
<212> TYPE: RNA
<213> ORGANISM: artificial
<220> FEATURE:
<223> OTHER INFORMATION: RNA Oligomer

<400> SEQUENCE: 11
aggagaaaau gacaaaagc                                              19

<210> SEQ ID NO 12
<211> LENGTH: 19
<212> TYPE: RNA
<213> ORGANISM: artificial
<220> FEATURE:
<223> OTHER INFORMATION: RNA Oligomer

<400> SEQUENCE: 12
```

-continued

```
gcucagaauu gcagaaaaa                                          19

<210> SEQ ID NO 13
<211> LENGTH: 19
<212> TYPE: RNA
<213> ORGANISM: artificial
<220> FEATURE:
<223> OTHER INFORMATION: RNA Oligomer

<400> SEQUENCE: 13
gagaaagaau ugccuguaa                                          19

<210> SEQ ID NO 14
<211> LENGTH: 19
<212> TYPE: RNA
<213> ORGANISM: artificial
<220> FEATURE:
<223> OTHER INFORMATION: RNA Oligomer

<400> SEQUENCE: 14
uccggcauuu cacuaaaca                                          19

<210> SEQ ID NO 15
<211> LENGTH: 19
<212> TYPE: RNA
<213> ORGANISM: artificial
<220> FEATURE:
<223> OTHER INFORMATION: RNA Oligomer

<400> SEQUENCE: 15
gaguuacagu gucuuaaua                                          19

<210> SEQ ID NO 16
<211> LENGTH: 19
<212> TYPE: RNA
<213> ORGANISM: artificial
<220> FEATURE:
<223> OTHER INFORMATION: RNA Oligomer

<400> SEQUENCE: 16
gccaaaacua guauagaaa                                          19

<210> SEQ ID NO 17
<211> LENGTH: 19
<212> TYPE: RNA
<213> ORGANISM: artificial
<220> FEATURE:
<223> OTHER INFORMATION: RNA Oligomer

<400> SEQUENCE: 17
agccagaugu uaagaaaaa                                          19

<210> SEQ ID NO 18
<211> LENGTH: 19
<212> TYPE: RNA
<213> ORGANISM: artificial
<220> FEATURE:
<223> OTHER INFORMATION: RNA Oligomer

<400> SEQUENCE: 18
gaagccagau guuaagaaa                                          19

<210> SEQ ID NO 19
<211> LENGTH: 19
<212> TYPE: RNA
<213> ORGANISM: artificial
```

```
<220> FEATURE:
<223> OTHER INFORMATION: RNA Oligomer

<400> SEQUENCE: 19
agaagccaga uguuaagaa                                                    19

<210> SEQ ID NO 20
<211> LENGTH: 19
<212> TYPE: RNA
<213> ORGANISM: artificial
<220> FEATURE:
<223> OTHER INFORMATION: RNA Oligomer

<400> SEQUENCE: 20
ucagaauugc agaaaaga                                                     19

<210> SEQ ID NO 21
<211> LENGTH: 19
<212> TYPE: RNA
<213> ORGANISM: artificial
<220> FEATURE:
<223> OTHER INFORMATION: RNA Oligomer

<400> SEQUENCE: 21
uaggaggggu aagaauaaa                                                    19

<210> SEQ ID NO 22
<211> LENGTH: 19
<212> TYPE: RNA
<213> ORGANISM: artificial
<220> FEATURE:
<223> OTHER INFORMATION: RNA Oligomer

<400> SEQUENCE: 22
cacucucuga acuucuaaa                                                    19

<210> SEQ ID NO 23
<211> LENGTH: 19
<212> TYPE: RNA
<213> ORGANISM: artificial
<220> FEATURE:
<223> OTHER INFORMATION: RNA Oligomer

<400> SEQUENCE: 23
uagccccugu ugauuuaga                                                    19

<210> SEQ ID NO 24
<211> LENGTH: 19
<212> TYPE: RNA
<213> ORGANISM: artificial
<220> FEATURE:
<223> OTHER INFORMATION: RNA Oligomer

<400> SEQUENCE: 24
gaucugccaa cuacuccca                                                    19

<210> SEQ ID NO 25
<211> LENGTH: 19
<212> TYPE: RNA
<213> ORGANISM: artificial
<220> FEATURE:
<223> OTHER INFORMATION: RNA Oligomer

<400> SEQUENCE: 25
gcaaaaucau agccaaaac                                                    19
```

```
<210> SEQ ID NO 26
<211> LENGTH: 19
<212> TYPE: RNA
<213> ORGANISM: artificial
<220> FEATURE:
<223> OTHER INFORMATION: RNA Oligomer

<400> SEQUENCE: 26
guaagaagcc agauguuaa                                                    19

<210> SEQ ID NO 27
<211> LENGTH: 19
<212> TYPE: RNA
<213> ORGANISM: artificial
<220> FEATURE:
<223> OTHER INFORMATION: RNA Oligomer

<400> SEQUENCE: 27
uaaaguggcu gcucagaau                                                    19

<210> SEQ ID NO 28
<211> LENGTH: 19
<212> TYPE: RNA
<213> ORGANISM: artificial
<220> FEATURE:
<223> OTHER INFORMATION: RNA Oligomer

<400> SEQUENCE: 28
agaauaaagu ggcugcuca                                                    19

<210> SEQ ID NO 29
<211> LENGTH: 19
<212> TYPE: RNA
<213> ORGANISM: artificial
<220> FEATURE:
<223> OTHER INFORMATION: RNA Oligomer

<400> SEQUENCE: 29
aggaaagaca agaacaacu                                                    19

<210> SEQ ID NO 30
<211> LENGTH: 19
<212> TYPE: RNA
<213> ORGANISM: artificial
<220> FEATURE:
<223> OTHER INFORMATION: RNA Oligomer

<400> SEQUENCE: 30
aaaggaaaga caagaacaa                                                    19

<210> SEQ ID NO 31
<211> LENGTH: 19
<212> TYPE: RNA
<213> ORGANISM: artificial
<220> FEATURE:
<223> OTHER INFORMATION: RNA Oligomer

<400> SEQUENCE: 31
aacuugaaaa ggaaagaca                                                    19

<210> SEQ ID NO 32
<211> LENGTH: 19
<212> TYPE: RNA
<213> ORGANISM: artificial
<220> FEATURE:
<223> OTHER INFORMATION: RNA Oligomer

<400> SEQUENCE: 32
```
gacaaacauu caagccgcu    19

<210> SEQ ID NO 33
<211> LENGTH: 19
<212> TYPE: RNA
<213> ORGANISM: artificial
<220> FEATURE:
<223> OTHER INFORMATION: RNA Oligomer

<400> SEQUENCE: 33
gacuccggca uuucacuaa    19

<210> SEQ ID NO 34
<211> LENGTH: 19
<212> TYPE: RNA
<213> ORGANISM: artificial
<220> FEATURE:
<223> OTHER INFORMATION: RNA Oligomer

<400> SEQUENCE: 34
accaaaacca cccugaaag    19

<210> SEQ ID NO 35
<211> LENGTH: 19
<212> TYPE: RNA
<213> ORGANISM: artificial
<220> FEATURE:
<223> OTHER INFORMATION: RNA Oligomer

<400> SEQUENCE: 35
acucucugaa cuucuaaau    19

<210> SEQ ID NO 36
<211> LENGTH: 19
<212> TYPE: RNA
<213> ORGANISM: artificial
<220> FEATURE:
<223> OTHER INFORMATION: RNA Oligomer

<400> SEQUENCE: 36
gacagugaac ucauuaaau    19

<210> SEQ ID NO 37
<211> LENGTH: 19
<212> TYPE: RNA
<213> ORGANISM: artificial
<220> FEATURE:
<223> OTHER INFORMATION: RNA Oligomer

<400> SEQUENCE: 37
aaguuuggga ggagcuauu    19

<210> SEQ ID NO 38
<211> LENGTH: 19
<212> TYPE: RNA
<213> ORGANISM: artificial
<220> FEATURE:
<223> OTHER INFORMATION: RNA Oligomer

<400> SEQUENCE: 38
uuguagauga caaugaggu    19

<210> SEQ ID NO 39
<211> LENGTH: 19
<212> TYPE: RNA
<213> ORGANISM: artificial

```
<220> FEATURE:
<223> OTHER INFORMATION: RNA Oligomer

<400> SEQUENCE: 39
aaacuaacca cuauguacu                                              19

<210> SEQ ID NO 40
<211> LENGTH: 19
<212> TYPE: RNA
<213> ORGANISM: artificial
<220> FEATURE:
<223> OTHER INFORMATION: RNA Oligomer

<400> SEQUENCE: 40
caaaaucaua gccaaaacu                                              19

<210> SEQ ID NO 41
<211> LENGTH: 19
<212> TYPE: RNA
<213> ORGANISM: artificial
<220> FEATURE:
<223> OTHER INFORMATION: RNA Oligomer

<400> SEQUENCE: 41
uaagaagcca gauguuaag                                              19

<210> SEQ ID NO 42
<211> LENGTH: 19
<212> TYPE: RNA
<213> ORGANISM: artificial
<220> FEATURE:
<223> OTHER INFORMATION: RNA Oligomer

<400> SEQUENCE: 42
acgugaugaa gauggaaaa                                              19

<210> SEQ ID NO 43
<211> LENGTH: 19
<212> TYPE: RNA
<213> ORGANISM: artificial
<220> FEATURE:
<223> OTHER INFORMATION: RNA Oligomer

<400> SEQUENCE: 43
cuggaaaaua uaguagaac                                              19

<210> SEQ ID NO 44
<211> LENGTH: 19
<212> TYPE: RNA
<213> ORGANISM: artificial
<220> FEATURE:
<223> OTHER INFORMATION: RNA Oligomer

<400> SEQUENCE: 44
gaaaaggaaa gacaagaac                                              19

<210> SEQ ID NO 45
<211> LENGTH: 19
<212> TYPE: RNA
<213> ORGANISM: artificial
<220> FEATURE:
<223> OTHER INFORMATION: RNA Oligomer

<400> SEQUENCE: 45
ugaaaaggaa agacaagaa                                              19
```

```
<210> SEQ ID NO 46
<211> LENGTH: 19
<212> TYPE: RNA
<213> ORGANISM: artificial
<220> FEATURE:
<223> OTHER INFORMATION: RNA Oligomer

<400> SEQUENCE: 46
uggagacaca cuacuuggc                                                  19

<210> SEQ ID NO 47
<211> LENGTH: 19
<212> TYPE: RNA
<213> ORGANISM: artificial
<220> FEATURE:
<223> OTHER INFORMATION: RNA Oligomer

<400> SEQUENCE: 47
ucaaccaaaa ccacccuga                                                  19

<210> SEQ ID NO 48
<211> LENGTH: 19
<212> TYPE: RNA
<213> ORGANISM: artificial
<220> FEATURE:
<223> OTHER INFORMATION: RNA Oligomer

<400> SEQUENCE: 48
cccucaccug cuacuuuaa                                                  19

<210> SEQ ID NO 49
<211> LENGTH: 19
<212> TYPE: RNA
<213> ORGANISM: artificial
<220> FEATURE:
<223> OTHER INFORMATION: RNA Oligomer

<400> SEQUENCE: 49
ugacagugaa cucauuaaa                                                  19

<210> SEQ ID NO 50
<211> LENGTH: 19
<212> TYPE: RNA
<213> ORGANISM: artificial
<220> FEATURE:
<223> OTHER INFORMATION: RNA Oligomer

<400> SEQUENCE: 50
uuggaggcaa gauauagau                                                  19

<210> SEQ ID NO 51
<211> LENGTH: 19
<212> TYPE: RNA
<213> ORGANISM: artificial
<220> FEATURE:
<223> OTHER INFORMATION: RNA Oligomer

<400> SEQUENCE: 51
gagcuauuau ccauuccug                                                  19

<210> SEQ ID NO 52
<211> LENGTH: 19
<212> TYPE: RNA
<213> ORGANISM: artificial
<220> FEATURE:
<223> OTHER INFORMATION: RNA Oligomer

<400> SEQUENCE: 52
```
uagaugacaa ugagguuuc                                                19

<210> SEQ ID NO 53
<211> LENGTH: 19
<212> TYPE: RNA
<213> ORGANISM: artificial
<220> FEATURE:
<223> OTHER INFORMATION: RNA Oligomer

<400> SEQUENCE: 53
ugcccacauu cccaaauca                                                19

<210> SEQ ID NO 54
<211> LENGTH: 19
<212> TYPE: RNA
<213> ORGANISM: artificial
<220> FEATURE:
<223> OTHER INFORMATION: RNA Oligomer

<400> SEQUENCE: 54
agccaaaacu aguauagaa                                                19

<210> SEQ ID NO 55
<211> LENGTH: 19
<212> TYPE: RNA
<213> ORGANISM: artificial
<220> FEATURE:
<223> OTHER INFORMATION: RNA Oligomer

<400> SEQUENCE: 55
aaaguaagaa gccagaugu                                                19

<210> SEQ ID NO 56
<211> LENGTH: 19
<212> TYPE: RNA
<213> ORGANISM: artificial
<220> FEATURE:
<223> OTHER INFORMATION: RNA Oligomer

<400> SEQUENCE: 56
ccaaaaguaa gaagccaga                                                19

<210> SEQ ID NO 57
<211> LENGTH: 19
<212> TYPE: RNA
<213> ORGANISM: artificial
<220> FEATURE:
<223> OTHER INFORMATION: RNA Oligomer

<400> SEQUENCE: 57
cccaaaagua agaagccag                                                19

<210> SEQ ID NO 58
<211> LENGTH: 19
<212> TYPE: RNA
<213> ORGANISM: artificial
<220> FEATURE:
<223> OTHER INFORMATION: RNA Oligomer

<400> SEQUENCE: 58
uacgugauga agauggaaa                                                19

<210> SEQ ID NO 59
<211> LENGTH: 19
<212> TYPE: RNA
<213> ORGANISM: artificial

```
<220> FEATURE:
<223> OTHER INFORMATION: RNA Oligomer

<400> SEQUENCE: 59
gcucaaagaa aaaggagaa                                                    19

<210> SEQ ID NO 60
<211> LENGTH: 19
<212> TYPE: RNA
<213> ORGANISM: artificial
<220> FEATURE:
<223> OTHER INFORMATION: RNA Oligomer

<400> SEQUENCE: 60
aacuagagca agauuuaga                                                    19

<210> SEQ ID NO 61
<211> LENGTH: 19
<212> TYPE: RNA
<213> ORGANISM: artificial
<220> FEATURE:
<223> OTHER INFORMATION: RNA Oligomer

<400> SEQUENCE: 61
aaguggcugc ucagaauug                                                    19

<210> SEQ ID NO 62
<211> LENGTH: 19
<212> TYPE: RNA
<213> ORGANISM: artificial
<220> FEATURE:
<223> OTHER INFORMATION: RNA Oligomer

<400> SEQUENCE: 62
guaggagggg uaagaauaa                                                    19

<210> SEQ ID NO 63
<211> LENGTH: 19
<212> TYPE: RNA
<213> ORGANISM: artificial
<220> FEATURE:
<223> OTHER INFORMATION: RNA Oligomer

<400> SEQUENCE: 63
ucaacuugca uuaauucgg                                                    19

<210> SEQ ID NO 64
<211> LENGTH: 19
<212> TYPE: RNA
<213> ORGANISM: artificial
<220> FEATURE:
<223> OTHER INFORMATION: RNA Oligomer

<400> SEQUENCE: 64
aaagacaaga acaacucca                                                    19

<210> SEQ ID NO 65
<211> LENGTH: 19
<212> TYPE: RNA
<213> ORGANISM: artificial
<220> FEATURE:
<223> OTHER INFORMATION: RNA Oligomer

<400> SEQUENCE: 65
agaaagaauu gccuguaag                                                    19
```

```
<210> SEQ ID NO 66
<211> LENGTH: 19
<212> TYPE: RNA
<213> ORGANISM: artificial
<220> FEATURE:
<223> OTHER INFORMATION: RNA Oligomer

<400> SEQUENCE: 66
acacaccaga gaaagaauu                                                  19

<210> SEQ ID NO 67
<211> LENGTH: 19
<212> TYPE: RNA
<213> ORGANISM: artificial
<220> FEATURE:
<223> OTHER INFORMATION: RNA Oligomer

<400> SEQUENCE: 67
aacaccagua cauucuucu                                                  19

<210> SEQ ID NO 68
<211> LENGTH: 19
<212> TYPE: RNA
<213> ORGANISM: artificial
<220> FEATURE:
<223> OTHER INFORMATION: RNA Oligomer

<400> SEQUENCE: 68
aaacaccagu acauucuuc                                                  19

<210> SEQ ID NO 69
<211> LENGTH: 19
<212> TYPE: RNA
<213> ORGANISM: artificial
<220> FEATURE:
<223> OTHER INFORMATION: RNA Oligomer

<400> SEQUENCE: 69
acagaauggu ccuaaaaca                                                  19

<210> SEQ ID NO 70
<211> LENGTH: 19
<212> TYPE: RNA
<213> ORGANISM: artificial
<220> FEATURE:
<223> OTHER INFORMATION: RNA Oligomer

<400> SEQUENCE: 70
aaaccacccu gaaagcaca                                                  19

<210> SEQ ID NO 71
<211> LENGTH: 19
<212> TYPE: RNA
<213> ORGANISM: artificial
<220> FEATURE:
<223> OTHER INFORMATION: RNA Oligomer

<400> SEQUENCE: 71
aaccaaaacc acccugaaa                                                  19

<210> SEQ ID NO 72
<211> LENGTH: 19
<212> TYPE: RNA
<213> ORGANISM: artificial
<220> FEATURE:
<223> OTHER INFORMATION: RNA Oligomer

<400> SEQUENCE: 72
```
ucucugaacu ucuaaaugg                                       19

<210> SEQ ID NO 73
<211> LENGTH: 19
<212> TYPE: RNA
<213> ORGANISM: artificial
<220> FEATURE:
<223> OTHER INFORMATION: RNA Oligomer

<400> SEQUENCE: 73
uucacucucu gaacuucua                                       19

<210> SEQ ID NO 74
<211> LENGTH: 19
<212> TYPE: RNA
<213> ORGANISM: artificial
<220> FEATURE:
<223> OTHER INFORMATION: RNA Oligomer

<400> SEQUENCE: 74
guaguccaca uuuucuuaa                                       19

<210> SEQ ID NO 75
<211> LENGTH: 19
<212> TYPE: RNA
<213> ORGANISM: artificial
<220> FEATURE:
<223> OTHER INFORMATION: RNA Oligomer

<400> SEQUENCE: 75
uugaaaauga caagcuggu                                       19

<210> SEQ ID NO 76
<211> LENGTH: 19
<212> TYPE: RNA
<213> ORGANISM: artificial
<220> FEATURE:
<223> OTHER INFORMATION: RNA Oligomer

<400> SEQUENCE: 76
cagucuucau ugcuacuaa                                       19

<210> SEQ ID NO 77
<211> LENGTH: 19
<212> TYPE: RNA
<213> ORGANISM: artificial
<220> FEATURE:
<223> OTHER INFORMATION: RNA Oligomer

<400> SEQUENCE: 77
augacaauga gguuucuuc                                       19

<210> SEQ ID NO 78
<211> LENGTH: 19
<212> TYPE: RNA
<213> ORGANISM: artificial
<220> FEATURE:
<223> OTHER INFORMATION: RNA Oligomer

<400> SEQUENCE: 78
agaugacaau gagguuucu                                       19

<210> SEQ ID NO 79
<211> LENGTH: 19
<212> TYPE: RNA
<213> ORGANISM: artificial

```
<220> FEATURE:
<223> OTHER INFORMATION: RNA Oligomer

<400> SEQUENCE: 79
guagaugaca augagguuu                                                     19

<210> SEQ ID NO 80
<211> LENGTH: 19
<212> TYPE: RNA
<213> ORGANISM: artificial
<220> FEATURE:
<223> OTHER INFORMATION: RNA Oligomer

<400> SEQUENCE: 80
ugccaacuac ucccagguu                                                     19

<210> SEQ ID NO 81
<211> LENGTH: 19
<212> TYPE: RNA
<213> ORGANISM: artificial
<220> FEATURE:
<223> OTHER INFORMATION: RNA Oligomer

<400> SEQUENCE: 81
aagccagaug uuaagaaaa                                                     19

<210> SEQ ID NO 82
<211> LENGTH: 19
<212> TYPE: RNA
<213> ORGANISM: artificial
<220> FEATURE:
<223> OTHER INFORMATION: RNA Oligomer

<400> SEQUENCE: 82
accuuauucu ccuagugaa                                                     19

<210> SEQ ID NO 83
<211> LENGTH: 19
<212> TYPE: RNA
<213> ORGANISM: artificial
<220> FEATURE:
<223> OTHER INFORMATION: RNA Oligomer

<400> SEQUENCE: 83
accuacugaa aaacaacu                                                      19

<210> SEQ ID NO 84
<211> LENGTH: 19
<212> TYPE: RNA
<213> ORGANISM: artificial
<220> FEATURE:
<223> OTHER INFORMATION: RNA Oligomer

<400> SEQUENCE: 84
acaaaagccu ucaccuacu                                                     19

<210> SEQ ID NO 85
<211> LENGTH: 19
<212> TYPE: RNA
<213> ORGANISM: artificial
<220> FEATURE:
<223> OTHER INFORMATION: RNA Oligomer

<400> SEQUENCE: 85
ugcucaaaga aaaaggaga                                                     19
```

```
<210> SEQ ID NO 86
<211> LENGTH: 19
<212> TYPE: RNA
<213> ORGANISM: artificial
<220> FEATURE:
<223> OTHER INFORMATION: RNA Oligomer

<400> SEQUENCE: 86
caacuugcau uaauucggg                                                    19

<210> SEQ ID NO 87
<211> LENGTH: 19
<212> TYPE: RNA
<213> ORGANISM: artificial
<220> FEATURE:
<223> OTHER INFORMATION: RNA Oligomer

<400> SEQUENCE: 87
ggaaagacaa gaacaacuc                                                    19

<210> SEQ ID NO 88
<211> LENGTH: 19
<212> TYPE: RNA
<213> ORGANISM: artificial
<220> FEATURE:
<223> OTHER INFORMATION: RNA Oligomer

<400> SEQUENCE: 88
uugaaaagga aagacaaga                                                    19

<210> SEQ ID NO 89
<211> LENGTH: 19
<212> TYPE: RNA
<213> ORGANISM: artificial
<220> FEATURE:
<223> OTHER INFORMATION: RNA Oligomer

<400> SEQUENCE: 89
caaaagacaa acauucaag                                                    19

<210> SEQ ID NO 90
<211> LENGTH: 19
<212> TYPE: RNA
<213> ORGANISM: artificial
<220> FEATURE:
<223> OTHER INFORMATION: RNA Oligomer

<400> SEQUENCE: 90
ucacaaaaga caaacauuc                                                    19

<210> SEQ ID NO 91
<211> LENGTH: 19
<212> TYPE: RNA
<213> ORGANISM: artificial
<220> FEATURE:
<223> OTHER INFORMATION: RNA Oligomer

<400> SEQUENCE: 91
accccauuca caaaagaca                                                    19

<210> SEQ ID NO 92
<211> LENGTH: 19
<212> TYPE: RNA
<213> ORGANISM: artificial
<220> FEATURE:
<223> OTHER INFORMATION: RNA Oligomer

<400> SEQUENCE: 92
```
agaauugccu guaaguccu					19

<210> SEQ ID NO 93
<211> LENGTH: 19
<212> TYPE: RNA
<213> ORGANISM: artificial
<220> FEATURE:
<223> OTHER INFORMATION: RNA Oligomer

<400> SEQUENCE: 93
agcgacggaa agaguauga					19

<210> SEQ ID NO 94
<211> LENGTH: 19
<212> TYPE: RNA
<213> ORGANISM: artificial
<220> FEATURE:
<223> OTHER INFORMATION: RNA Oligomer

<400> SEQUENCE: 94
aagcacagca gaauucaau					19

<210> SEQ ID NO 95
<211> LENGTH: 19
<212> TYPE: RNA
<213> ORGANISM: artificial
<220> FEATURE:
<223> OTHER INFORMATION: RNA Oligomer

<400> SEQUENCE: 95
cucugaacuu cuaaauggg					19

<210> SEQ ID NO 96
<211> LENGTH: 19
<212> TYPE: RNA
<213> ORGANISM: artificial
<220> FEATURE:
<223> OTHER INFORMATION: RNA Oligomer

<400> SEQUENCE: 96
uugacaguga acucauuaa					19

<210> SEQ ID NO 97
<211> LENGTH: 19
<212> TYPE: RNA
<213> ORGANISM: artificial
<220> FEATURE:
<223> OTHER INFORMATION: RNA Oligomer

<400> SEQUENCE: 97
uaagucgaga aguauuuga					19

<210> SEQ ID NO 98
<211> LENGTH: 19
<212> TYPE: RNA
<213> ORGANISM: artificial
<220> FEATURE:
<223> OTHER INFORMATION: RNA Oligomer

<400> SEQUENCE: 98
uggaguaagu cgagaagua					19

<210> SEQ ID NO 99
<211> LENGTH: 19
<212> TYPE: RNA
<213> ORGANISM: artificial

```
<220> FEATURE:
<223> OTHER INFORMATION: RNA Oligomer

<400> SEQUENCE: 99
uacucaucua uacccucaa                                                  19

<210> SEQ ID NO 100
<211> LENGTH: 19
<212> TYPE: RNA
<213> ORGANISM: artificial
<220> FEATURE:
<223> OTHER INFORMATION: RNA Oligomer

<400> SEQUENCE: 100
uccaagucca gaagccaaa                                                  19

<210> SEQ ID NO 101
<211> LENGTH: 19
<212> TYPE: RNA
<213> ORGANISM: artificial
<220> FEATURE:
<223> OTHER INFORMATION: RNA Oligomer

<400> SEQUENCE: 101
cuguugauuu agacgguau                                                  19

<210> SEQ ID NO 102
<211> LENGTH: 19
<212> TYPE: RNA
<213> ORGANISM: artificial
<220> FEATURE:
<223> OTHER INFORMATION: RNA Oligomer

<400> SEQUENCE: 102
uugcuacuaa ucaggcuca                                                  19

<210> SEQ ID NO 103
<211> LENGTH: 19
<212> TYPE: RNA
<213> ORGANISM: artificial
<220> FEATURE:
<223> OTHER INFORMATION: RNA Oligomer

<400> SEQUENCE: 103
gcccagucuu cauugcuac                                                  19

<210> SEQ ID NO 104
<211> LENGTH: 19
<212> TYPE: RNA
<213> ORGANISM: artificial
<220> FEATURE:
<223> OTHER INFORMATION: RNA Oligomer

<400> SEQUENCE: 104
cauucccguu uguagauga                                                  19

<210> SEQ ID NO 105
<211> LENGTH: 19
<212> TYPE: RNA
<213> ORGANISM: artificial
<220> FEATURE:
<223> OTHER INFORMATION: RNA Oligomer

<400> SEQUENCE: 105
augcuuugua cuuugauga                                                  19
```

<210> SEQ ID NO 106
<211> LENGTH: 19
<212> TYPE: RNA
<213> ORGANISM: artificial
<220> FEATURE:
<223> OTHER INFORMATION: RNA Oligomer

<400> SEQUENCE: 106
cagaugcuuu guacuuuga                                                  19

<210> SEQ ID NO 107
<211> LENGTH: 19
<212> TYPE: RNA
<213> ORGANISM: artificial
<220> FEATURE:
<223> OTHER INFORMATION: RNA Oligomer

<400> SEQUENCE: 107
aagagcuggu acuaauaaa                                                  19

<210> SEQ ID NO 108
<211> LENGTH: 19
<212> TYPE: RNA
<213> ORGANISM: artificial
<220> FEATURE:
<223> OTHER INFORMATION: RNA Oligomer

<400> SEQUENCE: 108
ggacaaaaaa uggcauuuu                                                  19

<210> SEQ ID NO 109
<211> LENGTH: 19
<212> TYPE: RNA
<213> ORGANISM: artificial
<220> FEATURE:
<223> OTHER INFORMATION: RNA Oligomer

<400> SEQUENCE: 109
gugaaaugcu cauacuuua                                                  19

<210> SEQ ID NO 110
<211> LENGTH: 19
<212> TYPE: RNA
<213> ORGANISM: artificial
<220> FEATURE:
<223> OTHER INFORMATION: RNA Oligomer

<400> SEQUENCE: 110
aaccuuauuc uccuaguga                                                  19

<210> SEQ ID NO 111
<211> LENGTH: 19
<212> TYPE: RNA
<213> ORGANISM: artificial
<220> FEATURE:
<223> OTHER INFORMATION: RNA Oligomer

<400> SEQUENCE: 111
aaaaccuuau ucuccuagu                                                  19

<210> SEQ ID NO 112
<211> LENGTH: 19
<212> TYPE: RNA
<213> ORGANISM: artificial
<220> FEATURE:
<223> OTHER INFORMATION: RNA Oligomer

<400> SEQUENCE: 112
aaacaacuca gcaccuuau                                                19

<210> SEQ ID NO 113
<211> LENGTH: 19
<212> TYPE: RNA
<213> ORGANISM: artificial
<220> FEATURE:
<223> OTHER INFORMATION: RNA Oligomer

<400> SEQUENCE: 113
caccuacuga aaaacaac                                                 19

<210> SEQ ID NO 114
<211> LENGTH: 19
<212> TYPE: RNA
<213> ORGANISM: artificial
<220> FEATURE:
<223> OTHER INFORMATION: RNA Oligomer

<400> SEQUENCE: 114
uucaccuacu gaaaaaaca                                                19

<210> SEQ ID NO 115
<211> LENGTH: 19
<212> TYPE: RNA
<213> ORGANISM: artificial
<220> FEATURE:
<223> OTHER INFORMATION: RNA Oligomer

<400> SEQUENCE: 115
acaagaacaa cuccaaaag                                                19

<210> SEQ ID NO 116
<211> LENGTH: 19
<212> TYPE: RNA
<213> ORGANISM: artificial
<220> FEATURE:
<223> OTHER INFORMATION: RNA Oligomer

<400> SEQUENCE: 116
uugcauuaau ucgggauau                                                19

<210> SEQ ID NO 117
<211> LENGTH: 19
<212> TYPE: RNA
<213> ORGANISM: artificial
<220> FEATURE:
<223> OTHER INFORMATION: RNA Oligomer

<400> SEQUENCE: 117
aacuugcauu aauucggga                                                19

<210> SEQ ID NO 118
<211> LENGTH: 19
<212> TYPE: RNA
<213> ORGANISM: artificial
<220> FEATURE:
<223> OTHER INFORMATION: RNA Oligomer

<400> SEQUENCE: 118
cacaaaagac aaacauuca                                                19

<210> SEQ ID NO 119
<211> LENGTH: 19
<212> TYPE: RNA
<213> ORGANISM: artificial

```
<220> FEATURE:
<223> OTHER INFORMATION: RNA Oligomer

<400> SEQUENCE: 119
cccauucaca aaagacaaa                                                    19

<210> SEQ ID NO 120
<211> LENGTH: 19
<212> TYPE: RNA
<213> ORGANISM: artificial
<220> FEATURE:
<223> OTHER INFORMATION: RNA Oligomer

<400> SEQUENCE: 120
gaacacacca gagaaagaa                                                    19

<210> SEQ ID NO 121
<211> LENGTH: 19
<212> TYPE: RNA
<213> ORGANISM: artificial
<220> FEATURE:
<223> OTHER INFORMATION: RNA Oligomer

<400> SEQUENCE: 121
acgguccaca gcucaucau                                                    19

<210> SEQ ID NO 122
<211> LENGTH: 19
<212> TYPE: RNA
<213> ORGANISM: artificial
<220> FEATURE:
<223> OTHER INFORMATION: RNA Oligomer

<400> SEQUENCE: 122
ugagaacaca ccagagaaa                                                    19

<210> SEQ ID NO 123
<211> LENGTH: 19
<212> TYPE: RNA
<213> ORGANISM: artificial
<220> FEATURE:
<223> OTHER INFORMATION: RNA Oligomer

<400> SEQUENCE: 123
gugauucuga aguggaaga                                                    19

<210> SEQ ID NO 124
<211> LENGTH: 19
<212> TYPE: RNA
<213> ORGANISM: artificial
<220> FEATURE:
<223> OTHER INFORMATION: RNA Oligomer

<400> SEQUENCE: 124
acagcagaau ucaaugauu                                                    19

<210> SEQ ID NO 125
<211> LENGTH: 19
<212> TYPE: RNA
<213> ORGANISM: artificial
<220> FEATURE:
<223> OTHER INFORMATION: RNA Oligomer

<400> SEQUENCE: 125
gcacagcaga auucaauga                                                    19
```

```
<210> SEQ ID NO 126
<211> LENGTH: 19
<212> TYPE: RNA
<213> ORGANISM: artificial
<220> FEATURE:
<223> OTHER INFORMATION: RNA Oligomer

<400> SEQUENCE: 126
cucauuaaau ucagaugcc                                              19

<210> SEQ ID NO 127
<211> LENGTH: 19
<212> TYPE: RNA
<213> ORGANISM: artificial
<220> FEATURE:
<223> OTHER INFORMATION: RNA Oligomer

<400> SEQUENCE: 127
acucauuaaa uucagaugc                                              19

<210> SEQ ID NO 128
<211> LENGTH: 19
<212> TYPE: RNA
<213> ORGANISM: artificial
<220> FEATURE:
<223> OTHER INFORMATION: RNA Oligomer

<400> SEQUENCE: 128
aaccaguuga cagugaacu                                              19

<210> SEQ ID NO 129
<211> LENGTH: 19
<212> TYPE: RNA
<213> ORGANISM: artificial
<220> FEATURE:
<223> OTHER INFORMATION: RNA Oligomer

<400> SEQUENCE: 129
uccuucagca gcauccucu                                              19

<210> SEQ ID NO 130
<211> LENGTH: 19
<212> TYPE: RNA
<213> ORGANISM: artificial
<220> FEATURE:
<223> OTHER INFORMATION: RNA Oligomer

<400> SEQUENCE: 130
gaggauuccu ucagcagca                                              19

<210> SEQ ID NO 131
<211> LENGTH: 19
<212> TYPE: RNA
<213> ORGANISM: artificial
<220> FEATURE:
<223> OTHER INFORMATION: RNA Oligomer

<400> SEQUENCE: 131
aguaagucga gaaguauuu                                              19

<210> SEQ ID NO 132
<211> LENGTH: 19
<212> TYPE: RNA
<213> ORGANISM: artificial
<220> FEATURE:
<223> OTHER INFORMATION: RNA Oligomer

<400> SEQUENCE: 132
```

```
gaguaagucg agaaguauu                                              19

<210> SEQ ID NO 133
<211> LENGTH: 19
<212> TYPE: RNA
<213> ORGANISM: artificial
<220> FEATURE:
<223> OTHER INFORMATION: RNA Oligomer

<400> SEQUENCE: 133
acucaucuau acccucaau                                              19

<210> SEQ ID NO 134
<211> LENGTH: 19
<212> TYPE: RNA
<213> ORGANISM: artificial
<220> FEATURE:
<223> OTHER INFORMATION: RNA Oligomer

<400> SEQUENCE: 134
uuacucaucu auacccuca                                              19

<210> SEQ ID NO 135
<211> LENGTH: 19
<212> TYPE: RNA
<213> ORGANISM: artificial
<220> FEATURE:
<223> OTHER INFORMATION: RNA Oligomer

<400> SEQUENCE: 135
ugaguuacag ugucuuaau                                              19

<210> SEQ ID NO 136
<211> LENGTH: 19
<212> TYPE: RNA
<213> ORGANISM: artificial
<220> FEATURE:
<223> OTHER INFORMATION: RNA Oligomer

<400> SEQUENCE: 136
uuuggaggca agauauaga                                              19

<210> SEQ ID NO 137
<211> LENGTH: 19
<212> TYPE: RNA
<213> ORGANISM: artificial
<220> FEATURE:
<223> OTHER INFORMATION: RNA Oligomer

<400> SEQUENCE: 137
aggacauuga gcaaguuug                                              19

<210> SEQ ID NO 138
<211> LENGTH: 19
<212> TYPE: RNA
<213> ORGANISM: artificial
<220> FEATURE:
<223> OTHER INFORMATION: RNA Oligomer

<400> SEQUENCE: 138
uagacgguau gcaacagga                                              19

<210> SEQ ID NO 139
<211> LENGTH: 19
<212> TYPE: RNA
<213> ORGANISM: artificial
```

```
<220> FEATURE:
<223> OTHER INFORMATION: RNA Oligomer

<400> SEQUENCE: 139
uugauuuaga cgguaugca                                                19

<210> SEQ ID NO 140
<211> LENGTH: 19
<212> TYPE: RNA
<213> ORGANISM: artificial
<220> FEATURE:
<223> OTHER INFORMATION: RNA Oligomer

<400> SEQUENCE: 140
uucauugcua cuaaucagg                                                19

<210> SEQ ID NO 141
<211> LENGTH: 19
<212> TYPE: RNA
<213> ORGANISM: artificial
<220> FEATURE:
<223> OTHER INFORMATION: RNA Oligomer

<400> SEQUENCE: 141
agucuucauu gcuacuaau                                                19

<210> SEQ ID NO 142
<211> LENGTH: 19
<212> TYPE: RNA
<213> ORGANISM: artificial
<220> FEATURE:
<223> OTHER INFORMATION: RNA Oligomer

<400> SEQUENCE: 142
cggcuacguu ucagucacu                                                19

<210> SEQ ID NO 143
<211> LENGTH: 19
<212> TYPE: RNA
<213> ORGANISM: artificial
<220> FEATURE:
<223> OTHER INFORMATION: RNA Oligomer

<400> SEQUENCE: 143
aggacaugga uuugauuga                                                19

<210> SEQ ID NO 144
<211> LENGTH: 19
<212> TYPE: RNA
<213> ORGANISM: artificial
<220> FEATURE:
<223> OTHER INFORMATION: RNA Oligomer

<400> SEQUENCE: 144
gcccacauuc ccaaaucag                                                19

<210> SEQ ID NO 145
<211> LENGTH: 19
<212> TYPE: RNA
<213> ORGANISM: artificial
<220> FEATURE:
<223> OTHER INFORMATION: RNA Oligomer

<400> SEQUENCE: 145
agcaggacau ggauuugau                                                19
```

```
<210> SEQ ID NO 146
<211> LENGTH: 19
<212> TYPE: RNA
<213> ORGANISM: artificial
<220> FEATURE:
<223> OTHER INFORMATION: RNA Oligomer

<400> SEQUENCE: 146
agcugguacu aauaaagga                                            19

<210> SEQ ID NO 147
<211> LENGTH: 19
<212> TYPE: RNA
<213> ORGANISM: artificial
<220> FEATURE:
<223> OTHER INFORMATION: RNA Oligomer

<400> SEQUENCE: 147
gagcugguac uaauaaagg                                            19

<210> SEQ ID NO 148
<211> LENGTH: 19
<212> TYPE: RNA
<213> ORGANISM: artificial
<220> FEATURE:
<223> OTHER INFORMATION: RNA Oligomer

<400> SEQUENCE: 148
agagcuggua cuaauaaag                                            19

<210> SEQ ID NO 149
<211> LENGTH: 19
<212> TYPE: RNA
<213> ORGANISM: artificial
<220> FEATURE:
<223> OTHER INFORMATION: RNA Oligomer

<400> SEQUENCE: 149
cuaaccacua uguacuuuu                                            19

<210> SEQ ID NO 150
<211> LENGTH: 19
<212> TYPE: RNA
<213> ORGANISM: artificial
<220> FEATURE:
<223> OTHER INFORMATION: RNA Oligomer

<400> SEQUENCE: 150
acaucuggcu aaaaagaaa                                            19

<210> SEQ ID NO 151
<211> LENGTH: 19
<212> TYPE: RNA
<213> ORGANISM: artificial
<220> FEATURE:
<223> OTHER INFORMATION: RNA Oligomer

<400> SEQUENCE: 151
cuguucuuau gucauuugu                                            19

<210> SEQ ID NO 152
<211> LENGTH: 19
<212> TYPE: RNA
<213> ORGANISM: artificial
<220> FEATURE:
<223> OTHER INFORMATION: RNA Oligomer

<400> SEQUENCE: 152
```

```
ugggcuaguu ucuguguaa                                              19

<210> SEQ ID NO 153
<211> LENGTH: 19
<212> TYPE: RNA
<213> ORGANISM: artificial
<220> FEATURE:
<223> OTHER INFORMATION: RNA Oligomer

<400> SEQUENCE: 153
guaaacaauu ucuuaggac                                              19

<210> SEQ ID NO 154
<211> LENGTH: 19
<212> TYPE: RNA
<213> ORGANISM: artificial
<220> FEATURE:
<223> OTHER INFORMATION: RNA Oligomer

<400> SEQUENCE: 154
cuguaaacaa uuucuuagg                                              19

<210> SEQ ID NO 155
<211> LENGTH: 19
<212> TYPE: RNA
<213> ORGANISM: artificial
<220> FEATURE:
<223> OTHER INFORMATION: RNA Oligomer

<400> SEQUENCE: 155
gucaguaugu ugaaucagu                                              19

<210> SEQ ID NO 156
<211> LENGTH: 19
<212> TYPE: RNA
<213> ORGANISM: artificial
<220> FEATURE:
<223> OTHER INFORMATION: RNA Oligomer

<400> SEQUENCE: 156
ggcaauguuu uccuuguuc                                              19

<210> SEQ ID NO 157
<211> LENGTH: 19
<212> TYPE: RNA
<213> ORGANISM: artificial
<220> FEATURE:
<223> OTHER INFORMATION: RNA Oligomer

<400> SEQUENCE: 157
gcaccuuaua ucucgaagu                                              19

<210> SEQ ID NO 158
<211> LENGTH: 19
<212> TYPE: RNA
<213> ORGANISM: artificial
<220> FEATURE:
<223> OTHER INFORMATION: RNA Oligomer

<400> SEQUENCE: 158
gaaaaaacaa cucagcacc                                              19

<210> SEQ ID NO 159
<211> LENGTH: 19
<212> TYPE: RNA
<213> ORGANISM: artificial
```

```
<220> FEATURE:
<223> OTHER INFORMATION: RNA Oligomer

<400> SEQUENCE: 159
agagcaagau uuagaucau                                                  19

<210> SEQ ID NO 160
<211> LENGTH: 19
<212> TYPE: RNA
<213> ORGANISM: artificial
<220> FEATURE:
<223> OTHER INFORMATION: RNA Oligomer

<400> SEQUENCE: 160
uagagcaaga uuuagauca                                                  19

<210> SEQ ID NO 161
<211> LENGTH: 19
<212> TYPE: RNA
<213> ORGANISM: artificial
<220> FEATURE:
<223> OTHER INFORMATION: RNA Oligomer

<400> SEQUENCE: 161
uagaacuaga gcaagauuu                                                  19

<210> SEQ ID NO 162
<211> LENGTH: 19
<212> TYPE: RNA
<213> ORGANISM: artificial
<220> FEATURE:
<223> OTHER INFORMATION: RNA Oligomer

<400> SEQUENCE: 162
acguaggagg gguaagaau                                                  19

<210> SEQ ID NO 163
<211> LENGTH: 19
<212> TYPE: RNA
<213> ORGANISM: artificial
<220> FEATURE:
<223> OTHER INFORMATION: RNA Oligomer

<400> SEQUENCE: 163
ucccuguugu ugacuucaa                                                  19

<210> SEQ ID NO 164
<211> LENGTH: 19
<212> TYPE: RNA
<213> ORGANISM: artificial
<220> FEATURE:
<223> OTHER INFORMATION: RNA Oligomer

<400> SEQUENCE: 164
ucccuguaga aaaaaucau                                                  19

<210> SEQ ID NO 165
<211> LENGTH: 19
<212> TYPE: RNA
<213> ORGANISM: artificial
<220> FEATURE:
<223> OTHER INFORMATION: RNA Oligomer

<400> SEQUENCE: 165
ucacaagaga ugaacuuag                                                  19
```

```
<210> SEQ ID NO 166
<211> LENGTH: 19
<212> TYPE: RNA
<213> ORGANISM: artificial
<220> FEATURE:
<223> OTHER INFORMATION: RNA Oligomer

<400> SEQUENCE: 166
agagaaagaa uugccugua                                               19

<210> SEQ ID NO 167
<211> LENGTH: 19
<212> TYPE: RNA
<213> ORGANISM: artificial
<220> FEATURE:
<223> OTHER INFORMATION: RNA Oligomer

<400> SEQUENCE: 167
accagagaaa gaauugccu                                               19

<210> SEQ ID NO 168
<211> LENGTH: 19
<212> TYPE: RNA
<213> ORGANISM: artificial
<220> FEATURE:
<223> OTHER INFORMATION: RNA Oligomer

<400> SEQUENCE: 168
caccagagaa agaauugcc                                               19

<210> SEQ ID NO 169
<211> LENGTH: 19
<212> TYPE: RNA
<213> ORGANISM: artificial
<220> FEATURE:
<223> OTHER INFORMATION: RNA Oligomer

<400> SEQUENCE: 169
aguaugagcu ggaaaaaca                                               19

<210> SEQ ID NO 170
<211> LENGTH: 19
<212> TYPE: RNA
<213> ORGANISM: artificial
<220> FEATURE:
<223> OTHER INFORMATION: RNA Oligomer

<400> SEQUENCE: 170
guacauucuu cugggdaua                                               19

<210> SEQ ID NO 171
<211> LENGTH: 19
<212> TYPE: RNA
<213> ORGANISM: artificial
<220> FEATURE:
<223> OTHER INFORMATION: RNA Oligomer

<400> SEQUENCE: 171
caaacagaau gguccuaaa                                               19

<210> SEQ ID NO 172
<211> LENGTH: 19
<212> TYPE: RNA
<213> ORGANISM: artificial
<220> FEATURE:
<223> OTHER INFORMATION: RNA Oligomer

<400> SEQUENCE: 172
```

```
cuggaagugu caaacagaa                                              19

<210> SEQ ID NO 173
<211> LENGTH: 19
<212> TYPE: RNA
<213> ORGANISM: artificial
<220> FEATURE:
<223> OTHER INFORMATION: RNA Oligomer

<400> SEQUENCE: 173
ggaaagagua ugagcugga                                              19

<210> SEQ ID NO 174
<211> LENGTH: 19
<212> TYPE: RNA
<213> ORGANISM: artificial
<220> FEATURE:
<223> OTHER INFORMATION: RNA Oligomer

<400> SEQUENCE: 174
cagugauucu gaaguggaa                                              19

<210> SEQ ID NO 175
<211> LENGTH: 19
<212> TYPE: RNA
<213> ORGANISM: artificial
<220> FEATURE:
<223> OTHER INFORMATION: RNA Oligomer

<400> SEQUENCE: 175
gacggaaaga guaugagcu                                              19

<210> SEQ ID NO 176
<211> LENGTH: 19
<212> TYPE: RNA
<213> ORGANISM: artificial
<220> FEATURE:
<223> OTHER INFORMATION: RNA Oligomer

<400> SEQUENCE: 176
cacagcagaa uucaaugau                                              19

<210> SEQ ID NO 177
<211> LENGTH: 19
<212> TYPE: RNA
<213> ORGANISM: artificial
<220> FEATURE:
<223> OTHER INFORMATION: RNA Oligomer

<400> SEQUENCE: 177
gccacaguca acacagauu                                              19

<210> SEQ ID NO 178
<211> LENGTH: 19
<212> TYPE: RNA
<213> ORGANISM: artificial
<220> FEATURE:
<223> OTHER INFORMATION: RNA Oligomer

<400> SEQUENCE: 178
uaaauucaga ugccacagu                                              19

<210> SEQ ID NO 179
<211> LENGTH: 19
<212> TYPE: RNA
<213> ORGANISM: artificial
```

```
<220> FEATURE:
<223> OTHER INFORMATION: RNA Oligomer

<400> SEQUENCE: 179
ccaguugaca gugaacuca                                                19

<210> SEQ ID NO 180
<211> LENGTH: 19
<212> TYPE: RNA
<213> ORGANISM: artificial
<220> FEATURE:
<223> OTHER INFORMATION: RNA Oligomer

<400> SEQUENCE: 180
gucgagaagu auuugacuu                                                19

<210> SEQ ID NO 181
<211> LENGTH: 19
<212> TYPE: RNA
<213> ORGANISM: artificial
<220> FEATURE:
<223> OTHER INFORMATION: RNA Oligomer

<400> SEQUENCE: 181
cuguagucca cauuuucuu                                                19

<210> SEQ ID NO 182
<211> LENGTH: 19
<212> TYPE: RNA
<213> ORGANISM: artificial
<220> FEATURE:
<223> OTHER INFORMATION: RNA Oligomer

<400> SEQUENCE: 182
ggaguaaguc gagaaguau                                                19

<210> SEQ ID NO 183
<211> LENGTH: 19
<212> TYPE: RNA
<213> ORGANISM: artificial
<220> FEATURE:
<223> OTHER INFORMATION: RNA Oligomer

<400> SEQUENCE: 183
gacagaaguu gacaauuau                                                19

<210> SEQ ID NO 184
<211> LENGTH: 19
<212> TYPE: RNA
<213> ORGANISM: artificial
<220> FEATURE:
<223> OTHER INFORMATION: RNA Oligomer

<400> SEQUENCE: 184
gagacuacca ugguuccaa                                                19

<210> SEQ ID NO 185
<211> LENGTH: 19
<212> TYPE: RNA
<213> ORGANISM: artificial
<220> FEATURE:
<223> OTHER INFORMATION: RNA Oligomer

<400> SEQUENCE: 185
cuauuaucca uuccugagu                                                19
```

```
<210> SEQ ID NO 186
<211> LENGTH: 19
<212> TYPE: RNA
<213> ORGANISM: artificial
<220> FEATURE:
<223> OTHER INFORMATION: RNA Oligomer

<400> SEQUENCE: 186
gacgguaugc aacaggaca                                                  19

<210> SEQ ID NO 187
<211> LENGTH: 19
<212> TYPE: RNA
<213> ORGANISM: artificial
<220> FEATURE:
<223> OTHER INFORMATION: RNA Oligomer

<400> SEQUENCE: 187
cgagagccca gucuucauu                                                  19

<210> SEQ ID NO 188
<211> LENGTH: 19
<212> TYPE: RNA
<213> ORGANISM: artificial
<220> FEATURE:
<223> OTHER INFORMATION: RNA Oligomer

<400> SEQUENCE: 188
uugauugaca uacuuugga                                                  19

<210> SEQ ID NO 189
<211> LENGTH: 19
<212> TYPE: RNA
<213> ORGANISM: artificial
<220> FEATURE:
<223> OTHER INFORMATION: RNA Oligomer

<400> SEQUENCE: 189
gucacuuguu ccugauauu                                                  19

<210> SEQ ID NO 190
<211> LENGTH: 19
<212> TYPE: RNA
<213> ORGANISM: artificial
<220> FEATURE:
<223> OTHER INFORMATION: RNA Oligomer

<400> SEQUENCE: 190
ucggcuacgu uucagucac                                                  19

<210> SEQ ID NO 191
<211> LENGTH: 19
<212> TYPE: RNA
<213> ORGANISM: artificial
<220> FEATURE:
<223> OTHER INFORMATION: RNA Oligomer

<400> SEQUENCE: 191
gagguuucuu cggcuacgu                                                  19

<210> SEQ ID NO 192
<211> LENGTH: 19
<212> TYPE: RNA
<213> ORGANISM: artificial
<220> FEATURE:
<223> OTHER INFORMATION: RNA Oligomer

<400> SEQUENCE: 192
```
gacauucccg uuuguagau                                              19

<210> SEQ ID NO 193
<211> LENGTH: 19
<212> TYPE: RNA
<213> ORGANISM: artificial
<220> FEATURE:
<223> OTHER INFORMATION: RNA Oligomer

<400> SEQUENCE: 193
gacauggauu ugauugaca                                              19

<210> SEQ ID NO 194
<211> LENGTH: 19
<212> TYPE: RNA
<213> ORGANISM: artificial
<220> FEATURE:
<223> OTHER INFORMATION: RNA Oligomer

<400> SEQUENCE: 194
ucagaugcuu uguacuuug                                              19

<210> SEQ ID NO 195
<211> LENGTH: 19
<212> TYPE: RNA
<213> ORGANISM: artificial
<220> FEATURE:
<223> OTHER INFORMATION: RNA Oligomer

<400> SEQUENCE: 195
cagcaggaca uggauuuga                                              19

<210> SEQ ID NO 196
<211> LENGTH: 19
<212> TYPE: RNA
<213> ORGANISM: artificial
<220> FEATURE:
<223> OTHER INFORMATION: RNA Oligomer

<400> SEQUENCE: 196
auggacaaaa aauggcauu                                              19

<210> SEQ ID NO 197
<211> LENGTH: 19
<212> TYPE: RNA
<213> ORGANISM: artificial
<220> FEATURE:
<223> OTHER INFORMATION: RNA Oligomer

<400> SEQUENCE: 197
guauggacaa aaauggca                                               19

<210> SEQ ID NO 198
<211> LENGTH: 19
<212> TYPE: RNA
<213> ORGANISM: artificial
<220> FEATURE:
<223> OTHER INFORMATION: RNA Oligomer

<400> SEQUENCE: 198
caucuggcua aaagaaau                                               19

<210> SEQ ID NO 199
<211> LENGTH: 19
<212> TYPE: RNA
<213> ORGANISM: artificial

```
<220> FEATURE:
<223> OTHER INFORMATION: RNA Oligomer

<400> SEQUENCE: 199
gacaucuggc uaaaaagaa                                                    19

<210> SEQ ID NO 200
<211> LENGTH: 19
<212> TYPE: RNA
<213> ORGANISM: artificial
<220> FEATURE:
<223> OTHER INFORMATION: RNA Oligomer

<400> SEQUENCE: 200
gagcuaguuu uuuuguacu                                                    19

<210> SEQ ID NO 201
<211> LENGTH: 19
<212> TYPE: RNA
<213> ORGANISM: artificial
<220> FEATURE:
<223> OTHER INFORMATION: RNA Oligomer

<400> SEQUENCE: 201
gaagauggaa aaccuuauu                                                    19

<210> SEQ ID NO 202
<211> LENGTH: 19
<212> TYPE: RNA
<213> ORGANISM: artificial
<220> FEATURE:
<223> OTHER INFORMATION: RNA Oligomer

<400> SEQUENCE: 202
gcuacgugau gaagaugga                                                    19

<210> SEQ ID NO 203
<211> LENGTH: 19
<212> TYPE: RNA
<213> ORGANISM: artificial
<220> FEATURE:
<223> OTHER INFORMATION: RNA Oligomer

<400> SEQUENCE: 203
ugcuacguga ugaagaugg                                                    19

<210> SEQ ID NO 204
<211> LENGTH: 19
<212> TYPE: RNA
<213> ORGANISM: artificial
<220> FEATURE:
<223> OTHER INFORMATION: RNA Oligomer

<400> SEQUENCE: 204
gagcaagauu uagaucauu                                                    19

<210> SEQ ID NO 205
<211> LENGTH: 19
<212> TYPE: RNA
<213> ORGANISM: artificial
<220> FEATURE:
<223> OTHER INFORMATION: RNA Oligomer

<400> SEQUENCE: 205
acuagagcaa gauuuagau                                                    19
```

```
<210> SEQ ID NO 206
<211> LENGTH: 19
<212> TYPE: RNA
<213> ORGANISM: artificial
<220> FEATURE:
<223> OTHER INFORMATION: RNA Oligomer

<400> SEQUENCE: 206
uaguagaacu agagcaaga                                                19

<210> SEQ ID NO 207
<211> LENGTH: 19
<212> TYPE: RNA
<213> ORGANISM: artificial
<220> FEATURE:
<223> OTHER INFORMATION: RNA Oligomer

<400> SEQUENCE: 207
auaucccauu cccuguaga                                                19

<210> SEQ ID NO 208
<211> LENGTH: 19
<212> TYPE: RNA
<213> ORGANISM: artificial
<220> FEATURE:
<223> OTHER INFORMATION: RNA Oligomer

<400> SEQUENCE: 208
ccauauccca uucccugua                                                19

<210> SEQ ID NO 209
<211> LENGTH: 19
<212> TYPE: RNA
<213> ORGANISM: artificial
<220> FEATURE:
<223> OTHER INFORMATION: RNA Oligomer

<400> SEQUENCE: 209
ccccauucac aaaagacaa                                                19

<210> SEQ ID NO 210
<211> LENGTH: 19
<212> TYPE: RNA
<213> ORGANISM: artificial
<220> FEATURE:
<223> OTHER INFORMATION: RNA Oligomer

<400> SEQUENCE: 210
acaccagaga aagaauugc                                                19

<210> SEQ ID NO 211
<211> LENGTH: 19
<212> TYPE: RNA
<213> ORGANISM: artificial
<220> FEATURE:
<223> OTHER INFORMATION: RNA Oligomer

<400> SEQUENCE: 211
ucaaacagaa ugguccuaa                                                19

<210> SEQ ID NO 212
<211> LENGTH: 19
<212> TYPE: RNA
<213> ORGANISM: artificial
<220> FEATURE:
<223> OTHER INFORMATION: RNA Oligomer

<400> SEQUENCE: 212
```
aagaguauga gcuggaaaa         19

<210> SEQ ID NO 213
<211> LENGTH: 19
<212> TYPE: RNA
<213> ORGANISM: artificial
<220> FEATURE:
<223> OTHER INFORMATION: RNA Oligomer

<400> SEQUENCE: 213
ugccccugga agugucaaa         19

<210> SEQ ID NO 214
<211> LENGTH: 19
<212> TYPE: RNA
<213> ORGANISM: artificial
<220> FEATURE:
<223> OTHER INFORMATION: RNA Oligomer

<400> SEQUENCE: 214
gcgacggaaa gaguaugag         19

<210> SEQ ID NO 215
<211> LENGTH: 19
<212> TYPE: RNA
<213> ORGANISM: artificial
<220> FEATURE:
<223> OTHER INFORMATION: RNA Oligomer

<400> SEQUENCE: 215
cugaacuucu aaaugggcc         19

<210> SEQ ID NO 216
<211> LENGTH: 19
<212> TYPE: RNA
<213> ORGANISM: artificial
<220> FEATURE:
<223> OTHER INFORMATION: RNA Oligomer

<400> SEQUENCE: 216
ccacagucaa cacagauuu         19

<210> SEQ ID NO 217
<211> LENGTH: 19
<212> TYPE: RNA
<213> ORGANISM: artificial
<220> FEATURE:
<223> OTHER INFORMATION: RNA Oligomer

<400> SEQUENCE: 217
augcuuuuga ggauuccuu         19

<210> SEQ ID NO 218
<211> LENGTH: 19
<212> TYPE: RNA
<213> ORGANISM: artificial
<220> FEATURE:
<223> OTHER INFORMATION: RNA Oligomer

<400> SEQUENCE: 218
cucaauggaa aaagaagua         19

<210> SEQ ID NO 219
<211> LENGTH: 19
<212> TYPE: RNA
<213> ORGANISM: artificial

```
<220> FEATURE:
<223> OTHER INFORMATION: RNA Oligomer

<400> SEQUENCE: 219
cucaucuaua cccucaaug                                               19

<210> SEQ ID NO 220
<211> LENGTH: 19
<212> TYPE: RNA
<213> ORGANISM: artificial
<220> FEATURE:
<223> OTHER INFORMATION: RNA Oligomer

<400> SEQUENCE: 220
acauugagca aguuuggga                                               19

<210> SEQ ID NO 221
<211> LENGTH: 19
<212> TYPE: RNA
<213> ORGANISM: artificial
<220> FEATURE:
<223> OTHER INFORMATION: RNA Oligomer

<400> SEQUENCE: 221
aacaggacau ugagcaagu                                               19

<210> SEQ ID NO 222
<211> LENGTH: 19
<212> TYPE: RNA
<213> ORGANISM: artificial
<220> FEATURE:
<223> OTHER INFORMATION: RNA Oligomer

<400> SEQUENCE: 222
uuagacggua ugcaacagg                                               19

<210> SEQ ID NO 223
<211> LENGTH: 19
<212> TYPE: RNA
<213> ORGANISM: artificial
<220> FEATURE:
<223> OTHER INFORMATION: RNA Oligomer

<400> SEQUENCE: 223
accugaaacu ucuguugcu                                               19

<210> SEQ ID NO 224
<211> LENGTH: 19
<212> TYPE: RNA
<213> ORGANISM: artificial
<220> FEATURE:
<223> OTHER INFORMATION: RNA Oligomer

<400> SEQUENCE: 224
ccagucuuca uugcuacua                                               19

<210> SEQ ID NO 225
<211> LENGTH: 19
<212> TYPE: RNA
<213> ORGANISM: artificial
<220> FEATURE:
<223> OTHER INFORMATION: RNA Oligomer

<400> SEQUENCE: 225
agagcccagu cuucauugc                                               19
```

```
<210> SEQ ID NO 226
<211> LENGTH: 19
<212> TYPE: RNA
<213> ORGANISM: artificial
<220> FEATURE:
<223> OTHER INFORMATION: RNA Oligomer

<400> SEQUENCE: 226
agucacuugu uccugauau                                                    19

<210> SEQ ID NO 227
<211> LENGTH: 19
<212> TYPE: RNA
<213> ORGANISM: artificial
<220> FEATURE:
<223> OTHER INFORMATION: RNA Oligomer

<400> SEQUENCE: 227
uggauuugau ugacauacu                                                    19

<210> SEQ ID NO 228
<211> LENGTH: 19
<212> TYPE: RNA
<213> ORGANISM: artificial
<220> FEATURE:
<223> OTHER INFORMATION: RNA Oligomer

<400> SEQUENCE: 228
caaugagguu ucuucggcu                                                    19

<210> SEQ ID NO 229
<211> LENGTH: 19
<212> TYPE: RNA
<213> ORGANISM: artificial
<220> FEATURE:
<223> OTHER INFORMATION: RNA Oligomer

<400> SEQUENCE: 229
acaaugaggu uucuucggc                                                    19

<210> SEQ ID NO 230
<211> LENGTH: 19
<212> TYPE: RNA
<213> ORGANISM: artificial
<220> FEATURE:
<223> OTHER INFORMATION: RNA Oligomer

<400> SEQUENCE: 230
agacauuccc guuuguaga                                                    19

<210> SEQ ID NO 231
<211> LENGTH: 19
<212> TYPE: RNA
<213> ORGANISM: artificial
<220> FEATURE:
<223> OTHER INFORMATION: RNA Oligomer

<400> SEQUENCE: 231
gcuuuguacu uugaugacu                                                    19

<210> SEQ ID NO 232
<211> LENGTH: 19
<212> TYPE: RNA
<213> ORGANISM: artificial
<220> FEATURE:
<223> OTHER INFORMATION: RNA Oligomer

<400> SEQUENCE: 232
```
cccacauucc caaaucaga                                              19

<210> SEQ ID NO 233
<211> LENGTH: 19
<212> TYPE: RNA
<213> ORGANISM: artificial
<220> FEATURE:
<223> OTHER INFORMATION: RNA Oligomer

<400> SEQUENCE: 233
acaacuagau gaagagaca                                              19

<210> SEQ ID NO 234
<211> LENGTH: 19
<212> TYPE: RNA
<213> ORGANISM: artificial
<220> FEATURE:
<223> OTHER INFORMATION: RNA Oligomer

<400> SEQUENCE: 234
uacaacuaga ugaagagac                                              19

<210> SEQ ID NO 235
<211> LENGTH: 19
<212> TYPE: RNA
<213> ORGANISM: artificial
<220> FEATURE:
<223> OTHER INFORMATION: RNA Oligomer

<400> SEQUENCE: 235
uuuaagagcu gguacuaau                                              19

<210> SEQ ID NO 236
<211> LENGTH: 19
<212> TYPE: RNA
<213> ORGANISM: artificial
<220> FEATURE:
<223> OTHER INFORMATION: RNA Oligomer

<400> SEQUENCE: 236
uggacaaaaa auggcauuu                                              19

<210> SEQ ID NO 237
<211> LENGTH: 19
<212> TYPE: RNA
<213> ORGANISM: artificial
<220> FEATURE:
<223> OTHER INFORMATION: RNA Oligomer

<400> SEQUENCE: 237
gggcuaguuu cuguguaag                                              19

<210> SEQ ID NO 238
<211> LENGTH: 19
<212> TYPE: RNA
<213> ORGANISM: artificial
<220> FEATURE:
<223> OTHER INFORMATION: RNA Oligomer

<400> SEQUENCE: 238
uugggcuagu uucugugua                                              19

<210> SEQ ID NO 239
<211> LENGTH: 19
<212> TYPE: RNA
<213> ORGANISM: artificial

```
<220> FEATURE:
<223> OTHER INFORMATION: RNA Oligomer

<400> SEQUENCE: 239
gugucaguau guugaauca                                                  19

<210> SEQ ID NO 240
<211> LENGTH: 19
<212> TYPE: RNA
<213> ORGANISM: artificial
<220> FEATURE:
<223> OTHER INFORMATION: RNA Oligomer

<400> SEQUENCE: 240
gaugugaaau gcucauacu                                                  19

<210> SEQ ID NO 241
<211> LENGTH: 19
<212> TYPE: RNA
<213> ORGANISM: artificial
<220> FEATURE:
<223> OTHER INFORMATION: RNA Oligomer

<400> SEQUENCE: 241
cuccuacugu gaugugaaa                                                  19

<210> SEQ ID NO 242
<211> LENGTH: 19
<212> TYPE: RNA
<213> ORGANISM: artificial
<220> FEATURE:
<223> OTHER INFORMATION: RNA Oligomer

<400> SEQUENCE: 242
agauuuagga ggauuugac                                                  19

<210> SEQ ID NO 243
<211> LENGTH: 19
<212> TYPE: RNA
<213> ORGANISM: artificial
<220> FEATURE:
<223> OTHER INFORMATION: RNA Oligomer

<400> SEQUENCE: 243
gcaauguuuu ccuuguucc                                                  19

<210> SEQ ID NO 244
<211> LENGTH: 19
<212> TYPE: RNA
<213> ORGANISM: artificial
<220> FEATURE:
<223> OTHER INFORMATION: RNA Oligomer

<400> SEQUENCE: 244
aacaagagau ggcaauguu                                                  19

<210> SEQ ID NO 245
<211> LENGTH: 19
<212> TYPE: RNA
<213> ORGANISM: artificial
<220> FEATURE:
<223> OTHER INFORMATION: RNA Oligomer

<400> SEQUENCE: 245
gcagcaaaca agagauggc                                                  19
```

```
<210> SEQ ID NO 246
<211> LENGTH: 19
<212> TYPE: RNA
<213> ORGANISM: artificial
<220> FEATURE:
<223> OTHER INFORMATION: RNA Oligomer

<400> SEQUENCE: 246
cuccuaguga auacucccu                                                  19

<210> SEQ ID NO 247
<211> LENGTH: 19
<212> TYPE: RNA
<213> ORGANISM: artificial
<220> FEATURE:
<223> OTHER INFORMATION: RNA Oligomer

<400> SEQUENCE: 247
cagcaccuua uaucucgaa                                                  19

<210> SEQ ID NO 248
<211> LENGTH: 19
<212> TYPE: RNA
<213> ORGANISM: artificial
<220> FEATURE:
<223> OTHER INFORMATION: RNA Oligomer

<400> SEQUENCE: 248
ucaccuacug aaaaaacaa                                                  19

<210> SEQ ID NO 249
<211> LENGTH: 19
<212> TYPE: RNA
<213> ORGANISM: artificial
<220> FEATURE:
<223> OTHER INFORMATION: RNA Oligomer

<400> SEQUENCE: 249
gcaagauuua gaucauuug                                                  19

<210> SEQ ID NO 250
<211> LENGTH: 19
<212> TYPE: RNA
<213> ORGANISM: artificial
<220> FEATURE:
<223> OTHER INFORMATION: RNA Oligomer

<400> SEQUENCE: 250 cagaaaaga aaacuggaa                                                   19

<210> SEQ ID NO 251
<211> LENGTH: 19
<212> TYPE: RNA
<213> ORGANISM: artificial
<220> FEATURE:
<223> OTHER INFORMATION: RNA Oligomer

<400> SEQUENCE: 251
auacguagga gggguaaga                                                  19

<210> SEQ ID NO 252
<211> LENGTH: 19
<212> TYPE: RNA
<213> ORGANISM: artificial
<220> FEATURE:
<223> OTHER INFORMATION: RNA Oligomer

<400> SEQUENCE: 252
```
ugcauuaauu cgggauaua                                                19

<210> SEQ ID NO 253
<211> LENGTH: 19
<212> TYPE: RNA
<213> ORGANISM: artificial
<220> FEATURE:
<223> OTHER INFORMATION: RNA Oligomer

<400> SEQUENCE: 253
aagcucucca uaucccauu                                                19

<210> SEQ ID NO 254
<211> LENGTH: 19
<212> TYPE: RNA
<213> ORGANISM: artificial
<220> FEATURE:
<223> OTHER INFORMATION: RNA Oligomer

<400> SEQUENCE: 254
cauucacaaa agacaaaca                                                19

<210> SEQ ID NO 255
<211> LENGTH: 19
<212> TYPE: RNA
<213> ORGANISM: artificial
<220> FEATURE:
<223> OTHER INFORMATION: RNA Oligomer

<400> SEQUENCE: 255
gaguaugagc uggaaaaac                                                19

<210> SEQ ID NO 256
<211> LENGTH: 19
<212> TYPE: RNA
<213> ORGANISM: artificial
<220> FEATURE:
<223> OTHER INFORMATION: RNA Oligomer

<400> SEQUENCE: 256
cagaaugguc cuaaaacac                                                19

<210> SEQ ID NO 257
<211> LENGTH: 19
<212> TYPE: RNA
<213> ORGANISM: artificial
<220> FEATURE:
<223> OTHER INFORMATION: RNA Oligomer

<400> SEQUENCE: 257
gugucaaaca gaauggucc                                                19

<210> SEQ ID NO 258
<211> LENGTH: 19
<212> TYPE: RNA
<213> ORGANISM: artificial
<220> FEATURE:
<223> OTHER INFORMATION: RNA Oligomer

<400> SEQUENCE: 258
gaagugucaa acagaaugg                                                19

<210> SEQ ID NO 259
<211> LENGTH: 19
<212> TYPE: RNA
<213> ORGANISM: artificial

```
<220> FEATURE:
<223> OTHER INFORMATION: RNA Oligomer

<400> SEQUENCE: 259
cugaagugga agagcuaga                                              19

<210> SEQ ID NO 260
<211> LENGTH: 19
<212> TYPE: RNA
<213> ORGANISM: artificial
<220> FEATURE:
<223> OTHER INFORMATION: RNA Oligomer

<400> SEQUENCE: 260
ccagaacacu caguggaau                                              19

<210> SEQ ID NO 261
<211> LENGTH: 19
<212> TYPE: RNA
<213> ORGANISM: artificial
<220> FEATURE:
<223> OTHER INFORMATION: RNA Oligomer

<400> SEQUENCE: 261
uucugacucc ggcauuuca                                              19

<210> SEQ ID NO 262
<211> LENGTH: 19
<212> TYPE: RNA
<213> ORGANISM: artificial
<220> FEATURE:
<223> OTHER INFORMATION: RNA Oligomer

<400> SEQUENCE: 262
augauucuga cuccggcau                                              19

<210> SEQ ID NO 263
<211> LENGTH: 19
<212> TYPE: RNA
<213> ORGANISM: artificial
<220> FEATURE:
<223> OTHER INFORMATION: RNA Oligomer

<400> SEQUENCE: 263
ggcccauuga uguuucuga                                              19

<210> SEQ ID NO 264
<211> LENGTH: 19
<212> TYPE: RNA
<213> ORGANISM: artificial
<220> FEATURE:
<223> OTHER INFORMATION: RNA Oligomer

<400> SEQUENCE: 264
cacagauuuu ggugaugaa                                              19

<210> SEQ ID NO 265
<211> LENGTH: 19
<212> TYPE: RNA
<213> ORGANISM: artificial
<220> FEATURE:
<223> OTHER INFORMATION: RNA Oligomer

<400> SEQUENCE: 265
caguugacag ugaacucau                                              19
```

```
<210> SEQ ID NO 266
<211> LENGTH: 19
<212> TYPE: RNA
<213> ORGANISM: artificial
<220> FEATURE:
<223> OTHER INFORMATION: RNA Oligomer

<400> SEQUENCE: 266
uuaaugcuuu ugaggauuc                                              19

<210> SEQ ID NO 267
<211> LENGTH: 19
<212> TYPE: RNA
<213> ORGANISM: artificial
<220> FEATURE:
<223> OTHER INFORMATION: RNA Oligomer

<400> SEQUENCE: 267
ucuuaaugcu uuugaggau                                              19

<210> SEQ ID NO 268
<211> LENGTH: 19
<212> TYPE: RNA
<213> ORGANISM: artificial
<220> FEATURE:
<223> OTHER INFORMATION: RNA Oligomer

<400> SEQUENCE: 268
aguccacauu uucuuaaug                                              19

<210> SEQ ID NO 269
<211> LENGTH: 19
<212> TYPE: RNA
<213> ORGANISM: artificial
<220> FEATURE:
<223> OTHER INFORMATION: RNA Oligomer

<400> SEQUENCE: 269
ugacagaagu ugacaauua                                              19

<210> SEQ ID NO 270
<211> LENGTH: 19
<212> TYPE: RNA
<213> ORGANISM: artificial
<220> FEATURE:
<223> OTHER INFORMATION: RNA Oligomer

<400> SEQUENCE: 270
ccaaacugac agaaguuga                                              19

<210> SEQ ID NO 271
<211> LENGTH: 19
<212> TYPE: RNA
<213> ORGANISM: artificial
<220> FEATURE:
<223> OTHER INFORMATION: RNA Oligomer

<400> SEQUENCE: 271
guugagacua ccauggduuc                                             19

<210> SEQ ID NO 272
<211> LENGTH: 19
<212> TYPE: RNA
<213> ORGANISM: artificial
<220> FEATURE:
<223> OTHER INFORMATION: RNA Oligomer

<400> SEQUENCE: 272
```
acaagcuggu ugagacuac                                             19

<210> SEQ ID NO 273
<211> LENGTH: 19
<212> TYPE: RNA
<213> ORGANISM: artificial
<220> FEATURE:
<223> OTHER INFORMATION: RNA Oligomer

<400> SEQUENCE: 273
auacuuugga ggcaagaua                                             19

<210> SEQ ID NO 274
<211> LENGTH: 19
<212> TYPE: RNA
<213> ORGANISM: artificial
<220> FEATURE:
<223> OTHER INFORMATION: RNA Oligomer

<400> SEQUENCE: 274
gacauacuuu ggaggcaag                                             19

<210> SEQ ID NO 275
<211> LENGTH: 19
<212> TYPE: RNA
<213> ORGANISM: artificial
<220> FEATURE:
<223> OTHER INFORMATION: RNA Oligomer

<400> SEQUENCE: 275
gucaccugaa acuucuguu                                             19

<210> SEQ ID NO 276
<211> LENGTH: 19
<212> TYPE: RNA
<213> ORGANISM: artificial
<220> FEATURE:
<223> OTHER INFORMATION: RNA Oligomer

<400> SEQUENCE: 276
ucgagagccc agucuucau                                             19

<210> SEQ ID NO 277
<211> LENGTH: 19
<212> TYPE: RNA
<213> ORGANISM: artificial
<220> FEATURE:
<223> OTHER INFORMATION: RNA Oligomer

<400> SEQUENCE: 277
guacuuugau gacugcaug                                             19

<210> SEQ ID NO 278
<211> LENGTH: 19
<212> TYPE: RNA
<213> ORGANISM: artificial
<220> FEATURE:
<223> OTHER INFORMATION: RNA Oligomer

<400> SEQUENCE: 278
uguacuuuga ugacugcau                                             19

<210> SEQ ID NO 279
<211> LENGTH: 19
<212> TYPE: RNA
<213> ORGANISM: artificial

```
<220> FEATURE:
<223> OTHER INFORMATION: RNA Oligomer

<400> SEQUENCE: 279
ggacauggau uugauugac                                                    19

<210> SEQ ID NO 280
<211> LENGTH: 19
<212> TYPE: RNA
<213> ORGANISM: artificial
<220> FEATURE:
<223> OTHER INFORMATION: RNA Oligomer

<400> SEQUENCE: 280
gaugcuuugu acuuugaug                                                    19

<210> SEQ ID NO 281
<211> LENGTH: 19
<212> TYPE: RNA
<213> ORGANISM: artificial
<220> FEATURE:
<223> OTHER INFORMATION: RNA Oligomer

<400> SEQUENCE: 281
aucagaugcu uuguacuuu                                                    19

<210> SEQ ID NO 282
<211> LENGTH: 19
<212> TYPE: RNA
<213> ORGANISM: artificial
<220> FEATURE:
<223> OTHER INFORMATION: RNA Oligomer

<400> SEQUENCE: 282
uucccaaauc agaugcuuu                                                    19

<210> SEQ ID NO 283
<211> LENGTH: 19
<212> TYPE: RNA
<213> ORGANISM: artificial
<220> FEATURE:
<223> OTHER INFORMATION: RNA Oligomer

<400> SEQUENCE: 283
cauucccaaa ucagaugcu                                                    19

<210> SEQ ID NO 284
<211> LENGTH: 19
<212> TYPE: RNA
<213> ORGANISM: artificial
<220> FEATURE:
<223> OTHER INFORMATION: RNA Oligomer

<400> SEQUENCE: 284
ccacauuccc aaaucagau                                                    19

<210> SEQ ID NO 285
<211> LENGTH: 19
<212> TYPE: RNA
<213> ORGANISM: artificial
<220> FEATURE:
<223> OTHER INFORMATION: RNA Oligomer

<400> SEQUENCE: 285
aguuacaacu agaugaaga                                                    19
```

```
<210> SEQ ID NO 286
<211> LENGTH: 19
<212> TYPE: RNA
<213> ORGANISM: artificial
<220> FEATURE:
<223> OTHER INFORMATION: RNA Oligomer

<400> SEQUENCE: 286
uauggacaaa aaauggcau                                               19

<210> SEQ ID NO 287
<211> LENGTH: 19
<212> TYPE: RNA
<213> ORGANISM: artificial
<220> FEATURE:
<223> OTHER INFORMATION: RNA Oligomer

<400> SEQUENCE: 287
acuguaugga caaaaaaug                                               19

<210> SEQ ID NO 288
<211> LENGTH: 19
<212> TYPE: RNA
<213> ORGANISM: artificial
<220> FEATURE:
<223> OTHER INFORMATION: RNA Oligomer

<400> SEQUENCE: 288
uaugacaucu ggcuaaaaa                                               19

<210> SEQ ID NO 289
<211> LENGTH: 19
<212> TYPE: RNA
<213> ORGANISM: artificial
<220> FEATURE:
<223> OTHER INFORMATION: RNA Oligomer

<400> SEQUENCE: 289
acuguucuua ugucauuug                                               19

<210> SEQ ID NO 290
<211> LENGTH: 19
<212> TYPE: RNA
<213> ORGANISM: artificial
<220> FEATURE:
<223> OTHER INFORMATION: RNA Oligomer

<400> SEQUENCE: 290
uaguuucugu guaagugua                                               19

<210> SEQ ID NO 291
<211> LENGTH: 19
<212> TYPE: RNA
<213> ORGANISM: artificial
<220> FEATURE:
<223> OTHER INFORMATION: RNA Oligomer

<400> SEQUENCE: 291
ggcuaguuuc uguguaagu                                               19

<210> SEQ ID NO 292
<211> LENGTH: 19
<212> TYPE: RNA
<213> ORGANISM: artificial
<220> FEATURE:
<223> OTHER INFORMATION: RNA Oligomer

<400> SEQUENCE: 292
```

```
caauuucuua ggacaccau                                                  19

<210> SEQ ID NO 293
<211> LENGTH: 19
<212> TYPE: RNA
<213> ORGANISM: artificial
<220> FEATURE:
<223> OTHER INFORMATION: RNA Oligomer

<400> SEQUENCE: 293
guauguugaa ucaguaguu                                                  19

<210> SEQ ID NO 294
<211> LENGTH: 19
<212> TYPE: RNA
<213> ORGANISM: artificial
<220> FEATURE:
<223> OTHER INFORMATION: RNA Oligomer

<400> SEQUENCE: 294
ucaguauguu gaaucagua                                                  19

<210> SEQ ID NO 295
<211> LENGTH: 19
<212> TYPE: RNA
<213> ORGANISM: artificial
<220> FEATURE:
<223> OTHER INFORMATION: RNA Oligomer

<400> SEQUENCE: 295
ugaugugaaa ugcucauac                                                  19

<210> SEQ ID NO 296
<211> LENGTH: 19
<212> TYPE: RNA
<213> ORGANISM: artificial
<220> FEATURE:
<223> OTHER INFORMATION: RNA Oligomer

<400> SEQUENCE: 296
aaagcuccua cugugaugu                                                  19

<210> SEQ ID NO 297
<211> LENGTH: 19
<212> TYPE: RNA
<213> ORGANISM: artificial
<220> FEATURE:
<223> OTHER INFORMATION: RNA Oligomer

<400> SEQUENCE: 297
uacuaaaagc uccuacugu                                                  19

<210> SEQ ID NO 298
<211> LENGTH: 19
<212> TYPE: RNA
<213> ORGANISM: artificial
<220> FEATURE:
<223> OTHER INFORMATION: RNA Oligomer

<400> SEQUENCE: 298
ggauuugacc uuuucugag                                                  19

<210> SEQ ID NO 299
<211> LENGTH: 19
<212> TYPE: RNA
<213> ORGANISM: artificial
```

```
<220> FEATURE:
<223> OTHER INFORMATION: RNA Oligomer

<400> SEQUENCE: 299
agagauggca auguuucc                                                   19

<210> SEQ ID NO 300
<211> LENGTH: 19
<212> TYPE: RNA
<213> ORGANISM: artificial
<220> FEATURE:
<223> OTHER INFORMATION: RNA Oligomer

<400> SEQUENCE: 300
aaacaagaga uggcaaugu                                                  19

<210> SEQ ID NO 301
<211> LENGTH: 19
<212> TYPE: RNA
<213> ORGANISM: artificial
<220> FEATURE:
<223> OTHER INFORMATION: RNA Oligomer

<400> SEQUENCE: 301
cagcaaacaa gagauggca                                                  19

<210> SEQ ID NO 302
<211> LENGTH: 19
<212> TYPE: RNA
<213> ORGANISM: artificial
<220> FEATURE:
<223> OTHER INFORMATION: RNA Oligomer

<400> SEQUENCE: 302
cuagugaaua cucccugca                                                  19

<210> SEQ ID NO 303
<211> LENGTH: 19
<212> TYPE: RNA
<213> ORGANISM: artificial
<220> FEATURE:
<223> OTHER INFORMATION: RNA Oligomer

<400> SEQUENCE: 303
aagauggaaa accuuauuc                                                  19

<210> SEQ ID NO 304
<211> LENGTH: 19
<212> TYPE: RNA
<213> ORGANISM: artificial
<220> FEATURE:
<223> OTHER INFORMATION: RNA Oligomer

<400> SEQUENCE: 304
cagcaugcua cgugaugaa                                                  19

<210> SEQ ID NO 305
<211> LENGTH: 19
<212> TYPE: RNA
<213> ORGANISM: artificial
<220> FEATURE:
<223> OTHER INFORMATION: RNA Oligomer

<400> SEQUENCE: 305
caccuuauau cucgaaguu                                                  19
```

```
<210> SEQ ID NO 306
<211> LENGTH: 19
<212> TYPE: RNA
<213> ORGANISM: artificial
<220> FEATURE:
<223> OTHER INFORMATION: RNA Oligomer

<400> SEQUENCE: 306
ucagcaccuu auaucucga                                               19

<210> SEQ ID NO 307
<211> LENGTH: 19
<212> TYPE: RNA
<213> ORGANISM: artificial
<220> FEATURE:
<223> OTHER INFORMATION: RNA Oligomer

<400> SEQUENCE: 307
auauaguaga acuagagca                                               19

<210> SEQ ID NO 308
<211> LENGTH: 19
<212> TYPE: RNA
<213> ORGANISM: artificial
<220> FEATURE:
<223> OTHER INFORMATION: RNA Oligomer

<400> SEQUENCE: 308
uugcagaaaa agaaaacug                                               19

<210> SEQ ID NO 309
<211> LENGTH: 19
<212> TYPE: RNA
<213> ORGANISM: artificial
<220> FEATURE:
<223> OTHER INFORMATION: RNA Oligomer

<400> SEQUENCE: 309
acgaaaugau guccaaaga                                               19

<210> SEQ ID NO 310
<211> LENGTH: 19
<212> TYPE: RNA
<213> ORGANISM: artificial
<220> FEATURE:
<223> OTHER INFORMATION: RNA Oligomer

<400> SEQUENCE: 310
accucccugu uguugacuu                                               19

<210> SEQ ID NO 311
<211> LENGTH: 19
<212> TYPE: RNA
<213> ORGANISM: artificial
<220> FEATURE:
<223> OTHER INFORMATION: RNA Oligomer

<400> SEQUENCE: 311
cccuguagaa aaaaucauu                                               19

<210> SEQ ID NO 312
<211> LENGTH: 19
<212> TYPE: RNA
<213> ORGANISM: artificial
<220> FEATURE:
<223> OTHER INFORMATION: RNA Oligomer

<400> SEQUENCE: 312
```
gagaugaacu uagggcaaa					19

<210> SEQ ID NO 313
<211> LENGTH: 19
<212> TYPE: RNA
<213> ORGANISM: artificial
<220> FEATURE:
<223> OTHER INFORMATION: RNA Oligomer

<400> SEQUENCE: 313
cacaagagau gaacuuagg					19

<210> SEQ ID NO 314
<211> LENGTH: 19
<212> TYPE: RNA
<213> ORGANISM: artificial
<220> FEATURE:
<223> OTHER INFORMATION: RNA Oligomer

<400> SEQUENCE: 314
aaccccauuc acaaaagac					19

<210> SEQ ID NO 315
<211> LENGTH: 19
<212> TYPE: RNA
<213> ORGANISM: artificial
<220> FEATURE:
<223> OTHER INFORMATION: RNA Oligomer

<400> SEQUENCE: 315
agaacacacc agagaaaga					19

<210> SEQ ID NO 316
<211> LENGTH: 19
<212> TYPE: RNA
<213> ORGANISM: artificial
<220> FEATURE:
<223> OTHER INFORMATION: RNA Oligomer

<400> SEQUENCE: 316
gucaaacaga augguccua					19

<210> SEQ ID NO 317
<211> LENGTH: 19
<212> TYPE: RNA
<213> ORGANISM: artificial
<220> FEATURE:
<223> OTHER INFORMATION: RNA Oligomer

<400> SEQUENCE: 317
ggaaguguca aacagaaug					19

<210> SEQ ID NO 318
<211> LENGTH: 19
<212> TYPE: RNA
<213> ORGANISM: artificial
<220> FEATURE:
<223> OTHER INFORMATION: RNA Oligomer

<400> SEQUENCE: 318
uggaaguguc aaacagaau					19

<210> SEQ ID NO 319
<211> LENGTH: 19
<212> TYPE: RNA
<213> ORGANISM: artificial

```
<220> FEATURE:
<223> OTHER INFORMATION: RNA Oligomer

<400> SEQUENCE: 319
cccuggaagu gucaaacag                                              19

<210> SEQ ID NO 320
<211> LENGTH: 19
<212> TYPE: RNA
<213> ORGANISM: artificial
<220> FEATURE:
<223> OTHER INFORMATION: RNA Oligomer

<400> SEQUENCE: 320
guggaagagc uagauagug                                              19

<210> SEQ ID NO 321
<211> LENGTH: 19
<212> TYPE: RNA
<213> ORGANISM: artificial
<220> FEATURE:
<223> OTHER INFORMATION: RNA Oligomer

<400> SEQUENCE: 321
accagaacac ucaguggaa                                              19

<210> SEQ ID NO 322
<211> LENGTH: 19
<212> TYPE: RNA
<213> ORGANISM: artificial
<220> FEATURE:
<223> OTHER INFORMATION: RNA Oligomer

<400> SEQUENCE: 322
cagcgacgga aagaguaug                                              19

<210> SEQ ID NO 323
<211> LENGTH: 19
<212> TYPE: RNA
<213> ORGANISM: artificial
<220> FEATURE:
<223> OTHER INFORMATION: RNA Oligomer

<400> SEQUENCE: 323
ugaucuauca cuuugcaaa                                              19

<210> SEQ ID NO 324
<211> LENGTH: 19
<212> TYPE: RNA
<213> ORGANISM: artificial
<220> FEATURE:
<223> OTHER INFORMATION: RNA Oligomer

<400> SEQUENCE: 324
gcccauugau guuucugau                                              19

<210> SEQ ID NO 325
<211> LENGTH: 19
<212> TYPE: RNA
<213> ORGANISM: artificial
<220> FEATURE:
<223> OTHER INFORMATION: RNA Oligomer

<400> SEQUENCE: 325
agucaacaca gauuuuggu                                              19
```

```
<210> SEQ ID NO 326
<211> LENGTH: 19
<212> TYPE: RNA
<213> ORGANISM: artificial
<220> FEATURE:
<223> OTHER INFORMATION: RNA Oligomer

<400> SEQUENCE: 326
aguugacagu gaacucauu                                                  19

<210> SEQ ID NO 327
<211> LENGTH: 19
<212> TYPE: RNA
<213> ORGANISM: artificial
<220> FEATURE:
<223> OTHER INFORMATION: RNA Oligomer

<400> SEQUENCE: 327
acuguagucc acauuuucu                                                  19

<210> SEQ ID NO 328
<211> LENGTH: 19
<212> TYPE: RNA
<213> ORGANISM: artificial
<220> FEATURE:
<223> OTHER INFORMATION: RNA Oligomer

<400> SEQUENCE: 328
caauggaaaa agaaguagg                                                  19

<210> SEQ ID NO 329
<211> LENGTH: 19
<212> TYPE: RNA
<213> ORGANISM: artificial
<220> FEATURE:
<223> OTHER INFORMATION: RNA Oligomer

<400> SEQUENCE: 329
caaacugaca gaaguugac                                                  19

<210> SEQ ID NO 330
<211> LENGTH: 19
<212> TYPE: RNA
<213> ORGANISM: artificial
<220> FEATURE:
<223> OTHER INFORMATION: RNA Oligomer

<400> SEQUENCE: 330
agacuaccau gguuccaag                                                  19

<210> SEQ ID NO 331
<211> LENGTH: 19
<212> TYPE: RNA
<213> ORGANISM: artificial
<220> FEATURE:
<223> OTHER INFORMATION: RNA Oligomer

<400> SEQUENCE: 331
acaggacauu gagcaaguu                                                  19

<210> SEQ ID NO 332
<211> LENGTH: 19
<212> TYPE: RNA
<213> ORGANISM: artificial
<220> FEATURE:
<223> OTHER INFORMATION: RNA Oligomer

<400> SEQUENCE: 332
```
ugacauacuu uggaggcaa                                              19

<210> SEQ ID NO 333
<211> LENGTH: 19
<212> TYPE: RNA
<213> ORGANISM: artificial
<220> FEATURE:
<223> OTHER INFORMATION: RNA Oligomer

<400> SEQUENCE: 333
acguuucagu cacuuguuc                                              19

<210> SEQ ID NO 334
<211> LENGTH: 19
<212> TYPE: RNA
<213> ORGANISM: artificial
<220> FEATURE:
<223> OTHER INFORMATION: RNA Oligomer

<400> SEQUENCE: 334
cuacguuuca gucacuugu                                              19

<210> SEQ ID NO 335
<211> LENGTH: 19
<212> TYPE: RNA
<213> ORGANISM: artificial
<220> FEATURE:
<223> OTHER INFORMATION: RNA Oligomer

<400> SEQUENCE: 335
ggcuacguuu cagucacuu                                              19

<210> SEQ ID NO 336
<211> LENGTH: 19
<212> TYPE: RNA
<213> ORGANISM: artificial
<220> FEATURE:
<223> OTHER INFORMATION: RNA Oligomer

<400> SEQUENCE: 336
ggauuugauu gacauacuu                                              19

<210> SEQ ID NO 337
<211> LENGTH: 19
<212> TYPE: RNA
<213> ORGANISM: artificial
<220> FEATURE:
<223> OTHER INFORMATION: RNA Oligomer

<400> SEQUENCE: 337
ucuucggcua cguuucagu                                              19

<210> SEQ ID NO 338
<211> LENGTH: 19
<212> TYPE: RNA
<213> ORGANISM: artificial
<220> FEATURE:
<223> OTHER INFORMATION: RNA Oligomer

<400> SEQUENCE: 338
cagucagaaa ccaguggau                                              19

<210> SEQ ID NO 339
<211> LENGTH: 19
<212> TYPE: RNA
<213> ORGANISM: artificial

```
<220> FEATURE:
<223> OTHER INFORMATION: RNA Oligomer

<400> SEQUENCE: 339
ugaagagaca ggugaauuu                                               19

<210> SEQ ID NO 340
<211> LENGTH: 19
<212> TYPE: RNA
<213> ORGANISM: artificial
<220> FEATURE:
<223> OTHER INFORMATION: RNA Oligomer

<400> SEQUENCE: 340
uagaugaaga gacagguga                                               19

<210> SEQ ID NO 341
<211> LENGTH: 19
<212> TYPE: RNA
<213> ORGANISM: artificial
<220> FEATURE:
<223> OTHER INFORMATION: RNA Oligomer

<400> SEQUENCE: 341
uaagagcugg uacuaauaa                                               19

<210> SEQ ID NO 342
<211> LENGTH: 19
<212> TYPE: RNA
<213> ORGANISM: artificial
<220> FEATURE:
<223> OTHER INFORMATION: RNA Oligomer

<400> SEQUENCE: 342
cuguauggac aaaaaaugg                                               19

<210> SEQ ID NO 343
<211> LENGTH: 19
<212> TYPE: RNA
<213> ORGANISM: artificial
<220> FEATURE:
<223> OTHER INFORMATION: RNA Oligomer

<400> SEQUENCE: 343
uggaguguca guauguuga                                               19

<210> SEQ ID NO 344
<211> LENGTH: 19
<212> TYPE: RNA
<213> ORGANISM: artificial
<220> FEATURE:
<223> OTHER INFORMATION: RNA Oligomer

<400> SEQUENCE: 344
ugugaaaugc ucauacuuu                                               19

<210> SEQ ID NO 345
<211> LENGTH: 19
<212> TYPE: RNA
<213> ORGANISM: artificial
<220> FEATURE:
<223> OTHER INFORMATION: RNA Oligomer

<400> SEQUENCE: 345
gugaugugaa augcucaua                                               19
```

```
<210> SEQ ID NO 346
<211> LENGTH: 19
<212> TYPE: RNA
<213> ORGANISM: artificial
<220> FEATURE:
<223> OTHER INFORMATION: RNA Oligomer

<400> SEQUENCE: 346 agccuuacu gugauguga                                                    19

<210> SEQ ID NO 347
<211> LENGTH: 19
<212> TYPE: RNA
<213> ORGANISM: artificial
<220> FEATURE:
<223> OTHER INFORMATION: RNA Oligomer

<400> SEQUENCE: 347
uccuagugaa uacucccug                                                   19

<210> SEQ ID NO 348
<211> LENGTH: 19
<212> TYPE: RNA
<213> ORGANISM: artificial
<220> FEATURE:
<223> OTHER INFORMATION: RNA Oligomer

<400> SEQUENCE: 348
uucuccuagu gaauacucc                                                   19

<210> SEQ ID NO 349
<211> LENGTH: 19
<212> TYPE: RNA
<213> ORGANISM: artificial
<220> FEATURE:
<223> OTHER INFORMATION: RNA Oligomer

<400> SEQUENCE: 349
caugcuacgu gaugaagau                                                   19

<210> SEQ ID NO 350
<211> LENGTH: 19
<212> TYPE: RNA
<213> ORGANISM: artificial
<220> FEATURE:
<223> OTHER INFORMATION: RNA Oligomer

<400> SEQUENCE: 350
gcaugcuacg ugaugaaga                                                   19

<210> SEQ ID NO 351
<211> LENGTH: 19
<212> TYPE: RNA
<213> ORGANISM: artificial
<220> FEATURE:
<223> OTHER INFORMATION: RNA Oligomer

<400> SEQUENCE: 351
agcaccuuau aucucgaag                                                   19

<210> SEQ ID NO 352
<211> LENGTH: 19
<212> TYPE: RNA
<213> ORGANISM: artificial
<220> FEATURE:
<223> OTHER INFORMATION: RNA Oligomer

<400> SEQUENCE: 352
```
agaaaaagga gaaaaugac                                               19

<210> SEQ ID NO 353
<211> LENGTH: 19
<212> TYPE: RNA
<213> ORGANISM: artificial
<220> FEATURE:
<223> OTHER INFORMATION: RNA Oligomer

<400> SEQUENCE: 353
ugcagaaaaa gaaaacugg                                               19

<210> SEQ ID NO 354
<211> LENGTH: 19
<212> TYPE: RNA
<213> ORGANISM: artificial
<220> FEATURE:
<223> OTHER INFORMATION: RNA Oligomer

<400> SEQUENCE: 354
ucauuaaccu cccuguugu                                               19

<210> SEQ ID NO 355
<211> LENGTH: 19
<212> TYPE: RNA
<213> ORGANISM: artificial
<220> FEATURE:
<223> OTHER INFORMATION: RNA Oligomer

<400> SEQUENCE: 355
aagugucaaa cagaauggu                                               19

<210> SEQ ID NO 356
<211> LENGTH: 19
<212> TYPE: RNA
<213> ORGANISM: artificial
<220> FEATURE:
<223> OTHER INFORMATION: RNA Oligomer

<400> SEQUENCE: 356
gaaagaguau gagcuggaa                                               19

<210> SEQ ID NO 357
<211> LENGTH: 19
<212> TYPE: RNA
<213> ORGANISM: artificial
<220> FEATURE:
<223> OTHER INFORMATION: RNA Oligomer

<400> SEQUENCE: 357
aaagcacagc agaauucaa                                               19

<210> SEQ ID NO 358
<211> LENGTH: 19
<212> TYPE: RNA
<213> ORGANISM: artificial
<220> FEATURE:
<223> OTHER INFORMATION: RNA Oligomer

<400> SEQUENCE: 358
auguuucuga ucuaucacu                                               19

<210> SEQ ID NO 359
<211> LENGTH: 19
<212> TYPE: RNA
<213> ORGANISM: artificial

```
<220> FEATURE:
<223> OTHER INFORMATION: RNA Oligomer

<400> SEQUENCE: 359
ugggcccauu gauguuucu                                                19

<210> SEQ ID NO 360
<211> LENGTH: 19
<212> TYPE: RNA
<213> ORGANISM: artificial
<220> FEATURE:
<223> OTHER INFORMATION: RNA Oligomer

<400> SEQUENCE: 360
cagucaacac agauuuugg                                                19

<210> SEQ ID NO 361
<211> LENGTH: 19
<212> TYPE: RNA
<213> ORGANISM: artificial
<220> FEATURE:
<223> OTHER INFORMATION: RNA Oligomer

<400> SEQUENCE: 361
acagucaaca cagauuuug                                                19

<210> SEQ ID NO 362
<211> LENGTH: 19
<212> TYPE: RNA
<213> ORGANISM: artificial
<220> FEATURE:
<223> OTHER INFORMATION: RNA Oligomer

<400> SEQUENCE: 362
cacagucaac acagauuuu                                                19

<210> SEQ ID NO 363
<211> LENGTH: 19
<212> TYPE: RNA
<213> ORGANISM: artificial
<220> FEATURE:
<223> OTHER INFORMATION: RNA Oligomer

<400> SEQUENCE: 363
acagaagacc ccaaccagu                                                19

<210> SEQ ID NO 364
<211> LENGTH: 19
<212> TYPE: RNA
<213> ORGANISM: artificial
<220> FEATURE:
<223> OTHER INFORMATION: RNA Oligomer

<400> SEQUENCE: 364
aggauuccuu cagcagcau                                                19

<210> SEQ ID NO 365
<211> LENGTH: 19
<212> TYPE: RNA
<213> ORGANISM: artificial
<220> FEATURE:
<223> OTHER INFORMATION: RNA Oligomer

<400> SEQUENCE: 365
aauggaaaaa gaaguaggu                                                19
```

```
<210> SEQ ID NO 366
<211> LENGTH: 19
<212> TYPE: RNA
<213> ORGANISM: artificial
<220> FEATURE:
<223> OTHER INFORMATION: RNA Oligomer

<400> SEQUENCE: 366
augacaagcu gguugagac                                                19

<210> SEQ ID NO 367
<211> LENGTH: 19
<212> TYPE: RNA
<213> ORGANISM: artificial
<220> FEATURE:
<223> OTHER INFORMATION: RNA Oligomer

<400> SEQUENCE: 367
uugagcaagu uugggagga                                                19

<210> SEQ ID NO 368
<211> LENGTH: 19
<212> TYPE: RNA
<213> ORGANISM: artificial
<220> FEATURE:
<223> OTHER INFORMATION: RNA Oligomer

<400> SEQUENCE: 368
cugaaacuuc uguugcuca                                                19

<210> SEQ ID NO 369
<211> LENGTH: 19
<212> TYPE: RNA
<213> ORGANISM: artificial
<220> FEATURE:
<223> OTHER INFORMATION: RNA Oligomer

<400> SEQUENCE: 369
ucaccugaaa cuucuguug                                                19

<210> SEQ ID NO 370
<211> LENGTH: 19
<212> TYPE: RNA
<213> ORGANISM: artificial
<220> FEATURE:
<223> OTHER INFORMATION: RNA Oligomer

<400> SEQUENCE: 370
uugacauacu uuggaggca                                                19

<210> SEQ ID NO 371
<211> LENGTH: 19
<212> TYPE: RNA
<213> ORGANISM: artificial
<220> FEATURE:
<223> OTHER INFORMATION: RNA Oligomer

<400> SEQUENCE: 371
ugauugacau acuuuggag                                                19

<210> SEQ ID NO 372
<211> LENGTH: 19
<212> TYPE: RNA
<213> ORGANISM: artificial
<220> FEATURE:
<223> OTHER INFORMATION: RNA Oligomer

<400> SEQUENCE: 372
```
agguuucuuc ggcuacguu                                             19

<210> SEQ ID NO 373
<211> LENGTH: 19
<212> TYPE: RNA
<213> ORGANISM: artificial
<220> FEATURE:
<223> OTHER INFORMATION: RNA Oligomer

<400> SEQUENCE: 373
auggauuuga uugacauac                                             19

<210> SEQ ID NO 374
<211> LENGTH: 19
<212> TYPE: RNA
<213> ORGANISM: artificial
<220> FEATURE:
<223> OTHER INFORMATION: RNA Oligomer

<400> SEQUENCE: 374
acauggauuu gauugacau                                             19

<210> SEQ ID NO 375
<211> LENGTH: 19
<212> TYPE: RNA
<213> ORGANISM: artificial
<220> FEATURE:
<223> OTHER INFORMATION: RNA Oligomer

<400> SEQUENCE: 375
uucucccaau ucagccagc                                             19

<210> SEQ ID NO 376
<211> LENGTH: 19
<212> TYPE: RNA
<213> ORGANISM: artificial
<220> FEATURE:
<223> OTHER INFORMATION: RNA Oligomer

<400> SEQUENCE: 376
aagagacagg ugaauuucu                                             19

<210> SEQ ID NO 377
<211> LENGTH: 19
<212> TYPE: RNA
<213> ORGANISM: artificial
<220> FEATURE:
<223> OTHER INFORMATION: RNA Oligomer

<400> SEQUENCE: 377
gaugaagaga caggugaau                                             19

<210> SEQ ID NO 378
<211> LENGTH: 19
<212> TYPE: RNA
<213> ORGANISM: artificial
<220> FEATURE:
<223> OTHER INFORMATION: RNA Oligomer

<400> SEQUENCE: 378
aacuagauga agagacagg                                             19

<210> SEQ ID NO 379
<211> LENGTH: 19
<212> TYPE: RNA
<213> ORGANISM: artificial

```
<220> FEATURE:
<223> OTHER INFORMATION: RNA Oligomer

<400> SEQUENCE: 379
uugcaaaacu aaccacuau                                                    19

<210> SEQ ID NO 380
<211> LENGTH: 19
<212> TYPE: RNA
<213> ORGANISM: artificial
<220> FEATURE:
<223> OTHER INFORMATION: RNA Oligomer

<400> SEQUENCE: 380
ugacaucugg cuaaaaga                                                     19

<210> SEQ ID NO 381
<211> LENGTH: 19
<212> TYPE: RNA
<213> ORGANISM: artificial
<220> FEATURE:
<223> OTHER INFORMATION: RNA Oligomer

<400> SEQUENCE: 381
gagugucagu auguugaau                                                    19

<210> SEQ ID NO 382
<211> LENGTH: 19
<212> TYPE: RNA
<213> ORGANISM: artificial
<220> FEATURE:
<223> OTHER INFORMATION: RNA Oligomer

<400> SEQUENCE: 382
aagcauugga gugucagua                                                    19

<210> SEQ ID NO 383
<211> LENGTH: 19
<212> TYPE: RNA
<213> ORGANISM: artificial
<220> FEATURE:
<223> OTHER INFORMATION: RNA Oligomer

<400> SEQUENCE: 383
gcuccuacug ugaugugaa                                                    19

<210> SEQ ID NO 384
<211> LENGTH: 19
<212> TYPE: RNA
<213> ORGANISM: artificial
<220> FEATURE:
<223> OTHER INFORMATION: RNA Oligomer

<400> SEQUENCE: 384
gaccuuuucu gagcuaguu                                                    19

<210> SEQ ID NO 385
<211> LENGTH: 19
<212> TYPE: RNA
<213> ORGANISM: artificial
<220> FEATURE:
<223> OTHER INFORMATION: RNA Oligomer

<400> SEQUENCE: 385
ugaccuuuuc ugagcuagu                                                    19
```

```
<210> SEQ ID NO 386
<211> LENGTH: 19
<212> TYPE: RNA
<213> ORGANISM: artificial
<220> FEATURE:
<223> OTHER INFORMATION: RNA Oligomer

<400> SEQUENCE: 386
ucaugaugga cuuggagcu                                                19

<210> SEQ ID NO 387
<211> LENGTH: 19
<212> TYPE: RNA
<213> ORGANISM: artificial
<220> FEATURE:
<223> OTHER INFORMATION: RNA Oligomer

<400> SEQUENCE: 387
ccuuauaucu cgaaguuuu                                                19

<210> SEQ ID NO 388
<211> LENGTH: 19
<212> TYPE: RNA
<213> ORGANISM: artificial
<220> FEATURE:
<223> OTHER INFORMATION: RNA Oligomer

<400> SEQUENCE: 388
cucagcaccu uauaucucg                                                19

<210> SEQ ID NO 389
<211> LENGTH: 19
<212> TYPE: RNA
<213> ORGANISM: artificial
<220> FEATURE:
<223> OTHER INFORMATION: RNA Oligomer

<400> SEQUENCE: 389
gacaagaaca acuccaaaa                                                19

<210> SEQ ID NO 390
<211> LENGTH: 19
<212> TYPE: RNA
<213> ORGANISM: artificial
<220> FEATURE:
<223> OTHER INFORMATION: RNA Oligomer

<400> SEQUENCE: 390
ucgggauaua cguaggagg                                                19

<210> SEQ ID NO 391
<211> LENGTH: 19
<212> TYPE: RNA
<213> ORGANISM: artificial
<220> FEATURE:
<223> OTHER INFORMATION: RNA Oligomer

<400> SEQUENCE: 391
uaauucggga uauacguag                                                19

<210> SEQ ID NO 392
<211> LENGTH: 19
<212> TYPE: RNA
<213> ORGANISM: artificial
<220> FEATURE:
<223> OTHER INFORMATION: RNA Oligomer

<400> SEQUENCE: 392
```
gaaaugaugu ccaaagagc                                                    19

<210> SEQ ID NO 393
<211> LENGTH: 19
<212> TYPE: RNA
<213> ORGANISM: artificial
<220> FEATURE:
<223> OTHER INFORMATION: RNA Oligomer

<400> SEQUENCE: 393
aacgaaauga uguccaaag                                                    19

<210> SEQ ID NO 394
<211> LENGTH: 19
<212> TYPE: RNA
<213> ORGANISM: artificial
<220> FEATURE:
<223> OTHER INFORMATION: RNA Oligomer

<400> SEQUENCE: 394
gaaaaaauca uuaaccucc                                                    19

<210> SEQ ID NO 395
<211> LENGTH: 19
<212> TYPE: RNA
<213> ORGANISM: artificial
<220> FEATURE:
<223> OTHER INFORMATION: RNA Oligomer

<400> SEQUENCE: 395
agcucuccau aucccauuc                                                    19

<210> SEQ ID NO 396
<211> LENGTH: 19
<212> TYPE: RNA
<213> ORGANISM: artificial
<220> FEATURE:
<223> OTHER INFORMATION: RNA Oligomer

<400> SEQUENCE: 396
gcaaaagcuc uccauaucc                                                    19

<210> SEQ ID NO 397
<211> LENGTH: 19
<212> TYPE: RNA
<213> ORGANISM: artificial
<220> FEATURE:
<223> OTHER INFORMATION: RNA Oligomer

<400> SEQUENCE: 397
aagagaugaa cuuagggca                                                    19

<210> SEQ ID NO 398
<211> LENGTH: 19
<212> TYPE: RNA
<213> ORGANISM: artificial
<220> FEATURE:
<223> OTHER INFORMATION: RNA Oligomer

<400> SEQUENCE: 398
cuggaaaaac agaaaaaac                                                    19

<210> SEQ ID NO 399
<211> LENGTH: 19
<212> TYPE: RNA
<213> ORGANISM: artificial

```
<220> FEATURE:
<223> OTHER INFORMATION: RNA Oligomer

<400> SEQUENCE: 399
gagcuggaaa aacagaaaa                                                19

<210> SEQ ID NO 400
<211> LENGTH: 19
<212> TYPE: RNA
<213> ORGANISM: artificial
<220> FEATURE:
<223> OTHER INFORMATION: RNA Oligomer

<400> SEQUENCE: 400 cccuggaag ugucaaaca                                                 19

<210> SEQ ID NO 401
<211> LENGTH: 19
<212> TYPE: RNA
<213> ORGANISM: artificial
<220> FEATURE:
<223> OTHER INFORMATION: RNA Oligomer

<400> SEQUENCE: 401
auucugaagu ggaagagcu                                                19

<210> SEQ ID NO 402
<211> LENGTH: 19
<212> TYPE: RNA
<213> ORGANISM: artificial
<220> FEATURE:
<223> OTHER INFORMATION: RNA Oligomer

<400> SEQUENCE: 402
caucaccaga acacucagu                                                19

<210> SEQ ID NO 403
<211> LENGTH: 19
<212> TYPE: RNA
<213> ORGANISM: artificial
<220> FEATURE:
<223> OTHER INFORMATION: RNA Oligomer

<400> SEQUENCE: 403
cugaucuauc acuuugcaa                                                19

<210> SEQ ID NO 404
<211> LENGTH: 19
<212> TYPE: RNA
<213> ORGANISM: artificial
<220> FEATURE:
<223> OTHER INFORMATION: RNA Oligomer

<400> SEQUENCE: 404
ucugaucuau cacuuugca                                                19

<210> SEQ ID NO 405
<211> LENGTH: 19
<212> TYPE: RNA
<213> ORGANISM: artificial
<220> FEATURE:
<223> OTHER INFORMATION: RNA Oligomer

<400> SEQUENCE: 405
uucugaucua ucacuuugc                                                19
```

```
<210> SEQ ID NO 406
<211> LENGTH: 19
<212> TYPE: RNA
<213> ORGANISM: artificial
<220> FEATURE:
<223> OTHER INFORMATION: RNA Oligomer

<400> SEQUENCE: 406
gagcccagua ucagcaaca                                              19

<210> SEQ ID NO 407
<211> LENGTH: 19
<212> TYPE: RNA
<213> ORGANISM: artificial
<220> FEATURE:
<223> OTHER INFORMATION: RNA Oligomer

<400> SEQUENCE: 407
gaaguaggua acuguaguc                                              19

<210> SEQ ID NO 408
<211> LENGTH: 19
<212> TYPE: RNA
<213> ORGANISM: artificial
<220> FEATURE:
<223> OTHER INFORMATION: RNA Oligomer

<400> SEQUENCE: 408
agaaguaggu aacuguagu                                              19

<210> SEQ ID NO 409
<211> LENGTH: 19
<212> TYPE: RNA
<213> ORGANISM: artificial
<220> FEATURE:
<223> OTHER INFORMATION: RNA Oligomer

<400> SEQUENCE: 409
aaaagaagua gguaacugu                                              19

<210> SEQ ID NO 410
<211> LENGTH: 19
<212> TYPE: RNA
<213> ORGANISM: artificial
<220> FEATURE:
<223> OTHER INFORMATION: RNA Oligomer

<400> SEQUENCE: 410
gcaacaggac auugagcaa                                              19

<210> SEQ ID NO 411
<211> LENGTH: 19
<212> TYPE: RNA
<213> ORGANISM: artificial
<220> FEATURE:
<223> OTHER INFORMATION: RNA Oligomer

<400> SEQUENCE: 411
cacuuguucc ugauauucc                                              19

<210> SEQ ID NO 412
<211> LENGTH: 19
<212> TYPE: RNA
<213> ORGANISM: artificial
<220> FEATURE:
<223> OTHER INFORMATION: RNA Oligomer

<400> SEQUENCE: 412
```
gcaggacaug gauuugauu                                                    19

<210> SEQ ID NO 413
<211> LENGTH: 19
<212> TYPE: RNA
<213> ORGANISM: artificial
<220> FEATURE:
<223> OTHER INFORMATION: RNA Oligomer

<400> SEQUENCE: 413
guuucugugu aaguguaaa                                                    19

<210> SEQ ID NO 414
<211> LENGTH: 19
<212> TYPE: RNA
<213> ORGANISM: artificial
<220> FEATURE:
<223> OTHER INFORMATION: RNA Oligomer

<400> SEQUENCE: 414
gcauuggagu gucaguaug                                                    19

<210> SEQ ID NO 415
<211> LENGTH: 19
<212> TYPE: RNA
<213> ORGANISM: artificial
<220> FEATURE:
<223> OTHER INFORMATION: RNA Oligomer

<400> SEQUENCE: 415
ugugauguga aaugcucau                                                    19

<210> SEQ ID NO 416
<211> LENGTH: 19
<212> TYPE: RNA
<213> ORGANISM: artificial
<220> FEATURE:
<223> OTHER INFORMATION: RNA Oligomer

<400> SEQUENCE: 416
acuagauuua ggaggauuu                                                    19

<210> SEQ ID NO 417
<211> LENGTH: 19
<212> TYPE: RNA
<213> ORGANISM: artificial
<220> FEATURE:
<223> OTHER INFORMATION: RNA Oligomer

<400> SEQUENCE: 417
cucgaaguuu ucagcaugc                                                    19

<210> SEQ ID NO 418
<211> LENGTH: 19
<212> TYPE: RNA
<213> ORGANISM: artificial
<220> FEATURE:
<223> OTHER INFORMATION: RNA Oligomer

<400> SEQUENCE: 418
aucucgaagu uuucagcau                                                    19

<210> SEQ ID NO 419
<211> LENGTH: 19
<212> TYPE: RNA
<213> ORGANISM: artificial

```
<220> FEATURE:
<223> OTHER INFORMATION: RNA Oligomer

<400> SEQUENCE: 419
gcagaaaaag aaaacugga                                                  19

<210> SEQ ID NO 420
<211> LENGTH: 19
<212> TYPE: RNA
<213> ORGANISM: artificial
<220> FEATURE:
<223> OTHER INFORMATION: RNA Oligomer

<400> SEQUENCE: 420
ggauauacgu aggaggggu                                                  19

<210> SEQ ID NO 421
<211> LENGTH: 19
<212> TYPE: RNA
<213> ORGANISM: artificial
<220> FEATURE:
<223> OTHER INFORMATION: RNA Oligomer

<400> SEQUENCE: 421
aagacaagaa caacuccaa                                                  19

<210> SEQ ID NO 422
<211> LENGTH: 19
<212> TYPE: RNA
<213> ORGANISM: artificial
<220> FEATURE:
<223> OTHER INFORMATION: RNA Oligomer

<400> SEQUENCE: 422
aaagagcagu ucaaugaag                                                  19

<210> SEQ ID NO 423
<211> LENGTH: 19
<212> TYPE: RNA
<213> ORGANISM: artificial
<220> FEATURE:
<223> OTHER INFORMATION: RNA Oligomer

<400> SEQUENCE: 423
ucaacgaaau gauguccaa                                                  19

<210> SEQ ID NO 424
<211> LENGTH: 19
<212> TYPE: RNA
<213> ORGANISM: artificial
<220> FEATURE:
<223> OTHER INFORMATION: RNA Oligomer

<400> SEQUENCE: 424
uaaccucccu guuguugac                                                  19

<210> SEQ ID NO 425
<211> LENGTH: 19
<212> TYPE: RNA
<213> ORGANISM: artificial
<220> FEATURE:
<223> OTHER INFORMATION: RNA Oligomer

<400> SEQUENCE: 425
caaaagcucu ccauauccc                                                  19
```

```
<210> SEQ ID NO 426
<211> LENGTH: 19
<212> TYPE: RNA
<213> ORGANISM: artificial
<220> FEATURE:
<223> OTHER INFORMATION: RNA Oligomer

<400> SEQUENCE: 426
agaugaacuu agggcaaaa                                              19

<210> SEQ ID NO 427
<211> LENGTH: 19
<212> TYPE: RNA
<213> ORGANISM: artificial
<220> FEATURE:
<223> OTHER INFORMATION: RNA Oligomer

<400> SEQUENCE: 427
agagaugaac uuagggcaa                                              19

<210> SEQ ID NO 428
<211> LENGTH: 19
<212> TYPE: RNA
<213> ORGANISM: artificial
<220> FEATURE:
<223> OTHER INFORMATION: RNA Oligomer

<400> SEQUENCE: 428
agcuggaaaa acagaaaaa                                              19

<210> SEQ ID NO 429
<211> LENGTH: 19
<212> TYPE: RNA
<213> ORGANISM: artificial
<220> FEATURE:
<223> OTHER INFORMATION: RNA Oligomer

<400> SEQUENCE: 429
uccuaaaaca ccaguacau                                              19

<210> SEQ ID NO 430
<211> LENGTH: 19
<212> TYPE: RNA
<213> ORGANISM: artificial
<220> FEATURE:
<223> OTHER INFORMATION: RNA Oligomer

<400> SEQUENCE: 430
ugauguuucu gaucuauca                                              19

<210> SEQ ID NO 431
<211> LENGTH: 19
<212> TYPE: RNA
<213> ORGANISM: artificial
<220> FEATURE:
<223> OTHER INFORMATION: RNA Oligomer

<400> SEQUENCE: 431
ccauugaugu uucugaucu                                              19

<210> SEQ ID NO 432
<211> LENGTH: 19
<212> TYPE: RNA
<213> ORGANISM: artificial
<220> FEATURE:
<223> OTHER INFORMATION: RNA Oligomer

<400> SEQUENCE: 432
```

```
aguauguuga aucaguagu                                                19

<210> SEQ ID NO 433
<211> LENGTH: 19
<212> TYPE: RNA
<213> ORGANISM: artificial
<220> FEATURE:
<223> OTHER INFORMATION: RNA Oligomer

<400> SEQUENCE: 433
uucugagcua guuuuuug                                                 19

<210> SEQ ID NO 434
<211> LENGTH: 19
<212> TYPE: RNA
<213> ORGANISM: artificial
<220> FEATURE:
<223> OTHER INFORMATION: RNA Oligomer

<400> SEQUENCE: 434
ucgaaguuuu cagcaugcu                                                19

<210> SEQ ID NO 435
<211> LENGTH: 19
<212> TYPE: RNA
<213> ORGANISM: artificial
<220> FEATURE:
<223> OTHER INFORMATION: RNA Oligomer

<400> SEQUENCE: 435
auucgggaua uacguagga                                                19

<210> SEQ ID NO 436
<211> LENGTH: 19
<212> TYPE: RNA
<213> ORGANISM: artificial
<220> FEATURE:
<223> OTHER INFORMATION: RNA Oligomer

<400> SEQUENCE: 436
uguccaaaga gcaguucaa                                                19

<210> SEQ ID NO 437
<211> LENGTH: 19
<212> TYPE: RNA
<213> ORGANISM: artificial
<220> FEATURE:
<223> OTHER INFORMATION: RNA Oligomer

<400> SEQUENCE: 437 uucugggau augguacaa                                                 19

<210> SEQ ID NO 438
<211> LENGTH: 19
<212> TYPE: RNA
<213> ORGANISM: artificial
<220> FEATURE:
<223> OTHER INFORMATION: RNA Oligomer

<400> SEQUENCE: 438
cuucugggga uaugguaca                                                19

<210> SEQ ID NO 439
<211> LENGTH: 19
<212> TYPE: RNA
<213> ORGANISM: artificial
```

```
<220> FEATURE:
<223> OTHER INFORMATION: RNA Oligomer

<400> SEQUENCE: 439
uguuucugau cuaucacuu                                                       19

<210> SEQ ID NO 440
<211> LENGTH: 19
<212> TYPE: RNA
<213> ORGANISM: artificial
<220> FEATURE:
<223> OTHER INFORMATION: RNA Oligomer

<400> SEQUENCE: 440
accugcuacu uuaagccau                                                       19

<210> SEQ ID NO 441
<211> LENGTH: 19
<212> TYPE: RNA
<213> ORGANISM: artificial
<220> FEATURE:
<223> OTHER INFORMATION: RNA Oligomer

<400> SEQUENCE: 441
guuucaguca cuuguuccu                                                       19

<210> SEQ ID NO 442
<211> LENGTH: 19
<212> TYPE: RNA
<213> ORGANISM: artificial
<220> FEATURE:
<223> OTHER INFORMATION: RNA Oligomer

<400> SEQUENCE: 442
cacauccagu cagaaacca                                                       19

<210> SEQ ID NO 443
<211> LENGTH: 19
<212> TYPE: RNA
<213> ORGANISM: artificial
<220> FEATURE:
<223> OTHER INFORMATION: RNA Oligomer

<400> SEQUENCE: 443
cugguacuaa uaaaggauu                                                       19

<210> SEQ ID NO 444
<211> LENGTH: 19
<212> TYPE: RNA
<213> ORGANISM: artificial
<220> FEATURE:
<223> OTHER INFORMATION: RNA Oligomer

<400> SEQUENCE: 444
agugucagua uguugaauc                                                       19

<210> SEQ ID NO 445
<211> LENGTH: 19
<212> TYPE: RNA
<213> ORGANISM: artificial
<220> FEATURE:
<223> OTHER INFORMATION: RNA Oligomer

<400> SEQUENCE: 445
aaacuagauu uaggaggau                                                       19
```

<210> SEQ ID NO 446
<211> LENGTH: 19
<212> TYPE: RNA
<213> ORGANISM: artificial
<220> FEATURE:
<223> OTHER INFORMATION: RNA Oligomer

<400> SEQUENCE: 446
aaaacuagau uuaggagga                                              19

<210> SEQ ID NO 447
<211> LENGTH: 19
<212> TYPE: RNA
<213> ORGANISM: artificial
<220> FEATURE:
<223> OTHER INFORMATION: RNA Oligomer

<400> SEQUENCE: 447
agcucaacuu gcauuaauu                                              19

<210> SEQ ID NO 448
<211> LENGTH: 19
<212> TYPE: RNA
<213> ORGANISM: artificial
<220> FEATURE:
<223> OTHER INFORMATION: RNA Oligomer

<400> SEQUENCE: 448
aagagcaguu caaugaagc                                              19

<210> SEQ ID NO 449
<211> LENGTH: 19
<212> TYPE: RNA
<213> ORGANISM: artificial
<220> FEATURE:
<223> OTHER INFORMATION: RNA Oligomer

<400> SEQUENCE: 449
ugauguccaa agagcaguu                                              19

<210> SEQ ID NO 450
<211> LENGTH: 19
<212> TYPE: RNA
<213> ORGANISM: artificial
<220> FEATURE:
<223> OTHER INFORMATION: RNA Oligomer

<400> SEQUENCE: 450
gaaaacccca uucacaaaa                                              19

<210> SEQ ID NO 451
<211> LENGTH: 19
<212> TYPE: RNA
<213> ORGANISM: artificial
<220> FEATURE:
<223> OTHER INFORMATION: RNA Oligomer

<400> SEQUENCE: 451
ugagcuggaa aaacagaaa                                              19

<210> SEQ ID NO 452
<211> LENGTH: 19
<212> TYPE: RNA
<213> ORGANISM: artificial
<220> FEATURE:
<223> OTHER INFORMATION: RNA Oligomer

<400> SEQUENCE: 452
uugauguuuc ugaucuauc                                              19

<210> SEQ ID NO 453
<211> LENGTH: 19
<212> TYPE: RNA
<213> ORGANISM: artificial
<220> FEATURE:
<223> OTHER INFORMATION: RNA Oligomer

<400> SEQUENCE: 453
uugcccacau ucccaaauc                                              19

<210> SEQ ID NO 454
<211> LENGTH: 19
<212> TYPE: RNA
<213> ORGANISM: artificial
<220> FEATURE:
<223> OTHER INFORMATION: RNA Oligomer

<400> SEQUENCE: 454
gcacauccag ucagaaacc                                              19

<210> SEQ ID NO 455
<211> LENGTH: 19
<212> TYPE: RNA
<213> ORGANISM: artificial
<220> FEATURE:
<223> OTHER INFORMATION: RNA Oligomer

<400> SEQUENCE: 455
gcugguacua auaaaggau                                              19

<210> SEQ ID NO 456
<211> LENGTH: 19
<212> TYPE: RNA
<213> ORGANISM: artificial
<220> FEATURE:
<223> OTHER INFORMATION: RNA Oligomer

<400> SEQUENCE: 456
ggagugucag uauguugaa                                              19

<210> SEQ ID NO 457
<211> LENGTH: 19
<212> TYPE: RNA
<213> ORGANISM: artificial
<220> FEATURE:
<223> OTHER INFORMATION: RNA Oligomer

<400> SEQUENCE: 457
ccuuuucuga gcuaguuuu                                              19

<210> SEQ ID NO 458
<211> LENGTH: 19
<212> TYPE: RNA
<213> ORGANISM: artificial
<220> FEATURE:
<223> OTHER INFORMATION: RNA Oligomer

<400> SEQUENCE: 458
cucaaagaaa aaggagaaa                                              19

<210> SEQ ID NO 459
<211> LENGTH: 19
<212> TYPE: RNA
<213> ORGANISM: artificial

<220> FEATURE:
<223> OTHER INFORMATION: RNA Oligomer

<400> SEQUENCE: 459
agacaagaac aacuccaaa                                                    19

<210> SEQ ID NO 460
<211> LENGTH: 19
<212> TYPE: RNA
<213> ORGANISM: artificial
<220> FEATURE:
<223> OTHER INFORMATION: RNA Oligomer

<400> SEQUENCE: 460
augaugucca aagagcagu                                                    19

<210> SEQ ID NO 461
<211> LENGTH: 19
<212> TYPE: RNA
<213> ORGANISM: artificial
<220> FEATURE:
<223> OTHER INFORMATION: RNA Oligomer

<400> SEQUENCE: 461
augagcugga aaaacagaa                                                    19

<210> SEQ ID NO 462
<211> LENGTH: 19
<212> TYPE: RNA
<213> ORGANISM: artificial
<220> FEATURE:
<223> OTHER INFORMATION: RNA Oligomer

<400> SEQUENCE: 462
guccuaaaac accaguaca                                                    19

<210> SEQ ID NO 463
<211> LENGTH: 19
<212> TYPE: RNA
<213> ORGANISM: artificial
<220> FEATURE:
<223> OTHER INFORMATION: RNA Oligomer

<400> SEQUENCE: 463
aucagcaaca gcaugcccu                                                    19

<210> SEQ ID NO 464
<211> LENGTH: 19
<212> TYPE: RNA
<213> ORGANISM: artificial
<220> FEATURE:
<223> OTHER INFORMATION: RNA Oligomer

<400> SEQUENCE: 464
aagccaaacu gacagaagu                                                    19

<210> SEQ ID NO 465
<211> LENGTH: 19
<212> TYPE: RNA
<213> ORGANISM: artificial
<220> FEATURE:
<223> OTHER INFORMATION: RNA Oligomer

<400> SEQUENCE: 465
cguuuguaga ugacaauga                                                    19

```
<210> SEQ ID NO 466
<211> LENGTH: 19
<212> TYPE: RNA
<213> ORGANISM: artificial
<220> FEATURE:
<223> OTHER INFORMATION: RNA Oligomer

<400> SEQUENCE: 466
guugcccaca uucccaaau                                                    19

<210> SEQ ID NO 467
<211> LENGTH: 19
<212> TYPE: RNA
<213> ORGANISM: artificial
<220> FEATURE:
<223> OTHER INFORMATION: RNA Oligomer

<400> SEQUENCE: 467
gcaaacaaga gauggcaau                                                    19

<210> SEQ ID NO 468
<211> LENGTH: 19
<212> TYPE: RNA
<213> ORGANISM: artificial
<220> FEATURE:
<223> OTHER INFORMATION: RNA Oligomer

<400> SEQUENCE: 468
auugcucaaa gaaaaagga                                                    19

<210> SEQ ID NO 469
<211> LENGTH: 19
<212> TYPE: RNA
<213> ORGANISM: artificial
<220> FEATURE:
<223> OTHER INFORMATION: RNA Oligomer

<400> SEQUENCE: 469
aaaccccauu cacaaaaga                                                    19

<210> SEQ ID NO 470
<211> LENGTH: 19
<212> TYPE: RNA
<213> ORGANISM: artificial
<220> FEATURE:
<223> OTHER INFORMATION: RNA Oligomer

<400> SEQUENCE: 470
aaguggaaga gcuagauag                                                    19

<210> SEQ ID NO 471
<211> LENGTH: 19
<212> TYPE: RNA
<213> ORGANISM: artificial
<220> FEATURE:
<223> OTHER INFORMATION: RNA Oligomer

<400> SEQUENCE: 471
ucacuaaaca caaguccca                                                    19

<210> SEQ ID NO 472
<211> LENGTH: 19
<212> TYPE: RNA
<213> ORGANISM: artificial
<220> FEATURE:
<223> OTHER INFORMATION: RNA Oligomer

<400> SEQUENCE: 472
```
cggcauuuca cuaaacaca                                         19

<210> SEQ ID NO 473
<211> LENGTH: 19
<212> TYPE: RNA
<213> ORGANISM: artificial
<220> FEATURE:
<223> OTHER INFORMATION: RNA Oligomer

<400> SEQUENCE: 473
uuuaagccau ucacucucu                                         19

<210> SEQ ID NO 474
<211> LENGTH: 19
<212> TYPE: RNA
<213> ORGANISM: artificial
<220> FEATURE:
<223> OTHER INFORMATION: RNA Oligomer

<400> SEQUENCE: 474
caccugcuac uuuaagcca                                         19

<210> SEQ ID NO 475
<211> LENGTH: 19
<212> TYPE: RNA
<213> ORGANISM: artificial
<220> FEATURE:
<223> OTHER INFORMATION: RNA Oligomer

<400> SEQUENCE: 475
ggaggagcua uuauccauu                                         19

<210> SEQ ID NO 476
<211> LENGTH: 19
<212> TYPE: RNA
<213> ORGANISM: artificial
<220> FEATURE:
<223> OTHER INFORMATION: RNA Oligomer

<400> SEQUENCE: 476
gggaggagcu auuauccau                                         19

<210> SEQ ID NO 477
<211> LENGTH: 19
<212> TYPE: RNA
<213> ORGANISM: artificial
<220> FEATURE:
<223> OTHER INFORMATION: RNA Oligomer

<400> SEQUENCE: 477
ucgcucaguu acaacuaga                                         19

<210> SEQ ID NO 478
<211> LENGTH: 19
<212> TYPE: RNA
<213> ORGANISM: artificial
<220> FEATURE:
<223> OTHER INFORMATION: RNA Oligomer

<400> SEQUENCE: 478
ugaagaugga aaaccuuau                                         19

<210> SEQ ID NO 479
<211> LENGTH: 19
<212> TYPE: RNA
<213> ORGANISM: artificial

```
<220> FEATURE:
<223> OTHER INFORMATION: RNA Oligomer

<400> SEQUENCE: 479
aagcucaacu ugcauuaau                                                    19

<210> SEQ ID NO 480
<211> LENGTH: 19
<212> TYPE: RNA
<213> ORGANISM: artificial
<220> FEATURE:
<223> OTHER INFORMATION: RNA Oligomer

<400> SEQUENCE: 480
aaaaccccau ucacaaaag                                                    19

<210> SEQ ID NO 481
<211> LENGTH: 19
<212> TYPE: RNA
<213> ORGANISM: artificial
<220> FEATURE:
<223> OTHER INFORMATION: RNA Oligomer

<400> SEQUENCE: 481
gcuauggaga cacacuacu                                                    19

<210> SEQ ID NO 482
<211> LENGTH: 19
<212> TYPE: RNA
<213> ORGANISM: artificial
<220> FEATURE:
<223> OTHER INFORMATION: RNA Oligomer

<400> SEQUENCE: 482
guauuugacu ucagucagc                                                    19

<210> SEQ ID NO 483
<211> LENGTH: 19
<212> TYPE: RNA
<213> ORGANISM: artificial
<220> FEATURE:
<223> OTHER INFORMATION: RNA Oligomer

<400> SEQUENCE: 483
ccugcuacuu uaagccauu                                                    19

<210> SEQ ID NO 484
<211> LENGTH: 19
<212> TYPE: RNA
<213> ORGANISM: artificial
<220> FEATURE:
<223> OTHER INFORMATION: RNA Oligomer

<400> SEQUENCE: 484
ugagcccagu aucagcaac                                                    19

<210> SEQ ID NO 485
<211> LENGTH: 19
<212> TYPE: RNA
<213> ORGANISM: artificial
<220> FEATURE:
<223> OTHER INFORMATION: RNA Oligomer

<400> SEQUENCE: 485
gagaaguauu ugacuucag                                                    19
```

```
<210> SEQ ID NO 486
<211> LENGTH: 19
<212> TYPE: RNA
<213> ORGANISM: artificial
<220> FEATURE:
<223> OTHER INFORMATION: RNA Oligomer

<400> SEQUENCE: 486
uggaaaaaga aguagguaa                                              19

<210> SEQ ID NO 487
<211> LENGTH: 19
<212> TYPE: RNA
<213> ORGANISM: artificial
<220> FEATURE:
<223> OTHER INFORMATION: RNA Oligomer

<400> SEQUENCE: 487
gaagccaaac ugacagaag                                              19

<210> SEQ ID NO 488
<211> LENGTH: 19
<212> TYPE: RNA
<213> ORGANISM: artificial
<220> FEATURE:
<223> OTHER INFORMATION: RNA Oligomer

<400> SEQUENCE: 488
cagaagccaa acugacaga                                              19

<210> SEQ ID NO 489
<211> LENGTH: 19
<212> TYPE: RNA
<213> ORGANISM: artificial
<220> FEATURE:
<223> OTHER INFORMATION: RNA Oligomer

<400> SEQUENCE: 489
gaaaaugaca agcugguug                                              19

<210> SEQ ID NO 490
<211> LENGTH: 19
<212> TYPE: RNA
<213> ORGANISM: artificial
<220> FEATURE:
<223> OTHER INFORMATION: RNA Oligomer

<400> SEQUENCE: 490
aaaaagcauu ggaguguca                                              19

<210> SEQ ID NO 491
<211> LENGTH: 19
<212> TYPE: RNA
<213> ORGANISM: artificial
<220> FEATURE:
<223> OTHER INFORMATION: RNA Oligomer

<400> SEQUENCE: 491
uaggaggauu ugaccuuuu                                              19

<210> SEQ ID NO 492
<211> LENGTH: 19
<212> TYPE: RNA
<213> ORGANISM: artificial
<220> FEATURE:
<223> OTHER INFORMATION: RNA Oligomer

<400> SEQUENCE: 492
```
agauggaaaa ccuuauucu                                              19

<210> SEQ ID NO 493
<211> LENGTH: 19
<212> TYPE: RNA
<213> ORGANISM: artificial
<220> FEATURE:
<223> OTHER INFORMATION: RNA Oligomer

<400> SEQUENCE: 493
gaagcucaac uugcauuaa                                              19

<210> SEQ ID NO 494
<211> LENGTH: 19
<212> TYPE: RNA
<213> ORGANISM: artificial
<220> FEATURE:
<223> OTHER INFORMATION: RNA Oligomer

<400> SEQUENCE: 494
gcucuccaua ucccauucc                                              19

<210> SEQ ID NO 495
<211> LENGTH: 19
<212> TYPE: RNA
<213> ORGANISM: artificial
<220> FEATURE:
<223> OTHER INFORMATION: RNA Oligomer

<400> SEQUENCE: 495
ggaaaacccc auucacaaa                                              19

<210> SEQ ID NO 496
<211> LENGTH: 19
<212> TYPE: RNA
<213> ORGANISM: artificial
<220> FEATURE:
<223> OTHER INFORMATION: RNA Oligomer

<400> SEQUENCE: 496
agagcacuca cgugcauga                                              19

<210> SEQ ID NO 497
<211> LENGTH: 19
<212> TYPE: RNA
<213> ORGANISM: artificial
<220> FEATURE:
<223> OTHER INFORMATION: RNA Oligomer

<400> SEQUENCE: 497
acccuuguca ccaucucag                                              19

<210> SEQ ID NO 498
<211> LENGTH: 19
<212> TYPE: RNA
<213> ORGANISM: artificial
<220> FEATURE:
<223> OTHER INFORMATION: RNA Oligomer

<400> SEQUENCE: 498
cuacuuggcc ucagugauu                                              19

<210> SEQ ID NO 499
<211> LENGTH: 19
<212> TYPE: RNA
<213> ORGANISM: artificial

```
<220> FEATURE:
<223> OTHER INFORMATION: RNA Oligomer

<400> SEQUENCE: 499
gugaacucau uaaauucag                                                  19

<210> SEQ ID NO 500
<211> LENGTH: 19
<212> TYPE: RNA
<213> ORGANISM: artificial
<220> FEATURE:
<223> OTHER INFORMATION: RNA Oligomer

<400> SEQUENCE: 500
ggaaaaagaa guagguaac                                                  19

<210> SEQ ID NO 501
<211> LENGTH: 19
<212> TYPE: RNA
<213> ORGANISM: artificial
<220> FEATURE:
<223> OTHER INFORMATION: RNA Oligomer

<400> SEQUENCE: 501
cccugucgaa aaaucauu                                                   19

<210> SEQ ID NO 502
<211> LENGTH: 19
<212> TYPE: RNA
<213> ORGANISM: artificial
<220> FEATURE:
<223> OTHER INFORMATION: RNA Oligomer

<400> SEQUENCE: 502
ucccugucga aaaaucau                                                   19

<210> SEQ ID NO 503
<211> LENGTH: 19
<212> TYPE: RNA
<213> ORGANISM: artificial
<220> FEATURE:
<223> OTHER INFORMATION: RNA Oligomer

<400> SEQUENCE: 503
ccugucgaaa aaucauua                                                   19

<210> SEQ ID NO 504
<211> LENGTH: 19
<212> TYPE: RNA
<213> ORGANISM: artificial
<220> FEATURE:
<223> OTHER INFORMATION: RNA Oligomer

<400> SEQUENCE: 504
gccacuuuau ucuuacccc                                                  19

<210> SEQ ID NO 505
<211> LENGTH: 19
<212> TYPE: RNA
<213> ORGANISM: artificial
<220> FEATURE:
<223> OTHER INFORMATION: RNA Oligomer

<400> SEQUENCE: 505
acuuuauucu uaccccucc                                                  19
```

```
<210> SEQ ID NO 506
<211> LENGTH: 19
<212> TYPE: RNA
<213> ORGANISM: artificial
<220> FEATURE:
<223> OTHER INFORMATION: RNA Oligomer

<400> SEQUENCE: 506
acauaguggu uaguuuugc                                              19

<210> SEQ ID NO 507
<211> LENGTH: 19
<212> TYPE: RNA
<213> ORGANISM: artificial
<220> FEATURE:
<223> OTHER INFORMATION: RNA Oligomer

<400> SEQUENCE: 507
cuuuugucau uuucuccuu                                              19

<210> SEQ ID NO 508
<211> LENGTH: 19
<212> TYPE: RNA
<213> ORGANISM: artificial
<220> FEATURE:
<223> OTHER INFORMATION: RNA Oligomer

<400> SEQUENCE: 508
uucuuuuucu gcaauucug                                              19

<210> SEQ ID NO 509
<211> LENGTH: 19
<212> TYPE: RNA
<213> ORGANISM: artificial
<220> FEATURE:
<223> OTHER INFORMATION: RNA Oligomer

<400> SEQUENCE: 509
agccacuuua uucuuaccc                                              19

<210> SEQ ID NO 510
<211> LENGTH: 19
<212> TYPE: RNA
<213> ORGANISM: artificial
<220> FEATURE:
<223> OTHER INFORMATION: RNA Oligomer

<400> SEQUENCE: 510
uaaaguagca ggugagggc                                              19

<210> SEQ ID NO 511
<211> LENGTH: 19
<212> TYPE: RNA
<213> ORGANISM: artificial
<220> FEATURE:
<223> OTHER INFORMATION: RNA Oligomer

<400> SEQUENCE: 511
ccacuuuauu cuuaccccu                                              19

<210> SEQ ID NO 512
<211> LENGTH: 19
<212> TYPE: RNA
<213> ORGANISM: artificial
<220> FEATURE:
<223> OTHER INFORMATION: RNA Oligomer

<400> SEQUENCE: 512
```
cuuuauucuu accccuccu                                              19

<210> SEQ ID NO 513
<211> LENGTH: 19
<212> TYPE: RNA
<213> ORGANISM: artificial
<220> FEATURE:
<223> OTHER INFORMATION: RNA Oligomer

<400> SEQUENCE: 513
uugucaucua caaacggga                                              19

<210> SEQ ID NO 514
<211> LENGTH: 19
<212> TYPE: RNA
<213> ORGANISM: artificial
<220> FEATURE:
<223> OTHER INFORMATION: RNA Oligomer

<400> SEQUENCE: 514
gcuuuuguca uuuucuccu                                              19

<210> SEQ ID NO 515
<211> LENGTH: 19
<212> TYPE: RNA
<213> ORGANISM: artificial
<220> FEATURE:
<223> OTHER INFORMATION: RNA Oligomer

<400> SEQUENCE: 515
uuuuucugca auucugagc                                              19

<210> SEQ ID NO 516
<211> LENGTH: 19
<212> TYPE: RNA
<213> ORGANISM: artificial
<220> FEATURE:
<223> OTHER INFORMATION: RNA Oligomer

<400> SEQUENCE: 516
uuacaggcaa uucuuucuc                                              19

<210> SEQ ID NO 517
<211> LENGTH: 19
<212> TYPE: RNA
<213> ORGANISM: artificial
<220> FEATURE:
<223> OTHER INFORMATION: RNA Oligomer

<400> SEQUENCE: 517
uguuuaguga aaugccgga                                              19

<210> SEQ ID NO 518
<211> LENGTH: 19
<212> TYPE: RNA
<213> ORGANISM: artificial
<220> FEATURE:
<223> OTHER INFORMATION: RNA Oligomer

<400> SEQUENCE: 518
uauuaagaca cuguaacuc                                              19

<210> SEQ ID NO 519
<211> LENGTH: 19
<212> TYPE: RNA
<213> ORGANISM: artificial

```
<220> FEATURE:
<223> OTHER INFORMATION: RNA Oligomer

<400> SEQUENCE: 519
uuucuauacu aguuuggc                                                  19

<210> SEQ ID NO 520
<211> LENGTH: 19
<212> TYPE: RNA
<213> ORGANISM: artificial
<220> FEATURE:
<223> OTHER INFORMATION: RNA Oligomer

<400> SEQUENCE: 520
uuuuucuuaa caucuggcu                                                 19

<210> SEQ ID NO 521
<211> LENGTH: 19
<212> TYPE: RNA
<213> ORGANISM: artificial
<220> FEATURE:
<223> OTHER INFORMATION: RNA Oligomer

<400> SEQUENCE: 521
uuucuuaaca ucuggcuuc                                                 19

<210> SEQ ID NO 522
<211> LENGTH: 19
<212> TYPE: RNA
<213> ORGANISM: artificial
<220> FEATURE:
<223> OTHER INFORMATION: RNA Oligomer

<400> SEQUENCE: 522
uucuuaacau cuggcuucu                                                 19

<210> SEQ ID NO 523
<211> LENGTH: 19
<212> TYPE: RNA
<213> ORGANISM: artificial
<220> FEATURE:
<223> OTHER INFORMATION: RNA Oligomer

<400> SEQUENCE: 523
ucuuuuucug caauucuga                                                 19

<210> SEQ ID NO 524
<211> LENGTH: 19
<212> TYPE: RNA
<213> ORGANISM: artificial
<220> FEATURE:
<223> OTHER INFORMATION: RNA Oligomer

<400> SEQUENCE: 524
uuuauucuua ccccuccua                                                 19

<210> SEQ ID NO 525
<211> LENGTH: 19
<212> TYPE: RNA
<213> ORGANISM: artificial
<220> FEATURE:
<223> OTHER INFORMATION: RNA Oligomer

<400> SEQUENCE: 525
uuuagaaguu cagagagug                                                 19
```

```
<210> SEQ ID NO 526
<211> LENGTH: 19
<212> TYPE: RNA
<213> ORGANISM: artificial
<220> FEATURE:
<223> OTHER INFORMATION: RNA Oligomer

<400> SEQUENCE: 526
ucuaaaucaa cagggggcua                                                19

<210> SEQ ID NO 527
<211> LENGTH: 19
<212> TYPE: RNA
<213> ORGANISM: artificial
<220> FEATURE:
<223> OTHER INFORMATION: RNA Oligomer

<400> SEQUENCE: 527
ugggaguagu uggcagauc                                                 19

<210> SEQ ID NO 528
<211> LENGTH: 19
<212> TYPE: RNA
<213> ORGANISM: artificial
<220> FEATURE:
<223> OTHER INFORMATION: RNA Oligomer

<400> SEQUENCE: 528
guuuuggcua ugauuugc                                                  19

<210> SEQ ID NO 529
<211> LENGTH: 19
<212> TYPE: RNA
<213> ORGANISM: artificial
<220> FEATURE:
<223> OTHER INFORMATION: RNA Oligomer

<400> SEQUENCE: 529
uuaacaucug gcuucuuac                                                 19

<210> SEQ ID NO 530
<211> LENGTH: 19
<212> TYPE: RNA
<213> ORGANISM: artificial
<220> FEATURE:
<223> OTHER INFORMATION: RNA Oligomer

<400> SEQUENCE: 530
auucugagca gccacuuua                                                 19

<210> SEQ ID NO 531
<211> LENGTH: 19
<212> TYPE: RNA
<213> ORGANISM: artificial
<220> FEATURE:
<223> OTHER INFORMATION: RNA Oligomer

<400> SEQUENCE: 531
ugagcagcca cuuuauucu                                                 19

<210> SEQ ID NO 532
<211> LENGTH: 19
<212> TYPE: RNA
<213> ORGANISM: artificial
<220> FEATURE:
<223> OTHER INFORMATION: RNA Oligomer

<400> SEQUENCE: 532
```
aguuguucuu gucuuuccu                                                19

<210> SEQ ID NO 533
<211> LENGTH: 19
<212> TYPE: RNA
<213> ORGANISM: artificial
<220> FEATURE:
<223> OTHER INFORMATION: RNA Oligomer

<400> SEQUENCE: 533
uuguucuugu cuuccuuu                                                 19

<210> SEQ ID NO 534
<211> LENGTH: 19
<212> TYPE: RNA
<213> ORGANISM: artificial
<220> FEATURE:
<223> OTHER INFORMATION: RNA Oligomer

<400> SEQUENCE: 534
ugucuuuccu uuucaaguu                                                19

<210> SEQ ID NO 535
<211> LENGTH: 19
<212> TYPE: RNA
<213> ORGANISM: artificial
<220> FEATURE:
<223> OTHER INFORMATION: RNA Oligomer

<400> SEQUENCE: 535
agcggcuuga auguuuguc                                                19

<210> SEQ ID NO 536
<211> LENGTH: 19
<212> TYPE: RNA
<213> ORGANISM: artificial
<220> FEATURE:
<223> OTHER INFORMATION: RNA Oligomer

<400> SEQUENCE: 536
uuagugaaau gccggaguc                                                19

<210> SEQ ID NO 537
<211> LENGTH: 19
<212> TYPE: RNA
<213> ORGANISM: artificial
<220> FEATURE:
<223> OTHER INFORMATION: RNA Oligomer

<400> SEQUENCE: 537
cuuucagggu gguuuggu                                                 19

<210> SEQ ID NO 538
<211> LENGTH: 19
<212> TYPE: RNA
<213> ORGANISM: artificial
<220> FEATURE:
<223> OTHER INFORMATION: RNA Oligomer

<400> SEQUENCE: 538
auuuagaagu ucagagagu                                                19

<210> SEQ ID NO 539
<211> LENGTH: 19
<212> TYPE: RNA
<213> ORGANISM: artificial

```
<220> FEATURE:
<223> OTHER INFORMATION: RNA Oligomer

<400> SEQUENCE: 539
auuuaaugag uucacuguc                                            19

<210> SEQ ID NO 540
<211> LENGTH: 19
<212> TYPE: RNA
<213> ORGANISM: artificial
<220> FEATURE:
<223> OTHER INFORMATION: RNA Oligomer

<400> SEQUENCE: 540
aauagcuccu cccaaacuu                                            19

<210> SEQ ID NO 541
<211> LENGTH: 19
<212> TYPE: RNA
<213> ORGANISM: artificial
<220> FEATURE:
<223> OTHER INFORMATION: RNA Oligomer

<400> SEQUENCE: 541
accucauugu caucuacaa                                            19

<210> SEQ ID NO 542
<211> LENGTH: 19
<212> TYPE: RNA
<213> ORGANISM: artificial
<220> FEATURE:
<223> OTHER INFORMATION: RNA Oligomer

<400> SEQUENCE: 542
aguacauagu gguuaguuu                                            19

<210> SEQ ID NO 543
<211> LENGTH: 19
<212> TYPE: RNA
<213> ORGANISM: artificial
<220> FEATURE:
<223> OTHER INFORMATION: RNA Oligomer

<400> SEQUENCE: 543
aguuuuggcu augauuuug                                            19

<210> SEQ ID NO 544
<211> LENGTH: 19
<212> TYPE: RNA
<213> ORGANISM: artificial
<220> FEATURE:
<223> OTHER INFORMATION: RNA Oligomer

<400> SEQUENCE: 544
cuuaacaucu ggcuucuua                                            19

<210> SEQ ID NO 545
<211> LENGTH: 19
<212> TYPE: RNA
<213> ORGANISM: artificial
<220> FEATURE:
<223> OTHER INFORMATION: RNA Oligomer

<400> SEQUENCE: 545
uuuuccaucu ucaucacgu                                            19
```

```
<210> SEQ ID NO 546
<211> LENGTH: 19
<212> TYPE: RNA
<213> ORGANISM: artificial
<220> FEATURE:
<223> OTHER INFORMATION: RNA Oligomer

<400> SEQUENCE: 546
guucuacuau auuuuccag                                                  19

<210> SEQ ID NO 547
<211> LENGTH: 19
<212> TYPE: RNA
<213> ORGANISM: artificial
<220> FEATURE:
<223> OTHER INFORMATION: RNA Oligomer

<400> SEQUENCE: 547
guucuugucu uccuuuuc                                                   19

<210> SEQ ID NO 548
<211> LENGTH: 19
<212> TYPE: RNA
<213> ORGANISM: artificial
<220> FEATURE:
<223> OTHER INFORMATION: RNA Oligomer

<400> SEQUENCE: 548
uucuugucuu uccuuuuca                                                  19

<210> SEQ ID NO 549
<211> LENGTH: 19
<212> TYPE: RNA
<213> ORGANISM: artificial
<220> FEATURE:
<223> OTHER INFORMATION: RNA Oligomer

<400> SEQUENCE: 549
gccaaguagu gugucucca                                                  19

<210> SEQ ID NO 550
<211> LENGTH: 19
<212> TYPE: RNA
<213> ORGANISM: artificial
<220> FEATURE:
<223> OTHER INFORMATION: RNA Oligomer

<400> SEQUENCE: 550
ucaggguggu uuugguuga                                                  19

<210> SEQ ID NO 551
<211> LENGTH: 19
<212> TYPE: RNA
<213> ORGANISM: artificial
<220> FEATURE:
<223> OTHER INFORMATION: RNA Oligomer

<400> SEQUENCE: 551
uuaaaguagc aggugaggg                                                  19

<210> SEQ ID NO 552
<211> LENGTH: 19
<212> TYPE: RNA
<213> ORGANISM: artificial
<220> FEATURE:
<223> OTHER INFORMATION: RNA Oligomer

<400> SEQUENCE: 552
```
uuuaaugagu ucacuguca                                    19

<210> SEQ ID NO 553
<211> LENGTH: 19
<212> TYPE: RNA
<213> ORGANISM: artificial
<220> FEATURE:
<223> OTHER INFORMATION: RNA Oligomer

<400> SEQUENCE: 553
aucuauaucu ugccuccaa                                    19

<210> SEQ ID NO 554
<211> LENGTH: 19
<212> TYPE: RNA
<213> ORGANISM: artificial
<220> FEATURE:
<223> OTHER INFORMATION: RNA Oligomer

<400> SEQUENCE: 554
caggaaugga uaauagcuc                                    19

<210> SEQ ID NO 555
<211> LENGTH: 19
<212> TYPE: RNA
<213> ORGANISM: artificial
<220> FEATURE:
<223> OTHER INFORMATION: RNA Oligomer

<400> SEQUENCE: 555
gaaaccucau ugucaucua                                    19

<210> SEQ ID NO 556
<211> LENGTH: 19
<212> TYPE: RNA
<213> ORGANISM: artificial
<220> FEATURE:
<223> OTHER INFORMATION: RNA Oligomer

<400> SEQUENCE: 556
ugauuuggga augugggca                                    19

<210> SEQ ID NO 557
<211> LENGTH: 19
<212> TYPE: RNA
<213> ORGANISM: artificial
<220> FEATURE:
<223> OTHER INFORMATION: RNA Oligomer

<400> SEQUENCE: 557
uucuauacua guuuuggcu                                    19

<210> SEQ ID NO 558
<211> LENGTH: 19
<212> TYPE: RNA
<213> ORGANISM: artificial
<220> FEATURE:
<223> OTHER INFORMATION: RNA Oligomer

<400> SEQUENCE: 558
acaucuggcu ucuuacuuu                                    19

<210> SEQ ID NO 559
<211> LENGTH: 19
<212> TYPE: RNA
<213> ORGANISM: artificial

<220> FEATURE:
<223> OTHER INFORMATION: RNA Oligomer

<400> SEQUENCE: 559
ucuggcuucu uacuuuugg                                                19

<210> SEQ ID NO 560
<211> LENGTH: 19
<212> TYPE: RNA
<213> ORGANISM: artificial
<220> FEATURE:
<223> OTHER INFORMATION: RNA Oligomer

<400> SEQUENCE: 560
cuggcuucuu acuuugggg                                                19

<210> SEQ ID NO 561
<211> LENGTH: 19
<212> TYPE: RNA
<213> ORGANISM: artificial
<220> FEATURE:
<223> OTHER INFORMATION: RNA Oligomer

<400> SEQUENCE: 561
uuuccaucuu caucacgua                                                19

<210> SEQ ID NO 562
<211> LENGTH: 19
<212> TYPE: RNA
<213> ORGANISM: artificial
<220> FEATURE:
<223> OTHER INFORMATION: RNA Oligomer

<400> SEQUENCE: 562
uucuccuuuu ucuuugagc                                                19

<210> SEQ ID NO 563
<211> LENGTH: 19
<212> TYPE: RNA
<213> ORGANISM: artificial
<220> FEATURE:
<223> OTHER INFORMATION: RNA Oligomer

<400> SEQUENCE: 563
ucuaaaucuu gcucuaguu                                                19

<210> SEQ ID NO 564
<211> LENGTH: 19
<212> TYPE: RNA
<213> ORGANISM: artificial
<220> FEATURE:
<223> OTHER INFORMATION: RNA Oligomer

<400> SEQUENCE: 564
caauucugag cagccacuu                                                19

<210> SEQ ID NO 565
<211> LENGTH: 19
<212> TYPE: RNA
<213> ORGANISM: artificial
<220> FEATURE:
<223> OTHER INFORMATION: RNA Oligomer

<400> SEQUENCE: 565
uuauucuuac cccuccuac                                                19

```
<210> SEQ ID NO 566
<211> LENGTH: 19
<212> TYPE: RNA
<213> ORGANISM: artificial
<220> FEATURE:
<223> OTHER INFORMATION: RNA Oligomer

<400> SEQUENCE: 566
ccgaauuaau gcaaguuga                                            19

<210> SEQ ID NO 567
<211> LENGTH: 19
<212> TYPE: RNA
<213> ORGANISM: artificial
<220> FEATURE:
<223> OTHER INFORMATION: RNA Oligomer

<400> SEQUENCE: 567
uggaguuguu cuugucuuu                                            19

<210> SEQ ID NO 568
<211> LENGTH: 19
<212> TYPE: RNA
<213> ORGANISM: artificial
<220> FEATURE:
<223> OTHER INFORMATION: RNA Oligomer

<400> SEQUENCE: 568
cuuacaggca auucuuucu                                            19

<210> SEQ ID NO 569
<211> LENGTH: 19
<212> TYPE: RNA
<213> ORGANISM: artificial
<220> FEATURE:
<223> OTHER INFORMATION: RNA Oligomer

<400> SEQUENCE: 569
aauucuuucu cuggugugu                                            19

<210> SEQ ID NO 570
<211> LENGTH: 19
<212> TYPE: RNA
<213> ORGANISM: artificial
<220> FEATURE:
<223> OTHER INFORMATION: RNA Oligomer

<400> SEQUENCE: 570
agaagaaugu acugguguu                                            19

<210> SEQ ID NO 571
<211> LENGTH: 19
<212> TYPE: RNA
<213> ORGANISM: artificial
<220> FEATURE:
<223> OTHER INFORMATION: RNA Oligomer

<400> SEQUENCE: 571
gaagaaugua cugguguuu                                            19

<210> SEQ ID NO 572
<211> LENGTH: 19
<212> TYPE: RNA
<213> ORGANISM: artificial
<220> FEATURE:
<223> OTHER INFORMATION: RNA Oligomer

<400> SEQUENCE: 572
```

```
uguuuuagga ccauucugu                                          19

<210> SEQ ID NO 573
<211> LENGTH: 19
<212> TYPE: RNA
<213> ORGANISM: artificial
<220> FEATURE:
<223> OTHER INFORMATION: RNA Oligomer

<400> SEQUENCE: 573
ugugcuuuca gggugguuu                                          19

<210> SEQ ID NO 574
<211> LENGTH: 19
<212> TYPE: RNA
<213> ORGANISM: artificial
<220> FEATURE:
<223> OTHER INFORMATION: RNA Oligomer

<400> SEQUENCE: 574
uuucagggug guuugguu                                           19

<210> SEQ ID NO 575
<211> LENGTH: 19
<212> TYPE: RNA
<213> ORGANISM: artificial
<220> FEATURE:
<223> OTHER INFORMATION: RNA Oligomer

<400> SEQUENCE: 575
ccauuuagaa guucagaga                                          19

<210> SEQ ID NO 576
<211> LENGTH: 19
<212> TYPE: RNA
<213> ORGANISM: artificial
<220> FEATURE:
<223> OTHER INFORMATION: RNA Oligomer

<400> SEQUENCE: 576
uagaaguuca gagagugaa                                          19

<210> SEQ ID NO 577
<211> LENGTH: 19
<212> TYPE: RNA
<213> ORGANISM: artificial
<220> FEATURE:
<223> OTHER INFORMATION: RNA Oligomer

<400> SEQUENCE: 577
uuaagaaaau guggacuac                                          19

<210> SEQ ID NO 578
<211> LENGTH: 19
<212> TYPE: RNA
<213> ORGANISM: artificial
<220> FEATURE:
<223> OTHER INFORMATION: RNA Oligomer

<400> SEQUENCE: 578
accagcuugu cauuuucaa                                          19

<210> SEQ ID NO 579
<211> LENGTH: 19
<212> TYPE: RNA
<213> ORGANISM: artificial
```

```
<220> FEATURE:
<223> OTHER INFORMATION: RNA Oligomer

<400> SEQUENCE: 579
uuaguagcaa ugaagacug                                                  19

<210> SEQ ID NO 580
<211> LENGTH: 19
<212> TYPE: RNA
<213> ORGANISM: artificial
<220> FEATURE:
<223> OTHER INFORMATION: RNA Oligomer

<400> SEQUENCE: 580
gaagaaaccu cauugucau                                                  19

<210> SEQ ID NO 581
<211> LENGTH: 19
<212> TYPE: RNA
<213> ORGANISM: artificial
<220> FEATURE:
<223> OTHER INFORMATION: RNA Oligomer

<400> SEQUENCE: 581
agaaaccuca uugucaucu                                                  19

<210> SEQ ID NO 582
<211> LENGTH: 19
<212> TYPE: RNA
<213> ORGANISM: artificial
<220> FEATURE:
<223> OTHER INFORMATION: RNA Oligomer

<400> SEQUENCE: 582
aaaccucauu gucaucuac                                                  19

<210> SEQ ID NO 583
<211> LENGTH: 19
<212> TYPE: RNA
<213> ORGANISM: artificial
<220> FEATURE:
<223> OTHER INFORMATION: RNA Oligomer

<400> SEQUENCE: 583
aaccugggag uaguuggca                                                  19

<210> SEQ ID NO 584
<211> LENGTH: 19
<212> TYPE: RNA
<213> ORGANISM: artificial
<220> FEATURE:
<223> OTHER INFORMATION: RNA Oligomer

<400> SEQUENCE: 584
uuuucuuaac aucuggcuu                                                  19

<210> SEQ ID NO 585
<211> LENGTH: 19
<212> TYPE: RNA
<213> ORGANISM: artificial
<220> FEATURE:
<223> OTHER INFORMATION: RNA Oligomer

<400> SEQUENCE: 585
uucacuagga gaauaaggu                                                  19
```

```
<210> SEQ ID NO 586
<211> LENGTH: 19
<212> TYPE: RNA
<213> ORGANISM: artificial
<220> FEATURE:
<223> OTHER INFORMATION: RNA Oligomer

<400> SEQUENCE: 586
aguuguuuuu ucaguaggu                                                    19

<210> SEQ ID NO 587
<211> LENGTH: 19
<212> TYPE: RNA
<213> ORGANISM: artificial
<220> FEATURE:
<223> OTHER INFORMATION: RNA Oligomer

<400> SEQUENCE: 587
aguaggugaa ggcuuuugu                                                    19

<210> SEQ ID NO 588
<211> LENGTH: 19
<212> TYPE: RNA
<213> ORGANISM: artificial
<220> FEATURE:
<223> OTHER INFORMATION: RNA Oligomer

<400> SEQUENCE: 588
ucuccuuuuu cuuugagca                                                    19

<210> SEQ ID NO 589
<211> LENGTH: 19
<212> TYPE: RNA
<213> ORGANISM: artificial
<220> FEATURE:
<223> OTHER INFORMATION: RNA Oligomer

<400> SEQUENCE: 589
cccgaauuaa ugcaaguug                                                    19

<210> SEQ ID NO 590
<211> LENGTH: 19
<212> TYPE: RNA
<213> ORGANISM: artificial
<220> FEATURE:
<223> OTHER INFORMATION: RNA Oligomer

<400> SEQUENCE: 590
gaguuguucu ugucuuucc                                                    19

<210> SEQ ID NO 591
<211> LENGTH: 19
<212> TYPE: RNA
<213> ORGANISM: artificial
<220> FEATURE:
<223> OTHER INFORMATION: RNA Oligomer

<400> SEQUENCE: 591
ucuugucuuu ccuuuucaa                                                    19

<210> SEQ ID NO 592
<211> LENGTH: 19
<212> TYPE: RNA
<213> ORGANISM: artificial
<220> FEATURE:
<223> OTHER INFORMATION: RNA Oligomer

<400> SEQUENCE: 592
```
cuugaauguu ugucuuuug                                                19

<210> SEQ ID NO 593
<211> LENGTH: 19
<212> TYPE: RNA
<213> ORGANISM: artificial
<220> FEATURE:
<223> OTHER INFORMATION: RNA Oligomer

<400> SEQUENCE: 593
gaauguuugu cuuuuguga                                                19

<210> SEQ ID NO 594
<211> LENGTH: 19
<212> TYPE: RNA
<213> ORGANISM: artificial
<220> FEATURE:
<223> OTHER INFORMATION: RNA Oligomer

<400> SEQUENCE: 594
ugucuuuugu gaaugggu                                                 19

<210> SEQ ID NO 595
<211> LENGTH: 19
<212> TYPE: RNA
<213> ORGANISM: artificial
<220> FEATURE:
<223> OTHER INFORMATION: RNA Oligomer

<400> SEQUENCE: 595
aggacuuaca ggcaauucu                                                19

<210> SEQ ID NO 596
<211> LENGTH: 19
<212> TYPE: RNA
<213> ORGANISM: artificial
<220> FEATURE:
<223> OTHER INFORMATION: RNA Oligomer

<400> SEQUENCE: 596
ucauacucuu uccgucgcu                                                19

<210> SEQ ID NO 597
<211> LENGTH: 19
<212> TYPE: RNA
<213> ORGANISM: artificial
<220> FEATURE:
<223> OTHER INFORMATION: RNA Oligomer

<400> SEQUENCE: 597
auugaauucu gcugugcuu                                                19

<210> SEQ ID NO 598
<211> LENGTH: 19
<212> TYPE: RNA
<213> ORGANISM: artificial
<220> FEATURE:
<223> OTHER INFORMATION: RNA Oligomer

<400> SEQUENCE: 598
cccauuuaga aguucagag                                                19

<210> SEQ ID NO 599
<211> LENGTH: 19
<212> TYPE: RNA
<213> ORGANISM: artificial

```
<220> FEATURE:
<223> OTHER INFORMATION: RNA Oligomer

<400> SEQUENCE: 599
uuaaugaguu cacugucaa                                                    19

<210> SEQ ID NO 600
<211> LENGTH: 19
<212> TYPE: RNA
<213> ORGANISM: artificial
<220> FEATURE:
<223> OTHER INFORMATION: RNA Oligomer

<400> SEQUENCE: 600
ucaaauacuu cucgacuua                                                    19

<210> SEQ ID NO 601
<211> LENGTH: 19
<212> TYPE: RNA
<213> ORGANISM: artificial
<220> FEATURE:
<223> OTHER INFORMATION: RNA Oligomer

<400> SEQUENCE: 601
uacuucucga cuuacucca                                                    19

<210> SEQ ID NO 602
<211> LENGTH: 19
<212> TYPE: RNA
<213> ORGANISM: artificial
<220> FEATURE:
<223> OTHER INFORMATION: RNA Oligomer

<400> SEQUENCE: 602
uugaggguau agaugagua                                                    19

<210> SEQ ID NO 603
<211> LENGTH: 19
<212> TYPE: RNA
<213> ORGANISM: artificial
<220> FEATURE:
<223> OTHER INFORMATION: RNA Oligomer

<400> SEQUENCE: 603
uuuggcuucu ggacuugga                                                    19

<210> SEQ ID NO 604
<211> LENGTH: 19
<212> TYPE: RNA
<213> ORGANISM: artificial
<220> FEATURE:
<223> OTHER INFORMATION: RNA Oligomer

<400> SEQUENCE: 604
auaccgucua aaucaacag                                                    19

<210> SEQ ID NO 605
<211> LENGTH: 19
<212> TYPE: RNA
<213> ORGANISM: artificial
<220> FEATURE:
<223> OTHER INFORMATION: RNA Oligomer

<400> SEQUENCE: 605
ugagccugau uaguagcaa                                                    19
```

<210> SEQ ID NO 606
<211> LENGTH: 19
<212> TYPE: RNA
<213> ORGANISM: artificial
<220> FEATURE:
<223> OTHER INFORMATION: RNA Oligomer

<400> SEQUENCE: 606
guagcaauga agacugggc                                                    19

<210> SEQ ID NO 607
<211> LENGTH: 19
<212> TYPE: RNA
<213> ORGANISM: artificial
<220> FEATURE:
<223> OTHER INFORMATION: RNA Oligomer

<400> SEQUENCE: 607
ucaucuacaa acgggaaug                                                    19

<210> SEQ ID NO 608
<211> LENGTH: 19
<212> TYPE: RNA
<213> ORGANISM: artificial
<220> FEATURE:
<223> OTHER INFORMATION: RNA Oligomer

<400> SEQUENCE: 608
ucaucaaagu acaaagcau                                                    19

<210> SEQ ID NO 609
<211> LENGTH: 19
<212> TYPE: RNA
<213> ORGANISM: artificial
<220> FEATURE:
<223> OTHER INFORMATION: RNA Oligomer

<400> SEQUENCE: 609
ucaaaguaca aagcaucug                                                    19

<210> SEQ ID NO 610
<211> LENGTH: 19
<212> TYPE: RNA
<213> ORGANISM: artificial
<220> FEATURE:
<223> OTHER INFORMATION: RNA Oligomer

<400> SEQUENCE: 610
uuuauuagua ccagcucuu                                                    19

<210> SEQ ID NO 611
<211> LENGTH: 19
<212> TYPE: RNA
<213> ORGANISM: artificial
<220> FEATURE:
<223> OTHER INFORMATION: RNA Oligomer

<400> SEQUENCE: 611
aaaaugccau uuuuugucc                                                    19

<210> SEQ ID NO 612
<211> LENGTH: 19
<212> TYPE: RNA
<213> ORGANISM: artificial
<220> FEATURE:
<223> OTHER INFORMATION: RNA Oligomer

<400> SEQUENCE: 612
uaaaguauga gcauuucac                                              19

<210> SEQ ID NO 613
<211> LENGTH: 19
<212> TYPE: RNA
<213> ORGANISM: artificial
<220> FEATURE:
<223> OTHER INFORMATION: RNA Oligomer

<400> SEQUENCE: 613
ucacuaggag aauaagguu                                              19

<210> SEQ ID NO 614
<211> LENGTH: 19
<212> TYPE: RNA
<213> ORGANISM: artificial
<220> FEATURE:
<223> OTHER INFORMATION: RNA Oligomer

<400> SEQUENCE: 614
acuaggagaa uaagguuuu                                              19

<210> SEQ ID NO 615
<211> LENGTH: 19
<212> TYPE: RNA
<213> ORGANISM: artificial
<220> FEATURE:
<223> OTHER INFORMATION: RNA Oligomer

<400> SEQUENCE: 615
auaaggugcu gaguuguuu                                              19

<210> SEQ ID NO 616
<211> LENGTH: 19
<212> TYPE: RNA
<213> ORGANISM: artificial
<220> FEATURE:
<223> OTHER INFORMATION: RNA Oligomer

<400> SEQUENCE: 616
guuguuuuuu caguaggug                                              19

<210> SEQ ID NO 617
<211> LENGTH: 19
<212> TYPE: RNA
<213> ORGANISM: artificial
<220> FEATURE:
<223> OTHER INFORMATION: RNA Oligomer

<400> SEQUENCE: 617
uguuuuuuca guaggugaa                                              19

<210> SEQ ID NO 618
<211> LENGTH: 19
<212> TYPE: RNA
<213> ORGANISM: artificial
<220> FEATURE:
<223> OTHER INFORMATION: RNA Oligomer

<400> SEQUENCE: 618
cuuuuggagu uguucuugu                                              19

<210> SEQ ID NO 619
<211> LENGTH: 19
<212> TYPE: RNA
<213> ORGANISM: artificial

```
<220> FEATURE:
<223> OTHER INFORMATION: RNA Oligomer

<400> SEQUENCE: 619
auaucccgaa uuaaugcaa                                                    19

<210> SEQ ID NO 620
<211> LENGTH: 19
<212> TYPE: RNA
<213> ORGANISM: artificial
<220> FEATURE:
<223> OTHER INFORMATION: RNA Oligomer

<400> SEQUENCE: 620
ucccgaauua augcaaguu                                                    19

<210> SEQ ID NO 621
<211> LENGTH: 19
<212> TYPE: RNA
<213> ORGANISM: artificial
<220> FEATURE:
<223> OTHER INFORMATION: RNA Oligomer

<400> SEQUENCE: 621
ugaauguuug ucuuuugug                                                    19

<210> SEQ ID NO 622
<211> LENGTH: 19
<212> TYPE: RNA
<213> ORGANISM: artificial
<220> FEATURE:
<223> OTHER INFORMATION: RNA Oligomer

<400> SEQUENCE: 622
uuugucuuuu gugaauggg                                                    19

<210> SEQ ID NO 623
<211> LENGTH: 19
<212> TYPE: RNA
<213> ORGANISM: artificial
<220> FEATURE:
<223> OTHER INFORMATION: RNA Oligomer

<400> SEQUENCE: 623
uucuuucucu gguguguuc                                                    19

<210> SEQ ID NO 624
<211> LENGTH: 19
<212> TYPE: RNA
<213> ORGANISM: artificial
<220> FEATURE:
<223> OTHER INFORMATION: RNA Oligomer

<400> SEQUENCE: 624
augaugagcu guggaccgu                                                    19

<210> SEQ ID NO 625
<211> LENGTH: 19
<212> TYPE: RNA
<213> ORGANISM: artificial
<220> FEATURE:
<223> OTHER INFORMATION: RNA Oligomer

<400> SEQUENCE: 625
uuucucuggu guguucuca                                                    19
```

<210> SEQ ID NO 626
<211> LENGTH: 19
<212> TYPE: RNA
<213> ORGANISM: artificial
<220> FEATURE:
<223> OTHER INFORMATION: RNA Oligomer

<400> SEQUENCE: 626
ucuuccacuu cagaaucac                                                  19

<210> SEQ ID NO 627
<211> LENGTH: 19
<212> TYPE: RNA
<213> ORGANISM: artificial
<220> FEATURE:
<223> OTHER INFORMATION: RNA Oligomer

<400> SEQUENCE: 627
aaucauugaa uucugcugu                                                  19

<210> SEQ ID NO 628
<211> LENGTH: 19
<212> TYPE: RNA
<213> ORGANISM: artificial
<220> FEATURE:
<223> OTHER INFORMATION: RNA Oligomer

<400> SEQUENCE: 628
ucauugaauu cugcugugc                                                  19

<210> SEQ ID NO 629
<211> LENGTH: 19
<212> TYPE: RNA
<213> ORGANISM: artificial
<220> FEATURE:
<223> OTHER INFORMATION: RNA Oligomer

<400> SEQUENCE: 629
ggcaucugaa uuuaaugag                                                  19

<210> SEQ ID NO 630
<211> LENGTH: 19
<212> TYPE: RNA
<213> ORGANISM: artificial
<220> FEATURE:
<223> OTHER INFORMATION: RNA Oligomer

<400> SEQUENCE: 630
gcaucugaau uuaaugagu                                                  19

<210> SEQ ID NO 631
<211> LENGTH: 19
<212> TYPE: RNA
<213> ORGANISM: artificial
<220> FEATURE:
<223> OTHER INFORMATION: RNA Oligomer

<400> SEQUENCE: 631
aguucacugu caacugguu                                                  19

<210> SEQ ID NO 632
<211> LENGTH: 19
<212> TYPE: RNA
<213> ORGANISM: artificial
<220> FEATURE:
<223> OTHER INFORMATION: RNA Oligomer

<400> SEQUENCE: 632

```
agaggaugcu gcugaagga                                                    19

<210> SEQ ID NO 633
<211> LENGTH: 19
<212> TYPE: RNA
<213> ORGANISM: artificial
<220> FEATURE:
<223> OTHER INFORMATION: RNA Oligomer

<400> SEQUENCE: 633
ugcugcugaa ggaauccuc                                                    19

<210> SEQ ID NO 634
<211> LENGTH: 19
<212> TYPE: RNA
<213> ORGANISM: artificial
<220> FEATURE:
<223> OTHER INFORMATION: RNA Oligomer

<400> SEQUENCE: 634
aaauacuucu cgacuuacu                                                    19

<210> SEQ ID NO 635
<211> LENGTH: 19
<212> TYPE: RNA
<213> ORGANISM: artificial
<220> FEATURE:
<223> OTHER INFORMATION: RNA Oligomer

<400> SEQUENCE: 635
aauacuucuc gacuuacuc                                                    19

<210> SEQ ID NO 636
<211> LENGTH: 19
<212> TYPE: RNA
<213> ORGANISM: artificial
<220> FEATURE:
<223> OTHER INFORMATION: RNA Oligomer

<400> SEQUENCE: 636
auugagggua uagaugagu                                                    19

<210> SEQ ID NO 637
<211> LENGTH: 19
<212> TYPE: RNA
<213> ORGANISM: artificial
<220> FEATURE:
<223> OTHER INFORMATION: RNA Oligomer

<400> SEQUENCE: 637
ugaggguaua gaugaguaa                                                    19

<210> SEQ ID NO 638
<211> LENGTH: 19
<212> TYPE: RNA
<213> ORGANISM: artificial
<220> FEATURE:
<223> OTHER INFORMATION: RNA Oligomer

<400> SEQUENCE: 638
auuaagacac uguaacuca                                                    19

<210> SEQ ID NO 639
<211> LENGTH: 19
<212> TYPE: RNA
<213> ORGANISM: artificial
```

```
<220> FEATURE:
<223> OTHER INFORMATION: RNA Oligomer

<400> SEQUENCE: 639
ucuauaucuu gccuccaaa                                                    19

<210> SEQ ID NO 640
<211> LENGTH: 19
<212> TYPE: RNA
<213> ORGANISM: artificial
<220> FEATURE:
<223> OTHER INFORMATION: RNA Oligomer

<400> SEQUENCE: 640
caaacuugcu caauguccu                                                    19

<210> SEQ ID NO 641
<211> LENGTH: 19
<212> TYPE: RNA
<213> ORGANISM: artificial
<220> FEATURE:
<223> OTHER INFORMATION: RNA Oligomer

<400> SEQUENCE: 641
uccuguugca uaccgucua                                                    19

<210> SEQ ID NO 642
<211> LENGTH: 19
<212> TYPE: RNA
<213> ORGANISM: artificial
<220> FEATURE:
<223> OTHER INFORMATION: RNA Oligomer

<400> SEQUENCE: 642
ugcauaccgu cuaaaucaa                                                    19

<210> SEQ ID NO 643
<211> LENGTH: 19
<212> TYPE: RNA
<213> ORGANISM: artificial
<220> FEATURE:
<223> OTHER INFORMATION: RNA Oligomer

<400> SEQUENCE: 643
ccugauuagu agcaaugaa                                                    19

<210> SEQ ID NO 644
<211> LENGTH: 19
<212> TYPE: RNA
<213> ORGANISM: artificial
<220> FEATURE:
<223> OTHER INFORMATION: RNA Oligomer

<400> SEQUENCE: 644
auuaguagca augaagacu                                                    19

<210> SEQ ID NO 645
<211> LENGTH: 19
<212> TYPE: RNA
<213> ORGANISM: artificial
<220> FEATURE:
<223> OTHER INFORMATION: RNA Oligomer

<400> SEQUENCE: 645
agugacugaa acguagccg                                                    19
```

```
<210> SEQ ID NO 646
<211> LENGTH: 19
<212> TYPE: RNA
<213> ORGANISM: artificial
<220> FEATURE:
<223> OTHER INFORMATION: RNA Oligomer

<400> SEQUENCE: 646
ucaaucaaau ccauguccu                                                  19

<210> SEQ ID NO 647
<211> LENGTH: 19
<212> TYPE: RNA
<213> ORGANISM: artificial
<220> FEATURE:
<223> OTHER INFORMATION: RNA Oligomer

<400> SEQUENCE: 647
cugauuuggg aaugugggc                                                  19

<210> SEQ ID NO 648
<211> LENGTH: 19
<212> TYPE: RNA
<213> ORGANISM: artificial
<220> FEATURE:
<223> OTHER INFORMATION: RNA Oligomer

<400> SEQUENCE: 648
aucaaaucca uguccugcu                                                  19

<210> SEQ ID NO 649
<211> LENGTH: 19
<212> TYPE: RNA
<213> ORGANISM: artificial
<220> FEATURE:
<223> OTHER INFORMATION: RNA Oligomer

<400> SEQUENCE: 649
uccuuuauua guaccagcu                                                  19

<210> SEQ ID NO 650
<211> LENGTH: 19
<212> TYPE: RNA
<213> ORGANISM: artificial
<220> FEATURE:
<223> OTHER INFORMATION: RNA Oligomer

<400> SEQUENCE: 650
ccuuuauuag uaccagcuc                                                  19

<210> SEQ ID NO 651
<211> LENGTH: 19
<212> TYPE: RNA
<213> ORGANISM: artificial
<220> FEATURE:
<223> OTHER INFORMATION: RNA Oligomer

<400> SEQUENCE: 651
cuuuauuagu accagcucu                                                  19

<210> SEQ ID NO 652
<211> LENGTH: 19
<212> TYPE: RNA
<213> ORGANISM: artificial
<220> FEATURE:
<223> OTHER INFORMATION: RNA Oligomer

<400> SEQUENCE: 652
```
aaaaguacau agugguuag 19

<210> SEQ ID NO 653
<211> LENGTH: 19
<212> TYPE: RNA
<213> ORGANISM: artificial
<220> FEATURE:
<223> OTHER INFORMATION: RNA Oligomer

<400> SEQUENCE: 653
uuucuuuuua gccagaugu 19

<210> SEQ ID NO 654
<211> LENGTH: 19
<212> TYPE: RNA
<213> ORGANISM: artificial
<220> FEATURE:
<223> OTHER INFORMATION: RNA Oligomer

<400> SEQUENCE: 654
acaaaugaca uaagaacag 19

<210> SEQ ID NO 655
<211> LENGTH: 19
<212> TYPE: RNA
<213> ORGANISM: artificial
<220> FEATURE:
<223> OTHER INFORMATION: RNA Oligomer

<400> SEQUENCE: 655
uuacacagaa acuagccca 19

<210> SEQ ID NO 656
<211> LENGTH: 19
<212> TYPE: RNA
<213> ORGANISM: artificial
<220> FEATURE:
<223> OTHER INFORMATION: RNA Oligomer

<400> SEQUENCE: 656
guccuaagaa auuguuuac 19

<210> SEQ ID NO 657
<211> LENGTH: 19
<212> TYPE: RNA
<213> ORGANISM: artificial
<220> FEATURE:
<223> OTHER INFORMATION: RNA Oligomer

<400> SEQUENCE: 657
ccuaagaaau uguuuacag 19

<210> SEQ ID NO 658
<211> LENGTH: 19
<212> TYPE: RNA
<213> ORGANISM: artificial
<220> FEATURE:
<223> OTHER INFORMATION: RNA Oligomer

<400> SEQUENCE: 658
acugauucaa cauacugac 19

<210> SEQ ID NO 659
<211> LENGTH: 19
<212> TYPE: RNA
<213> ORGANISM: artificial

```
<220> FEATURE:
<223> OTHER INFORMATION: RNA Oligomer

<400> SEQUENCE: 659
gaacaaggaa aacauugcc                                                19

<210> SEQ ID NO 660
<211> LENGTH: 19
<212> TYPE: RNA
<213> ORGANISM: artificial
<220> FEATURE:
<223> OTHER INFORMATION: RNA Oligomer

<400> SEQUENCE: 660
acuucgagau auaaggugc                                                19

<210> SEQ ID NO 661
<211> LENGTH: 19
<212> TYPE: RNA
<213> ORGANISM: artificial
<220> FEATURE:
<223> OTHER INFORMATION: RNA Oligomer

<400> SEQUENCE: 661
ggugcugagu uguuuuuc                                                 19

<210> SEQ ID NO 662
<211> LENGTH: 19
<212> TYPE: RNA
<213> ORGANISM: artificial
<220> FEATURE:
<223> OTHER INFORMATION: RNA Oligomer

<400> SEQUENCE: 662
augaucuaaa ucuugcucu                                                19

<210> SEQ ID NO 663
<211> LENGTH: 19
<212> TYPE: RNA
<213> ORGANISM: artificial
<220> FEATURE:
<223> OTHER INFORMATION: RNA Oligomer

<400> SEQUENCE: 663
ugaucuaaau cuugcucua                                                19

<210> SEQ ID NO 664
<211> LENGTH: 19
<212> TYPE: RNA
<213> ORGANISM: artificial
<220> FEATURE:
<223> OTHER INFORMATION: RNA Oligomer

<400> SEQUENCE: 664
aaaucuugcu cuaguucua                                                19

<210> SEQ ID NO 665
<211> LENGTH: 19
<212> TYPE: RNA
<213> ORGANISM: artificial
<220> FEATURE:
<223> OTHER INFORMATION: RNA Oligomer

<400> SEQUENCE: 665
auucuuaccc cuccuacgu                                                19
```

```
<210> SEQ ID NO 666
<211> LENGTH: 19
<212> TYPE: RNA
<213> ORGANISM: artificial
<220> FEATURE:
<223> OTHER INFORMATION: RNA Oligomer

<400> SEQUENCE: 666
uugaagucaa caacaggga                                                   19

<210> SEQ ID NO 667
<211> LENGTH: 19
<212> TYPE: RNA
<213> ORGANISM: artificial
<220> FEATURE:
<223> OTHER INFORMATION: RNA Oligomer

<400> SEQUENCE: 667
augauuuuuu cuacaggga                                                   19

<210> SEQ ID NO 668
<211> LENGTH: 19
<212> TYPE: RNA
<213> ORGANISM: artificial
<220> FEATURE:
<223> OTHER INFORMATION: RNA Oligomer

<400> SEQUENCE: 668
cuaaguucau cucuuguga                                                   19

<210> SEQ ID NO 669
<211> LENGTH: 19
<212> TYPE: RNA
<213> ORGANISM: artificial
<220> FEATURE:
<223> OTHER INFORMATION: RNA Oligomer

<400> SEQUENCE: 669
uacaggcaau ucuuucucu                                                   19

<210> SEQ ID NO 670
<211> LENGTH: 19
<212> TYPE: RNA
<213> ORGANISM: artificial
<220> FEATURE:
<223> OTHER INFORMATION: RNA Oligomer

<400> SEQUENCE: 670
aggcaauucu uucucuggu                                                   19

<210> SEQ ID NO 671
<211> LENGTH: 19
<212> TYPE: RNA
<213> ORGANISM: artificial
<220> FEATURE:
<223> OTHER INFORMATION: RNA Oligomer

<400> SEQUENCE: 671
ggcaauucuu ucucuggug                                                   19

<210> SEQ ID NO 672
<211> LENGTH: 19
<212> TYPE: RNA
<213> ORGANISM: artificial
<220> FEATURE:
<223> OTHER INFORMATION: RNA Oligomer

<400> SEQUENCE: 672
```
uguuuuucca gcucauacu                                                19

<210> SEQ ID NO 673
<211> LENGTH: 19
<212> TYPE: RNA
<213> ORGANISM: artificial
<220> FEATURE:
<223> OTHER INFORMATION: RNA Oligomer

<400> SEQUENCE: 673 uaucccaga agaauguac                                                 19

<210> SEQ ID NO 674
<211> LENGTH: 19
<212> TYPE: RNA
<213> ORGANISM: artificial
<220> FEATURE:
<223> OTHER INFORMATION: RNA Oligomer

<400> SEQUENCE: 674
uuuaggacca uucuguuug                                                19

<210> SEQ ID NO 675
<211> LENGTH: 19
<212> TYPE: RNA
<213> ORGANISM: artificial
<220> FEATURE:
<223> OTHER INFORMATION: RNA Oligomer

<400> SEQUENCE: 675
uucuguuuga cacuuccag                                                19

<210> SEQ ID NO 676
<211> LENGTH: 19
<212> TYPE: RNA
<213> ORGANISM: artificial
<220> FEATURE:
<223> OTHER INFORMATION: RNA Oligomer

<400> SEQUENCE: 676
uccagcucau acucuuucc                                                19

<210> SEQ ID NO 677
<211> LENGTH: 19
<212> TYPE: RNA
<213> ORGANISM: artificial
<220> FEATURE:
<223> OTHER INFORMATION: RNA Oligomer

<400> SEQUENCE: 677
uuccacuuca gaaucacug                                                19

<210> SEQ ID NO 678
<211> LENGTH: 19
<212> TYPE: RNA
<213> ORGANISM: artificial
<220> FEATURE:
<223> OTHER INFORMATION: RNA Oligomer

<400> SEQUENCE: 678
agcucauacu cuuccguc                                                 19

<210> SEQ ID NO 679
<211> LENGTH: 19
<212> TYPE: RNA
<213> ORGANISM: artificial

-continued

```
<220> FEATURE:
<223> OTHER INFORMATION: RNA Oligomer

<400> SEQUENCE: 679
aucauugaau ucugcugug                                                    19

<210> SEQ ID NO 680
<211> LENGTH: 19
<212> TYPE: RNA
<213> ORGANISM: artificial
<220> FEATURE:
<223> OTHER INFORMATION: RNA Oligomer

<400> SEQUENCE: 680
aaucuguguu gacugggc                                                     19

<210> SEQ ID NO 681
<211> LENGTH: 19
<212> TYPE: RNA
<213> ORGANISM: artificial
<220> FEATURE:
<223> OTHER INFORMATION: RNA Oligomer

<400> SEQUENCE: 681
acuguggcau cugaauuua                                                    19

<210> SEQ ID NO 682
<211> LENGTH: 19
<212> TYPE: RNA
<213> ORGANISM: artificial
<220> FEATURE:
<223> OTHER INFORMATION: RNA Oligomer

<400> SEQUENCE: 682
ugaguucacu gucaacugg                                                    19

<210> SEQ ID NO 683
<211> LENGTH: 19
<212> TYPE: RNA
<213> ORGANISM: artificial
<220> FEATURE:
<223> OTHER INFORMATION: RNA Oligomer

<400> SEQUENCE: 683
aagucaaaua cuucucgac                                                    19

<210> SEQ ID NO 684
<211> LENGTH: 19
<212> TYPE: RNA
<213> ORGANISM: artificial
<220> FEATURE:
<223> OTHER INFORMATION: RNA Oligomer

<400> SEQUENCE: 684
aagaaaaugu ggacuacag                                                    19

<210> SEQ ID NO 685
<211> LENGTH: 19
<212> TYPE: RNA
<213> ORGANISM: artificial
<220> FEATURE:
<223> OTHER INFORMATION: RNA Oligomer

<400> SEQUENCE: 685
auacuucucg acuuacucc                                                    19
```

```
<210> SEQ ID NO 686
<211> LENGTH: 19
<212> TYPE: RNA
<213> ORGANISM: artificial
<220> FEATURE:
<223> OTHER INFORMATION: RNA Oligomer

<400> SEQUENCE: 686
auaauuguca acuucuguc                                                19

<210> SEQ ID NO 687
<211> LENGTH: 19
<212> TYPE: RNA
<213> ORGANISM: artificial
<220> FEATURE:
<223> OTHER INFORMATION: RNA Oligomer

<400> SEQUENCE: 687
uuggaaccau gguagucuc                                                19

<210> SEQ ID NO 688
<211> LENGTH: 19
<212> TYPE: RNA
<213> ORGANISM: artificial
<220> FEATURE:
<223> OTHER INFORMATION: RNA Oligomer

<400> SEQUENCE: 688
acucaggaau ggauaauag                                                19

<210> SEQ ID NO 689
<211> LENGTH: 19
<212> TYPE: RNA
<213> ORGANISM: artificial
<220> FEATURE:
<223> OTHER INFORMATION: RNA Oligomer

<400> SEQUENCE: 689
uguccuguug cauaccguc                                                19

<210> SEQ ID NO 690
<211> LENGTH: 19
<212> TYPE: RNA
<213> ORGANISM: artificial
<220> FEATURE:
<223> OTHER INFORMATION: RNA Oligomer

<400> SEQUENCE: 690
aaugaagacu gggcucucg                                                19

<210> SEQ ID NO 691
<211> LENGTH: 19
<212> TYPE: RNA
<213> ORGANISM: artificial
<220> FEATURE:
<223> OTHER INFORMATION: RNA Oligomer

<400> SEQUENCE: 691
uccaaaguau gucaaucaa                                                19

<210> SEQ ID NO 692
<211> LENGTH: 19
<212> TYPE: RNA
<213> ORGANISM: artificial
<220> FEATURE:
<223> OTHER INFORMATION: RNA Oligomer

<400> SEQUENCE: 692
```
aauaucagga acaagugac                                          19

<210> SEQ ID NO 693
<211> LENGTH: 19
<212> TYPE: RNA
<213> ORGANISM: artificial
<220> FEATURE:
<223> OTHER INFORMATION: RNA Oligomer

<400> SEQUENCE: 693
gugacugaaa cguagccga                                          19

<210> SEQ ID NO 694
<211> LENGTH: 19
<212> TYPE: RNA
<213> ORGANISM: artificial
<220> FEATURE:
<223> OTHER INFORMATION: RNA Oligomer

<400> SEQUENCE: 694
acguagccga agaaaccuc                                          19

<210> SEQ ID NO 695
<211> LENGTH: 19
<212> TYPE: RNA
<213> ORGANISM: artificial
<220> FEATURE:
<223> OTHER INFORMATION: RNA Oligomer

<400> SEQUENCE: 695
aucuacaaac gggaauguc                                          19

<210> SEQ ID NO 696
<211> LENGTH: 19
<212> TYPE: RNA
<213> ORGANISM: artificial
<220> FEATURE:
<223> OTHER INFORMATION: RNA Oligomer

<400> SEQUENCE: 696
ugucaaucaa auccauguc                                          19

<210> SEQ ID NO 697
<211> LENGTH: 19
<212> TYPE: RNA
<213> ORGANISM: artificial
<220> FEATURE:
<223> OTHER INFORMATION: RNA Oligomer

<400> SEQUENCE: 697
caaaguacaa agcaucuga                                          19

<210> SEQ ID NO 698
<211> LENGTH: 19
<212> TYPE: RNA
<213> ORGANISM: artificial
<220> FEATURE:
<223> OTHER INFORMATION: RNA Oligomer

<400> SEQUENCE: 698
ucaaauccau guccugcug                                          19

<210> SEQ ID NO 699
<211> LENGTH: 19
<212> TYPE: RNA
<213> ORGANISM: artificial

```
<220> FEATURE:
<223> OTHER INFORMATION: RNA Oligomer

<400> SEQUENCE: 699
aaugccauuu uuuguccau                                                       19

<210> SEQ ID NO 700
<211> LENGTH: 19
<212> TYPE: RNA
<213> ORGANISM: artificial
<220> FEATURE:
<223> OTHER INFORMATION: RNA Oligomer

<400> SEQUENCE: 700
ugccauuuuu uguccauac                                                       19

<210> SEQ ID NO 701
<211> LENGTH: 19
<212> TYPE: RNA
<213> ORGANISM: artificial
<220> FEATURE:
<223> OTHER INFORMATION: RNA Oligomer

<400> SEQUENCE: 701
auuucuuuuu agccagaug                                                       19

<210> SEQ ID NO 702
<211> LENGTH: 19
<212> TYPE: RNA
<213> ORGANISM: artificial
<220> FEATURE:
<223> OTHER INFORMATION: RNA Oligomer

<400> SEQUENCE: 702
uucuuuuuag ccagauguc                                                       19

<210> SEQ ID NO 703
<211> LENGTH: 19
<212> TYPE: RNA
<213> ORGANISM: artificial
<220> FEATURE:
<223> OTHER INFORMATION: RNA Oligomer

<400> SEQUENCE: 703
aguacaaaaa aacuagcuc                                                       19

<210> SEQ ID NO 704
<211> LENGTH: 19
<212> TYPE: RNA
<213> ORGANISM: artificial
<220> FEATURE:
<223> OTHER INFORMATION: RNA Oligomer

<400> SEQUENCE: 704
aauaagguuu uccaucuuc                                                       19

<210> SEQ ID NO 705
<211> LENGTH: 19
<212> TYPE: RNA
<213> ORGANISM: artificial
<220> FEATURE:
<223> OTHER INFORMATION: RNA Oligomer

<400> SEQUENCE: 705
uccaucuuca ucacguagc                                                       19
```

```
<210> SEQ ID NO 706
<211> LENGTH: 19
<212> TYPE: RNA
<213> ORGANISM: artificial
<220> FEATURE:
<223> OTHER INFORMATION: RNA Oligomer

<400> SEQUENCE: 706
ccaucuucau cacguagca                                              19

<210> SEQ ID NO 707
<211> LENGTH: 19
<212> TYPE: RNA
<213> ORGANISM: artificial
<220> FEATURE:
<223> OTHER INFORMATION: RNA Oligomer

<400> SEQUENCE: 707
aaugaucuaa aucuugcuc                                              19

<210> SEQ ID NO 708
<211> LENGTH: 19
<212> TYPE: RNA
<213> ORGANISM: artificial
<220> FEATURE:
<223> OTHER INFORMATION: RNA Oligomer

<400> SEQUENCE: 708
aucuaaaucu ugcucuagu                                              19

<210> SEQ ID NO 709
<211> LENGTH: 19
<212> TYPE: RNA
<213> ORGANISM: artificial
<220> FEATURE:
<223> OTHER INFORMATION: RNA Oligomer

<400> SEQUENCE: 709
ucuugcucua guucuacua                                              19

<210> SEQ ID NO 710
<211> LENGTH: 19
<212> TYPE: RNA
<213> ORGANISM: artificial
<220> FEATURE:
<223> OTHER INFORMATION: RNA Oligomer

<400> SEQUENCE: 710
ucuacaggga augggauau                                              19

<210> SEQ ID NO 711
<211> LENGTH: 19
<212> TYPE: RNA
<213> ORGANISM: artificial
<220> FEATURE:
<223> OTHER INFORMATION: RNA Oligomer

<400> SEQUENCE: 711
uacagggaau gggauaugg                                              19

<210> SEQ ID NO 712
<211> LENGTH: 19
<212> TYPE: RNA
<213> ORGANISM: artificial
<220> FEATURE:
<223> OTHER INFORMATION: RNA Oligomer

<400> SEQUENCE: 712
```
uugucuuuug ugaaugggg                                                  19

<210> SEQ ID NO 713
<211> LENGTH: 19
<212> TYPE: RNA
<213> ORGANISM: artificial
<220> FEATURE:
<223> OTHER INFORMATION: RNA Oligomer

<400> SEQUENCE: 713 gcaaucuuu cucggugu                                                    19

<210> SEQ ID NO 714
<211> LENGTH: 19
<212> TYPE: RNA
<213> ORGANISM: artificial
<220> FEATURE:
<223> OTHER INFORMATION: RNA Oligomer

<400> SEQUENCE: 714
uuaggaccau ucuguuuga                                                  19

<210> SEQ ID NO 715
<211> LENGTH: 19
<212> TYPE: RNA
<213> ORGANISM: artificial
<220> FEATURE:
<223> OTHER INFORMATION: RNA Oligomer

<400> SEQUENCE: 715
uuuuccagcu cauacucuu                                                  19

<210> SEQ ID NO 716
<211> LENGTH: 19
<212> TYPE: RNA
<213> ORGANISM: artificial
<220> FEATURE:
<223> OTHER INFORMATION: RNA Oligomer

<400> SEQUENCE: 716
uuugacacuu ccaggggca                                                  19

<210> SEQ ID NO 717
<211> LENGTH: 19
<212> TYPE: RNA
<213> ORGANISM: artificial
<220> FEATURE:
<223> OTHER INFORMATION: RNA Oligomer

<400> SEQUENCE: 717
cucauacucu uuccgucgc                                                  19

<210> SEQ ID NO 718
<211> LENGTH: 19
<212> TYPE: RNA
<213> ORGANISM: artificial
<220> FEATURE:
<223> OTHER INFORMATION: RNA Oligomer

<400> SEQUENCE: 718
ggcccauuua gaaguucag                                                  19

<210> SEQ ID NO 719
<211> LENGTH: 19
<212> TYPE: RNA
<213> ORGANISM: artificial

```
<220> FEATURE:
<223> OTHER INFORMATION: RNA Oligomer

<400> SEQUENCE: 719
aaaucugugu ugacugugg                                              19

<210> SEQ ID NO 720
<211> LENGTH: 19
<212> TYPE: RNA
<213> ORGANISM: artificial
<220> FEATURE:
<223> OTHER INFORMATION: RNA Oligomer

<400> SEQUENCE: 720
aaggaauccu caaaagcau                                              19

<210> SEQ ID NO 721
<211> LENGTH: 19
<212> TYPE: RNA
<213> ORGANISM: artificial
<220> FEATURE:
<223> OTHER INFORMATION: RNA Oligomer

<400> SEQUENCE: 721
uacuucuuuu uccauugag                                              19

<210> SEQ ID NO 722
<211> LENGTH: 19
<212> TYPE: RNA
<213> ORGANISM: artificial
<220> FEATURE:
<223> OTHER INFORMATION: RNA Oligomer

<400> SEQUENCE: 722
cauugagggu auagaugag                                              19

<210> SEQ ID NO 723
<211> LENGTH: 19
<212> TYPE: RNA
<213> ORGANISM: artificial
<220> FEATURE:
<223> OTHER INFORMATION: RNA Oligomer

<400> SEQUENCE: 723
ucccaaacuu gcucaaugu                                              19

<210> SEQ ID NO 724
<211> LENGTH: 19
<212> TYPE: RNA
<213> ORGANISM: artificial
<220> FEATURE:
<223> OTHER INFORMATION: RNA Oligomer

<400> SEQUENCE: 724
acuugcucaa uguccuguu                                              19

<210> SEQ ID NO 725
<211> LENGTH: 19
<212> TYPE: RNA
<213> ORGANISM: artificial
<220> FEATURE:
<223> OTHER INFORMATION: RNA Oligomer

<400> SEQUENCE: 725
ccuguugcau accgucuaa                                              19
```

```
<210> SEQ ID NO 726
<211> LENGTH: 19
<212> TYPE: RNA
<213> ORGANISM: artificial
<220> FEATURE:
<223> OTHER INFORMATION: RNA Oligomer

<400> SEQUENCE: 726
agcaacagaa guucaggu                                                   19

<210> SEQ ID NO 727
<211> LENGTH: 19
<212> TYPE: RNA
<213> ORGANISM: artificial
<220> FEATURE:
<223> OTHER INFORMATION: RNA Oligomer

<400> SEQUENCE: 727
uaguagcaau gaagacugg                                                  19

<210> SEQ ID NO 728
<211> LENGTH: 19
<212> TYPE: RNA
<213> ORGANISM: artificial
<220> FEATURE:
<223> OTHER INFORMATION: RNA Oligomer

<400> SEQUENCE: 728
gcaaugaaga cugggcucu                                                  19

<210> SEQ ID NO 729
<211> LENGTH: 19
<212> TYPE: RNA
<213> ORGANISM: artificial
<220> FEATURE:
<223> OTHER INFORMATION: RNA Oligomer

<400> SEQUENCE: 729
auaucaggaa caagugacu                                                  19

<210> SEQ ID NO 730
<211> LENGTH: 19
<212> TYPE: RNA
<213> ORGANISM: artificial
<220> FEATURE:
<223> OTHER INFORMATION: RNA Oligomer

<400> SEQUENCE: 730
aguaugucaa ucaaaucca                                                  19

<210> SEQ ID NO 731
<211> LENGTH: 19
<212> TYPE: RNA
<213> ORGANISM: artificial
<220> FEATURE:
<223> OTHER INFORMATION: RNA Oligomer

<400> SEQUENCE: 731
agccgaagaa accucauug                                                  19

<210> SEQ ID NO 732
<211> LENGTH: 19
<212> TYPE: RNA
<213> ORGANISM: artificial
<220> FEATURE:
<223> OTHER INFORMATION: RNA Oligomer

<400> SEQUENCE: 732
```

-continued gccgaagaaa ccucauugu                                           19

<210> SEQ ID NO 733
<211> LENGTH: 19
<212> TYPE: RNA
<213> ORGANISM: artificial
<220> FEATURE:
<223> OTHER INFORMATION: RNA Oligomer

<400> SEQUENCE: 733
ucuacaaacg ggaaugucu                                           19

<210> SEQ ID NO 734
<211> LENGTH: 19
<212> TYPE: RNA
<213> ORGANISM: artificial
<220> FEATURE:
<223> OTHER INFORMATION: RNA Oligomer

<400> SEQUENCE: 734
agucaucaaa guacaaagc                                           19

<210> SEQ ID NO 735
<211> LENGTH: 19
<212> TYPE: RNA
<213> ORGANISM: artificial
<220> FEATURE:
<223> OTHER INFORMATION: RNA Oligomer

<400> SEQUENCE: 735
ucugauuugg gaauguggg                                           19

<210> SEQ ID NO 736
<211> LENGTH: 19
<212> TYPE: RNA
<213> ORGANISM: artificial
<220> FEATURE:
<223> OTHER INFORMATION: RNA Oligomer

<400> SEQUENCE: 736
ugucucuuca ucuaguugu                                           19

<210> SEQ ID NO 737
<211> LENGTH: 19
<212> TYPE: RNA
<213> ORGANISM: artificial
<220> FEATURE:
<223> OTHER INFORMATION: RNA Oligomer

<400> SEQUENCE: 737
gucucuucau cuaguugua                                           19

<210> SEQ ID NO 738
<211> LENGTH: 19
<212> TYPE: RNA
<213> ORGANISM: artificial
<220> FEATURE:
<223> OTHER INFORMATION: RNA Oligomer

<400> SEQUENCE: 738
auuaguacca gcucuuaaa                                           19

<210> SEQ ID NO 739
<211> LENGTH: 19
<212> TYPE: RNA
<213> ORGANISM: artificial

```
<220> FEATURE:
<223> OTHER INFORMATION: RNA Oligomer

<400> SEQUENCE: 739
aaaugccauu uuuugucca                                              19

<210> SEQ ID NO 740
<211> LENGTH: 19
<212> TYPE: RNA
<213> ORGANISM: artificial
<220> FEATURE:
<223> OTHER INFORMATION: RNA Oligomer

<400> SEQUENCE: 740
cuuacacaga aacuagccc                                              19

<210> SEQ ID NO 741
<211> LENGTH: 19
<212> TYPE: RNA
<213> ORGANISM: artificial
<220> FEATURE:
<223> OTHER INFORMATION: RNA Oligomer

<400> SEQUENCE: 741
uacacagaaa cuagcccaa                                              19

<210> SEQ ID NO 742
<211> LENGTH: 19
<212> TYPE: RNA
<213> ORGANISM: artificial
<220> FEATURE:
<223> OTHER INFORMATION: RNA Oligomer

<400> SEQUENCE: 742
ugauucaaca uacugacac                                              19

<210> SEQ ID NO 743
<211> LENGTH: 19
<212> TYPE: RNA
<213> ORGANISM: artificial
<220> FEATURE:
<223> OTHER INFORMATION: RNA Oligomer

<400> SEQUENCE: 743
aguaugagca uuucacauc                                              19

<210> SEQ ID NO 744
<211> LENGTH: 19
<212> TYPE: RNA
<213> ORGANISM: artificial
<220> FEATURE:
<223> OTHER INFORMATION: RNA Oligomer

<400> SEQUENCE: 744
uuucacauca caguaggag                                              19

<210> SEQ ID NO 745
<211> LENGTH: 19
<212> TYPE: RNA
<213> ORGANISM: artificial
<220> FEATURE:
<223> OTHER INFORMATION: RNA Oligomer

<400> SEQUENCE: 745
gucaaauccu ccuaaaucu                                              19
```

-continued

```
<210> SEQ ID NO 746
<211> LENGTH: 19
<212> TYPE: RNA
<213> ORGANISM: artificial
<220> FEATURE:
<223> OTHER INFORMATION: RNA Oligomer

<400> SEQUENCE: 746
ggaacaagga aaacauugc                                               19

<210> SEQ ID NO 747
<211> LENGTH: 19
<212> TYPE: RNA
<213> ORGANISM: artificial
<220> FEATURE:
<223> OTHER INFORMATION: RNA Oligomer

<400> SEQUENCE: 747
aacauugcca ucucuuguu                                               19

<210> SEQ ID NO 748
<211> LENGTH: 19
<212> TYPE: RNA
<213> ORGANISM: artificial
<220> FEATURE:
<223> OTHER INFORMATION: RNA Oligomer

<400> SEQUENCE: 748
gccaucucuu guuugcugc                                               19

<210> SEQ ID NO 749
<211> LENGTH: 19
<212> TYPE: RNA
<213> ORGANISM: artificial
<220> FEATURE:
<223> OTHER INFORMATION: RNA Oligomer

<400> SEQUENCE: 749
agggaguauu cacuaggag                                               19

<210> SEQ ID NO 750
<211> LENGTH: 19
<212> TYPE: RNA
<213> ORGANISM: artificial
<220> FEATURE:
<223> OTHER INFORMATION: RNA Oligomer

<400> SEQUENCE: 750
uucgagauau aaggugcug                                               19

<210> SEQ ID NO 751
<211> LENGTH: 19
<212> TYPE: RNA
<213> ORGANISM: artificial
<220> FEATURE:
<223> OTHER INFORMATION: RNA Oligomer

<400> SEQUENCE: 751
uuguuuuuuc aguagguga                                               19

<210> SEQ ID NO 752
<211> LENGTH: 19
<212> TYPE: RNA
<213> ORGANISM: artificial
<220> FEATURE:
<223> OTHER INFORMATION: RNA Oligomer

<400> SEQUENCE: 752
```
caaaugaucu aaaucuugc                                                19

<210> SEQ ID NO 753
<211> LENGTH: 19
<212> TYPE: RNA
<213> ORGANISM: artificial
<220> FEATURE:
<223> OTHER INFORMATION: RNA Oligomer

<400> SEQUENCE: 753
uuccaguuuu cuuuucug                                                 19

<210> SEQ ID NO 754
<211> LENGTH: 19
<212> TYPE: RNA
<213> ORGANISM: artificial
<220> FEATURE:
<223> OTHER INFORMATION: RNA Oligomer

<400> SEQUENCE: 754
ucuuaccccu ccuacguau                                                19

<210> SEQ ID NO 755
<211> LENGTH: 19
<212> TYPE: RNA
<213> ORGANISM: artificial
<220> FEATURE:
<223> OTHER INFORMATION: RNA Oligomer

<400> SEQUENCE: 755
uauaucccga auuaaugca                                                19

<210> SEQ ID NO 756
<211> LENGTH: 19
<212> TYPE: RNA
<213> ORGANISM: artificial
<220> FEATURE:
<223> OTHER INFORMATION: RNA Oligomer

<400> SEQUENCE: 756
aaugggauau ggagagcuu                                                19

<210> SEQ ID NO 757
<211> LENGTH: 19
<212> TYPE: RNA
<213> ORGANISM: artificial
<220> FEATURE:
<223> OTHER INFORMATION: RNA Oligomer

<400> SEQUENCE: 757
uguuugucuu uugugaaug                                                19

<210> SEQ ID NO 758
<211> LENGTH: 19
<212> TYPE: RNA
<213> ORGANISM: artificial
<220> FEATURE:
<223> OTHER INFORMATION: RNA Oligomer

<400> SEQUENCE: 758
guuuuuccag cucauacuc                                                19

<210> SEQ ID NO 759
<211> LENGTH: 19
<212> TYPE: RNA
<213> ORGANISM: artificial

```
<220> FEATURE:
<223> OTHER INFORMATION: RNA Oligomer

<400> SEQUENCE: 759
guguuuuagg accauucug                                              19

<210> SEQ ID NO 760
<211> LENGTH: 19
<212> TYPE: RNA
<213> ORGANISM: artificial
<220> FEATURE:
<223> OTHER INFORMATION: RNA Oligomer

<400> SEQUENCE: 760
ggaccauucu guuugacac                                              19

<210> SEQ ID NO 761
<211> LENGTH: 19
<212> TYPE: RNA
<213> ORGANISM: artificial
<220> FEATURE:
<223> OTHER INFORMATION: RNA Oligomer

<400> SEQUENCE: 761
ccauucuguu ugacacuuc                                              19

<210> SEQ ID NO 762
<211> LENGTH: 19
<212> TYPE: RNA
<213> ORGANISM: artificial
<220> FEATURE:
<223> OTHER INFORMATION: RNA Oligomer

<400> SEQUENCE: 762
ucuagcucuu ccacuucag                                              19

<210> SEQ ID NO 763
<211> LENGTH: 19
<212> TYPE: RNA
<213> ORGANISM: artificial
<220> FEATURE:
<223> OTHER INFORMATION: RNA Oligomer

<400> SEQUENCE: 763
auuccacuga guguucugg                                              19

<210> SEQ ID NO 764
<211> LENGTH: 19
<212> TYPE: RNA
<213> ORGANISM: artificial
<220> FEATURE:
<223> OTHER INFORMATION: RNA Oligomer

<400> SEQUENCE: 764
ugaaaugccg gagucagaa                                              19

<210> SEQ ID NO 765
<211> LENGTH: 19
<212> TYPE: RNA
<213> ORGANISM: artificial
<220> FEATURE:
<223> OTHER INFORMATION: RNA Oligomer

<400> SEQUENCE: 765
augccggagu cagaaucau                                              19
```

```
<210> SEQ ID NO 766
<211> LENGTH: 19
<212> TYPE: RNA
<213> ORGANISM: artificial
<220> FEATURE:
<223> OTHER INFORMATION: RNA Oligomer

<400> SEQUENCE: 766
ucagaaacau caaugggcc                                                19

<210> SEQ ID NO 767
<211> LENGTH: 19
<212> TYPE: RNA
<213> ORGANISM: artificial
<220> FEATURE:
<223> OTHER INFORMATION: RNA Oligomer

<400> SEQUENCE: 767
uucaucacca aaaucugug                                                19

<210> SEQ ID NO 768
<211> LENGTH: 19
<212> TYPE: RNA
<213> ORGANISM: artificial
<220> FEATURE:
<223> OTHER INFORMATION: RNA Oligomer

<400> SEQUENCE: 768
augaguucac ugucaacug                                                19

<210> SEQ ID NO 769
<211> LENGTH: 19
<212> TYPE: RNA
<213> ORGANISM: artificial
<220> FEATURE:
<223> OTHER INFORMATION: RNA Oligomer

<400> SEQUENCE: 769
gaauccucaa aagcauuaa                                                19

<210> SEQ ID NO 770
<211> LENGTH: 19
<212> TYPE: RNA
<213> ORGANISM: artificial
<220> FEATURE:
<223> OTHER INFORMATION: RNA Oligomer

<400> SEQUENCE: 770
auccucaaaa gcauuaaga                                                19

<210> SEQ ID NO 771
<211> LENGTH: 19
<212> TYPE: RNA
<213> ORGANISM: artificial
<220> FEATURE:
<223> OTHER INFORMATION: RNA Oligomer

<400> SEQUENCE: 771
cauuaagaaa auggacu                                                  19

<210> SEQ ID NO 772
<211> LENGTH: 19
<212> TYPE: RNA
<213> ORGANISM: artificial
<220> FEATURE:
<223> OTHER INFORMATION: RNA Oligomer

<400> SEQUENCE: 772
```

```
uaauugucaa cuucuguca                                              19

<210> SEQ ID NO 773
<211> LENGTH: 19
<212> TYPE: RNA
<213> ORGANISM: artificial
<220> FEATURE:
<223> OTHER INFORMATION: RNA Oligomer

<400> SEQUENCE: 773
ucaacuucug ucaguuugg                                              19

<210> SEQ ID NO 774
<211> LENGTH: 19
<212> TYPE: RNA
<213> ORGANISM: artificial
<220> FEATURE:
<223> OTHER INFORMATION: RNA Oligomer

<400> SEQUENCE: 774
gaaccauggu agucucaac                                              19

<210> SEQ ID NO 775
<211> LENGTH: 19
<212> TYPE: RNA
<213> ORGANISM: artificial
<220> FEATURE:
<223> OTHER INFORMATION: RNA Oligomer

<400> SEQUENCE: 775
guagucucaa ccagcuugu                                              19

<210> SEQ ID NO 776
<211> LENGTH: 19
<212> TYPE: RNA
<213> ORGANISM: artificial
<220> FEATURE:
<223> OTHER INFORMATION: RNA Oligomer

<400> SEQUENCE: 776
uaucuugccu ccaaaguau                                              19

<210> SEQ ID NO 777
<211> LENGTH: 19
<212> TYPE: RNA
<213> ORGANISM: artificial
<220> FEATURE:
<223> OTHER INFORMATION: RNA Oligomer

<400> SEQUENCE: 777
cuugccucca aaguauguc                                              19

<210> SEQ ID NO 778
<211> LENGTH: 19
<212> TYPE: RNA
<213> ORGANISM: artificial
<220> FEATURE:
<223> OTHER INFORMATION: RNA Oligomer

<400> SEQUENCE: 778
aacagaaguu ucaggugac                                              19

<210> SEQ ID NO 779
<211> LENGTH: 19
<212> TYPE: RNA
<213> ORGANISM: artificial
```

```
<220> FEATURE:
<223> OTHER INFORMATION: RNA Oligomer

<400> SEQUENCE: 779
augaagacug ggcucucga                                              19

<210> SEQ ID NO 780
<211> LENGTH: 19
<212> TYPE: RNA
<213> ORGANISM: artificial
<220> FEATURE:
<223> OTHER INFORMATION: RNA Oligomer

<400> SEQUENCE: 780
caugcaguca ucaaaguac                                              19

<210> SEQ ID NO 781
<211> LENGTH: 19
<212> TYPE: RNA
<213> ORGANISM: artificial
<220> FEATURE:
<223> OTHER INFORMATION: RNA Oligomer

<400> SEQUENCE: 781
augcagucau caaaguaca                                              19

<210> SEQ ID NO 782
<211> LENGTH: 19
<212> TYPE: RNA
<213> ORGANISM: artificial
<220> FEATURE:
<223> OTHER INFORMATION: RNA Oligomer

<400> SEQUENCE: 782
gucaaucaaa uccaugucc                                              19

<210> SEQ ID NO 783
<211> LENGTH: 19
<212> TYPE: RNA
<213> ORGANISM: artificial
<220> FEATURE:
<223> OTHER INFORMATION: RNA Oligomer

<400> SEQUENCE: 783
caucaaagua caaagcauc                                              19

<210> SEQ ID NO 784
<211> LENGTH: 19
<212> TYPE: RNA
<213> ORGANISM: artificial
<220> FEATURE:
<223> OTHER INFORMATION: RNA Oligomer

<400> SEQUENCE: 784
aaaguacaaa gcaucugau                                              19

<210> SEQ ID NO 785
<211> LENGTH: 19
<212> TYPE: RNA
<213> ORGANISM: artificial
<220> FEATURE:
<223> OTHER INFORMATION: RNA Oligomer

<400> SEQUENCE: 785
aaagcaucug auuugggaa                                              19
```

```
<210> SEQ ID NO 786
<211> LENGTH: 19
<212> TYPE: RNA
<213> ORGANISM: artificial
<220> FEATURE:
<223> OTHER INFORMATION: RNA Oligomer

<400> SEQUENCE: 786
agcaucugau uugggaaug                                               19

<210> SEQ ID NO 787
<211> LENGTH: 19
<212> TYPE: RNA
<213> ORGANISM: artificial
<220> FEATURE:
<223> OTHER INFORMATION: RNA Oligomer

<400> SEQUENCE: 787
aucugauuug ggaugugg                                                19

<210> SEQ ID NO 788
<211> LENGTH: 19
<212> TYPE: RNA
<213> ORGANISM: artificial
<220> FEATURE:
<223> OTHER INFORMATION: RNA Oligomer

<400> SEQUENCE: 788
ucuucaucua guuguaacu                                               19

<210> SEQ ID NO 789
<211> LENGTH: 19
<212> TYPE: RNA
<213> ORGANISM: artificial
<220> FEATURE:
<223> OTHER INFORMATION: RNA Oligomer

<400> SEQUENCE: 789
augccauuuu uuguccaua                                               19

<210> SEQ ID NO 790
<211> LENGTH: 19
<212> TYPE: RNA
<213> ORGANISM: artificial
<220> FEATURE:
<223> OTHER INFORMATION: RNA Oligomer

<400> SEQUENCE: 790 cauuuuugu ccauacagu                                                19

<210> SEQ ID NO 791
<211> LENGTH: 19
<212> TYPE: RNA
<213> ORGANISM: artificial
<220> FEATURE:
<223> OTHER INFORMATION: RNA Oligomer

<400> SEQUENCE: 791
uuuuuagcca gaugucaua                                               19

<210> SEQ ID NO 792
<211> LENGTH: 19
<212> TYPE: RNA
<213> ORGANISM: artificial
<220> FEATURE:
<223> OTHER INFORMATION: RNA Oligomer

<400> SEQUENCE: 792
```
caaaugacau aagaacagu                                            19

<210> SEQ ID NO 793
<211> LENGTH: 19
<212> TYPE: RNA
<213> ORGANISM: artificial
<220> FEATURE:
<223> OTHER INFORMATION: RNA Oligomer

<400> SEQUENCE: 793
uacacuuaca cagaaacua                                            19

<210> SEQ ID NO 794
<211> LENGTH: 19
<212> TYPE: RNA
<213> ORGANISM: artificial
<220> FEATURE:
<223> OTHER INFORMATION: RNA Oligomer

<400> SEQUENCE: 794
acuuacacag aaacuagcc                                            19

<210> SEQ ID NO 795
<211> LENGTH: 19
<212> TYPE: RNA
<213> ORGANISM: artificial
<220> FEATURE:
<223> OTHER INFORMATION: RNA Oligomer

<400> SEQUENCE: 795
augguguccu aagaaauug                                            19

<210> SEQ ID NO 796
<211> LENGTH: 19
<212> TYPE: RNA
<213> ORGANISM: artificial
<220> FEATURE:
<223> OTHER INFORMATION: RNA Oligomer

<400> SEQUENCE: 796
aacuacugau ucaacauac                                            19

<210> SEQ ID NO 797
<211> LENGTH: 19
<212> TYPE: RNA
<213> ORGANISM: artificial
<220> FEATURE:
<223> OTHER INFORMATION: RNA Oligomer

<400> SEQUENCE: 797
uacugauuca acauacuga                                            19

<210> SEQ ID NO 798
<211> LENGTH: 19
<212> TYPE: RNA
<213> ORGANISM: artificial
<220> FEATURE:
<223> OTHER INFORMATION: RNA Oligomer

<400> SEQUENCE: 798
guaugagcau uucacauca                                            19

<210> SEQ ID NO 799
<211> LENGTH: 19
<212> TYPE: RNA
<213> ORGANISM: artificial

```
<220> FEATURE:
<223> OTHER INFORMATION: RNA Oligomer

<400> SEQUENCE: 799
acaucacagu aggagcuuu                                                19

<210> SEQ ID NO 800
<211> LENGTH: 19
<212> TYPE: RNA
<213> ORGANISM: artificial
<220> FEATURE:
<223> OTHER INFORMATION: RNA Oligomer

<400> SEQUENCE: 800
acaguaggag cuuuuagua                                                19

<210> SEQ ID NO 801
<211> LENGTH: 19
<212> TYPE: RNA
<213> ORGANISM: artificial
<220> FEATURE:
<223> OTHER INFORMATION: RNA Oligomer

<400> SEQUENCE: 801
cucagaaaag gucaaaucc                                                19

<210> SEQ ID NO 802
<211> LENGTH: 19
<212> TYPE: RNA
<213> ORGANISM: artificial
<220> FEATURE:
<223> OTHER INFORMATION: RNA Oligomer

<400> SEQUENCE: 802
ggaaaacauu gccaucucu                                                19

<210> SEQ ID NO 803
<211> LENGTH: 19
<212> TYPE: RNA
<213> ORGANISM: artificial
<220> FEATURE:
<223> OTHER INFORMATION: RNA Oligomer

<400> SEQUENCE: 803
acauugccau cucuuguuu                                                19

<210> SEQ ID NO 804
<211> LENGTH: 19
<212> TYPE: RNA
<213> ORGANISM: artificial
<220> FEATURE:
<223> OTHER INFORMATION: RNA Oligomer

<400> SEQUENCE: 804
ugccaucucu uguuugcug                                                19

<210> SEQ ID NO 805
<211> LENGTH: 19
<212> TYPE: RNA
<213> ORGANISM: artificial
<220> FEATURE:
<223> OTHER INFORMATION: RNA Oligomer

<400> SEQUENCE: 805
ugcagggagu auucacuag                                                19
```

```
<210> SEQ ID NO 806
<211> LENGTH: 19
<212> TYPE: RNA
<213> ORGANISM: artificial
<220> FEATURE:
<223> OTHER INFORMATION: RNA Oligomer

<400> SEQUENCE: 806
gaauaagguu uuccaucuu                                            19

<210> SEQ ID NO 807
<211> LENGTH: 19
<212> TYPE: RNA
<213> ORGANISM: artificial
<220> FEATURE:
<223> OTHER INFORMATION: RNA Oligomer

<400> SEQUENCE: 807
uucaucacgu agcaugcug                                            19

<210> SEQ ID NO 808
<211> LENGTH: 19
<212> TYPE: RNA
<213> ORGANISM: artificial
<220> FEATURE:
<223> OTHER INFORMATION: RNA Oligomer

<400> SEQUENCE: 808
aacuucgaga uauaaggug                                            19

<210> SEQ ID NO 809
<211> LENGTH: 19
<212> TYPE: RNA
<213> ORGANISM: artificial
<220> FEATURE:
<223> OTHER INFORMATION: RNA Oligomer

<400> SEQUENCE: 809
ucgagauaua aggugcuga                                            19

<210> SEQ ID NO 810
<211> LENGTH: 19
<212> TYPE: RNA
<213> ORGANISM: artificial
<220> FEATURE:
<223> OTHER INFORMATION: RNA Oligomer

<400> SEQUENCE: 810
ugcucuaguu cuacuauau                                            19

<210> SEQ ID NO 811
<211> LENGTH: 19
<212> TYPE: RNA
<213> ORGANISM: artificial
<220> FEATURE:
<223> OTHER INFORMATION: RNA Oligomer

<400> SEQUENCE: 811
caguuuucuu uuucugcaa                                            19

<210> SEQ ID NO 812
<211> LENGTH: 19
<212> TYPE: RNA
<213> ORGANISM: artificial
<220> FEATURE:
<223> OTHER INFORMATION: RNA Oligomer

<400> SEQUENCE: 812
```
ucuuuggaca ucauuucgu                                                19

<210> SEQ ID NO 813
<211> LENGTH: 19
<212> TYPE: RNA
<213> ORGANISM: artificial
<220> FEATURE:
<223> OTHER INFORMATION: RNA Oligomer

<400> SEQUENCE: 813
aagucaacaa cagggaggu                                                19

<210> SEQ ID NO 814
<211> LENGTH: 19
<212> TYPE: RNA
<213> ORGANISM: artificial
<220> FEATURE:
<223> OTHER INFORMATION: RNA Oligomer

<400> SEQUENCE: 814
aaugauuuuu ucuacaggg                                                19

<210> SEQ ID NO 815
<211> LENGTH: 19
<212> TYPE: RNA
<213> ORGANISM: artificial
<220> FEATURE:
<223> OTHER INFORMATION: RNA Oligomer

<400> SEQUENCE: 815
uuugcccuaa guucaucuc                                                19

<210> SEQ ID NO 816
<211> LENGTH: 19
<212> TYPE: RNA
<213> ORGANISM: artificial
<220> FEATURE:
<223> OTHER INFORMATION: RNA Oligomer

<400> SEQUENCE: 816
ccuaaguuca ucucuugug                                                19

<210> SEQ ID NO 817
<211> LENGTH: 19
<212> TYPE: RNA
<213> ORGANISM: artificial
<220> FEATURE:
<223> OTHER INFORMATION: RNA Oligomer

<400> SEQUENCE: 817
gucuuuugug aauggggguu                                               19

<210> SEQ ID NO 818
<211> LENGTH: 19
<212> TYPE: RNA
<213> ORGANISM: artificial
<220> FEATURE:
<223> OTHER INFORMATION: RNA Oligomer

<400> SEQUENCE: 818
ucuuucucug guguguucu                                                19

<210> SEQ ID NO 819
<211> LENGTH: 19
<212> TYPE: RNA
<213> ORGANISM: artificial

```
<220> FEATURE:
<223> OTHER INFORMATION: RNA Oligomer

<400> SEQUENCE: 819
uaggaccauu cguuugac                                                    19

<210> SEQ ID NO 820
<211> LENGTH: 19
<212> TYPE: RNA
<213> ORGANISM: artificial
<220> FEATURE:
<223> OTHER INFORMATION: RNA Oligomer

<400> SEQUENCE: 820
cauucuguuu gacacuucc                                                   19

<210> SEQ ID NO 821
<211> LENGTH: 19
<212> TYPE: RNA
<213> ORGANISM: artificial
<220> FEATURE:
<223> OTHER INFORMATION: RNA Oligomer

<400> SEQUENCE: 821
auucuguuug acacuucca                                                   19

<210> SEQ ID NO 822
<211> LENGTH: 19
<212> TYPE: RNA
<213> ORGANISM: artificial
<220> FEATURE:
<223> OTHER INFORMATION: RNA Oligomer

<400> SEQUENCE: 822
cuguuugaca cuuccaggg                                                   19

<210> SEQ ID NO 823
<211> LENGTH: 19
<212> TYPE: RNA
<213> ORGANISM: artificial
<220> FEATURE:
<223> OTHER INFORMATION: RNA Oligomer

<400> SEQUENCE: 823
cacuaucuag cucuuccac                                                   19

<210> SEQ ID NO 824
<211> LENGTH: 19
<212> TYPE: RNA
<213> ORGANISM: artificial
<220> FEATURE:
<223> OTHER INFORMATION: RNA Oligomer

<400> SEQUENCE: 824
uuccacugag uguucggu                                                    19

<210> SEQ ID NO 825
<211> LENGTH: 19
<212> TYPE: RNA
<213> ORGANISM: artificial
<220> FEATURE:
<223> OTHER INFORMATION: RNA Oligomer

<400> SEQUENCE: 825
cauacucuuu ccgucgcug                                                   19
```

```
<210> SEQ ID NO 826
<211> LENGTH: 19
<212> TYPE: RNA
<213> ORGANISM: artificial
<220> FEATURE:
<223> OTHER INFORMATION: RNA Oligomer

<400> SEQUENCE: 826
uuugcaaagu gauagauca                                                 19

<210> SEQ ID NO 827
<211> LENGTH: 19
<212> TYPE: RNA
<213> ORGANISM: artificial
<220> FEATURE:
<223> OTHER INFORMATION: RNA Oligomer

<400> SEQUENCE: 827
aucagaaaca ucaaugggc                                                 19

<210> SEQ ID NO 828
<211> LENGTH: 19
<212> TYPE: RNA
<213> ORGANISM: artificial
<220> FEATURE:
<223> OTHER INFORMATION: RNA Oligomer

<400> SEQUENCE: 828
accaaaaucu guguugacu                                                 19

<210> SEQ ID NO 829
<211> LENGTH: 19
<212> TYPE: RNA
<213> ORGANISM: artificial
<220> FEATURE:
<223> OTHER INFORMATION: RNA Oligomer

<400> SEQUENCE: 829
aaugaguuca cugucaacu                                                 19

<210> SEQ ID NO 830
<211> LENGTH: 19
<212> TYPE: RNA
<213> ORGANISM: artificial
<220> FEATURE:
<223> OTHER INFORMATION: RNA Oligomer

<400> SEQUENCE: 830 agaaaugug gacuacagu                                                  19

<210> SEQ ID NO 831
<211> LENGTH: 19
<212> TYPE: RNA
<213> ORGANISM: artificial
<220> FEATURE:
<223> OTHER INFORMATION: RNA Oligomer

<400> SEQUENCE: 831
ccuacuucuu uuuccauug                                                 19

<210> SEQ ID NO 832
<211> LENGTH: 19
<212> TYPE: RNA
<213> ORGANISM: artificial
<220> FEATURE:
<223> OTHER INFORMATION: RNA Oligomer

<400> SEQUENCE: 832
```

```
gucaacuucu gucaguuug                                             19
```

<210> SEQ ID NO 833
<211> LENGTH: 19
<212> TYPE: RNA
<213> ORGANISM: artificial
<220> FEATURE:
<223> OTHER INFORMATION: RNA Oligomer

<400> SEQUENCE: 833

```
cuuggaacca ugguagucu                                             19
```

<210> SEQ ID NO 834
<211> LENGTH: 19
<212> TYPE: RNA
<213> ORGANISM: artificial
<220> FEATURE:
<223> OTHER INFORMATION: RNA Oligomer

<400> SEQUENCE: 834

```
aacuugcuca auguccugu                                             19
```

<210> SEQ ID NO 835
<211> LENGTH: 19
<212> TYPE: RNA
<213> ORGANISM: artificial
<220> FEATURE:
<223> OTHER INFORMATION: RNA Oligomer

<400> SEQUENCE: 835

```
uugccuccaa aguauguca                                             19
```

<210> SEQ ID NO 836
<211> LENGTH: 19
<212> TYPE: RNA
<213> ORGANISM: artificial
<220> FEATURE:
<223> OTHER INFORMATION: RNA Oligomer

<400> SEQUENCE: 836

```
gaacaaguga cugaaacgu                                             19
```

<210> SEQ ID NO 837
<211> LENGTH: 19
<212> TYPE: RNA
<213> ORGANISM: artificial
<220> FEATURE:
<223> OTHER INFORMATION: RNA Oligomer

<400> SEQUENCE: 837

```
acaagugacu gaaacguag                                             19
```

<210> SEQ ID NO 838
<211> LENGTH: 19
<212> TYPE: RNA
<213> ORGANISM: artificial
<220> FEATURE:
<223> OTHER INFORMATION: RNA Oligomer

<400> SEQUENCE: 838

```
aagugacuga aacguagcc                                             19
```

<210> SEQ ID NO 839
<211> LENGTH: 19
<212> TYPE: RNA
<213> ORGANISM: artificial

```
<220> FEATURE:
<223> OTHER INFORMATION: RNA Oligomer

<400> SEQUENCE: 839
aaguauguca aucaaaucc                                                    19

<210> SEQ ID NO 840
<211> LENGTH: 19
<212> TYPE: RNA
<213> ORGANISM: artificial
<220> FEATURE:
<223> OTHER INFORMATION: RNA Oligomer

<400> SEQUENCE: 840
acugaaacgu agccgaaga                                                    19

<210> SEQ ID NO 841
<211> LENGTH: 19
<212> TYPE: RNA
<213> ORGANISM: artificial
<220> FEATURE:
<223> OTHER INFORMATION: RNA Oligomer

<400> SEQUENCE: 841
auccacuggu uucugacug                                                    19

<210> SEQ ID NO 842
<211> LENGTH: 19
<212> TYPE: RNA
<213> ORGANISM: artificial
<220> FEATURE:
<223> OTHER INFORMATION: RNA Oligomer

<400> SEQUENCE: 842
aaauucaccu gucucuuca                                                    19

<210> SEQ ID NO 843
<211> LENGTH: 19
<212> TYPE: RNA
<213> ORGANISM: artificial
<220> FEATURE:
<223> OTHER INFORMATION: RNA Oligomer

<400> SEQUENCE: 843
ucaccugucu cuucaucua                                                    19

<210> SEQ ID NO 844
<211> LENGTH: 19
<212> TYPE: RNA
<213> ORGANISM: artificial
<220> FEATURE:
<223> OTHER INFORMATION: RNA Oligomer

<400> SEQUENCE: 844
uuauuaguac cagcucuua                                                    19

<210> SEQ ID NO 845
<211> LENGTH: 19
<212> TYPE: RNA
<213> ORGANISM: artificial
<220> FEATURE:
<223> OTHER INFORMATION: RNA Oligomer

<400> SEQUENCE: 845 ccauuuuug uccauacag                                                     19
```

```
<210> SEQ ID NO 846
<211> LENGTH: 19
<212> TYPE: RNA
<213> ORGANISM: artificial
<220> FEATURE:
<223> OTHER INFORMATION: RNA Oligomer

<400> SEQUENCE: 846
ucaacauacu gacacucca                                              19

<210> SEQ ID NO 847
<211> LENGTH: 19
<212> TYPE: RNA
<213> ORGANISM: artificial
<220> FEATURE:
<223> OTHER INFORMATION: RNA Oligomer

<400> SEQUENCE: 847
aaaguaugag cauuucaca                                              19

<210> SEQ ID NO 848
<211> LENGTH: 19
<212> TYPE: RNA
<213> ORGANISM: artificial
<220> FEATURE:
<223> OTHER INFORMATION: RNA Oligomer

<400> SEQUENCE: 848
uaugagcauu ucacaucac                                              19

<210> SEQ ID NO 849
<211> LENGTH: 19
<212> TYPE: RNA
<213> ORGANISM: artificial
<220> FEATURE:
<223> OTHER INFORMATION: RNA Oligomer

<400> SEQUENCE: 849
ucacaucaca guaggagcu                                              19

<210> SEQ ID NO 850
<211> LENGTH: 19
<212> TYPE: RNA
<213> ORGANISM: artificial
<220> FEATURE:
<223> OTHER INFORMATION: RNA Oligomer

<400> SEQUENCE: 850
cagggaguau ucacuagga                                              19

<210> SEQ ID NO 851
<211> LENGTH: 19
<212> TYPE: RNA
<213> ORGANISM: artificial
<220> FEATURE:
<223> OTHER INFORMATION: RNA Oligomer

<400> SEQUENCE: 851
ggaguauuca cuaggagaa                                              19

<210> SEQ ID NO 852
<211> LENGTH: 19
<212> TYPE: RNA
<213> ORGANISM: artificial
<220> FEATURE:
<223> OTHER INFORMATION: RNA Oligomer

<400> SEQUENCE: 852
```

-continued aucuucauca cguagcaug                                             19

<210> SEQ ID NO 853
<211> LENGTH: 19
<212> TYPE: RNA
<213> ORGANISM: artificial
<220> FEATURE:
<223> OTHER INFORMATION: RNA Oligomer

<400> SEQUENCE: 853
ucuucaucac guagcaugc                                             19

<210> SEQ ID NO 854
<211> LENGTH: 19
<212> TYPE: RNA
<213> ORGANISM: artificial
<220> FEATURE:
<223> OTHER INFORMATION: RNA Oligomer

<400> SEQUENCE: 854
cuucgagaua uaaggugcu                                             19

<210> SEQ ID NO 855
<211> LENGTH: 19
<212> TYPE: RNA
<213> ORGANISM: artificial
<220> FEATURE:
<223> OTHER INFORMATION: RNA Oligomer

<400> SEQUENCE: 855
gucauuuucu ccuuuuucu                                             19

<210> SEQ ID NO 856
<211> LENGTH: 19
<212> TYPE: RNA
<213> ORGANISM: artificial
<220> FEATURE:
<223> OTHER INFORMATION: RNA Oligomer

<400> SEQUENCE: 856
ccaguuuucu uuuucugca                                             19

<210> SEQ ID NO 857
<211> LENGTH: 19
<212> TYPE: RNA
<213> ORGANISM: artificial
<220> FEATURE:
<223> OTHER INFORMATION: RNA Oligomer

<400> SEQUENCE: 857
acaacaggga gguuaauga                                             19

<210> SEQ ID NO 858
<211> LENGTH: 19
<212> TYPE: RNA
<213> ORGANISM: artificial
<220> FEATURE:
<223> OTHER INFORMATION: RNA Oligomer

<400> SEQUENCE: 858
accauucugu uugacacuu                                             19

<210> SEQ ID NO 859
<211> LENGTH: 19
<212> TYPE: RNA
<213> ORGANISM: artificial

<220> FEATURE:
<223> OTHER INFORMATION: RNA Oligomer

<400> SEQUENCE: 859
uuccagcuca uacucuuuc                                                19

<210> SEQ ID NO 860
<211> LENGTH: 19
<212> TYPE: RNA
<213> ORGANISM: artificial
<220> FEATURE:
<223> OTHER INFORMATION: RNA Oligomer

<400> SEQUENCE: 860
uugaauucug cugugcuuu                                                19

<210> SEQ ID NO 861
<211> LENGTH: 19
<212> TYPE: RNA
<213> ORGANISM: artificial
<220> FEATURE:
<223> OTHER INFORMATION: RNA Oligomer

<400> SEQUENCE: 861
agugauagau cagaaacau                                                19

<210> SEQ ID NO 862
<211> LENGTH: 19
<212> TYPE: RNA
<213> ORGANISM: artificial
<220> FEATURE:
<223> OTHER INFORMATION: RNA Oligomer

<400> SEQUENCE: 862
agaaacauca augggccca                                                19

<210> SEQ ID NO 863
<211> LENGTH: 19
<212> TYPE: RNA
<213> ORGANISM: artificial
<220> FEATURE:
<223> OTHER INFORMATION: RNA Oligomer

<400> SEQUENCE: 863
ccaaaaucug uguugacug                                                19

<210> SEQ ID NO 864
<211> LENGTH: 19
<212> TYPE: RNA
<213> ORGANISM: artificial
<220> FEATURE:
<223> OTHER INFORMATION: RNA Oligomer

<400> SEQUENCE: 864
caaaaucugu guugacugu                                                19

<210> SEQ ID NO 865
<211> LENGTH: 19
<212> TYPE: RNA
<213> ORGANISM: artificial
<220> FEATURE:
<223> OTHER INFORMATION: RNA Oligomer

<400> SEQUENCE: 865
aaaaucugug uugacugug                                                19

```
<210> SEQ ID NO 866
<211> LENGTH: 19
<212> TYPE: RNA
<213> ORGANISM: artificial
<220> FEATURE:
<223> OTHER INFORMATION: RNA Oligomer

<400> SEQUENCE: 866
acugguuggg gcuucugu                                              19

<210> SEQ ID NO 867
<211> LENGTH: 19
<212> TYPE: RNA
<213> ORGANISM: artificial
<220> FEATURE:
<223> OTHER INFORMATION: RNA Oligomer

<400> SEQUENCE: 867
augcugcuga aggaauccu                                             19

<210> SEQ ID NO 868
<211> LENGTH: 19
<212> TYPE: RNA
<213> ORGANISM: artificial
<220> FEATURE:
<223> OTHER INFORMATION: RNA Oligomer

<400> SEQUENCE: 868
accuacuucu uuuccauu                                              19

<210> SEQ ID NO 869
<211> LENGTH: 19
<212> TYPE: RNA
<213> ORGANISM: artificial
<220> FEATURE:
<223> OTHER INFORMATION: RNA Oligomer

<400> SEQUENCE: 869
gucucaacca gcuugucau                                             19

<210> SEQ ID NO 870
<211> LENGTH: 19
<212> TYPE: RNA
<213> ORGANISM: artificial
<220> FEATURE:
<223> OTHER INFORMATION: RNA Oligomer

<400> SEQUENCE: 870
uccucccaaa cuugcucaa                                             19

<210> SEQ ID NO 871
<211> LENGTH: 19
<212> TYPE: RNA
<213> ORGANISM: artificial
<220> FEATURE:
<223> OTHER INFORMATION: RNA Oligomer

<400> SEQUENCE: 871
ugagcaacag aaguuucag                                             19

<210> SEQ ID NO 872
<211> LENGTH: 19
<212> TYPE: RNA
<213> ORGANISM: artificial
<220> FEATURE:
<223> OTHER INFORMATION: RNA Oligomer

<400> SEQUENCE: 872
```
caacagaagu uucagguga                                              19

<210> SEQ ID NO 873
<211> LENGTH: 19
<212> TYPE: RNA
<213> ORGANISM: artificial
<220> FEATURE:
<223> OTHER INFORMATION: RNA Oligomer

<400> SEQUENCE: 873
ugccuccaaa guaugucaa                                              19

<210> SEQ ID NO 874
<211> LENGTH: 19
<212> TYPE: RNA
<213> ORGANISM: artificial
<220> FEATURE:
<223> OTHER INFORMATION: RNA Oligomer

<400> SEQUENCE: 874
cuccaaagua ugucaauca                                              19

<210> SEQ ID NO 875
<211> LENGTH: 19
<212> TYPE: RNA
<213> ORGANISM: artificial
<220> FEATURE:
<223> OTHER INFORMATION: RNA Oligomer

<400> SEQUENCE: 875
aacguagccg aagaaaccu                                              19

<210> SEQ ID NO 876
<211> LENGTH: 19
<212> TYPE: RNA
<213> ORGANISM: artificial
<220> FEATURE:
<223> OTHER INFORMATION: RNA Oligomer

<400> SEQUENCE: 876
guaugucaau caaauccau                                              19

<210> SEQ ID NO 877
<211> LENGTH: 19
<212> TYPE: RNA
<213> ORGANISM: artificial
<220> FEATURE:
<223> OTHER INFORMATION: RNA Oligomer

<400> SEQUENCE: 877
augucaauca aauccaugu                                              19

<210> SEQ ID NO 878
<211> LENGTH: 19
<212> TYPE: RNA
<213> ORGANISM: artificial
<220> FEATURE:
<223> OTHER INFORMATION: RNA Oligomer

<400> SEQUENCE: 878
gcuggcugaa uugggagaa                                              19

<210> SEQ ID NO 879
<211> LENGTH: 19
<212> TYPE: RNA
<213> ORGANISM: artificial

```
<220> FEATURE:
<223> OTHER INFORMATION: RNA Oligomer

<400> SEQUENCE: 879
agaaauucac cugucucuu                                                19

<210> SEQ ID NO 880
<211> LENGTH: 19
<212> TYPE: RNA
<213> ORGANISM: artificial
<220> FEATURE:
<223> OTHER INFORMATION: RNA Oligomer

<400> SEQUENCE: 880
auucaccugu cucuucauc                                                19

<210> SEQ ID NO 881
<211> LENGTH: 19
<212> TYPE: RNA
<213> ORGANISM: artificial
<220> FEATURE:
<223> OTHER INFORMATION: RNA Oligomer

<400> SEQUENCE: 881
ccugucucuu caucuaguu                                                19

<210> SEQ ID NO 882
<211> LENGTH: 19
<212> TYPE: RNA
<213> ORGANISM: artificial
<220> FEATURE:
<223> OTHER INFORMATION: RNA Oligomer

<400> SEQUENCE: 882
auagugguua guuuugcaa                                                19

<210> SEQ ID NO 883
<211> LENGTH: 19
<212> TYPE: RNA
<213> ORGANISM: artificial
<220> FEATURE:
<223> OTHER INFORMATION: RNA Oligomer

<400> SEQUENCE: 883
ucuuuuuagc cagauguca                                                19

<210> SEQ ID NO 884
<211> LENGTH: 19
<212> TYPE: RNA
<213> ORGANISM: artificial
<220> FEATURE:
<223> OTHER INFORMATION: RNA Oligomer

<400> SEQUENCE: 884
auucaacaua cugacacuc                                                19

<210> SEQ ID NO 885
<211> LENGTH: 19
<212> TYPE: RNA
<213> ORGANISM: artificial
<220> FEATURE:
<223> OTHER INFORMATION: RNA Oligomer

<400> SEQUENCE: 885
uacugacacu ccaaugcuu                                                19
```

```
<210> SEQ ID NO 886
<211> LENGTH: 19
<212> TYPE: RNA
<213> ORGANISM: artificial
<220> FEATURE:
<223> OTHER INFORMATION: RNA Oligomer

<400> SEQUENCE: 886
uucacaucac aguaggagc                                              19

<210> SEQ ID NO 887
<211> LENGTH: 19
<212> TYPE: RNA
<213> ORGANISM: artificial
<220> FEATURE:
<223> OTHER INFORMATION: RNA Oligomer

<400> SEQUENCE: 887
aacuagcuca gaaaagguc                                              19

<210> SEQ ID NO 888
<211> LENGTH: 19
<212> TYPE: RNA
<213> ORGANISM: artificial
<220> FEATURE:
<223> OTHER INFORMATION: RNA Oligomer

<400> SEQUENCE: 888
acuagcucag aaaagguca                                              19

<210> SEQ ID NO 889
<211> LENGTH: 19
<212> TYPE: RNA
<213> ORGANISM: artificial
<220> FEATURE:
<223> OTHER INFORMATION: RNA Oligomer

<400> SEQUENCE: 889
agcuccaagu ccaucauga                                              19

<210> SEQ ID NO 890
<211> LENGTH: 19
<212> TYPE: RNA
<213> ORGANISM: artificial
<220> FEATURE:
<223> OTHER INFORMATION: RNA Oligomer

<400> SEQUENCE: 890
aaaacuucga gauauaagg                                              19

<210> SEQ ID NO 891
<211> LENGTH: 19
<212> TYPE: RNA
<213> ORGANISM: artificial
<220> FEATURE:
<223> OTHER INFORMATION: RNA Oligomer

<400> SEQUENCE: 891
cgagauauaa ggugcugag                                              19

<210> SEQ ID NO 892
<211> LENGTH: 19
<212> TYPE: RNA
<213> ORGANISM: artificial
<220> FEATURE:
<223> OTHER INFORMATION: RNA Oligomer

<400> SEQUENCE: 892
```
uuuuggaguu guucuuguc						19

<210> SEQ ID NO 893
<211> LENGTH: 19
<212> TYPE: RNA
<213> ORGANISM: artificial
<220> FEATURE:
<223> OTHER INFORMATION: RNA Oligomer

<400> SEQUENCE: 893
ccuccuacgu auaucccga						19

<210> SEQ ID NO 894
<211> LENGTH: 19
<212> TYPE: RNA
<213> ORGANISM: artificial
<220> FEATURE:
<223> OTHER INFORMATION: RNA Oligomer

<400> SEQUENCE: 894
cuacguauau cccgaauua						19

<210> SEQ ID NO 895
<211> LENGTH: 19
<212> TYPE: RNA
<213> ORGANISM: artificial
<220> FEATURE:
<223> OTHER INFORMATION: RNA Oligomer

<400> SEQUENCE: 895
gcucuuugga caucauuuc						19

<210> SEQ ID NO 896
<211> LENGTH: 19
<212> TYPE: RNA
<213> ORGANISM: artificial
<220> FEATURE:
<223> OTHER INFORMATION: RNA Oligomer

<400> SEQUENCE: 896
cuuuggacau cauuucguu						19

<210> SEQ ID NO 897
<211> LENGTH: 19
<212> TYPE: RNA
<213> ORGANISM: artificial
<220> FEATURE:
<223> OTHER INFORMATION: RNA Oligomer

<400> SEQUENCE: 897
ggagguuaau gauuuuuc						19

<210> SEQ ID NO 898
<211> LENGTH: 19
<212> TYPE: RNA
<213> ORGANISM: artificial
<220> FEATURE:
<223> OTHER INFORMATION: RNA Oligomer

<400> SEQUENCE: 898
gaaugggaua uggagagcu						19

<210> SEQ ID NO 899
<211> LENGTH: 19
<212> TYPE: RNA
<213> ORGANISM: artificial

```
<220> FEATURE:
<223> OTHER INFORMATION: RNA Oligomer

<400> SEQUENCE: 899
ggauauggag agcuuuugc                                                19

<210> SEQ ID NO 900
<211> LENGTH: 19
<212> TYPE: RNA
<213> ORGANISM: artificial
<220> FEATURE:
<223> OTHER INFORMATION: RNA Oligomer

<400> SEQUENCE: 900
ugcccuaagu ucaucucuu                                                19

<210> SEQ ID NO 901
<211> LENGTH: 19
<212> TYPE: RNA
<213> ORGANISM: artificial
<220> FEATURE:
<223> OTHER INFORMATION: RNA Oligomer

<400> SEQUENCE: 901
guuuuuucug uuuuuccag                                                19

<210> SEQ ID NO 902
<211> LENGTH: 19
<212> TYPE: RNA
<213> ORGANISM: artificial
<220> FEATURE:
<223> OTHER INFORMATION: RNA Oligomer

<400> SEQUENCE: 902
uuuucuguuu uuccagcuc                                                19

<210> SEQ ID NO 903
<211> LENGTH: 19
<212> TYPE: RNA
<213> ORGANISM: artificial
<220> FEATURE:
<223> OTHER INFORMATION: RNA Oligomer

<400> SEQUENCE: 903
uguuugacac uuccagggg                                                19

<210> SEQ ID NO 904
<211> LENGTH: 19
<212> TYPE: RNA
<213> ORGANISM: artificial
<220> FEATURE:
<223> OTHER INFORMATION: RNA Oligomer

<400> SEQUENCE: 904
agcucuucca cuucagaau                                                19

<210> SEQ ID NO 905
<211> LENGTH: 19
<212> TYPE: RNA
<213> ORGANISM: artificial
<220> FEATURE:
<223> OTHER INFORMATION: RNA Oligomer

<400> SEQUENCE: 905
acugaguguu cuggugaug                                                19
```

```
<210> SEQ ID NO 906
<211> LENGTH: 19
<212> TYPE: RNA
<213> ORGANISM: artificial
<220> FEATURE:
<223> OTHER INFORMATION: RNA Oligomer

<400> SEQUENCE: 906
uugcaaagug auagaucag                                               19

<210> SEQ ID NO 907
<211> LENGTH: 19
<212> TYPE: RNA
<213> ORGANISM: artificial
<220> FEATURE:
<223> OTHER INFORMATION: RNA Oligomer

<400> SEQUENCE: 907
ugcaaaguga uagaucaga                                               19

<210> SEQ ID NO 908
<211> LENGTH: 19
<212> TYPE: RNA
<213> ORGANISM: artificial
<220> FEATURE:
<223> OTHER INFORMATION: RNA Oligomer

<400> SEQUENCE: 908
gcaaagugau agaucagaa                                               19

<210> SEQ ID NO 909
<211> LENGTH: 19
<212> TYPE: RNA
<213> ORGANISM: artificial
<220> FEATURE:
<223> OTHER INFORMATION: RNA Oligomer

<400> SEQUENCE: 909
uguugcugau acugggcuc                                               19

<210> SEQ ID NO 910
<211> LENGTH: 19
<212> TYPE: RNA
<213> ORGANISM: artificial
<220> FEATURE:
<223> OTHER INFORMATION: RNA Oligomer

<400> SEQUENCE: 910
gacuacaguu accuacuuc                                               19

<210> SEQ ID NO 911
<211> LENGTH: 19
<212> TYPE: RNA
<213> ORGANISM: artificial
<220> FEATURE:
<223> OTHER INFORMATION: RNA Oligomer

<400> SEQUENCE: 911
acuacaguua ccuacuucu                                               19

<210> SEQ ID NO 912
<211> LENGTH: 19
<212> TYPE: RNA
<213> ORGANISM: artificial
<220> FEATURE:
<223> OTHER INFORMATION: RNA Oligomer

<400> SEQUENCE: 912
```
acaguuaccu acucuuuu                                          19

<210> SEQ ID NO 913
<211> LENGTH: 19
<212> TYPE: RNA
<213> ORGANISM: artificial
<220> FEATURE:
<223> OTHER INFORMATION: RNA Oligomer

<400> SEQUENCE: 913
uugcucaaug uccuguugc                                         19

<210> SEQ ID NO 914
<211> LENGTH: 19
<212> TYPE: RNA
<213> ORGANISM: artificial
<220> FEATURE:
<223> OTHER INFORMATION: RNA Oligomer

<400> SEQUENCE: 914
ggaauaucag gaacaagug                                         19

<210> SEQ ID NO 915
<211> LENGTH: 19
<212> TYPE: RNA
<213> ORGANISM: artificial
<220> FEATURE:
<223> OTHER INFORMATION: RNA Oligomer

<400> SEQUENCE: 915
aaucaaaucc auguccugc                                         19

<210> SEQ ID NO 916
<211> LENGTH: 19
<212> TYPE: RNA
<213> ORGANISM: artificial
<220> FEATURE:
<223> OTHER INFORMATION: RNA Oligomer

<400> SEQUENCE: 916
uuuacacuua cacagaaac                                         19

<210> SEQ ID NO 917
<211> LENGTH: 19
<212> TYPE: RNA
<213> ORGANISM: artificial
<220> FEATURE:
<223> OTHER INFORMATION: RNA Oligomer

<400> SEQUENCE: 917
cauacugaca cuccaaugc                                         19

<210> SEQ ID NO 918
<211> LENGTH: 19
<212> TYPE: RNA
<213> ORGANISM: artificial
<220> FEATURE:
<223> OTHER INFORMATION: RNA Oligomer

<400> SEQUENCE: 918
augagcauuu cacaucaca                                         19

<210> SEQ ID NO 919
<211> LENGTH: 19
<212> TYPE: RNA
<213> ORGANISM: artificial

```
<220> FEATURE:
<223> OTHER INFORMATION: RNA Oligomer

<400> SEQUENCE: 919
aaauccuccu aaaucuagu                                               19

<210> SEQ ID NO 920
<211> LENGTH: 19
<212> TYPE: RNA
<213> ORGANISM: artificial
<220> FEATURE:
<223> OTHER INFORMATION: RNA Oligomer

<400> SEQUENCE: 920
gcaugcugaa aacuucgag                                               19

<210> SEQ ID NO 921
<211> LENGTH: 19
<212> TYPE: RNA
<213> ORGANISM: artificial
<220> FEATURE:
<223> OTHER INFORMATION: RNA Oligomer

<400> SEQUENCE: 921
augcugaaaa cuucgagau                                               19

<210> SEQ ID NO 922
<211> LENGTH: 19
<212> TYPE: RNA
<213> ORGANISM: artificial
<220> FEATURE:
<223> OTHER INFORMATION: RNA Oligomer

<400> SEQUENCE: 922
uccaguuuuc uuuuucugc                                               19

<210> SEQ ID NO 923
<211> LENGTH: 19
<212> TYPE: RNA
<213> ORGANISM: artificial
<220> FEATURE:
<223> OTHER INFORMATION: RNA Oligomer

<400> SEQUENCE: 923
accccuccua cguauaucc                                               19

<210> SEQ ID NO 924
<211> LENGTH: 19
<212> TYPE: RNA
<213> ORGANISM: artificial
<220> FEATURE:
<223> OTHER INFORMATION: RNA Oligomer

<400> SEQUENCE: 924
uuggaguugu ucuugucuu                                               19

<210> SEQ ID NO 925
<211> LENGTH: 19
<212> TYPE: RNA
<213> ORGANISM: artificial
<220> FEATURE:
<223> OTHER INFORMATION: RNA Oligomer

<400> SEQUENCE: 925
cuucauugaa cugcucuuu                                               19
```

```
<210> SEQ ID NO 926
<211> LENGTH: 19
<212> TYPE: RNA
<213> ORGANISM: artificial
<220> FEATURE:
<223> OTHER INFORMATION: RNA Oligomer

<400> SEQUENCE: 926
uuggacauca uuucguuga                                              19

<210> SEQ ID NO 927
<211> LENGTH: 19
<212> TYPE: RNA
<213> ORGANISM: artificial
<220> FEATURE:
<223> OTHER INFORMATION: RNA Oligomer

<400> SEQUENCE: 927
gucaacaaca gggagguua                                              19

<210> SEQ ID NO 928
<211> LENGTH: 19
<212> TYPE: RNA
<213> ORGANISM: artificial
<220> FEATURE:
<223> OTHER INFORMATION: RNA Oligomer

<400> SEQUENCE: 928
gggauaugga gagcuuuug                                              19

<210> SEQ ID NO 929
<211> LENGTH: 19
<212> TYPE: RNA
<213> ORGANISM: artificial
<220> FEATURE:
<223> OTHER INFORMATION: RNA Oligomer

<400> SEQUENCE: 929
uuuugcccua aguucaucu                                              19

<210> SEQ ID NO 930
<211> LENGTH: 19
<212> TYPE: RNA
<213> ORGANISM: artificial
<220> FEATURE:
<223> OTHER INFORMATION: RNA Oligomer

<400> SEQUENCE: 930
uugcccuaag uucaucucu                                              19

<210> SEQ ID NO 931
<211> LENGTH: 19
<212> TYPE: RNA
<213> ORGANISM: artificial
<220> FEATURE:
<223> OTHER INFORMATION: RNA Oligomer

<400> SEQUENCE: 931
uuuuucuguu uuuccagcu                                              19

<210> SEQ ID NO 932
<211> LENGTH: 19
<212> TYPE: RNA
<213> ORGANISM: artificial
<220> FEATURE:
<223> OTHER INFORMATION: RNA Oligomer

<400> SEQUENCE: 932
```
auguacuggu guuuuagga                                       19

<210> SEQ ID NO 933
<211> LENGTH: 19
<212> TYPE: RNA
<213> ORGANISM: artificial
<220> FEATURE:
<223> OTHER INFORMATION: RNA Oligomer

<400> SEQUENCE: 933
ugauagauca gaaacauca                                       19

<210> SEQ ID NO 934
<211> LENGTH: 19
<212> TYPE: RNA
<213> ORGANISM: artificial
<220> FEATURE:
<223> OTHER INFORMATION: RNA Oligomer

<400> SEQUENCE: 934
agaucagaaa caucaaugg                                       19

<210> SEQ ID NO 935
<211> LENGTH: 19
<212> TYPE: RNA
<213> ORGANISM: artificial
<220> FEATURE:
<223> OTHER INFORMATION: RNA Oligomer

<400> SEQUENCE: 935
acuacugauu caacauacu                                       19

<210> SEQ ID NO 936
<211> LENGTH: 19
<212> TYPE: RNA
<213> ORGANISM: artificial
<220> FEATURE:
<223> OTHER INFORMATION: RNA Oligomer

<400> SEQUENCE: 936
caaaaaaacu agcucagaa                                       19

<210> SEQ ID NO 937
<211> LENGTH: 19
<212> TYPE: RNA
<213> ORGANISM: artificial
<220> FEATURE:
<223> OTHER INFORMATION: RNA Oligomer

<400> SEQUENCE: 937
agcaugcuga aaacuucga                                       19

<210> SEQ ID NO 938
<211> LENGTH: 19
<212> TYPE: RNA
<213> ORGANISM: artificial
<220> FEATURE:
<223> OTHER INFORMATION: RNA Oligomer

<400> SEQUENCE: 938
uccuacguau aucccgaau                                       19

<210> SEQ ID NO 939
<211> LENGTH: 19
<212> TYPE: RNA
<213> ORGANISM: artificial

```
<220> FEATURE:
<223> OTHER INFORMATION: RNA Oligomer

<400> SEQUENCE: 939
uugaacugcu cuuuggaca                                                  19

<210> SEQ ID NO 940
<211> LENGTH: 19
<212> TYPE: RNA
<213> ORGANISM: artificial
<220> FEATURE:
<223> OTHER INFORMATION: RNA Oligomer

<400> SEQUENCE: 940
uuguaccaua uccccagaa                                                  19

<210> SEQ ID NO 941
<211> LENGTH: 19
<212> TYPE: RNA
<213> ORGANISM: artificial
<220> FEATURE:
<223> OTHER INFORMATION: RNA Oligomer

<400> SEQUENCE: 941
uguaccauau ccccagaag                                                  19

<210> SEQ ID NO 942
<211> LENGTH: 19
<212> TYPE: RNA
<213> ORGANISM: artificial
<220> FEATURE:
<223> OTHER INFORMATION: RNA Oligomer

<400> SEQUENCE: 942
aagugauaga ucagaaaca                                                  19

<210> SEQ ID NO 943
<211> LENGTH: 19
<212> TYPE: RNA
<213> ORGANISM: artificial
<220> FEATURE:
<223> OTHER INFORMATION: RNA Oligomer

<400> SEQUENCE: 943
auggcuuaaa guagcaggu                                                  19

<210> SEQ ID NO 944
<211> LENGTH: 19
<212> TYPE: RNA
<213> ORGANISM: artificial
<220> FEATURE:
<223> OTHER INFORMATION: RNA Oligomer

<400> SEQUENCE: 944
aggaacaagu gacugaaac                                                  19

<210> SEQ ID NO 945
<211> LENGTH: 19
<212> TYPE: RNA
<213> ORGANISM: artificial
<220> FEATURE:
<223> OTHER INFORMATION: RNA Oligomer

<400> SEQUENCE: 945
ugguuucuga cuggaugug                                                  19
```

```
<210> SEQ ID NO 946
<211> LENGTH: 19
<212> TYPE: RNA
<213> ORGANISM: artificial
<220> FEATURE:
<223> OTHER INFORMATION: RNA Oligomer

<400> SEQUENCE: 946
aauccuuuau uaguaccag                                                19

<210> SEQ ID NO 947
<211> LENGTH: 19
<212> TYPE: RNA
<213> ORGANISM: artificial
<220> FEATURE:
<223> OTHER INFORMATION: RNA Oligomer

<400> SEQUENCE: 947
gauucaacau acugacacu                                                19

<210> SEQ ID NO 948
<211> LENGTH: 19
<212> TYPE: RNA
<213> ORGANISM: artificial
<220> FEATURE:
<223> OTHER INFORMATION: RNA Oligomer

<400> SEQUENCE: 948
auccuccuaa aucuaguuu                                                19

<210> SEQ ID NO 949
<211> LENGTH: 19
<212> TYPE: RNA
<213> ORGANISM: artificial
<220> FEATURE:
<223> OTHER INFORMATION: RNA Oligomer

<400> SEQUENCE: 949
uccuccuaaa ucuaguuuu                                                19

<210> SEQ ID NO 950
<211> LENGTH: 19
<212> TYPE: RNA
<213> ORGANISM: artificial
<220> FEATURE:
<223> OTHER INFORMATION: RNA Oligomer

<400> SEQUENCE: 950
aauuaaugca aguugagcu                                                19

<210> SEQ ID NO 951
<211> LENGTH: 19
<212> TYPE: RNA
<213> ORGANISM: artificial
<220> FEATURE:
<223> OTHER INFORMATION: RNA Oligomer

<400> SEQUENCE: 951
gcuucauuga acugcucuu                                                19

<210> SEQ ID NO 952
<211> LENGTH: 19
<212> TYPE: RNA
<213> ORGANISM: artificial
<220> FEATURE:
<223> OTHER INFORMATION: RNA Oligomer

<400> SEQUENCE: 952
```
aacugcucuu uggacauca 19

<210> SEQ ID NO 953
<211> LENGTH: 19
<212> TYPE: RNA
<213> ORGANISM: artificial
<220> FEATURE:
<223> OTHER INFORMATION: RNA Oligomer

<400> SEQUENCE: 953
uuuugugaau gggguuuuc 19

<210> SEQ ID NO 954
<211> LENGTH: 19
<212> TYPE: RNA
<213> ORGANISM: artificial
<220> FEATURE:
<223> OTHER INFORMATION: RNA Oligomer

<400> SEQUENCE: 954
uuucuguuuu uccagcuca 19

<210> SEQ ID NO 955
<211> LENGTH: 19
<212> TYPE: RNA
<213> ORGANISM: artificial
<220> FEATURE:
<223> OTHER INFORMATION: RNA Oligomer

<400> SEQUENCE: 955
gauagaucag aaacaucaa 19

<210> SEQ ID NO 956
<211> LENGTH: 19
<212> TYPE: RNA
<213> ORGANISM: artificial
<220> FEATURE:
<223> OTHER INFORMATION: RNA Oligomer

<400> SEQUENCE: 956
gauuugggaa ugugggcaa 19

<210> SEQ ID NO 957
<211> LENGTH: 19
<212> TYPE: RNA
<213> ORGANISM: artificial
<220> FEATURE:
<223> OTHER INFORMATION: RNA Oligomer

<400> SEQUENCE: 957
gguuucugac uggaugugc 19

<210> SEQ ID NO 958
<211> LENGTH: 19
<212> TYPE: RNA
<213> ORGANISM: artificial
<220> FEATURE:
<223> OTHER INFORMATION: RNA Oligomer

<400> SEQUENCE: 958
auccuuuauu aguaccagc 19

<210> SEQ ID NO 959
<211> LENGTH: 19
<212> TYPE: RNA
<213> ORGANISM: artificial

```
<220> FEATURE:
<223> OTHER INFORMATION: RNA Oligomer

<400> SEQUENCE: 959
uucaacauac ugacacucc                                                   19

<210> SEQ ID NO 960
<211> LENGTH: 19
<212> TYPE: RNA
<213> ORGANISM: artificial
<220> FEATURE:
<223> OTHER INFORMATION: RNA Oligomer

<400> SEQUENCE: 960
aaaacuagcu cagaaaagg                                                   19

<210> SEQ ID NO 961
<211> LENGTH: 19
<212> TYPE: RNA
<213> ORGANISM: artificial
<220> FEATURE:
<223> OTHER INFORMATION: RNA Oligomer

<400> SEQUENCE: 961
uuucuccuuu uucuuugag                                                   19

<210> SEQ ID NO 962
<211> LENGTH: 19
<212> TYPE: RNA
<213> ORGANISM: artificial
<220> FEATURE:
<223> OTHER INFORMATION: RNA Oligomer

<400> SEQUENCE: 962
uuuggaguug uucuugucu                                                   19

<210> SEQ ID NO 963
<211> LENGTH: 19
<212> TYPE: RNA
<213> ORGANISM: artificial
<220> FEATURE:
<223> OTHER INFORMATION: RNA Oligomer

<400> SEQUENCE: 963
acugcucuuu ggacaucau                                                   19

<210> SEQ ID NO 964
<211> LENGTH: 19
<212> TYPE: RNA
<213> ORGANISM: artificial
<220> FEATURE:
<223> OTHER INFORMATION: RNA Oligomer

<400> SEQUENCE: 964
uucuguuuuu ccagcucau                                                   19

<210> SEQ ID NO 965
<211> LENGTH: 19
<212> TYPE: RNA
<213> ORGANISM: artificial
<220> FEATURE:
<223> OTHER INFORMATION: RNA Oligomer

<400> SEQUENCE: 965
uguacuggug uuuuaggac                                                   19
```

```
<210> SEQ ID NO 966
<211> LENGTH: 19
<212> TYPE: RNA
<213> ORGANISM: artificial
<220> FEATURE:
<223> OTHER INFORMATION: RNA Oligomer

<400> SEQUENCE: 966
agggcaugcu guugcugau                                                    19

<210> SEQ ID NO 967
<211> LENGTH: 19
<212> TYPE: RNA
<213> ORGANISM: artificial
<220> FEATURE:
<223> OTHER INFORMATION: RNA Oligomer

<400> SEQUENCE: 967
acuucuguca guuuggcuu                                                    19

<210> SEQ ID NO 968
<211> LENGTH: 19
<212> TYPE: RNA
<213> ORGANISM: artificial
<220> FEATURE:
<223> OTHER INFORMATION: RNA Oligomer

<400> SEQUENCE: 968
ucauugucau cuacaaacg                                                    19

<210> SEQ ID NO 969
<211> LENGTH: 19
<212> TYPE: RNA
<213> ORGANISM: artificial
<220> FEATURE:
<223> OTHER INFORMATION: RNA Oligomer

<400> SEQUENCE: 969
auuugggaau gugggcaac                                                    19

<210> SEQ ID NO 970
<211> LENGTH: 19
<212> TYPE: RNA
<213> ORGANISM: artificial
<220> FEATURE:
<223> OTHER INFORMATION: RNA Oligomer

<400> SEQUENCE: 970
auugccaucu cuuguuugc                                                    19

<210> SEQ ID NO 971
<211> LENGTH: 19
<212> TYPE: RNA
<213> ORGANISM: artificial
<220> FEATURE:
<223> OTHER INFORMATION: RNA Oligomer

<400> SEQUENCE: 971
uccuuuuucu uugagcaau                                                    19

<210> SEQ ID NO 972
<211> LENGTH: 19
<212> TYPE: RNA
<213> ORGANISM: artificial
<220> FEATURE:
<223> OTHER INFORMATION: RNA Oligomer

<400> SEQUENCE: 972
```
ucuuuuguga auggggbuuu                                              19

<210> SEQ ID NO 973
<211> LENGTH: 19
<212> TYPE: RNA
<213> ORGANISM: artificial
<220> FEATURE:
<223> OTHER INFORMATION: RNA Oligomer

<400> SEQUENCE: 973
cuaucuagcu cuuccacuu                                               19

<210> SEQ ID NO 974
<211> LENGTH: 19
<212> TYPE: RNA
<213> ORGANISM: artificial
<220> FEATURE:
<223> OTHER INFORMATION: RNA Oligomer

<400> SEQUENCE: 974
ugggacuugu guuuaguga                                               19

<210> SEQ ID NO 975
<211> LENGTH: 19
<212> TYPE: RNA
<213> ORGANISM: artificial
<220> FEATURE:
<223> OTHER INFORMATION: RNA Oligomer

<400> SEQUENCE: 975
uguguuuagu gaaaugccg                                               19

<210> SEQ ID NO 976
<211> LENGTH: 19
<212> TYPE: RNA
<213> ORGANISM: artificial
<220> FEATURE:
<223> OTHER INFORMATION: RNA Oligomer

<400> SEQUENCE: 976
agagagugaa uggcuuaaa                                               19

<210> SEQ ID NO 977
<211> LENGTH: 19
<212> TYPE: RNA
<213> ORGANISM: artificial
<220> FEATURE:
<223> OTHER INFORMATION: RNA Oligomer

<400> SEQUENCE: 977
uggcuuaaag uagcaggug                                               19

<210> SEQ ID NO 978
<211> LENGTH: 19
<212> TYPE: RNA
<213> ORGANISM: artificial
<220> FEATURE:
<223> OTHER INFORMATION: RNA Oligomer

<400> SEQUENCE: 978
aauggauaau agcuccucc                                               19

<210> SEQ ID NO 979
<211> LENGTH: 19
<212> TYPE: RNA
<213> ORGANISM: artificial

```
<220> FEATURE:
<223> OTHER INFORMATION: RNA Oligomer

<400> SEQUENCE: 979
auggauaaua gcuccuccc                                                    19

<210> SEQ ID NO 980
<211> LENGTH: 19
<212> TYPE: RNA
<213> ORGANISM: artificial
<220> FEATURE:
<223> OTHER INFORMATION: RNA Oligomer

<400> SEQUENCE: 980
ucuaguugua acugagcga                                                    19

<210> SEQ ID NO 981
<211> LENGTH: 19
<212> TYPE: RNA
<213> ORGANISM: artificial
<220> FEATURE:
<223> OTHER INFORMATION: RNA Oligomer

<400> SEQUENCE: 981
auaagguuuu ccaucuuca                                                    19

<210> SEQ ID NO 982
<211> LENGTH: 19
<212> TYPE: RNA
<213> ORGANISM: artificial
<220> FEATURE:
<223> OTHER INFORMATION: RNA Oligomer

<400> SEQUENCE: 982
auuaaugcaa guugagcuu                                                    19

<210> SEQ ID NO 983
<211> LENGTH: 19
<212> TYPE: RNA
<213> ORGANISM: artificial
<220> FEATURE:
<223> OTHER INFORMATION: RNA Oligomer

<400> SEQUENCE: 983
cuuuugugaa uggguuuu                                                     19

<210> SEQ ID NO 984
<211> LENGTH: 19
<212> TYPE: RNA
<213> ORGANISM: artificial
<220> FEATURE:
<223> OTHER INFORMATION: RNA Oligomer

<400> SEQUENCE: 984
aguagugugu cuccauagc                                                    19

<210> SEQ ID NO 985
<211> LENGTH: 19
<212> TYPE: RNA
<213> ORGANISM: artificial
<220> FEATURE:
<223> OTHER INFORMATION: RNA Oligomer

<400> SEQUENCE: 985
gcugacugaa gucaaauac                                                    19
```

```
<210> SEQ ID NO 986
<211> LENGTH: 19
<212> TYPE: RNA
<213> ORGANISM: artificial
<220> FEATURE:
<223> OTHER INFORMATION: RNA Oligomer

<400> SEQUENCE: 986
aauggcuuaa aguagcagg                                              19

<210> SEQ ID NO 987
<211> LENGTH: 19
<212> TYPE: RNA
<213> ORGANISM: artificial
<220> FEATURE:
<223> OTHER INFORMATION: RNA Oligomer

<400> SEQUENCE: 987
guugcugaua cugggcuca                                              19

<210> SEQ ID NO 988
<211> LENGTH: 19
<212> TYPE: RNA
<213> ORGANISM: artificial
<220> FEATURE:
<223> OTHER INFORMATION: RNA Oligomer

<400> SEQUENCE: 988
cugaagucaa auacuucuc                                              19

<210> SEQ ID NO 989
<211> LENGTH: 19
<212> TYPE: RNA
<213> ORGANISM: artificial
<220> FEATURE:
<223> OTHER INFORMATION: RNA Oligomer

<400> SEQUENCE: 989
uuaccuacuu cuuuuucca                                              19

<210> SEQ ID NO 990
<211> LENGTH: 19
<212> TYPE: RNA
<213> ORGANISM: artificial
<220> FEATURE:
<223> OTHER INFORMATION: RNA Oligomer

<400> SEQUENCE: 990
cuucugucag uuuggcuuc                                              19

<210> SEQ ID NO 991
<211> LENGTH: 19
<212> TYPE: RNA
<213> ORGANISM: artificial
<220> FEATURE:
<223> OTHER INFORMATION: RNA Oligomer

<400> SEQUENCE: 991
ucugucaguu uggcuucug                                              19

<210> SEQ ID NO 992
<211> LENGTH: 19
<212> TYPE: RNA
<213> ORGANISM: artificial
<220> FEATURE:
<223> OTHER INFORMATION: RNA Oligomer

<400> SEQUENCE: 992
```

-continued caaccagcuu gucauuuuc                                        19

<210> SEQ ID NO 993
<211> LENGTH: 19
<212> TYPE: RNA
<213> ORGANISM: artificial
<220> FEATURE:
<223> OTHER INFORMATION: RNA Oligomer

<400> SEQUENCE: 993
ugacacucca augcuuuuu                                        19

<210> SEQ ID NO 994
<211> LENGTH: 19
<212> TYPE: RNA
<213> ORGANISM: artificial
<220> FEATURE:
<223> OTHER INFORMATION: RNA Oligomer

<400> SEQUENCE: 994
aaaaggucaa auccuccua                                        19

<210> SEQ ID NO 995
<211> LENGTH: 19
<212> TYPE: RNA
<213> ORGANISM: artificial
<220> FEATURE:
<223> OTHER INFORMATION: RNA Oligomer

<400> SEQUENCE: 995
agaauaaggu uuuccaucu                                        19

<210> SEQ ID NO 996
<211> LENGTH: 19
<212> TYPE: RNA
<213> ORGANISM: artificial
<220> FEATURE:
<223> OTHER INFORMATION: RNA Oligomer

<400> SEQUENCE: 996
uuaaugcaag uugagcuuc                                        19

<210> SEQ ID NO 997
<211> LENGTH: 19
<212> TYPE: RNA
<213> ORGANISM: artificial
<220> FEATURE:
<223> OTHER INFORMATION: RNA Oligomer

<400> SEQUENCE: 997
ggaaugggau auggagagc                                        19

<210> SEQ ID NO 998
<211> LENGTH: 19
<212> TYPE: RNA
<213> ORGANISM: artificial
<220> FEATURE:
<223> OTHER INFORMATION: RNA Oligomer

<400> SEQUENCE: 998
uuugugaaug ggguuuucc                                        19

<210> SEQ ID NO 999
<211> LENGTH: 19
<212> TYPE: RNA
<213> ORGANISM: artificial

```
<220> FEATURE:
<223> OTHER INFORMATION: RNA Oligomer

<400> SEQUENCE: 999
ucaugcacgu gagugcucu                                                    19

<210> SEQ ID NO 1000
<211> LENGTH: 19
<212> TYPE: RNA
<213> ORGANISM: artificial
<220> FEATURE:
<223> OTHER INFORMATION: RNA Oligomer

<400> SEQUENCE: 1000
cugagauggu gacaagggu                                                    19

<210> SEQ ID NO 1001
<211> LENGTH: 19
<212> TYPE: RNA
<213> ORGANISM: artificial
<220> FEATURE:
<223> OTHER INFORMATION: RNA Oligomer

<400> SEQUENCE: 1001
aaucacugag gccaaguag                                                    19

<210> SEQ ID NO 1002
<211> LENGTH: 19
<212> TYPE: RNA
<213> ORGANISM: artificial
<220> FEATURE:
<223> OTHER INFORMATION: RNA Oligomer

<400> SEQUENCE: 1002
cugaauuuaa ugaguucac                                                    19

<210> SEQ ID NO 1003
<211> LENGTH: 19
<212> TYPE: RNA
<213> ORGANISM: artificial
<220> FEATURE:
<223> OTHER INFORMATION: RNA Oligomer

<400> SEQUENCE: 1003
guuaccuacu ucuuuuucc                                                    19

<210> SEQ ID NO 1004
<211> LENGTH: 19
<212> TYPE: RNA
<213> ORGANISM: artificial
<220> FEATURE:
<223> OTHER INFORMATION: RNA Oligomer

<400> SEQUENCE: 1004
aaugauuuuu ucgacaggg                                                    19

<210> SEQ ID NO 1005
<211> LENGTH: 19
<212> TYPE: RNA
<213> ORGANISM: artificial
<220> FEATURE:
<223> OTHER INFORMATION: RNA Oligomer

<400> SEQUENCE: 1005
augauuuuuu cgacaggga                                                    19
```

-continued

<210> SEQ ID NO 1006
<211> LENGTH: 19
<212> TYPE: RNA
<213> ORGANISM: artificial
<220> FEATURE:
<223> OTHER INFORMATION: RNA Oligomer

<400> SEQUENCE: 1006
uaaugauuuu uucgacagg                                              19

<210> SEQ ID NO 1007
<211> LENGTH: 21
<212> TYPE: RNA
<213> ORGANISM: artificial
<220> FEATURE:
<223> OTHER INFORMATION: RNA Oligomer

<400> SEQUENCE: 1007
uaggaggggu aagaauaaag u                                           21

<210> SEQ ID NO 1008
<211> LENGTH: 21
<212> TYPE: RNA
<213> ORGANISM: artificial
<220> FEATURE:
<223> OTHER INFORMATION: RNA Oligomer

<400> SEQUENCE: 1008 aggguaaga auaaaguggc u                                            21

<210> SEQ ID NO 1009
<211> LENGTH: 21
<212> TYPE: RNA
<213> ORGANISM: artificial
<220> FEATURE:
<223> OTHER INFORMATION: RNA Oligomer

<400> SEQUENCE: 1009
aagaagccag auguuaagaa a                                           21

<210> SEQ ID NO 1010
<211> LENGTH: 21
<212> TYPE: RNA
<213> ORGANISM: artificial
<220> FEATURE:
<223> OTHER INFORMATION: RNA Oligomer

<400> SEQUENCE: 1010
aaaggagaaa augacaaaag c                                           21

<210> SEQ ID NO 1011
<211> LENGTH: 21
<212> TYPE: RNA
<213> ORGANISM: artificial
<220> FEATURE:
<223> OTHER INFORMATION: RNA Oligomer

<400> SEQUENCE: 1011
gagggguaag aauaaagugg c                                           21

<210> SEQ ID NO 1012
<211> LENGTH: 21
<212> TYPE: RNA
<213> ORGANISM: artificial
<220> FEATURE:
<223> OTHER INFORMATION: RNA Oligomer

<400> SEQUENCE: 1012
guaggagggg uaagaauaaa g					21

<210> SEQ ID NO 1013
<211> LENGTH: 21
<212> TYPE: RNA
<213> ORGANISM: artificial
<220> FEATURE:
<223> OTHER INFORMATION: RNA Oligomer

<400> SEQUENCE: 1013
auaaaguggc ugcucagaau u					21

<210> SEQ ID NO 1014
<211> LENGTH: 21
<212> TYPE: RNA
<213> ORGANISM: artificial
<220> FEATURE:
<223> OTHER INFORMATION: RNA Oligomer

<400> SEQUENCE: 1014 aggagggua agaauaaagu g					21

<210> SEQ ID NO 1015
<211> LENGTH: 21
<212> TYPE: RNA
<213> ORGANISM: artificial
<220> FEATURE:
<223> OTHER INFORMATION: RNA Oligomer

<400> SEQUENCE: 1015
gagaaagaau ugccuguaag u					21

<210> SEQ ID NO 1016
<211> LENGTH: 21
<212> TYPE: RNA
<213> ORGANISM: artificial
<220> FEATURE:
<223> OTHER INFORMATION: RNA Oligomer

<400> SEQUENCE: 1016
ucacucucug aacuucuaaa u					21

<210> SEQ ID NO 1017
<211> LENGTH: 21
<212> TYPE: RNA
<213> ORGANISM: artificial
<220> FEATURE:
<223> OTHER INFORMATION: RNA Oligomer

<400> SEQUENCE: 1017
gacauucccg uuuguagaug a					21

<210> SEQ ID NO 1018
<211> LENGTH: 21
<212> TYPE: RNA
<213> ORGANISM: artificial
<220> FEATURE:
<223> OTHER INFORMATION: RNA Oligomer

<400> SEQUENCE: 1018
agaagccaga uguuaagaaa a					21

<210> SEQ ID NO 1019
<211> LENGTH: 21
<212> TYPE: RNA
<213> ORGANISM: artificial

```
<220> FEATURE:
<223> OTHER INFORMATION: RNA Oligomer

<400> SEQUENCE: 1019
cucagaauug cagaaaaga a                                          21

<210> SEQ ID NO 1020
<211> LENGTH: 21
<212> TYPE: RNA
<213> ORGANISM: artificial
<220> FEATURE:
<223> OTHER INFORMATION: RNA Oligomer

<400> SEQUENCE: 1020
aagaauaaag uggcugcuca g                                         21

<210> SEQ ID NO 1021
<211> LENGTH: 21
<212> TYPE: RNA
<213> ORGANISM: artificial
<220> FEATURE:
<223> OTHER INFORMATION: RNA Oligomer

<400> SEQUENCE: 1021
ggguaagaau aaaguggcug c                                         21

<210> SEQ ID NO 1022
<211> LENGTH: 21
<212> TYPE: RNA
<213> ORGANISM: artificial
<220> FEATURE:
<223> OTHER INFORMATION: RNA Oligomer

<400> SEQUENCE: 1022
ugaaaaggaa agacaagaac a                                         21

<210> SEQ ID NO 1023
<211> LENGTH: 21
<212> TYPE: RNA
<213> ORGANISM: artificial
<220> FEATURE:
<223> OTHER INFORMATION: RNA Oligomer

<400> SEQUENCE: 1023
gcccucaccu gcuacuuuaa g                                         21

<210> SEQ ID NO 1024
<211> LENGTH: 21
<212> TYPE: RNA
<213> ORGANISM: artificial
<220> FEATURE:
<223> OTHER INFORMATION: RNA Oligomer

<400> SEQUENCE: 1024
guagaugaca augagguuuc u                                         21

<210> SEQ ID NO 1025
<211> LENGTH: 21
<212> TYPE: RNA
<213> ORGANISM: artificial
<220> FEATURE:
<223> OTHER INFORMATION: RNA Oligomer

<400> SEQUENCE: 1025
guaagaagcc agauguuaag a                                         21
```

```
<210> SEQ ID NO 1026
<211> LENGTH: 21
<212> TYPE: RNA
<213> ORGANISM: artificial
<220> FEATURE:
<223> OTHER INFORMATION: RNA Oligomer

<400> SEQUENCE: 1026
aaguaagaag ccagauguua a                                          21

<210> SEQ ID NO 1027
<211> LENGTH: 21
<212> TYPE: RNA
<213> ORGANISM: artificial
<220> FEATURE:
<223> OTHER INFORMATION: RNA Oligomer

<400> SEQUENCE: 1027
gggguaagaa uaaaguggcu g                                          21

<210> SEQ ID NO 1028
<211> LENGTH: 21
<212> TYPE: RNA
<213> ORGANISM: artificial
<220> FEATURE:
<223> OTHER INFORMATION: RNA Oligomer

<400> SEQUENCE: 1028
agagaaagaa uugccuguaa g                                          21

<210> SEQ ID NO 1029
<211> LENGTH: 21
<212> TYPE: RNA
<213> ORGANISM: artificial
<220> FEATURE:
<223> OTHER INFORMATION: RNA Oligomer

<400> SEQUENCE: 1029
cucucugaac uucuaaaugg g                                          21

<210> SEQ ID NO 1030
<211> LENGTH: 21
<212> TYPE: RNA
<213> ORGANISM: artificial
<220> FEATURE:
<223> OTHER INFORMATION: RNA Oligomer

<400> SEQUENCE: 1030
uuacucaucu auacccucaa u                                          21

<210> SEQ ID NO 1031
<211> LENGTH: 21
<212> TYPE: RNA
<213> ORGANISM: artificial
<220> FEATURE:
<223> OTHER INFORMATION: RNA Oligomer

<400> SEQUENCE: 1031
ccagucuuca uugcuacuaa u                                          21

<210> SEQ ID NO 1032
<211> LENGTH: 21
<212> TYPE: RNA
<213> ORGANISM: artificial
<220> FEATURE:
<223> OTHER INFORMATION: RNA Oligomer

<400> SEQUENCE: 1032
```
uagaugacaa ugagguuucu u                     21

<210> SEQ ID NO 1033
<211> LENGTH: 21
<212> TYPE: RNA
<213> ORGANISM: artificial
<220> FEATURE:
<223> OTHER INFORMATION: RNA Oligomer

<400> SEQUENCE: 1033
acauucccgu uuguagauga c                     21

<210> SEQ ID NO 1034
<211> LENGTH: 21
<212> TYPE: RNA
<213> ORGANISM: artificial
<220> FEATURE:
<223> OTHER INFORMATION: RNA Oligomer

<400> SEQUENCE: 1034
gcaaaacuaa ccacuaugua c                     21

<210> SEQ ID NO 1035
<211> LENGTH: 21
<212> TYPE: RNA
<213> ORGANISM: artificial
<220> FEATURE:
<223> OTHER INFORMATION: RNA Oligomer

<400> SEQUENCE: 1035
aaaaguaaga agccagaugu u                     21

<210> SEQ ID NO 1036
<211> LENGTH: 21
<212> TYPE: RNA
<213> ORGANISM: artificial
<220> FEATURE:
<223> OTHER INFORMATION: RNA Oligomer

<400> SEQUENCE: 1036
cccaaaagua agaagccaga u                     21

<210> SEQ ID NO 1037
<211> LENGTH: 21
<212> TYPE: RNA
<213> ORGANISM: artificial
<220> FEATURE:
<223> OTHER INFORMATION: RNA Oligomer

<400> SEQUENCE: 1037
uugcucaaag aaaaaggaga a                     21

<210> SEQ ID NO 1038
<211> LENGTH: 21
<212> TYPE: RNA
<213> ORGANISM: artificial
<220> FEATURE:
<223> OTHER INFORMATION: RNA Oligomer

<400> SEQUENCE: 1038
gaacuagagc aagauuuaga u                     21

<210> SEQ ID NO 1039
<211> LENGTH: 21
<212> TYPE: RNA
<213> ORGANISM: artificial

```
<220> FEATURE:
<223> OTHER INFORMATION: RNA Oligomer

<400> SEQUENCE: 1039
gcucagaauu gcagaaaaag a                                              21

<210> SEQ ID NO 1040
<211> LENGTH: 21
<212> TYPE: RNA
<213> ORGANISM: artificial
<220> FEATURE:
<223> OTHER INFORMATION: RNA Oligomer

<400> SEQUENCE: 1040
uugaaaagga aagacaagaa c                                              21

<210> SEQ ID NO 1041
<211> LENGTH: 21
<212> TYPE: RNA
<213> ORGANISM: artificial
<220> FEATURE:
<223> OTHER INFORMATION: RNA Oligomer

<400> SEQUENCE: 1041
agaacacacc agagaaagaa u                                              21

<210> SEQ ID NO 1042
<211> LENGTH: 21
<212> TYPE: RNA
<213> ORGANISM: artificial
<220> FEATURE:
<223> OTHER INFORMATION: RNA Oligomer

<400> SEQUENCE: 1042
aaaacaccag uacauucuuc u                                              21

<210> SEQ ID NO 1043
<211> LENGTH: 21
<212> TYPE: RNA
<213> ORGANISM: artificial
<220> FEATURE:
<223> OTHER INFORMATION: RNA Oligomer

<400> SEQUENCE: 1043
gucaaacaga augguccuaa a                                              21

<210> SEQ ID NO 1044
<211> LENGTH: 21
<212> TYPE: RNA
<213> ORGANISM: artificial
<220> FEATURE:
<223> OTHER INFORMATION: RNA Oligomer

<400> SEQUENCE: 1044
aaccaaaacc acccugaaag c                                              21

<210> SEQ ID NO 1045
<211> LENGTH: 21
<212> TYPE: RNA
<213> ORGANISM: artificial
<220> FEATURE:
<223> OTHER INFORMATION: RNA Oligomer

<400> SEQUENCE: 1045
uucaaccaaa accaccuga a                                               21
```

```
<210> SEQ ID NO 1046
<211> LENGTH: 21
<212> TYPE: RNA
<213> ORGANISM: artificial
<220> FEATURE:
<223> OTHER INFORMATION: RNA Oligomer

<400> SEQUENCE: 1046
cacucucuga acuucuaaau g                                              21

<210> SEQ ID NO 1047
<211> LENGTH: 21
<212> TYPE: RNA
<213> ORGANISM: artificial
<220> FEATURE:
<223> OTHER INFORMATION: RNA Oligomer

<400> SEQUENCE: 1047
gaguaagucg agaaguauuu g                                              21

<210> SEQ ID NO 1048
<211> LENGTH: 21
<212> TYPE: RNA
<213> ORGANISM: artificial
<220> FEATURE:
<223> OTHER INFORMATION: RNA Oligomer

<400> SEQUENCE: 1048
gacaaugagg uuucuucggc u                                              21

<210> SEQ ID NO 1049
<211> LENGTH: 21
<212> TYPE: RNA
<213> ORGANISM: artificial
<220> FEATURE:
<223> OTHER INFORMATION: RNA Oligomer

<400> SEQUENCE: 1049
ucagaugcuu uguacuuuga u                                              21

<210> SEQ ID NO 1050
<211> LENGTH: 21
<212> TYPE: RNA
<213> ORGANISM: artificial
<220> FEATURE:
<223> OTHER INFORMATION: RNA Oligomer

<400> SEQUENCE: 1050
gacaucuggc uaaaaagaaa u                                              21

<210> SEQ ID NO 1051
<211> LENGTH: 21
<212> TYPE: RNA
<213> ORGANISM: artificial
<220> FEATURE:
<223> OTHER INFORMATION: RNA Oligomer

<400> SEQUENCE: 1051
gaagccagau guuaagaaaa a                                              21

<210> SEQ ID NO 1052
<211> LENGTH: 21
<212> TYPE: RNA
<213> ORGANISM: artificial
<220> FEATURE:
<223> OTHER INFORMATION: RNA Oligomer

<400> SEQUENCE: 1052
```

-continued caaaaguaag aagccagaug u                                      21

<210> SEQ ID NO 1053
<211> LENGTH: 21
<212> TYPE: RNA
<213> ORGANISM: artificial
<220> FEATURE:
<223> OTHER INFORMATION: RNA Oligomer

<400> SEQUENCE: 1053
aaaaccuuau ucuccagug a                                       21

<210> SEQ ID NO 1054
<211> LENGTH: 21
<212> TYPE: RNA
<213> ORGANISM: artificial
<220> FEATURE:
<223> OTHER INFORMATION: RNA Oligomer

<400> SEQUENCE: 1054
acguaggagg gguaagaaua a                                      21

<210> SEQ ID NO 1055
<211> LENGTH: 21
<212> TYPE: RNA
<213> ORGANISM: artificial
<220> FEATURE:
<223> OTHER INFORMATION: RNA Oligomer

<400> SEQUENCE: 1055
aaggaaagac aagaacaacu c                                      21

<210> SEQ ID NO 1056
<211> LENGTH: 21
<212> TYPE: RNA
<213> ORGANISM: artificial
<220> FEATURE:
<223> OTHER INFORMATION: RNA Oligomer

<400> SEQUENCE: 1056
cacaaaagac aaacauucaa g                                      21

<210> SEQ ID NO 1057
<211> LENGTH: 21
<212> TYPE: RNA
<213> ORGANISM: artificial
<220> FEATURE:
<223> OTHER INFORMATION: RNA Oligomer

<400> SEQUENCE: 1057
cccauucaca aaagacaaac a                                      21

<210> SEQ ID NO 1058
<211> LENGTH: 21
<212> TYPE: RNA
<213> ORGANISM: artificial
<220> FEATURE:
<223> OTHER INFORMATION: RNA Oligomer

<400> SEQUENCE: 1058
aaccccauuc acaaaagaca a                                      21

<210> SEQ ID NO 1059
<211> LENGTH: 21
<212> TYPE: RNA
<213> ORGANISM: artificial

```
<220> FEATURE:
<223> OTHER INFORMATION: RNA Oligomer

<400> SEQUENCE: 1059
acaccagaga aagaauugcc u                                          21

<210> SEQ ID NO 1060
<211> LENGTH: 21
<212> TYPE: RNA
<213> ORGANISM: artificial
<220> FEATURE:
<223> OTHER INFORMATION: RNA Oligomer

<400> SEQUENCE: 1060
aacacaccag agaaagaauu g                                          21

<210> SEQ ID NO 1061
<211> LENGTH: 21
<212> TYPE: RNA
<213> ORGANISM: artificial
<220> FEATURE:
<223> OTHER INFORMATION: RNA Oligomer

<400> SEQUENCE: 1061
ucaaacagaa ugguccuaaa a                                          21

<210> SEQ ID NO 1062
<211> LENGTH: 21
<212> TYPE: RNA
<213> ORGANISM: artificial
<220> FEATURE:
<223> OTHER INFORMATION: RNA Oligomer

<400> SEQUENCE: 1062
ucagcgacgg aaagaguaug a                                          21

<210> SEQ ID NO 1063
<211> LENGTH: 21
<212> TYPE: RNA
<213> ORGANISM: artificial
<220> FEATURE:
<223> OTHER INFORMATION: RNA Oligomer

<400> SEQUENCE: 1063
gcacagcaga auucaaugau u                                          21

<210> SEQ ID NO 1064
<211> LENGTH: 21
<212> TYPE: RNA
<213> ORGANISM: artificial
<220> FEATURE:
<223> OTHER INFORMATION: RNA Oligomer

<400> SEQUENCE: 1064
gcuuucaacc aaaaccaccc u                                          21

<210> SEQ ID NO 1065
<211> LENGTH: 21
<212> TYPE: RNA
<213> ORGANISM: artificial
<220> FEATURE:
<223> OTHER INFORMATION: RNA Oligomer

<400> SEQUENCE: 1065
gccacaguca acacagauuu u                                          21
```

-continued

<210> SEQ ID NO 1066
<211> LENGTH: 21
<212> TYPE: RNA
<213> ORGANISM: artificial
<220> FEATURE:
<223> OTHER INFORMATION: RNA Oligomer

<400> SEQUENCE: 1066
aacucauuaa auucagaugc c                                             21

<210> SEQ ID NO 1067
<211> LENGTH: 21
<212> TYPE: RNA
<213> ORGANISM: artificial
<220> FEATURE:
<223> OTHER INFORMATION: RNA Oligomer

<400> SEQUENCE: 1067
guugacagug aacucauuaa a                                             21

<210> SEQ ID NO 1068
<211> LENGTH: 21
<212> TYPE: RNA
<213> ORGANISM: artificial
<220> FEATURE:
<223> OTHER INFORMATION: RNA Oligomer

<400> SEQUENCE: 1068
gcuauuaucc auuccugagu u                                             21

<210> SEQ ID NO 1069
<211> LENGTH: 21
<212> TYPE: RNA
<213> ORGANISM: artificial
<220> FEATURE:
<223> OTHER INFORMATION: RNA Oligomer

<400> SEQUENCE: 1069
aaguuuggga ggagcuauua u                                             21

<210> SEQ ID NO 1070
<211> LENGTH: 21
<212> TYPE: RNA
<213> ORGANISM: artificial
<220> FEATURE:
<223> OTHER INFORMATION: RNA Oligomer

<400> SEQUENCE: 1070
caaguuuggg aggagcuauu a                                             21

<210> SEQ ID NO 1071
<211> LENGTH: 21
<212> TYPE: RNA
<213> ORGANISM: artificial
<220> FEATURE:
<223> OTHER INFORMATION: RNA Oligomer

<400> SEQUENCE: 1071
gucuucauug cuacuaauca g                                             21

<210> SEQ ID NO 1072
<211> LENGTH: 21
<212> TYPE: RNA
<213> ORGANISM: artificial
<220> FEATURE:
<223> OTHER INFORMATION: RNA Oligomer

<400> SEQUENCE: 1072

-continued gaugacaaug agguuucuuc g                                             21

<210> SEQ ID NO 1073
<211> LENGTH: 21
<212> TYPE: RNA
<213> ORGANISM: artificial
<220> FEATURE:
<223> OTHER INFORMATION: RNA Oligomer

<400> SEQUENCE: 1073
aucagaugcu uuguacuuug a                                             21

<210> SEQ ID NO 1074
<211> LENGTH: 21
<212> TYPE: RNA
<213> ORGANISM: artificial
<220> FEATURE:
<223> OTHER INFORMATION: RNA Oligomer

<400> SEQUENCE: 1074
gcccacauuc ccaaaucaga u                                             21

<210> SEQ ID NO 1075
<211> LENGTH: 21
<212> TYPE: RNA
<213> ORGANISM: artificial
<220> FEATURE:
<223> OTHER INFORMATION: RNA Oligomer

<400> SEQUENCE: 1075
gugaugugaa augcucauac u                                             21

<210> SEQ ID NO 1076
<211> LENGTH: 21
<212> TYPE: RNA
<213> ORGANISM: artificial
<220> FEATURE:
<223> OTHER INFORMATION: RNA Oligomer

<400> SEQUENCE: 1076
aagcuccuac ugugauguga a                                             21

<210> SEQ ID NO 1077
<211> LENGTH: 21
<212> TYPE: RNA
<213> ORGANISM: artificial
<220> FEATURE:
<223> OTHER INFORMATION: RNA Oligomer

<400> SEQUENCE: 1077
cuacgugaug aagauggaaa a                                             21

<210> SEQ ID NO 1078
<211> LENGTH: 21
<212> TYPE: RNA
<213> ORGANISM: artificial
<220> FEATURE:
<223> OTHER INFORMATION: RNA Oligomer

<400> SEQUENCE: 1078
augcuacgug augaagaugg a                                             21

<210> SEQ ID NO 1079
<211> LENGTH: 21
<212> TYPE: RNA
<213> ORGANISM: artificial

```
<220> FEATURE:
<223> OTHER INFORMATION: RNA Oligomer

<400> SEQUENCE: 1079
ugaaaaaaca acucagcacc u                                              21

<210> SEQ ID NO 1080
<211> LENGTH: 21
<212> TYPE: RNA
<213> ORGANISM: artificial
<220> FEATURE:
<223> OTHER INFORMATION: RNA Oligomer

<400> SEQUENCE: 1080
ucaccuacug aaaaaacaac u                                              21

<210> SEQ ID NO 1081
<211> LENGTH: 21
<212> TYPE: RNA
<213> ORGANISM: artificial
<220> FEATURE:
<223> OTHER INFORMATION: RNA Oligomer

<400> SEQUENCE: 1081
guagaacuag agcaagauuu a                                              21

<210> SEQ ID NO 1082
<211> LENGTH: 21
<212> TYPE: RNA
<213> ORGANISM: artificial
<220> FEATURE:
<223> OTHER INFORMATION: RNA Oligomer

<400> SEQUENCE: 1082
ucaacuugca uuaauucggg a                                              21

<210> SEQ ID NO 1083
<211> LENGTH: 21
<212> TYPE: RNA
<213> ORGANISM: artificial
<220> FEATURE:
<223> OTHER INFORMATION: RNA Oligomer

<400> SEQUENCE: 1083
aaaggaaaga caagaacaac u                                              21

<210> SEQ ID NO 1084
<211> LENGTH: 21
<212> TYPE: RNA
<213> ORGANISM: artificial
<220> FEATURE:
<223> OTHER INFORMATION: RNA Oligomer

<400> SEQUENCE: 1084
ccauucacaa aagacaaaca u                                              21

<210> SEQ ID NO 1085
<211> LENGTH: 21
<212> TYPE: RNA
<213> ORGANISM: artificial
<220> FEATURE:
<223> OTHER INFORMATION: RNA Oligomer

<400> SEQUENCE: 1085
cacaccagag aaagaauugc c                                              21
```

```
<210> SEQ ID NO 1086
<211> LENGTH: 21
<212> TYPE: RNA
<213> ORGANISM: artificial
<220> FEATURE:
<223> OTHER INFORMATION: RNA Oligomer

<400> SEQUENCE: 1086
aacagaaugg uccuaaaaca c                                              21

<210> SEQ ID NO 1087
<211> LENGTH: 21
<212> TYPE: RNA
<213> ORGANISM: artificial
<220> FEATURE:
<223> OTHER INFORMATION: RNA Oligomer

<400> SEQUENCE: 1087
ggaaagagua ugagcuggaa a                                              21

<210> SEQ ID NO 1088
<211> LENGTH: 21
<212> TYPE: RNA
<213> ORGANISM: artificial
<220> FEATURE:
<223> OTHER INFORMATION: RNA Oligomer

<400> SEQUENCE: 1088
caguugacag ugaacucauu a                                              21

<210> SEQ ID NO 1089
<211> LENGTH: 21
<212> TYPE: RNA
<213> ORGANISM: artificial
<220> FEATURE:
<223> OTHER INFORMATION: RNA Oligomer

<400> SEQUENCE: 1089
ggaguaaguc gagaaguauu u                                              21

<210> SEQ ID NO 1090
<211> LENGTH: 21
<212> TYPE: RNA
<213> ORGANISM: artificial
<220> FEATURE:
<223> OTHER INFORMATION: RNA Oligomer

<400> SEQUENCE: 1090
uggaguaagu cgagaaguau u                                              21

<210> SEQ ID NO 1091
<211> LENGTH: 21
<212> TYPE: RNA
<213> ORGANISM: artificial
<220> FEATURE:
<223> OTHER INFORMATION: RNA Oligomer

<400> SEQUENCE: 1091
uuggaguaag ucgagaagua u                                              21

<210> SEQ ID NO 1092
<211> LENGTH: 21
<212> TYPE: RNA
<213> ORGANISM: artificial
<220> FEATURE:
<223> OTHER INFORMATION: RNA Oligomer

<400> SEQUENCE: 1092
```

-continued cuauuaucca uuccugaguu a                                    21

<210> SEQ ID NO 1093
<211> LENGTH: 21
<212> TYPE: RNA
<213> ORGANISM: artificial
<220> FEATURE:
<223> OTHER INFORMATION: RNA Oligomer

<400> SEQUENCE: 1093
gcaacaggac auugagcaag u                                    21

<210> SEQ ID NO 1094
<211> LENGTH: 21
<212> TYPE: RNA
<213> ORGANISM: artificial
<220> FEATURE:
<223> OTHER INFORMATION: RNA Oligomer

<400> SEQUENCE: 1094
guugauuuag acgguaugca a                                    21

<210> SEQ ID NO 1095
<211> LENGTH: 21
<212> TYPE: RNA
<213> ORGANISM: artificial
<220> FEATURE:
<223> OTHER INFORMATION: RNA Oligomer

<400> SEQUENCE: 1095
cagucuucau ugcuacuaau c                                    21

<210> SEQ ID NO 1096
<211> LENGTH: 21
<212> TYPE: RNA
<213> ORGANISM: artificial
<220> FEATURE:
<223> OTHER INFORMATION: RNA Oligomer

<400> SEQUENCE: 1096
ucacaucgag agcccagucu u                                    21

<210> SEQ ID NO 1097
<211> LENGTH: 21
<212> TYPE: RNA
<213> ORGANISM: artificial
<220> FEATURE:
<223> OTHER INFORMATION: RNA Oligomer

<400> SEQUENCE: 1097
aggacaugga uuugauugac a                                    21

<210> SEQ ID NO 1098
<211> LENGTH: 21
<212> TYPE: RNA
<213> ORGANISM: artificial
<220> FEATURE:
<223> OTHER INFORMATION: RNA Oligomer

<400> SEQUENCE: 1098
ugcccacauu cccaaaucag a                                    21

<210> SEQ ID NO 1099
<211> LENGTH: 21
<212> TYPE: RNA
<213> ORGANISM: artificial

```
<220> FEATURE:
<223> OTHER INFORMATION: RNA Oligomer

<400> SEQUENCE: 1099
uacucccagg uugcccacau u                                              21

<210> SEQ ID NO 1100
<211> LENGTH: 21
<212> TYPE: RNA
<213> ORGANISM: artificial
<220> FEATURE:
<223> OTHER INFORMATION: RNA Oligomer

<400> SEQUENCE: 1100
aagagcuggu acuaauaaag g                                              21

<210> SEQ ID NO 1101
<211> LENGTH: 21
<212> TYPE: RNA
<213> ORGANISM: artificial
<220> FEATURE:
<223> OTHER INFORMATION: RNA Oligomer

<400> SEQUENCE: 1101
uaagagcugg uacuaauaaa g                                              21

<210> SEQ ID NO 1102
<211> LENGTH: 21
<212> TYPE: RNA
<213> ORGANISM: artificial
<220> FEATURE:
<223> OTHER INFORMATION: RNA Oligomer

<400> SEQUENCE: 1102
cuguauggac aaaaaauggc a                                              21

<210> SEQ ID NO 1103
<211> LENGTH: 21
<212> TYPE: RNA
<213> ORGANISM: artificial
<220> FEATURE:
<223> OTHER INFORMATION: RNA Oligomer

<400> SEQUENCE: 1103
ggauuugacc uuuucugagc u                                              21

<210> SEQ ID NO 1104
<211> LENGTH: 21
<212> TYPE: RNA
<213> ORGANISM: artificial
<220> FEATURE:
<223> OTHER INFORMATION: RNA Oligomer

<400> SEQUENCE: 1104
aaaccuuauu cuccuaguga a                                              21

<210> SEQ ID NO 1105
<211> LENGTH: 21
<212> TYPE: RNA
<213> ORGANISM: artificial
<220> FEATURE:
<223> OTHER INFORMATION: RNA Oligomer

<400> SEQUENCE: 1105
aaaaaacaac ucagcaccuu a                                              21
```

<210> SEQ ID NO 1106
<211> LENGTH: 21
<212> TYPE: RNA
<213> ORGANISM: artificial
<220> FEATURE:
<223> OTHER INFORMATION: RNA Oligomer

<400> SEQUENCE: 1106
cuagagcaag auuuagauca u                                              21

<210> SEQ ID NO 1107
<211> LENGTH: 21
<212> TYPE: RNA
<213> ORGANISM: artificial
<220> FEATURE:
<223> OTHER INFORMATION: RNA Oligomer

<400> SEQUENCE: 1107
gcagaaaaag aaaacuggaa a                                              21

<210> SEQ ID NO 1108
<211> LENGTH: 21
<212> TYPE: RNA
<213> ORGANISM: artificial
<220> FEATURE:
<223> OTHER INFORMATION: RNA Oligomer

<400> SEQUENCE: 1108
aacuugcauu aauucgggau a                                              21

<210> SEQ ID NO 1109
<211> LENGTH: 21
<212> TYPE: RNA
<213> ORGANISM: artificial
<220> FEATURE:
<223> OTHER INFORMATION: RNA Oligomer

<400> SEQUENCE: 1109
caacuugcau uaauucggga u                                              21

<210> SEQ ID NO 1110
<211> LENGTH: 21
<212> TYPE: RNA
<213> ORGANISM: artificial
<220> FEATURE:
<223> OTHER INFORMATION: RNA Oligomer

<400> SEQUENCE: 1110
ccauauccca uucccuguag a                                              21

<210> SEQ ID NO 1111
<211> LENGTH: 21
<212> TYPE: RNA
<213> ORGANISM: artificial
<220> FEATURE:
<223> OTHER INFORMATION: RNA Oligomer

<400> SEQUENCE: 1111
acaaaagaca aacauucaag c                                              21

<210> SEQ ID NO 1112
<211> LENGTH: 21
<212> TYPE: RNA
<213> ORGANISM: artificial
<220> FEATURE:
<223> OTHER INFORMATION: RNA Oligomer

<400> SEQUENCE: 1112
accccauuca caaaagacaa a                     21

<210> SEQ ID NO 1113
<211> LENGTH: 21
<212> TYPE: RNA
<213> ORGANISM: artificial
<220> FEATURE:
<223> OTHER INFORMATION: RNA Oligomer

<400> SEQUENCE: 1113
aagaauugcc uguaaguccu g                     21

<210> SEQ ID NO 1114
<211> LENGTH: 21
<212> TYPE: RNA
<213> ORGANISM: artificial
<220> FEATURE:
<223> OTHER INFORMATION: RNA Oligomer

<400> SEQUENCE: 1114
aaagaauugc cuguaagucc u                     21

<210> SEQ ID NO 1115
<211> LENGTH: 21
<212> TYPE: RNA
<213> ORGANISM: artificial
<220> FEATURE:
<223> OTHER INFORMATION: RNA Oligomer

<400> SEQUENCE: 1115
gaacacacca gagaaagaau u                     21

<210> SEQ ID NO 1116
<211> LENGTH: 21
<212> TYPE: RNA
<213> ORGANISM: artificial
<220> FEATURE:
<223> OTHER INFORMATION: RNA Oligomer

<400> SEQUENCE: 1116
agaguaugag cuggaaaaac a                     21

<210> SEQ ID NO 1117
<211> LENGTH: 21
<212> TYPE: RNA
<213> ORGANISM: artificial
<220> FEATURE:
<223> OTHER INFORMATION: RNA Oligomer

<400> SEQUENCE: 1117
guaguccaca uuuucuuaau g                     21

<210> SEQ ID NO 1118
<211> LENGTH: 21
<212> TYPE: RNA
<213> ORGANISM: artificial
<220> FEATURE:
<223> OTHER INFORMATION: RNA Oligomer

<400> SEQUENCE: 1118
uacucaucua uacccucaau g                     21

<210> SEQ ID NO 1119
<211> LENGTH: 21
<212> TYPE: RNA
<213> ORGANISM: artificial -continued

```
<220> FEATURE:
<223> OTHER INFORMATION: RNA Oligomer

<400> SEQUENCE: 1119
caggacauug agcaaguuug g                                              21

<210> SEQ ID NO 1120
<211> LENGTH: 21
<212> TYPE: RNA
<213> ORGANISM: artificial
<220> FEATURE:
<223> OTHER INFORMATION: RNA Oligomer

<400> SEQUENCE: 1120
uucggcuacg uuucagucac u                                              21

<210> SEQ ID NO 1121
<211> LENGTH: 21
<212> TYPE: RNA
<213> ORGANISM: artificial
<220> FEATURE:
<223> OTHER INFORMATION: RNA Oligomer

<400> SEQUENCE: 1121
acaaugaggu uucuucggcu a                                              21

<210> SEQ ID NO 1122
<211> LENGTH: 21
<212> TYPE: RNA
<213> ORGANISM: artificial
<220> FEATURE:
<223> OTHER INFORMATION: RNA Oligomer

<400> SEQUENCE: 1122
ggacauggau uugauugaca u                                              21

<210> SEQ ID NO 1123
<211> LENGTH: 21
<212> TYPE: RNA
<213> ORGANISM: artificial
<220> FEATURE:
<223> OTHER INFORMATION: RNA Oligomer

<400> SEQUENCE: 1123
uacuguaugg acaaaaaaug g                                              21

<210> SEQ ID NO 1124
<211> LENGTH: 21
<212> TYPE: RNA
<213> ORGANISM: artificial
<220> FEATURE:
<223> OTHER INFORMATION: RNA Oligomer

<400> SEQUENCE: 1124
aacaauuucu uaggacacca u                                              21

<210> SEQ ID NO 1125
<211> LENGTH: 21
<212> TYPE: RNA
<213> ORGANISM: artificial
<220> FEATURE:
<223> OTHER INFORMATION: RNA Oligomer

<400> SEQUENCE: 1125
cuguaaacaa uuucuuagga c                                              21
```

```
<210> SEQ ID NO 1126
<211> LENGTH: 21
<212> TYPE: RNA
<213> ORGANISM: artificial
<220> FEATURE:
<223> OTHER INFORMATION: RNA Oligomer

<400> SEQUENCE: 1126
gaagauggaa aaccuuauuc u                                              21

<210> SEQ ID NO 1127
<211> LENGTH: 21
<212> TYPE: RNA
<213> ORGANISM: artificial
<220> FEATURE:
<223> OTHER INFORMATION: RNA Oligomer

<400> SEQUENCE: 1127
uacgugauga agauggaaaa c                                              21

<210> SEQ ID NO 1128
<211> LENGTH: 21
<212> TYPE: RNA
<213> ORGANISM: artificial
<220> FEATURE:
<223> OTHER INFORMATION: RNA Oligomer

<400> SEQUENCE: 1128
agcaccuuau aucucgaagu u                                              21

<210> SEQ ID NO 1129
<211> LENGTH: 21
<212> TYPE: RNA
<213> ORGANISM: artificial
<220> FEATURE:
<223> OTHER INFORMATION: RNA Oligomer

<400> SEQUENCE: 1129
aaaacaacuc agcaccuuau a                                              21

<210> SEQ ID NO 1130
<211> LENGTH: 21
<212> TYPE: RNA
<213> ORGANISM: artificial
<220> FEATURE:
<223> OTHER INFORMATION: RNA Oligomer

<400> SEQUENCE: 1130
gagcaagauu uagaucauuu g                                              21

<210> SEQ ID NO 1131
<211> LENGTH: 21
<212> TYPE: RNA
<213> ORGANISM: artificial
<220> FEATURE:
<223> OTHER INFORMATION: RNA Oligomer

<400> SEQUENCE: 1131
agaacuagag caagauuuag a                                              21

<210> SEQ ID NO 1132
<211> LENGTH: 21
<212> TYPE: RNA
<213> ORGANISM: artificial
<220> FEATURE:
<223> OTHER INFORMATION: RNA Oligomer

<400> SEQUENCE: 1132
```
uugcagaaaa agaaaacugg a                                    21

<210> SEQ ID NO 1133
<211> LENGTH: 21
<212> TYPE: RNA
<213> ORGANISM: artificial
<220> FEATURE:
<223> OTHER INFORMATION: RNA Oligomer

<400> SEQUENCE: 1133
uccauauccc auucccugua g                                    21

<210> SEQ ID NO 1134
<211> LENGTH: 21
<212> TYPE: RNA
<213> ORGANISM: artificial
<220> FEATURE:
<223> OTHER INFORMATION: RNA Oligomer

<400> SEQUENCE: 1134
ccccauucac aaaagacaaa c                                    21

<210> SEQ ID NO 1135
<211> LENGTH: 21
<212> TYPE: RNA
<213> ORGANISM: artificial
<220> FEATURE:
<223> OTHER INFORMATION: RNA Oligomer

<400> SEQUENCE: 1135
gagaacacac cagagaaaga a                                    21

<210> SEQ ID NO 1136
<211> LENGTH: 21
<212> TYPE: RNA
<213> ORGANISM: artificial
<220> FEATURE:
<223> OTHER INFORMATION: RNA Oligomer

<400> SEQUENCE: 1136
caguacauuc uucuggggau a                                    21

<210> SEQ ID NO 1137
<211> LENGTH: 21
<212> TYPE: RNA
<213> ORGANISM: artificial
<220> FEATURE:
<223> OTHER INFORMATION: RNA Oligomer

<400> SEQUENCE: 1137
acggaaagag uaugagcugg a                                    21

<210> SEQ ID NO 1138
<211> LENGTH: 21
<212> TYPE: RNA
<213> ORGANISM: artificial
<220> FEATURE:
<223> OTHER INFORMATION: RNA Oligomer

<400> SEQUENCE: 1138
cugacuccgg cauuucacua a                                    21

<210> SEQ ID NO 1139
<211> LENGTH: 21
<212> TYPE: RNA
<213> ORGANISM: artificial

```
<220> FEATURE:
<223> OTHER INFORMATION: RNA Oligomer

<400> SEQUENCE: 1139
agcacagcag aauucaauga u                                              21

<210> SEQ ID NO 1140
<211> LENGTH: 21
<212> TYPE: RNA
<213> ORGANISM: artificial
<220> FEATURE:
<223> OTHER INFORMATION: RNA Oligomer

<400> SEQUENCE: 1140
uaaauucaga ugccacaguc a                                              21

<210> SEQ ID NO 1141
<211> LENGTH: 21
<212> TYPE: RNA
<213> ORGANISM: artificial
<220> FEATURE:
<223> OTHER INFORMATION: RNA Oligomer

<400> SEQUENCE: 1141
cucauuaaau ucagaugcca c                                              21

<210> SEQ ID NO 1142
<211> LENGTH: 21
<212> TYPE: RNA
<213> ORGANISM: artificial
<220> FEATURE:
<223> OTHER INFORMATION: RNA Oligomer

<400> SEQUENCE: 1142
acuguagucc acauuuucuu a                                              21

<210> SEQ ID NO 1143
<211> LENGTH: 21
<212> TYPE: RNA
<213> ORGANISM: artificial
<220> FEATURE:
<223> OTHER INFORMATION: RNA Oligomer

<400> SEQUENCE: 1143
ucaauggaaa aagaaguagg u                                              21

<210> SEQ ID NO 1144
<211> LENGTH: 21
<212> TYPE: RNA
<213> ORGANISM: artificial
<220> FEATURE:
<223> OTHER INFORMATION: RNA Oligomer

<400> SEQUENCE: 1144
gagcuauuau ccauuccuga g                                              21

<210> SEQ ID NO 1145
<211> LENGTH: 21
<212> TYPE: RNA
<213> ORGANISM: artificial
<220> FEATURE:
<223> OTHER INFORMATION: RNA Oligomer

<400> SEQUENCE: 1145
aacaggacau ugagcaaguu u                                              21
```

```
<210> SEQ ID NO 1146
<211> LENGTH: 21
<212> TYPE: RNA
<213> ORGANISM: artificial
<220> FEATURE:
<223> OTHER INFORMATION: RNA Oligomer

<400> SEQUENCE: 1146
uuagacggua ugcaacagga c                                              21

<210> SEQ ID NO 1147
<211> LENGTH: 21
<212> TYPE: RNA
<213> ORGANISM: artificial
<220> FEATURE:
<223> OTHER INFORMATION: RNA Oligomer

<400> SEQUENCE: 1147
uuuagacggu augcaacagg a                                              21

<210> SEQ ID NO 1148
<211> LENGTH: 21
<212> TYPE: RNA
<213> ORGANISM: artificial
<220> FEATURE:
<223> OTHER INFORMATION: RNA Oligomer

<400> SEQUENCE: 1148
ugagguuucu ucggcuacgu u                                              21

<210> SEQ ID NO 1149
<211> LENGTH: 21
<212> TYPE: RNA
<213> ORGANISM: artificial
<220> FEATURE:
<223> OTHER INFORMATION: RNA Oligomer

<400> SEQUENCE: 1149
augagguuuc uucggcuacg u                                              21

<210> SEQ ID NO 1150
<211> LENGTH: 21
<212> TYPE: RNA
<213> ORGANISM: artificial
<220> FEATURE:
<223> OTHER INFORMATION: RNA Oligomer

<400> SEQUENCE: 1150
ugcuuuguac uuugaugacu g                                              21

<210> SEQ ID NO 1151
<211> LENGTH: 21
<212> TYPE: RNA
<213> ORGANISM: artificial
<220> FEATURE:
<223> OTHER INFORMATION: RNA Oligomer

<400> SEQUENCE: 1151
agaugcuuug uacuuugaug a                                              21

<210> SEQ ID NO 1152
<211> LENGTH: 21
<212> TYPE: RNA
<213> ORGANISM: artificial
<220> FEATURE:
<223> OTHER INFORMATION: RNA Oligomer

<400> SEQUENCE: 1152
```
cagcaggaca uggauuugau u               21

<210> SEQ ID NO 1153
<211> LENGTH: 21
<212> TYPE: RNA
<213> ORGANISM: artificial
<220> FEATURE:
<223> OTHER INFORMATION: RNA Oligomer

<400> SEQUENCE: 1153
uuacaacuag augaagagac a               21

<210> SEQ ID NO 1154
<211> LENGTH: 21
<212> TYPE: RNA
<213> ORGANISM: artificial
<220> FEATURE:
<223> OTHER INFORMATION: RNA Oligomer

<400> SEQUENCE: 1154
agagcuggua cuaauaaagg a               21

<210> SEQ ID NO 1155
<211> LENGTH: 21
<212> TYPE: RNA
<213> ORGANISM: artificial
<220> FEATURE:
<223> OTHER INFORMATION: RNA Oligomer

<400> SEQUENCE: 1155
ugacaucugg cuaaaaagaa a               21

<210> SEQ ID NO 1156
<211> LENGTH: 21
<212> TYPE: RNA
<213> ORGANISM: artificial
<220> FEATURE:
<223> OTHER INFORMATION: RNA Oligomer

<400> SEQUENCE: 1156
cuaguuucug uguaagugua a               21

<210> SEQ ID NO 1157
<211> LENGTH: 21
<212> TYPE: RNA
<213> ORGANISM: artificial
<220> FEATURE:
<223> OTHER INFORMATION: RNA Oligomer

<400> SEQUENCE: 1157
ggcuaguuuc uguguaagug u               21

<210> SEQ ID NO 1158
<211> LENGTH: 21
<212> TYPE: RNA
<213> ORGANISM: artificial
<220> FEATURE:
<223> OTHER INFORMATION: RNA Oligomer

<400> SEQUENCE: 1158
ugggcuaguu ucuguguaag u               21

<210> SEQ ID NO 1159
<211> LENGTH: 21
<212> TYPE: RNA
<213> ORGANISM: artificial

```
<220> FEATURE:
<223> OTHER INFORMATION: RNA Oligomer

<400> SEQUENCE: 1159
aaacaauuuc uuaggacacc a                                              21

<210> SEQ ID NO 1160
<211> LENGTH: 21
<212> TYPE: RNA
<213> ORGANISM: artificial
<220> FEATURE:
<223> OTHER INFORMATION: RNA Oligomer

<400> SEQUENCE: 1160
gagugucagu auguugaauc a                                              21

<210> SEQ ID NO 1161
<211> LENGTH: 21
<212> TYPE: RNA
<213> ORGANISM: artificial
<220> FEATURE:
<223> OTHER INFORMATION: RNA Oligomer

<400> SEQUENCE: 1161
uacuaaaagc uccuacugug a                                              21

<210> SEQ ID NO 1162
<211> LENGTH: 21
<212> TYPE: RNA
<213> ORGANISM: artificial
<220> FEATURE:
<223> OTHER INFORMATION: RNA Oligomer

<400> SEQUENCE: 1162
ugcuacguga ugaagaugga a                                              21

<210> SEQ ID NO 1163
<211> LENGTH: 21
<212> TYPE: RNA
<213> ORGANISM: artificial
<220> FEATURE:
<223> OTHER INFORMATION: RNA Oligomer

<400> SEQUENCE: 1163
gcaccuuaua ucucgaaguu u                                              21

<210> SEQ ID NO 1164
<211> LENGTH: 21
<212> TYPE: RNA
<213> ORGANISM: artificial
<220> FEATURE:
<223> OTHER INFORMATION: RNA Oligomer

<400> SEQUENCE: 1164
cagcaccuua uaucucgaag u                                              21

<210> SEQ ID NO 1165
<211> LENGTH: 21
<212> TYPE: RNA
<213> ORGANISM: artificial
<220> FEATURE:
<223> OTHER INFORMATION: RNA Oligomer

<400> SEQUENCE: 1165
caccuacuga aaaacaacu c                                               21
```

```
<210> SEQ ID NO 1166
<211> LENGTH: 21
<212> TYPE: RNA
<213> ORGANISM: artificial
<220> FEATURE:
<223> OTHER INFORMATION: RNA Oligomer

<400> SEQUENCE: 1166
aacuagagca agauuuagau c                                              21

<210> SEQ ID NO 1167
<211> LENGTH: 21
<212> TYPE: RNA
<213> ORGANISM: artificial
<220> FEATURE:
<223> OTHER INFORMATION: RNA Oligomer

<400> SEQUENCE: 1167
uaguagaacu agagcaagau u                                              21

<210> SEQ ID NO 1168
<211> LENGTH: 21
<212> TYPE: RNA
<213> ORGANISM: artificial
<220> FEATURE:
<223> OTHER INFORMATION: RNA Oligomer

<400> SEQUENCE: 1168
gggauauacg uaggaggggu a                                              21

<210> SEQ ID NO 1169
<211> LENGTH: 21
<212> TYPE: RNA
<213> ORGANISM: artificial
<220> FEATURE:
<223> OTHER INFORMATION: RNA Oligomer

<400> SEQUENCE: 1169
ugagaacaca ccagagaaag a                                              21

<210> SEQ ID NO 1170
<211> LENGTH: 21
<212> TYPE: RNA
<213> ORGANISM: artificial
<220> FEATURE:
<223> OTHER INFORMATION: RNA Oligomer

<400> SEQUENCE: 1170
aaagaguaug agcuggaaaa a                                              21

<210> SEQ ID NO 1171
<211> LENGTH: 21
<212> TYPE: RNA
<213> ORGANISM: artificial
<220> FEATURE:
<223> OTHER INFORMATION: RNA Oligomer

<400> SEQUENCE: 1171
cggaaagagu augagcugga a                                              21

<210> SEQ ID NO 1172
<211> LENGTH: 21
<212> TYPE: RNA
<213> ORGANISM: artificial
<220> FEATURE:
<223> OTHER INFORMATION: RNA Oligomer

<400> SEQUENCE: 1172
```
ugccccugga agugucaaac a            21

<210> SEQ ID NO 1173
<211> LENGTH: 21
<212> TYPE: RNA
<213> ORGANISM: artificial
<220> FEATURE:
<223> OTHER INFORMATION: RNA Oligomer

<400> SEQUENCE: 1173
auagugcccc uggaaguguc a            21

<210> SEQ ID NO 1174
<211> LENGTH: 21
<212> TYPE: RNA
<213> ORGANISM: artificial
<220> FEATURE:
<223> OTHER INFORMATION: RNA Oligomer

<400> SEQUENCE: 1174
agcgacggaa agaguaugag c            21

<210> SEQ ID NO 1175
<211> LENGTH: 21
<212> TYPE: RNA
<213> ORGANISM: artificial
<220> FEATURE:
<223> OTHER INFORMATION: RNA Oligomer

<400> SEQUENCE: 1175
cagcgacgga aagaguauga g            21

<210> SEQ ID NO 1176
<211> LENGTH: 21
<212> TYPE: RNA
<213> ORGANISM: artificial
<220> FEATURE:
<223> OTHER INFORMATION: RNA Oligomer

<400> SEQUENCE: 1176
gggcccauug auguuucuga u            21

<210> SEQ ID NO 1177
<211> LENGTH: 21
<212> TYPE: RNA
<213> ORGANISM: artificial
<220> FEATURE:
<223> OTHER INFORMATION: RNA Oligomer

<400> SEQUENCE: 1177
cuguagucca cauuuucuua a            21

<210> SEQ ID NO 1178
<211> LENGTH: 21
<212> TYPE: RNA
<213> ORGANISM: artificial
<220> FEATURE:
<223> OTHER INFORMATION: RNA Oligomer

<400> SEQUENCE: 1178
cucaauggaa aaagaaguag g            21

<210> SEQ ID NO 1179
<211> LENGTH: 21
<212> TYPE: RNA
<213> ORGANISM: artificial

```
<220> FEATURE:
<223> OTHER INFORMATION: RNA Oligomer

<400> SEQUENCE: 1179
gaucuuggag uaagucgaga a                                              21

<210> SEQ ID NO 1180
<211> LENGTH: 21
<212> TYPE: RNA
<213> ORGANISM: artificial
<220> FEATURE:
<223> OTHER INFORMATION: RNA Oligomer

<400> SEQUENCE: 1180
cuuuggaggc aagauauaga u                                              21

<210> SEQ ID NO 1181
<211> LENGTH: 21
<212> TYPE: RNA
<213> ORGANISM: artificial
<220> FEATURE:
<223> OTHER INFORMATION: RNA Oligomer

<400> SEQUENCE: 1181
gacauugagc aaguuuggga g                                              21

<210> SEQ ID NO 1182
<211> LENGTH: 21
<212> TYPE: RNA
<213> ORGANISM: artificial
<220> FEATURE:
<223> OTHER INFORMATION: RNA Oligomer

<400> SEQUENCE: 1182
ggacauugag caaguuuggg a                                              21

<210> SEQ ID NO 1183
<211> LENGTH: 21
<212> TYPE: RNA
<213> ORGANISM: artificial
<220> FEATURE:
<223> OTHER INFORMATION: RNA Oligomer

<400> SEQUENCE: 1183
gucaccugaa acuucuguug c                                              21

<210> SEQ ID NO 1184
<211> LENGTH: 21
<212> TYPE: RNA
<213> ORGANISM: artificial
<220> FEATURE:
<223> OTHER INFORMATION: RNA Oligomer

<400> SEQUENCE: 1184
gcccagucuu cauugcuacu a                                              21

<210> SEQ ID NO 1185
<211> LENGTH: 21
<212> TYPE: RNA
<213> ORGANISM: artificial
<220> FEATURE:
<223> OTHER INFORMATION: RNA Oligomer

<400> SEQUENCE: 1185
ucgagagccc agucuucauu g                                              21
```

<210> SEQ ID NO 1186
<211> LENGTH: 21
<212> TYPE: RNA
<213> ORGANISM: artificial
<220> FEATURE:
<223> OTHER INFORMATION: RNA Oligomer

<400> SEQUENCE: 1186
ucggcuacgu uucagucacu u                                           21

<210> SEQ ID NO 1187
<211> LENGTH: 21
<212> TYPE: RNA
<213> ORGANISM: artificial
<220> FEATURE:
<223> OTHER INFORMATION: RNA Oligomer

<400> SEQUENCE: 1187
gagguuucuu cggcuacguu u                                           21

<210> SEQ ID NO 1188
<211> LENGTH: 21
<212> TYPE: RNA
<213> ORGANISM: artificial
<220> FEATURE:
<223> OTHER INFORMATION: RNA Oligomer

<400> SEQUENCE: 1188
uuguacuuug augacugcau g                                           21

<210> SEQ ID NO 1189
<211> LENGTH: 21
<212> TYPE: RNA
<213> ORGANISM: artificial
<220> FEATURE:
<223> OTHER INFORMATION: RNA Oligomer

<400> SEQUENCE: 1189
augcuuugua cuuugaugac u                                           21

<210> SEQ ID NO 1190
<211> LENGTH: 21
<212> TYPE: RNA
<213> ORGANISM: artificial
<220> FEATURE:
<223> OTHER INFORMATION: RNA Oligomer

<400> SEQUENCE: 1190
gaugcuuugu acuuugauga c                                           21

<210> SEQ ID NO 1191
<211> LENGTH: 21
<212> TYPE: RNA
<213> ORGANISM: artificial
<220> FEATURE:
<223> OTHER INFORMATION: RNA Oligomer

<400> SEQUENCE: 1191
cuagaugaag agacagguga a                                           21

<210> SEQ ID NO 1192
<211> LENGTH: 21
<212> TYPE: RNA
<213> ORGANISM: artificial
<220> FEATURE:
<223> OTHER INFORMATION: RNA Oligomer

<400> SEQUENCE: 1192
guauggacaa aaaauggcau u    21

<210> SEQ ID NO 1193
<211> LENGTH: 21
<212> TYPE: RNA
<213> ORGANISM: artificial
<220> FEATURE:
<223> OTHER INFORMATION: RNA Oligomer

<400> SEQUENCE: 1193
uguauggaca aaaaauggca u    21

<210> SEQ ID NO 1194
<211> LENGTH: 21
<212> TYPE: RNA
<213> ORGANISM: artificial
<220> FEATURE:
<223> OTHER INFORMATION: RNA Oligomer

<400> SEQUENCE: 1194
acaauuucuu aggacaccau u    21

<210> SEQ ID NO 1195
<211> LENGTH: 21
<212> TYPE: RNA
<213> ORGANISM: artificial
<220> FEATURE:
<223> OTHER INFORMATION: RNA Oligomer

<400> SEQUENCE: 1195
ugaugugaaa ugcucauacu u    21

<210> SEQ ID NO 1196
<211> LENGTH: 21
<212> TYPE: RNA
<213> ORGANISM: artificial
<220> FEATURE:
<223> OTHER INFORMATION: RNA Oligomer

<400> SEQUENCE: 1196
uccuacugug augugaaaug c    21

<210> SEQ ID NO 1197
<211> LENGTH: 21
<212> TYPE: RNA
<213> ORGANISM: artificial
<220> FEATURE:
<223> OTHER INFORMATION: RNA Oligomer

<400> SEQUENCE: 1197
uccuagugaa uacucccugc a    21

<210> SEQ ID NO 1198
<211> LENGTH: 21
<212> TYPE: RNA
<213> ORGANISM: artificial
<220> FEATURE:
<223> OTHER INFORMATION: RNA Oligomer

<400> SEQUENCE: 1198
acacggucca cagcucauca u    21

<210> SEQ ID NO 1199
<211> LENGTH: 21
<212> TYPE: RNA
<213> ORGANISM: artificial

```
<220> FEATURE:
<223> OTHER INFORMATION: RNA Oligomer

<400> SEQUENCE: 1199
gaagugucaa acagaauggu c                                              21

<210> SEQ ID NO 1200
<211> LENGTH: 21
<212> TYPE: RNA
<213> ORGANISM: artificial
<220> FEATURE:
<223> OTHER INFORMATION: RNA Oligomer

<400> SEQUENCE: 1200
uggaaguguc aaacagaaug g                                              21

<210> SEQ ID NO 1201
<211> LENGTH: 21
<212> TYPE: RNA
<213> ORGANISM: artificial
<220> FEATURE:
<223> OTHER INFORMATION: RNA Oligomer

<400> SEQUENCE: 1201
gugauucuga aguggaagag c                                              21

<210> SEQ ID NO 1202
<211> LENGTH: 21
<212> TYPE: RNA
<213> ORGANISM: artificial
<220> FEATURE:
<223> OTHER INFORMATION: RNA Oligomer

<400> SEQUENCE: 1202
gaaagcacag cagaauucaa u                                              21

<210> SEQ ID NO 1203
<211> LENGTH: 21
<212> TYPE: RNA
<213> ORGANISM: artificial
<220> FEATURE:
<223> OTHER INFORMATION: RNA Oligomer

<400> SEQUENCE: 1203
cacagucaac acagauuuug g                                              21

<210> SEQ ID NO 1204
<211> LENGTH: 21
<212> TYPE: RNA
<213> ORGANISM: artificial
<220> FEATURE:
<223> OTHER INFORMATION: RNA Oligomer

<400> SEQUENCE: 1204
cagaagccaa acugacagaa g                                              21

<210> SEQ ID NO 1205
<211> LENGTH: 21
<212> TYPE: RNA
<213> ORGANISM: artificial
<220> FEATURE:
<223> OTHER INFORMATION: RNA Oligomer

<400> SEQUENCE: 1205
accugaaacu ucuguugcuc a                                              21
```

```
<210> SEQ ID NO 1206
<211> LENGTH: 21
<212> TYPE: RNA
<213> ORGANISM: artificial
<220> FEATURE:
<223> OTHER INFORMATION: RNA Oligomer

<400> SEQUENCE: 1206
uugacauacu uuggaggcaa g                                              21

<210> SEQ ID NO 1207
<211> LENGTH: 21
<212> TYPE: RNA
<213> ORGANISM: artificial
<220> FEATURE:
<223> OTHER INFORMATION: RNA Oligomer

<400> SEQUENCE: 1207
uugauugaca uacuuuggag g                                              21

<210> SEQ ID NO 1208
<211> LENGTH: 21
<212> TYPE: RNA
<213> ORGANISM: artificial
<220> FEATURE:
<223> OTHER INFORMATION: RNA Oligomer

<400> SEQUENCE: 1208
gucacuuguu ccugauauuc c                                              21

<210> SEQ ID NO 1209
<211> LENGTH: 21
<212> TYPE: RNA
<213> ORGANISM: artificial
<220> FEATURE:
<223> OTHER INFORMATION: RNA Oligomer

<400> SEQUENCE: 1209
gcuuuguacu uugaugacug c                                              21

<210> SEQ ID NO 1210
<211> LENGTH: 21
<212> TYPE: RNA
<213> ORGANISM: artificial
<220> FEATURE:
<223> OTHER INFORMATION: RNA Oligomer

<400> SEQUENCE: 1210
caggacaugg auuugauuga c                                              21

<210> SEQ ID NO 1211
<211> LENGTH: 21
<212> TYPE: RNA
<213> ORGANISM: artificial
<220> FEATURE:
<223> OTHER INFORMATION: RNA Oligomer

<400> SEQUENCE: 1211
caguuacaac uagaugaaga g                                              21

<210> SEQ ID NO 1212
<211> LENGTH: 21
<212> TYPE: RNA
<213> ORGANISM: artificial
<220> FEATURE:
<223> OTHER INFORMATION: RNA Oligomer

<400> SEQUENCE: 1212
```

-continued gauaugacau cuggcuaaaa a                                            21

<210> SEQ ID NO 1213
<211> LENGTH: 21
<212> TYPE: RNA
<213> ORGANISM: artificial
<220> FEATURE:
<223> OTHER INFORMATION: RNA Oligomer

<400> SEQUENCE: 1213
caguauguug aaucaguagu u                                            21

<210> SEQ ID NO 1214
<211> LENGTH: 21
<212> TYPE: RNA
<213> ORGANISM: artificial
<220> FEATURE:
<223> OTHER INFORMATION: RNA Oligomer

<400> SEQUENCE: 1214
agcauuggag ugucaguaug u                                            21

<210> SEQ ID NO 1215
<211> LENGTH: 21
<212> TYPE: RNA
<213> ORGANISM: artificial
<220> FEATURE:
<223> OTHER INFORMATION: RNA Oligomer

<400> SEQUENCE: 1215
aaagcauugg agugucagua u                                            21

<210> SEQ ID NO 1216
<211> LENGTH: 21
<212> TYPE: RNA
<213> ORGANISM: artificial
<220> FEATURE:
<223> OTHER INFORMATION: RNA Oligomer

<400> SEQUENCE: 1216
ccuacuguga ugugaaaugc u                                            21

<210> SEQ ID NO 1217
<211> LENGTH: 21
<212> TYPE: RNA
<213> ORGANISM: artificial
<220> FEATURE:
<223> OTHER INFORMATION: RNA Oligomer

<400> SEQUENCE: 1217
ugaccuuuuc ugagcuaguu u                                            21

<210> SEQ ID NO 1218
<211> LENGTH: 21
<212> TYPE: RNA
<213> ORGANISM: artificial
<220> FEATURE:
<223> OTHER INFORMATION: RNA Oligomer

<400> SEQUENCE: 1218
gauuugaccu uuucugagcu a                                            21

<210> SEQ ID NO 1219
<211> LENGTH: 21
<212> TYPE: RNA
<213> ORGANISM: artificial

```
<220> FEATURE:
<223> OTHER INFORMATION: RNA Oligomer

<400> SEQUENCE: 1219
cagcaugcua cgugaugaag a                                               21

<210> SEQ ID NO 1220
<211> LENGTH: 21
<212> TYPE: RNA
<213> ORGANISM: artificial
<220> FEATURE:
<223> OTHER INFORMATION: RNA Oligomer

<400> SEQUENCE: 1220
caccuuauau cucgaaguuu u                                               21

<210> SEQ ID NO 1221
<211> LENGTH: 21
<212> TYPE: RNA
<213> ORGANISM: artificial
<220> FEATURE:
<223> OTHER INFORMATION: RNA Oligomer

<400> SEQUENCE: 1221
ucagcaccuu auaucucgaa g                                               21

<210> SEQ ID NO 1222
<211> LENGTH: 21
<212> TYPE: RNA
<213> ORGANISM: artificial
<220> FEATURE:
<223> OTHER INFORMATION: RNA Oligomer

<400> SEQUENCE: 1222
acucagcacc uuauaucucg a                                               21

<210> SEQ ID NO 1223
<211> LENGTH: 21
<212> TYPE: RNA
<213> ORGANISM: artificial
<220> FEATURE:
<223> OTHER INFORMATION: RNA Oligomer

<400> SEQUENCE: 1223
auaguagaac uagagcaaga u                                               21

<210> SEQ ID NO 1224
<211> LENGTH: 21
<212> TYPE: RNA
<213> ORGANISM: artificial
<220> FEATURE:
<223> OTHER INFORMATION: RNA Oligomer

<400> SEQUENCE: 1224
ggauauacgu aggaggggua a                                               21

<210> SEQ ID NO 1225
<211> LENGTH: 21
<212> TYPE: RNA
<213> ORGANISM: artificial
<220> FEATURE:
<223> OTHER INFORMATION: RNA Oligomer

<400> SEQUENCE: 1225
aaagcucucc auaucccauu c                                               21
```

```
<210> SEQ ID NO 1226
<211> LENGTH: 21
<212> TYPE: RNA
<213> ORGANISM: artificial
<220> FEATURE:
<223> OTHER INFORMATION: RNA Oligomer

<400> SEQUENCE: 1226
gcaaaagcuc uccauauccc a                                              21

<210> SEQ ID NO 1227
<211> LENGTH: 21
<212> TYPE: RNA
<213> ORGANISM: artificial
<220> FEATURE:
<223> OTHER INFORMATION: RNA Oligomer

<400> SEQUENCE: 1227
agagaugaac uuagggcaaa a                                              21

<210> SEQ ID NO 1228
<211> LENGTH: 21
<212> TYPE: RNA
<213> ORGANISM: artificial
<220> FEATURE:
<223> OTHER INFORMATION: RNA Oligomer

<400> SEQUENCE: 1228
caagagauga acuuagggca a                                              21

<210> SEQ ID NO 1229
<211> LENGTH: 21
<212> TYPE: RNA
<213> ORGANISM: artificial
<220> FEATURE:
<223> OTHER INFORMATION: RNA Oligomer

<400> SEQUENCE: 1229
ucacaagaga ugaacuuagg g                                              21

<210> SEQ ID NO 1230
<211> LENGTH: 21
<212> TYPE: RNA
<213> ORGANISM: artificial
<220> FEATURE:
<223> OTHER INFORMATION: RNA Oligomer

<400> SEQUENCE: 1230
ggaaguguca aacagaaugg u                                              21

<210> SEQ ID NO 1231
<211> LENGTH: 21
<212> TYPE: RNA
<213> ORGANISM: artificial
<220> FEATURE:
<223> OTHER INFORMATION: RNA Oligomer

<400> SEQUENCE: 1231
ccuggaagug ucaaacagaa u                                              21

<210> SEQ ID NO 1232
<211> LENGTH: 21
<212> TYPE: RNA
<213> ORGANISM: artificial
<220> FEATURE:
<223> OTHER INFORMATION: RNA Oligomer

<400> SEQUENCE: 1232
```
gauucugaag uggaagagcu a    21

<210> SEQ ID NO 1233
<211> LENGTH: 21
<212> TYPE: RNA
<213> ORGANISM: artificial
<220> FEATURE:
<223> OTHER INFORMATION: RNA Oligomer

<400> SEQUENCE: 1233
gcgacggaaa gaguaugagc u    21

<210> SEQ ID NO 1234
<211> LENGTH: 21
<212> TYPE: RNA
<213> ORGANISM: artificial
<220> FEATURE:
<223> OTHER INFORMATION: RNA Oligomer

<400> SEQUENCE: 1234
uucugaucua ucacuuugca a    21

<210> SEQ ID NO 1235
<211> LENGTH: 21
<212> TYPE: RNA
<213> ORGANISM: artificial
<220> FEATURE:
<223> OTHER INFORMATION: RNA Oligomer

<400> SEQUENCE: 1235
aucuuggagu aagucgagaa g    21

<210> SEQ ID NO 1236
<211> LENGTH: 21
<212> TYPE: RNA
<213> ORGANISM: artificial
<220> FEATURE:
<223> OTHER INFORMATION: RNA Oligomer

<400> SEQUENCE: 1236
caacaggaca uugagcaagu u    21

<210> SEQ ID NO 1237
<211> LENGTH: 21
<212> TYPE: RNA
<213> ORGANISM: artificial
<220> FEATURE:
<223> OTHER INFORMATION: RNA Oligomer

<400> SEQUENCE: 1237
ucaccugaaa cuucuguugc u    21

<210> SEQ ID NO 1238
<211> LENGTH: 21
<212> TYPE: RNA
<213> ORGANISM: artificial
<220> FEATURE:
<223> OTHER INFORMATION: RNA Oligomer

<400> SEQUENCE: 1238
aucgagagcc cagucuucau u    21

<210> SEQ ID NO 1239
<211> LENGTH: 21
<212> TYPE: RNA
<213> ORGANISM: artificial

```
<220> FEATURE:
<223> OTHER INFORMATION: RNA Oligomer

<400> SEQUENCE: 1239
uacguuucag ucacuuguuc c                                              21

<210> SEQ ID NO 1240
<211> LENGTH: 21
<212> TYPE: RNA
<213> ORGANISM: artificial
<220> FEATURE:
<223> OTHER INFORMATION: RNA Oligomer

<400> SEQUENCE: 1240
gcuacguuuc agucacuugu u                                              21

<210> SEQ ID NO 1241
<211> LENGTH: 21
<212> TYPE: RNA
<213> ORGANISM: artificial
<220> FEATURE:
<223> OTHER INFORMATION: RNA Oligomer

<400> SEQUENCE: 1241
ggcuacguuu cagucacuug u                                              21

<210> SEQ ID NO 1242
<211> LENGTH: 21
<212> TYPE: RNA
<213> ORGANISM: artificial
<220> FEATURE:
<223> OTHER INFORMATION: RNA Oligomer

<400> SEQUENCE: 1242
cggcuacguu ucagucacuu g                                              21

<210> SEQ ID NO 1243
<211> LENGTH: 21
<212> TYPE: RNA
<213> ORGANISM: artificial
<220> FEATURE:
<223> OTHER INFORMATION: RNA Oligomer

<400> SEQUENCE: 1243
uuucuucggc uacguuucag u                                              21

<210> SEQ ID NO 1244
<211> LENGTH: 21
<212> TYPE: RNA
<213> ORGANISM: artificial
<220> FEATURE:
<223> OTHER INFORMATION: RNA Oligomer

<400> SEQUENCE: 1244
gacauggauu ugauugacau a                                              21

<210> SEQ ID NO 1245
<211> LENGTH: 21
<212> TYPE: RNA
<213> ORGANISM: artificial
<220> FEATURE:
<223> OTHER INFORMATION: RNA Oligomer

<400> SEQUENCE: 1245
auaugacauc uggcuaaaaa g                                              21
```

```
<210> SEQ ID NO 1246
<211> LENGTH: 21
<212> TYPE: RNA
<213> ORGANISM: artificial
<220> FEATURE:
<223> OTHER INFORMATION: RNA Oligomer

<400> SEQUENCE: 1246
uugggcuagu uucuguguaa g                                              21

<210> SEQ ID NO 1247
<211> LENGTH: 21
<212> TYPE: RNA
<213> ORGANISM: artificial
<220> FEATURE:
<223> OTHER INFORMATION: RNA Oligomer

<400> SEQUENCE: 1247
gucaguaugu ugaaucagua g                                              21

<210> SEQ ID NO 1248
<211> LENGTH: 21
<212> TYPE: RNA
<213> ORGANISM: artificial
<220> FEATURE:
<223> OTHER INFORMATION: RNA Oligomer

<400> SEQUENCE: 1248
ugucaguaug uugaaucagu a                                              21

<210> SEQ ID NO 1249
<211> LENGTH: 21
<212> TYPE: RNA
<213> ORGANISM: artificial
<220> FEATURE:
<223> OTHER INFORMATION: RNA Oligomer

<400> SEQUENCE: 1249
gugucaguau guugaaucag u                                              21

<210> SEQ ID NO 1250
<211> LENGTH: 21
<212> TYPE: RNA
<213> ORGANISM: artificial
<220> FEATURE:
<223> OTHER INFORMATION: RNA Oligomer

<400> SEQUENCE: 1250
uuggaguguc aguauguuga a                                              21

<210> SEQ ID NO 1251
<211> LENGTH: 21
<212> TYPE: RNA
<213> ORGANISM: artificial
<220> FEATURE:
<223> OTHER INFORMATION: RNA Oligomer

<400> SEQUENCE: 1251
uacugugaug ugaaaugcuc a                                              21

<210> SEQ ID NO 1252
<211> LENGTH: 21
<212> TYPE: RNA
<213> ORGANISM: artificial
<220> FEATURE:
<223> OTHER INFORMATION: RNA Oligomer

<400> SEQUENCE: 1252
```
accuuuucug agcuaguuuu u                                            21

<210> SEQ ID NO 1253
<211> LENGTH: 21
<212> TYPE: RNA
<213> ORGANISM: artificial
<220> FEATURE:
<223> OTHER INFORMATION: RNA Oligomer

<400> SEQUENCE: 1253
uuugaccuuu ucugagcuag u                                            21

<210> SEQ ID NO 1254
<211> LENGTH: 21
<212> TYPE: RNA
<213> ORGANISM: artificial
<220> FEATURE:
<223> OTHER INFORMATION: RNA Oligomer

<400> SEQUENCE: 1254
ugcagcaaac aagagauggc a                                            21

<210> SEQ ID NO 1255
<211> LENGTH: 21
<212> TYPE: RNA
<213> ORGANISM: artificial
<220> FEATURE:
<223> OTHER INFORMATION: RNA Oligomer

<400> SEQUENCE: 1255
cuccuaguga auacucccug c                                            21

<210> SEQ ID NO 1256
<211> LENGTH: 21
<212> TYPE: RNA
<213> ORGANISM: artificial
<220> FEATURE:
<223> OTHER INFORMATION: RNA Oligomer

<400> SEQUENCE: 1256
gcaugcuacg ugaugaagau g                                            21

<210> SEQ ID NO 1257
<211> LENGTH: 21
<212> TYPE: RNA
<213> ORGANISM: artificial
<220> FEATURE:
<223> OTHER INFORMATION: RNA Oligomer

<400> SEQUENCE: 1257
accuuauauc ucgaaguuuu c                                            21

<210> SEQ ID NO 1258
<211> LENGTH: 21
<212> TYPE: RNA
<213> ORGANISM: artificial
<220> FEATURE:
<223> OTHER INFORMATION: RNA Oligomer

<400> SEQUENCE: 1258
uuaauucggg auauacguag g                                            21

<210> SEQ ID NO 1259
<211> LENGTH: 21
<212> TYPE: RNA
<213> ORGANISM: artificial

```
<220> FEATURE:
<223> OTHER INFORMATION: RNA Oligomer

<400> SEQUENCE: 1259
caacgaaaug auguccaaag a                                              21

<210> SEQ ID NO 1260
<211> LENGTH: 21
<212> TYPE: RNA
<213> ORGANISM: artificial
<220> FEATURE:
<223> OTHER INFORMATION: RNA Oligomer

<400> SEQUENCE: 1260
aaccucccug uuguugacuu c                                              21

<210> SEQ ID NO 1261
<211> LENGTH: 21
<212> TYPE: RNA
<213> ORGANISM: artificial
<220> FEATURE:
<223> OTHER INFORMATION: RNA Oligomer

<400> SEQUENCE: 1261
gagaugaacu uagggcaaaa g                                              21

<210> SEQ ID NO 1262
<211> LENGTH: 21
<212> TYPE: RNA
<213> ORGANISM: artificial
<220> FEATURE:
<223> OTHER INFORMATION: RNA Oligomer

<400> SEQUENCE: 1262
acaagagaug aacuuagggc a                                              21

<210> SEQ ID NO 1263
<211> LENGTH: 21
<212> TYPE: RNA
<213> ORGANISM: artificial
<220> FEATURE:
<223> OTHER INFORMATION: RNA Oligomer

<400> SEQUENCE: 1263
aaagcacagc agaauucaau g                                              21

<210> SEQ ID NO 1264
<211> LENGTH: 21
<212> TYPE: RNA
<213> ORGANISM: artificial
<220> FEATURE:
<223> OTHER INFORMATION: RNA Oligomer

<400> SEQUENCE: 1264
gauguuucug aucuaucacu u                                              21

<210> SEQ ID NO 1265
<211> LENGTH: 21
<212> TYPE: RNA
<213> ORGANISM: artificial
<220> FEATURE:
<223> OTHER INFORMATION: RNA Oligomer

<400> SEQUENCE: 1265
acagucaaca cagauuuugg u                                              21
```

<210> SEQ ID NO 1266
<211> LENGTH: 21
<212> TYPE: RNA
<213> ORGANISM: artificial
<220> FEATURE:
<223> OTHER INFORMATION: RNA Oligomer

<400> SEQUENCE: 1266
ugaggauucc uucagcagca u                                              21

<210> SEQ ID NO 1267
<211> LENGTH: 21
<212> TYPE: RNA
<213> ORGANISM: artificial
<220> FEATURE:
<223> OTHER INFORMATION: RNA Oligomer

<400> SEQUENCE: 1267
ugacauacuu uggaggcaag a                                              21

<210> SEQ ID NO 1268
<211> LENGTH: 21
<212> TYPE: RNA
<213> ORGANISM: artificial
<220> FEATURE:
<223> OTHER INFORMATION: RNA Oligomer

<400> SEQUENCE: 1268
cauggauuug auugacauac u                                              21

<210> SEQ ID NO 1269
<211> LENGTH: 21
<212> TYPE: RNA
<213> ORGANISM: artificial
<220> FEATURE:
<223> OTHER INFORMATION: RNA Oligomer

<400> SEQUENCE: 1269
gcaggacaug gauuugauug a                                              21

<210> SEQ ID NO 1270
<211> LENGTH: 21
<212> TYPE: RNA
<213> ORGANISM: artificial
<220> FEATURE:
<223> OTHER INFORMATION: RNA Oligomer

<400> SEQUENCE: 1270
augaagagac aggugaauuu c                                              21

<210> SEQ ID NO 1271
<211> LENGTH: 21
<212> TYPE: RNA
<213> ORGANISM: artificial
<220> FEATURE:
<223> OTHER INFORMATION: RNA Oligomer

<400> SEQUENCE: 1271
agaugaagag acaggugaau u                                              21

<210> SEQ ID NO 1272
<211> LENGTH: 21
<212> TYPE: RNA
<213> ORGANISM: artificial
<220> FEATURE:
<223> OTHER INFORMATION: RNA Oligomer

<400> SEQUENCE: 1272
uugcaaaacu aaccacuaug u                                              21

<210> SEQ ID NO 1273
<211> LENGTH: 21
<212> TYPE: RNA
<213> ORGANISM: artificial
<220> FEATURE:
<223> OTHER INFORMATION: RNA Oligomer

<400> SEQUENCE: 1273
augacaucug gcuaaaaga a                                               21

<210> SEQ ID NO 1274
<211> LENGTH: 21
<212> TYPE: RNA
<213> ORGANISM: artificial
<220> FEATURE:
<223> OTHER INFORMATION: RNA Oligomer

<400> SEQUENCE: 1274
gggcuaguuu cuguguaagu g                                              21

<210> SEQ ID NO 1275
<211> LENGTH: 21
<212> TYPE: RNA
<213> ORGANISM: artificial
<220> FEATURE:
<223> OTHER INFORMATION: RNA Oligomer

<400> SEQUENCE: 1275
uuugggcuag uuucugugua a                                              21

<210> SEQ ID NO 1276
<211> LENGTH: 21
<212> TYPE: RNA
<213> ORGANISM: artificial
<220> FEATURE:
<223> OTHER INFORMATION: RNA Oligomer

<400> SEQUENCE: 1276
ggagugucag uauguugaau c                                              21

<210> SEQ ID NO 1277
<211> LENGTH: 21
<212> TYPE: RNA
<213> ORGANISM: artificial
<220> FEATURE:
<223> OTHER INFORMATION: RNA Oligomer

<400> SEQUENCE: 1277
ugugauguga aaugcucaua c                                              21

<210> SEQ ID NO 1278
<211> LENGTH: 21
<212> TYPE: RNA
<213> ORGANISM: artificial
<220> FEATURE:
<223> OTHER INFORMATION: RNA Oligomer

<400> SEQUENCE: 1278
cucagcaccu uauaucucga a                                              21

<210> SEQ ID NO 1279
<211> LENGTH: 21
<212> TYPE: RNA
<213> ORGANISM: artificial

```
<220> FEATURE:
<223> OTHER INFORMATION: RNA Oligomer

<400> SEQUENCE: 1279
uaauucggga uauacguagg a                                              21

<210> SEQ ID NO 1280
<211> LENGTH: 21
<212> TYPE: RNA
<213> ORGANISM: artificial
<220> FEATURE:
<223> OTHER INFORMATION: RNA Oligomer

<400> SEQUENCE: 1280
aaagacaaga acaacuccaa a                                              21

<210> SEQ ID NO 1281
<211> LENGTH: 21
<212> TYPE: RNA
<213> ORGANISM: artificial
<220> FEATURE:
<223> OTHER INFORMATION: RNA Oligomer

<400> SEQUENCE: 1281
gaaagacaag aacaacucca a                                              21

<210> SEQ ID NO 1282
<211> LENGTH: 21
<212> TYPE: RNA
<213> ORGANISM: artificial
<220> FEATURE:
<223> OTHER INFORMATION: RNA Oligomer

<400> SEQUENCE: 1282
cgaaaugaug uccaaagagc a                                              21

<210> SEQ ID NO 1283
<211> LENGTH: 21
<212> TYPE: RNA
<213> ORGANISM: artificial
<220> FEATURE:
<223> OTHER INFORMATION: RNA Oligomer

<400> SEQUENCE: 1283
aacgaaauga uguccaaaga g                                              21

<210> SEQ ID NO 1284
<211> LENGTH: 21
<212> TYPE: RNA
<213> ORGANISM: artificial
<220> FEATURE:
<223> OTHER INFORMATION: RNA Oligomer

<400> SEQUENCE: 1284
accucccugu uguugacuuc a                                              21

<210> SEQ ID NO 1285
<211> LENGTH: 21
<212> TYPE: RNA
<213> ORGANISM: artificial
<220> FEATURE:
<223> OTHER INFORMATION: RNA Oligomer

<400> SEQUENCE: 1285
aucauuaacc ucccuguugu u                                              21
```

```
<210> SEQ ID NO 1286
<211> LENGTH: 21
<212> TYPE: RNA
<213> ORGANISM: artificial
<220> FEATURE:
<223> OTHER INFORMATION: RNA Oligomer

<400> SEQUENCE: 1286
uuucugaucu aucacuuugc a                                              21

<210> SEQ ID NO 1287
<211> LENGTH: 21
<212> TYPE: RNA
<213> ORGANISM: artificial
<220> FEATURE:
<223> OTHER INFORMATION: RNA Oligomer

<400> SEQUENCE: 1287
cacuuguucc ugauauuccc g                                              21

<210> SEQ ID NO 1288
<211> LENGTH: 21
<212> TYPE: RNA
<213> ORGANISM: artificial
<220> FEATURE:
<223> OTHER INFORMATION: RNA Oligomer

<400> SEQUENCE: 1288
gauuugauug acauacuuug g                                              21

<210> SEQ ID NO 1289
<211> LENGTH: 21
<212> TYPE: RNA
<213> ORGANISM: artificial
<220> FEATURE:
<223> OTHER INFORMATION: RNA Oligomer

<400> SEQUENCE: 1289
acguuucagu cacuuguucc u                                              21

<210> SEQ ID NO 1290
<211> LENGTH: 21
<212> TYPE: RNA
<213> ORGANISM: artificial
<220> FEATURE:
<223> OTHER INFORMATION: RNA Oligomer

<400> SEQUENCE: 1290
acaggugaau uucucccaau u                                              21

<210> SEQ ID NO 1291
<211> LENGTH: 21
<212> TYPE: RNA
<213> ORGANISM: artificial
<220> FEATURE:
<223> OTHER INFORMATION: RNA Oligomer

<400> SEQUENCE: 1291
gagcugguac uaauaaagga u                                              21

<210> SEQ ID NO 1292
<211> LENGTH: 21
<212> TYPE: RNA
<213> ORGANISM: artificial
<220> FEATURE:
<223> OTHER INFORMATION: RNA Oligomer

<400> SEQUENCE: 1292
```
cugugaugug aaaugcucau a                                          21

<210> SEQ ID NO 1293
<211> LENGTH: 21
<212> TYPE: RNA
<213> ORGANISM: artificial
<220> FEATURE:
<223> OTHER INFORMATION: RNA Oligomer

<400> SEQUENCE: 1293
gaaaaacuag auuuaggagg a                                          21

<210> SEQ ID NO 1294
<211> LENGTH: 21
<212> TYPE: RNA
<213> ORGANISM: artificial
<220> FEATURE:
<223> OTHER INFORMATION: RNA Oligomer

<400> SEQUENCE: 1294
gcucaaagaa aaaggagaaa a                                          21

<210> SEQ ID NO 1295
<211> LENGTH: 21
<212> TYPE: RNA
<213> ORGANISM: artificial
<220> FEATURE:
<223> OTHER INFORMATION: RNA Oligomer

<400> SEQUENCE: 1295
agacaagaac aacuccaaaa g                                          21

<210> SEQ ID NO 1296
<211> LENGTH: 21
<212> TYPE: RNA
<213> ORGANISM: artificial
<220> FEATURE:
<223> OTHER INFORMATION: RNA Oligomer

<400> SEQUENCE: 1296
uucgggauau acguaggagg g                                          21

<210> SEQ ID NO 1297
<211> LENGTH: 21
<212> TYPE: RNA
<213> ORGANISM: artificial
<220> FEATURE:
<223> OTHER INFORMATION: RNA Oligomer

<400> SEQUENCE: 1297
auguccaaag agcaguucaa u                                          21

<210> SEQ ID NO 1298
<211> LENGTH: 21
<212> TYPE: RNA
<213> ORGANISM: artificial
<220> FEATURE:
<223> OTHER INFORMATION: RNA Oligomer

<400> SEQUENCE: 1298
ugauguccaa agagcaguuc a                                          21

<210> SEQ ID NO 1299
<211> LENGTH: 21
<212> TYPE: RNA
<213> ORGANISM: artificial

```
<220> FEATURE:
<223> OTHER INFORMATION: RNA Oligomer

<400> SEQUENCE: 1299
gagcuggaaa aacagaaaaa a                                              21

<210> SEQ ID NO 1300
<211> LENGTH: 21
<212> TYPE: RNA
<213> ORGANISM: artificial
<220> FEATURE:
<223> OTHER INFORMATION: RNA Oligomer

<400> SEQUENCE: 1300
ccggcauuuc acuaaacaca a                                              21

<210> SEQ ID NO 1301
<211> LENGTH: 21
<212> TYPE: RNA
<213> ORGANISM: artificial
<220> FEATURE:
<223> OTHER INFORMATION: RNA Oligomer

<400> SEQUENCE: 1301
uugauguuuc ugaucuauca c                                              21

<210> SEQ ID NO 1302
<211> LENGTH: 21
<212> TYPE: RNA
<213> ORGANISM: artificial
<220> FEATURE:
<223> OTHER INFORMATION: RNA Oligomer

<400> SEQUENCE: 1302
ccauugaugu uucugaucua u                                              21

<210> SEQ ID NO 1303
<211> LENGTH: 21
<212> TYPE: RNA
<213> ORGANISM: artificial
<220> FEATURE:
<223> OTHER INFORMATION: RNA Oligomer

<400> SEQUENCE: 1303
cccauugaug uuucugaucu a                                              21

<210> SEQ ID NO 1304
<211> LENGTH: 21
<212> TYPE: RNA
<213> ORGANISM: artificial
<220> FEATURE:
<223> OTHER INFORMATION: RNA Oligomer

<400> SEQUENCE: 1304
ggcccauuga uguuucugau c                                              21

<210> SEQ ID NO 1305
<211> LENGTH: 21
<212> TYPE: RNA
<213> ORGANISM: artificial
<220> FEATURE:
<223> OTHER INFORMATION: RNA Oligomer

<400> SEQUENCE: 1305
aagaaguagg uaacuguagu c                                              21
```

-continued

<210> SEQ ID NO 1306
<211> LENGTH: 21
<212> TYPE: RNA
<213> ORGANISM: artificial
<220> FEATURE:
<223> OTHER INFORMATION: RNA Oligomer

<400> SEQUENCE: 1306
gaccuuuucu gagcuaguuu u                                        21

<210> SEQ ID NO 1307
<211> LENGTH: 21
<212> TYPE: RNA
<213> ORGANISM: artificial
<220> FEATURE:
<223> OTHER INFORMATION: RNA Oligomer

<400> SEQUENCE: 1307
aucucgaagu uuucagcaug c                                        21

<210> SEQ ID NO 1308
<211> LENGTH: 21
<212> TYPE: RNA
<213> ORGANISM: artificial
<220> FEATURE:
<223> OTHER INFORMATION: RNA Oligomer

<400> SEQUENCE: 1308
aagacaagaa caacuccaaa a                                        21

<210> SEQ ID NO 1309
<211> LENGTH: 21
<212> TYPE: RNA
<213> ORGANISM: artificial
<220> FEATURE:
<223> OTHER INFORMATION: RNA Oligomer

<400> SEQUENCE: 1309
gaaaacccca uucacaaaag a                                        21

<210> SEQ ID NO 1310
<211> LENGTH: 21
<212> TYPE: RNA
<213> ORGANISM: artificial
<220> FEATURE:
<223> OTHER INFORMATION: RNA Oligomer

<400> SEQUENCE: 1310
gauauggtac aacccuuguc a                                        21

<210> SEQ ID NO 1311
<211> LENGTH: 21
<212> TYPE: RNA
<213> ORGANISM: artificial
<220> FEATURE:
<223> OTHER INFORMATION: RNA Oligomer

<400> SEQUENCE: 1311
gaaguggaag agcuagauag u                                        21

<210> SEQ ID NO 1312
<211> LENGTH: 21
<212> TYPE: RNA
<213> ORGANISM: artificial
<220> FEATURE:
<223> OTHER INFORMATION: RNA Oligomer

<400> SEQUENCE: 1312
guuucugauc uaucacuuug c                          21

<210> SEQ ID NO 1313
<211> LENGTH: 21
<212> TYPE: RNA
<213> ORGANISM: artificial
<220> FEATURE:
<223> OTHER INFORMATION: RNA Oligomer

<400> SEQUENCE: 1313
gcccauugau guuucugauc u                          21

<210> SEQ ID NO 1314
<211> LENGTH: 21
<212> TYPE: RNA
<213> ORGANISM: artificial
<220> FEATURE:
<223> OTHER INFORMATION: RNA Oligomer

<400> SEQUENCE: 1314
uugcccacau ucccaaauca g                          21

<210> SEQ ID NO 1315
<211> LENGTH: 21
<212> TYPE: RNA
<213> ORGANISM: artificial
<220> FEATURE:
<223> OTHER INFORMATION: RNA Oligomer

<400> SEQUENCE: 1315
guugcccaca uucccaaauc a                          21

<210> SEQ ID NO 1316
<211> LENGTH: 21
<212> TYPE: RNA
<213> ORGANISM: artificial
<220> FEATURE:
<223> OTHER INFORMATION: RNA Oligomer

<400> SEQUENCE: 1316
gcagcaaaca agagauggca a                          21

<210> SEQ ID NO 1317
<211> LENGTH: 21
<212> TYPE: RNA
<213> ORGANISM: artificial
<220> FEATURE:
<223> OTHER INFORMATION: RNA Oligomer

<400> SEQUENCE: 1317
ugcucaaaga aaaaggagaa a                          21

<210> SEQ ID NO 1318
<211> LENGTH: 21
<212> TYPE: RNA
<213> ORGANISM: artificial
<220> FEATURE:
<223> OTHER INFORMATION: RNA Oligomer

<400> SEQUENCE: 1318
gaagcucaac uugcauuaau u                          21

<210> SEQ ID NO 1319
<211> LENGTH: 21
<212> TYPE: RNA
<213> ORGANISM: artificial

```
<220> FEATURE:
<223> OTHER INFORMATION: RNA Oligomer

<400> SEQUENCE: 1319
caaagagcag uucaaugaag c                                              21

<210> SEQ ID NO 1320
<211> LENGTH: 21
<212> TYPE: RNA
<213> ORGANISM: artificial
<220> FEATURE:
<223> OTHER INFORMATION: RNA Oligomer

<400> SEQUENCE: 1320
ggaaaacccc auucacaaaa g                                              21

<210> SEQ ID NO 1321
<211> LENGTH: 21
<212> TYPE: RNA
<213> ORGANISM: artificial
<220> FEATURE:
<223> OTHER INFORMATION: RNA Oligomer

<400> SEQUENCE: 1321
ugagcuggaa aaacagaaaa a                                              21

<210> SEQ ID NO 1322
<211> LENGTH: 21
<212> TYPE: RNA
<213> ORGANISM: artificial
<220> FEATURE:
<223> OTHER INFORMATION: RNA Oligomer

<400> SEQUENCE: 1322
gcccaguauc agcaacagca u                                              21

<210> SEQ ID NO 1323
<211> LENGTH: 21
<212> TYPE: RNA
<213> ORGANISM: artificial
<220> FEATURE:
<223> OTHER INFORMATION: RNA Oligomer

<400> SEQUENCE: 1323
uagguaacug uaguccacau u                                              21

<210> SEQ ID NO 1324
<211> LENGTH: 21
<212> TYPE: RNA
<213> ORGANISM: artificial
<220> FEATURE:
<223> OTHER INFORMATION: RNA Oligomer

<400> SEQUENCE: 1324
cauuccugag uuacaguguc u                                              21

<210> SEQ ID NO 1325
<211> LENGTH: 21
<212> TYPE: RNA
<213> ORGANISM: artificial
<220> FEATURE:
<223> OTHER INFORMATION: RNA Oligomer

<400> SEQUENCE: 1325
ccguuuguag augacaauga g                                              21
```

```
<210> SEQ ID NO 1326
<211> LENGTH: 21
<212> TYPE: RNA
<213> ORGANISM: artificial
<220> FEATURE:
<223> OTHER INFORMATION: RNA Oligomer

<400> SEQUENCE: 1326
gcugguacua auaaaggauu a                                              21

<210> SEQ ID NO 1327
<211> LENGTH: 21
<212> TYPE: RNA
<213> ORGANISM: artificial
<220> FEATURE:
<223> OTHER INFORMATION: RNA Oligomer

<400> SEQUENCE: 1327
aggacaccau uugggcuagu u                                              21

<210> SEQ ID NO 1328
<211> LENGTH: 21
<212> TYPE: RNA
<213> ORGANISM: artificial
<220> FEATURE:
<223> OTHER INFORMATION: RNA Oligomer

<400> SEQUENCE: 1328
gcucuccaua ucccauuccc u                                              21

<210> SEQ ID NO 1329
<211> LENGTH: 21
<212> TYPE: RNA
<213> ORGANISM: artificial
<220> FEATURE:
<223> OTHER INFORMATION: RNA Oligomer

<400> SEQUENCE: 1329
ugggcccauu gauguuucug a                                              21

<210> SEQ ID NO 1330
<211> LENGTH: 21
<212> TYPE: RNA
<213> ORGANISM: artificial
<220> FEATURE:
<223> OTHER INFORMATION: RNA Oligomer

<400> SEQUENCE: 1330
acuuuaagcc auucacucuc u                                              21

<210> SEQ ID NO 1331
<211> LENGTH: 21
<212> TYPE: RNA
<213> ORGANISM: artificial
<220> FEATURE:
<223> OTHER INFORMATION: RNA Oligomer

<400> SEQUENCE: 1331
caccugcuac uuuaagccau u                                              21

<210> SEQ ID NO 1332
<211> LENGTH: 21
<212> TYPE: RNA
<213> ORGANISM: artificial
<220> FEATURE:
<223> OTHER INFORMATION: RNA Oligomer

<400> SEQUENCE: 1332
```
cucaccugcu acuuuaagcc a         21

<210> SEQ ID NO 1333
<211> LENGTH: 21
<212> TYPE: RNA
<213> ORGANISM: artificial
<220> FEATURE:
<223> OTHER INFORMATION: RNA Oligomer

<400> SEQUENCE: 1333
ugaaaaugac aagcugguug a         21

<210> SEQ ID NO 1334
<211> LENGTH: 21
<212> TYPE: RNA
<213> ORGANISM: artificial
<220> FEATURE:
<223> OTHER INFORMATION: RNA Oligomer

<400> SEQUENCE: 1334
agcugguacu aauaaaggau u         21

<210> SEQ ID NO 1335
<211> LENGTH: 21
<212> TYPE: RNA
<213> ORGANISM: artificial
<220> FEATURE:
<223> OTHER INFORMATION: RNA Oligomer

<400> SEQUENCE: 1335
augcaaaauc auagccaaaa c         21

<210> SEQ ID NO 1336
<211> LENGTH: 21
<212> TYPE: RNA
<213> ORGANISM: artificial
<220> FEATURE:
<223> OTHER INFORMATION: RNA Oligomer

<400> SEQUENCE: 1336
caaacaagag auggcaaugu u         21

<210> SEQ ID NO 1337
<211> LENGTH: 21
<212> TYPE: RNA
<213> ORGANISM: artificial
<220> FEATURE:
<223> OTHER INFORMATION: RNA Oligomer

<400> SEQUENCE: 1337
gaaaaugaca aaagccuuca c         21

<210> SEQ ID NO 1338
<211> LENGTH: 21
<212> TYPE: RNA
<213> ORGANISM: artificial
<220> FEATURE:
<223> OTHER INFORMATION: RNA Oligomer

<400> SEQUENCE: 1338
aaaaccccau ucacaaaaga c         21

<210> SEQ ID NO 1339
<211> LENGTH: 21
<212> TYPE: RNA
<213> ORGANISM: artificial

```
<220> FEATURE:
<223> OTHER INFORMATION: RNA Oligomer

<400> SEQUENCE: 1339
augagcugga aaaacagaaa a                                              21

<210> SEQ ID NO 1340
<211> LENGTH: 21
<212> TYPE: RNA
<213> ORGANISM: artificial
<220> FEATURE:
<223> OTHER INFORMATION: RNA Oligomer

<400> SEQUENCE: 1340
cugaagugga agagcuagau a                                              21

<210> SEQ ID NO 1341
<211> LENGTH: 21
<212> TYPE: RNA
<213> ORGANISM: artificial
<220> FEATURE:
<223> OTHER INFORMATION: RNA Oligomer

<400> SEQUENCE: 1341
acuccggcau uucacuaaac a                                              21

<210> SEQ ID NO 1342
<211> LENGTH: 21
<212> TYPE: RNA
<213> ORGANISM: artificial
<220> FEATURE:
<223> OTHER INFORMATION: RNA Oligomer

<400> SEQUENCE: 1342
ccauucacuc ucugaacuuc u                                              21

<210> SEQ ID NO 1343
<211> LENGTH: 21
<212> TYPE: RNA
<213> ORGANISM: artificial
<220> FEATURE:
<223> OTHER INFORMATION: RNA Oligomer

<400> SEQUENCE: 1343
agccauucac ucucugaacu u                                              21

<210> SEQ ID NO 1344
<211> LENGTH: 21
<212> TYPE: RNA
<213> ORGANISM: artificial
<220> FEATURE:
<223> OTHER INFORMATION: RNA Oligomer

<400> SEQUENCE: 1344
cugcuacuuu aagccauuca c                                              21

<210> SEQ ID NO 1345
<211> LENGTH: 21
<212> TYPE: RNA
<213> ORGANISM: artificial
<220> FEATURE:
<223> OTHER INFORMATION: RNA Oligomer

<400> SEQUENCE: 1345
ucaccugcua cuuuaagcca u                                              21
```

```
<210> SEQ ID NO 1346
<211> LENGTH: 21
<212> TYPE: RNA
<213> ORGANISM: artificial
<220> FEATURE:
<223> OTHER INFORMATION: RNA Oligomer

<400> SEQUENCE: 1346
ugcccucacc ugcuacuuua a                                              21

<210> SEQ ID NO 1347
<211> LENGTH: 21
<212> TYPE: RNA
<213> ORGANISM: artificial
<220> FEATURE:
<223> OTHER INFORMATION: RNA Oligomer

<400> SEQUENCE: 1347
augcccucac cugcuacuuu a                                              21

<210> SEQ ID NO 1348
<211> LENGTH: 21
<212> TYPE: RNA
<213> ORGANISM: artificial
<220> FEATURE:
<223> OTHER INFORMATION: RNA Oligomer

<400> SEQUENCE: 1348
auggaaaaag aaguagguaa c                                              21

<210> SEQ ID NO 1349
<211> LENGTH: 21
<212> TYPE: RNA
<213> ORGANISM: artificial
<220> FEATURE:
<223> OTHER INFORMATION: RNA Oligomer

<400> SEQUENCE: 1349
gaagccaaac ugacagaagu u                                              21

<210> SEQ ID NO 1350
<211> LENGTH: 21
<212> TYPE: RNA
<213> ORGANISM: artificial
<220> FEATURE:
<223> OTHER INFORMATION: RNA Oligomer

<400> SEQUENCE: 1350
uuaaaaagca uuggaguguc a                                              21

<210> SEQ ID NO 1351
<211> LENGTH: 21
<212> TYPE: RNA
<213> ORGANISM: artificial
<220> FEATURE:
<223> OTHER INFORMATION: RNA Oligomer

<400> SEQUENCE: 1351
ggcaauguuu uccuuguucc c                                              21

<210> SEQ ID NO 1352
<211> LENGTH: 21
<212> TYPE: RNA
<213> ORGANISM: artificial
<220> FEATURE:
<223> OTHER INFORMATION: RNA Oligomer

<400> SEQUENCE: 1352
```
acaacucagc accuuauauc u                                               21

<210> SEQ ID NO 1353
<211> LENGTH: 21
<212> TYPE: RNA
<213> ORGANISM: artificial
<220> FEATURE:
<223> OTHER INFORMATION: RNA Oligomer

<400> SEQUENCE: 1353
ggcugcucag aauugcagaa a                                               21

<210> SEQ ID NO 1354
<211> LENGTH: 21
<212> TYPE: RNA
<213> ORGANISM: artificial
<220> FEATURE:
<223> OTHER INFORMATION: RNA Oligomer

<400> SEQUENCE: 1354
agcucuccau aucccauucc c                                               21

<210> SEQ ID NO 1355
<211> LENGTH: 21
<212> TYPE: RNA
<213> ORGANISM: artificial
<220> FEATURE:
<223> OTHER INFORMATION: RNA Oligomer

<400> SEQUENCE: 1355
aagcucucca uaucccauuc c                                               21

<210> SEQ ID NO 1356
<211> LENGTH: 21
<212> TYPE: RNA
<213> ORGANISM: artificial
<220> FEATURE:
<223> OTHER INFORMATION: RNA Oligomer

<400> SEQUENCE: 1356
aagacaaaca uucaagccgc u                                               21

<210> SEQ ID NO 1357
<211> LENGTH: 21
<212> TYPE: RNA
<213> ORGANISM: artificial
<220> FEATURE:
<223> OTHER INFORMATION: RNA Oligomer

<400> SEQUENCE: 1357
aaaccccauu cacaaaagac a                                               21

<210> SEQ ID NO 1358
<211> LENGTH: 21
<212> TYPE: RNA
<213> ORGANISM: artificial
<220> FEATURE:
<223> OTHER INFORMATION: RNA Oligomer

<400> SEQUENCE: 1358
cggcauuuca cuaaacacaa g                                               21

<210> SEQ ID NO 1359
<211> LENGTH: 21
<212> TYPE: RNA
<213> ORGANISM: artificial

```
<220> FEATURE:
<223> OTHER INFORMATION: RNA Oligomer

<400> SEQUENCE: 1359
cccguuugua gaugacaaug a                                              21

<210> SEQ ID NO 1360
<211> LENGTH: 21
<212> TYPE: RNA
<213> ORGANISM: artificial
<220> FEATURE:
<223> OTHER INFORMATION: RNA Oligomer

<400> SEQUENCE: 1360
ucccguuugu agaugacaau g                                              21

<210> SEQ ID NO 1361
<211> LENGTH: 21
<212> TYPE: RNA
<213> ORGANISM: artificial
<220> FEATURE:
<223> OTHER INFORMATION: RNA Oligomer

<400> SEQUENCE: 1361
aucugccaac uacucccagg u                                              21

<210> SEQ ID NO 1362
<211> LENGTH: 21
<212> TYPE: RNA
<213> ORGANISM: artificial
<220> FEATURE:
<223> OTHER INFORMATION: RNA Oligomer

<400> SEQUENCE: 1362
gccagauguu aagaaaaacu a                                              21

<210> SEQ ID NO 1363
<211> LENGTH: 21
<212> TYPE: RNA
<213> ORGANISM: artificial
<220> FEATURE:
<223> OTHER INFORMATION: RNA Oligomer

<400> SEQUENCE: 1363
aaaugacaaa agccuucacc u                                              21

<210> SEQ ID NO 1364
<211> LENGTH: 21
<212> TYPE: RNA
<213> ORGANISM: artificial
<220> FEATURE:
<223> OTHER INFORMATION: RNA Oligomer

<400> SEQUENCE: 1364
cugcucagaa uugcagaaaa a                                              21

<210> SEQ ID NO 1365
<211> LENGTH: 21
<212> TYPE: RNA
<213> ORGANISM: artificial
<220> FEATURE:
<223> OTHER INFORMATION: RNA Oligomer

<400> SEQUENCE: 1365
aagcucaacu ugcauuaauu c                                              21
```

```
<210> SEQ ID NO 1366
<211> LENGTH: 21
<212> TYPE: RNA
<213> ORGANISM: artificial
<220> FEATURE:
<223> OTHER INFORMATION: RNA Oligomer

<400> SEQUENCE: 1366
gucaucggaa aaccccauuc a                                          21

<210> SEQ ID NO 1367
<211> LENGTH: 21
<212> TYPE: RNA
<213> ORGANISM: artificial
<220> FEATURE:
<223> OTHER INFORMATION: RNA Oligomer

<400> SEQUENCE: 1367
ccccaaccag uugacaguga a                                          21

<210> SEQ ID NO 1368
<211> LENGTH: 21
<212> TYPE: RNA
<213> ORGANISM: artificial
<220> FEATURE:
<223> OTHER INFORMATION: RNA Oligomer

<400> SEQUENCE: 1368 gaaaagaag uagguaacug u                                           21

<210> SEQ ID NO 1369
<211> LENGTH: 21
<212> TYPE: RNA
<213> ORGANISM: artificial
<220> FEATURE:
<223> OTHER INFORMATION: RNA Oligomer

<400> SEQUENCE: 1369 uggaaaaga aguaggguaac u                                          21

<210> SEQ ID NO 1370
<211> LENGTH: 21
<212> TYPE: RNA
<213> ORGANISM: artificial
<220> FEATURE:
<223> OTHER INFORMATION: RNA Oligomer

<400> SEQUENCE: 1370
caaguccaga agccaaacug a                                          21

<210> SEQ ID NO 1371
<211> LENGTH: 21
<212> TYPE: RNA
<213> ORGANISM: artificial
<220> FEATURE:
<223> OTHER INFORMATION: RNA Oligomer

<400> SEQUENCE: 1371
ugggaggagc uauuauccau u                                          21

<210> SEQ ID NO 1372
<211> LENGTH: 21
<212> TYPE: RNA
<213> ORGANISM: artificial
<220> FEATURE:
<223> OTHER INFORMATION: RNA Oligomer

<400> SEQUENCE: 1372
```
ugcaaaacua accacuaugu a                                    21

<210> SEQ ID NO 1373
<211> LENGTH: 21
<212> TYPE: RNA
<213> ORGANISM: artificial
<220> FEATURE:
<223> OTHER INFORMATION: RNA Oligomer

<400> SEQUENCE: 1373
auggaaaacc uuauucuccu a                                    21

<210> SEQ ID NO 1374
<211> LENGTH: 21
<212> TYPE: RNA
<213> ORGANISM: artificial
<220> FEATURE:
<223> OTHER INFORMATION: RNA Oligomer

<400> SEQUENCE: 1374
agccuucacc uacugaaaaa a                                    21

<210> SEQ ID NO 1375
<211> LENGTH: 21
<212> TYPE: RNA
<213> ORGANISM: artificial
<220> FEATURE:
<223> OTHER INFORMATION: RNA Oligomer

<400> SEQUENCE: 1375
aaggagaaaa ugacaaaagc c                                    21

<210> SEQ ID NO 1376
<211> LENGTH: 21
<212> TYPE: RNA
<213> ORGANISM: artificial
<220> FEATURE:
<223> OTHER INFORMATION: RNA Oligomer

<400> SEQUENCE: 1376
aaagacaaac auucaagccg c                                    21

<210> SEQ ID NO 1377
<211> LENGTH: 21
<212> TYPE: RNA
<213> ORGANISM: artificial
<220> FEATURE:
<223> OTHER INFORMATION: RNA Oligomer

<400> SEQUENCE: 1377
uaaguccugg ucaucggaaa a                                    21

<210> SEQ ID NO 1378
<211> LENGTH: 21
<212> TYPE: RNA
<213> ORGANISM: artificial
<220> FEATURE:
<223> OTHER INFORMATION: RNA Oligomer

<400> SEQUENCE: 1378
uaugagcugg aaaaacagaa a                                    21

<210> SEQ ID NO 1379
<211> LENGTH: 21
<212> TYPE: RNA
<213> ORGANISM: artificial

```
<220> FEATURE:
<223> OTHER INFORMATION: RNA Oligomer

<400> SEQUENCE: 1379
acaacccuug ucaccaucuc a                                              21

<210> SEQ ID NO 1380
<211> LENGTH: 21
<212> TYPE: RNA
<213> ORGANISM: artificial
<220> FEATURE:
<223> OTHER INFORMATION: RNA Oligomer

<400> SEQUENCE: 1380
guacaacccu ugucaccauc u                                              21

<210> SEQ ID NO 1381
<211> LENGTH: 21
<212> TYPE: RNA
<213> ORGANISM: artificial
<220> FEATURE:
<223> OTHER INFORMATION: RNA Oligomer

<400> SEQUENCE: 1381
gacacacuac uuggccucag u                                              21

<210> SEQ ID NO 1382
<211> LENGTH: 21
<212> TYPE: RNA
<213> ORGANISM: artificial
<220> FEATURE:
<223> OTHER INFORMATION: RNA Oligomer

<400> SEQUENCE: 1382
cugaucuauc acuuugcaaa g                                              21

<210> SEQ ID NO 1383
<211> LENGTH: 21
<212> TYPE: RNA
<213> ORGANISM: artificial
<220> FEATURE:
<223> OTHER INFORMATION: RNA Oligomer

<400> SEQUENCE: 1383
ccugcuacuu uaagccauuc a                                              21

<210> SEQ ID NO 1384
<211> LENGTH: 21
<212> TYPE: RNA
<213> ORGANISM: artificial
<220> FEATURE:
<223> OTHER INFORMATION: RNA Oligomer

<400> SEQUENCE: 1384
cgagaaguau uugacuucag u                                              21

<210> SEQ ID NO 1385
<211> LENGTH: 21
<212> TYPE: RNA
<213> ORGANISM: artificial
<220> FEATURE:
<223> OTHER INFORMATION: RNA Oligomer

<400> SEQUENCE: 1385
uucccguuug uagaugacaa u                                              21
```

```
<210> SEQ ID NO 1386
<211> LENGTH: 21
<212> TYPE: RNA
<213> ORGANISM: artificial
<220> FEATURE:
<223> OTHER INFORMATION: RNA Oligomer

<400> SEQUENCE: 1386
gcgcagacau ucccguuugu a                                              21

<210> SEQ ID NO 1387
<211> LENGTH: 21
<212> TYPE: RNA
<213> ORGANISM: artificial
<220> FEATURE:
<223> OTHER INFORMATION: RNA Oligomer

<400> SEQUENCE: 1387
uggaucugcc aacuacuccc a                                              21

<210> SEQ ID NO 1388
<211> LENGTH: 21
<212> TYPE: RNA
<213> ORGANISM: artificial
<220> FEATURE:
<223> OTHER INFORMATION: RNA Oligomer

<400> SEQUENCE: 1388
gcucaguuac aacuagauga a                                              21

<210> SEQ ID NO 1389
<211> LENGTH: 21
<212> TYPE: RNA
<213> ORGANISM: artificial
<220> FEATURE:
<223> OTHER INFORMATION: RNA Oligomer

<400> SEQUENCE: 1389
gcaaaaucau agccaaaacu a                                              21

<210> SEQ ID NO 1390
<211> LENGTH: 21
<212> TYPE: RNA
<213> ORGANISM: artificial
<220> FEATURE:
<223> OTHER INFORMATION: RNA Oligomer

<400> SEQUENCE: 1390
cugagcuagu uuuuuguac u                                               21

<210> SEQ ID NO 1391
<211> LENGTH: 21
<212> TYPE: RNA
<213> ORGANISM: artificial
<220> FEATURE:
<223> OTHER INFORMATION: RNA Oligomer

<400> SEQUENCE: 1391
ggaggauuug accuuuucug a                                              21

<210> SEQ ID NO 1392
<211> LENGTH: 21
<212> TYPE: RNA
<213> ORGANISM: artificial
<220> FEATURE:
<223> OTHER INFORMATION: RNA Oligomer

<400> SEQUENCE: 1392
```

```
uaggaggauu ugaccuuuuc u                                          21

<210> SEQ ID NO 1393
<211> LENGTH: 21
<212> TYPE: RNA
<213> ORGANISM: artificial
<220> FEATURE:
<223> OTHER INFORMATION: RNA Oligomer

<400> SEQUENCE: 1393
gcugcucaga auugcagaaa a                                          21

<210> SEQ ID NO 1394
<211> LENGTH: 21
<212> TYPE: RNA
<213> ORGANISM: artificial
<220> FEATURE:
<223> OTHER INFORMATION: RNA Oligomer

<400> SEQUENCE: 1394
guggcugcuc agaauugcag a                                          21

<210> SEQ ID NO 1395
<211> LENGTH: 21
<212> TYPE: RNA
<213> ORGANISM: artificial
<220> FEATURE:
<223> OTHER INFORMATION: RNA Oligomer

<400> SEQUENCE: 1395
aaguggcugc ucagaauugc a                                          21

<210> SEQ ID NO 1396
<211> LENGTH: 21
<212> TYPE: RNA
<213> ORGANISM: artificial
<220> FEATURE:
<223> OTHER INFORMATION: RNA Oligomer

<400> SEQUENCE: 1396
ugguccuaaa acaccaguac a                                          21

<210> SEQ ID NO 1397
<211> LENGTH: 21
<212> TYPE: RNA
<213> ORGANISM: artificial
<220> FEATURE:
<223> OTHER INFORMATION: RNA Oligomer

<400> SEQUENCE: 1397
gaaugguccu aaaacaccag u                                          21

<210> SEQ ID NO 1398
<211> LENGTH: 21
<212> TYPE: RNA
<213> ORGANISM: artificial
<220> FEATURE:
<223> OTHER INFORMATION: RNA Oligomer

<400> SEQUENCE: 1398
ggccucagug auucugaagu g                                          21

<210> SEQ ID NO 1399
<211> LENGTH: 21
<212> TYPE: RNA
<213> ORGANISM: artificial
```

-continued

```
<220> FEATURE:
<223> OTHER INFORMATION: RNA Oligomer

<400> SEQUENCE: 1399
ucuuccagcu auggagacac a                                              21

<210> SEQ ID NO 1400
<211> LENGTH: 21
<212> TYPE: RNA
<213> ORGANISM: artificial
<220> FEATURE:
<223> OTHER INFORMATION: RNA Oligomer

<400> SEQUENCE: 1400
ggcauuucac uaaacacaag u                                              21

<210> SEQ ID NO 1401
<211> LENGTH: 21
<212> TYPE: RNA
<213> ORGANISM: artificial
<220> FEATURE:
<223> OTHER INFORMATION: RNA Oligomer

<400> SEQUENCE: 1401
gacuccggca uuucacuaaa c                                              21

<210> SEQ ID NO 1402
<211> LENGTH: 21
<212> TYPE: RNA
<213> ORGANISM: artificial
<220> FEATURE:
<223> OTHER INFORMATION: RNA Oligomer

<400> SEQUENCE: 1402
ugcuacuuua agccauucac u                                              21

<210> SEQ ID NO 1403
<211> LENGTH: 21
<212> TYPE: RNA
<213> ORGANISM: artificial
<220> FEATURE:
<223> OTHER INFORMATION: RNA Oligomer

<400> SEQUENCE: 1403
guauuugacu ucagucagcg a                                              21

<210> SEQ ID NO 1404
<211> LENGTH: 21
<212> TYPE: RNA
<213> ORGANISM: artificial
<220> FEATURE:
<223> OTHER INFORMATION: RNA Oligomer

<400> SEQUENCE: 1404
ugagcccagu aucagcaaca g                                              21

<210> SEQ ID NO 1405
<211> LENGTH: 21
<212> TYPE: RNA
<213> ORGANISM: artificial
<220> FEATURE:
<223> OTHER INFORMATION: RNA Oligomer

<400> SEQUENCE: 1405
gagaaguauu ugacuucagu c                                              21
```

```
<210> SEQ ID NO 1406
<211> LENGTH: 21
<212> TYPE: RNA
<213> ORGANISM: artificial
<220> FEATURE:
<223> OTHER INFORMATION: RNA Oligomer

<400> SEQUENCE: 1406
ucgagaagua uuugacuuca g                                              21

<210> SEQ ID NO 1407
<211> LENGTH: 21
<212> TYPE: RNA
<213> ORGANISM: artificial
<220> FEATURE:
<223> OTHER INFORMATION: RNA Oligomer

<400> SEQUENCE: 1407
cagugaacuc auuaaauuca g                                              21

<210> SEQ ID NO 1408
<211> LENGTH: 21
<212> TYPE: RNA
<213> ORGANISM: artificial
<220> FEATURE:
<223> OTHER INFORMATION: RNA Oligomer

<400> SEQUENCE: 1408
agaagccaaa cugacagaag u                                              21

<210> SEQ ID NO 1409
<211> LENGTH: 21
<212> TYPE: RNA
<213> ORGANISM: artificial
<220> FEATURE:
<223> OTHER INFORMATION: RNA Oligomer

<400> SEQUENCE: 1409
gggaggagcu auuauccauu c                                              21

<210> SEQ ID NO 1410
<211> LENGTH: 21
<212> TYPE: RNA
<213> ORGANISM: artificial
<220> FEATURE:
<223> OTHER INFORMATION: RNA Oligomer

<400> SEQUENCE: 1410
uugggaggag cuauuaucca u                                              21

<210> SEQ ID NO 1411
<211> LENGTH: 21
<212> TYPE: RNA
<213> ORGANISM: artificial
<220> FEATURE:
<223> OTHER INFORMATION: RNA Oligomer

<400> SEQUENCE: 1411
gccccuguug auuuagacgg u                                              21

<210> SEQ ID NO 1412
<211> LENGTH: 21
<212> TYPE: RNA
<213> ORGANISM: artificial
<220> FEATURE:
<223> OTHER INFORMATION: RNA Oligomer

<400> SEQUENCE: 1412
```
gacaggugaa uuucucccaa u                                     21

<210> SEQ ID NO 1413
<211> LENGTH: 21
<212> TYPE: RNA
<213> ORGANISM: artificial
<220> FEATURE:
<223> OTHER INFORMATION: RNA Oligomer

<400> SEQUENCE: 1413
ugcaaaauca uagccaaaac u                                     21

<210> SEQ ID NO 1414
<211> LENGTH: 21
<212> TYPE: RNA
<213> ORGANISM: artificial
<220> FEATURE:
<223> OTHER INFORMATION: RNA Oligomer

<400> SEQUENCE: 1414
ucccaaaagu aagaagccag a                                     21

<210> SEQ ID NO 1415
<211> LENGTH: 21
<212> TYPE: RNA
<213> ORGANISM: artificial
<220> FEATURE:
<223> OTHER INFORMATION: RNA Oligomer

<400> SEQUENCE: 1415
uuguucccaa aaguaagaag c                                     21

<210> SEQ ID NO 1416
<211> LENGTH: 21
<212> TYPE: RNA
<213> ORGANISM: artificial
<220> FEATURE:
<223> OTHER INFORMATION: RNA Oligomer

<400> SEQUENCE: 1416
acaacuccaa aaggagcaag a                                     21

<210> SEQ ID NO 1417
<211> LENGTH: 21
<212> TYPE: RNA
<213> ORGANISM: artificial
<220> FEATURE:
<223> OTHER INFORMATION: RNA Oligomer

<400> SEQUENCE: 1417
ucccauuccc uguagaaaaa a                                     21

<210> SEQ ID NO 1418
<211> LENGTH: 21
<212> TYPE: RNA
<213> ORGANISM: artificial
<220> FEATURE:
<223> OTHER INFORMATION: RNA Oligomer

<400> SEQUENCE: 1418
ucaucggaaa accccauuca c                                     21

<210> SEQ ID NO 1419
<211> LENGTH: 21
<212> TYPE: RNA
<213> ORGANISM: artificial

```
<220> FEATURE:
<223> OTHER INFORMATION: RNA Oligomer

<400> SEQUENCE: 1419
cagagaaaga auugccugua a                                              21

<210> SEQ ID NO 1420
<211> LENGTH: 21
<212> TYPE: RNA
<213> ORGANISM: artificial
<220> FEATURE:
<223> OTHER INFORMATION: RNA Oligomer

<400> SEQUENCE: 1420
cagagcacuc acgugcauga u                                              21

<210> SEQ ID NO 1421
<211> LENGTH: 21
<212> TYPE: RNA
<213> ORGANISM: artificial
<220> FEATURE:
<223> OTHER INFORMATION: RNA Oligomer

<400> SEQUENCE: 1421
caccaguaca uucuucuggg g                                              21

<210> SEQ ID NO 1422
<211> LENGTH: 21
<212> TYPE: RNA
<213> ORGANISM: artificial
<220> FEATURE:
<223> OTHER INFORMATION: RNA Oligomer

<400> SEQUENCE: 1422
uccggcauuu cacuaaacac a                                              21

<210> SEQ ID NO 1423
<211> LENGTH: 21
<212> TYPE: RNA
<213> ORGANISM: artificial
<220> FEATURE:
<223> OTHER INFORMATION: RNA Oligomer

<400> SEQUENCE: 1423
ugacuccggc auuucacuaa a                                              21

<210> SEQ ID NO 1424
<211> LENGTH: 21
<212> TYPE: RNA
<213> ORGANISM: artificial
<220> FEATURE:
<223> OTHER INFORMATION: RNA Oligomer

<400> SEQUENCE: 1424
cccucaccug cuacuuuaag c                                              21

<210> SEQ ID NO 1425
<211> LENGTH: 21
<212> TYPE: RNA
<213> ORGANISM: artificial
<220> FEATURE:
<223> OTHER INFORMATION: RNA Oligomer

<400> SEQUENCE: 1425
guccagaagc caaacugaca g                                              21
```

```
<210> SEQ ID NO 1426
<211> LENGTH: 21
<212> TYPE: RNA
<213> ORGANISM: artificial
<220> FEATURE:
<223> OTHER INFORMATION: RNA Oligomer

<400> SEQUENCE: 1426
gcugguugag acuaccaugg u                                              21

<210> SEQ ID NO 1427
<211> LENGTH: 21
<212> TYPE: RNA
<213> ORGANISM: artificial
<220> FEATURE:
<223> OTHER INFORMATION: RNA Oligomer

<400> SEQUENCE: 1427
uuccugaguu acagugucuu a                                              21

<210> SEQ ID NO 1428
<211> LENGTH: 21
<212> TYPE: RNA
<213> ORGANISM: artificial
<220> FEATURE:
<223> OTHER INFORMATION: RNA Oligomer

<400> SEQUENCE: 1428
ccccuguuga uuuagacggu a                                              21

<210> SEQ ID NO 1429
<211> LENGTH: 21
<212> TYPE: RNA
<213> ORGANISM: artificial
<220> FEATURE:
<223> OTHER INFORMATION: RNA Oligomer

<400> SEQUENCE: 1429
ccaguggauc ugccaacuac u                                              21

<210> SEQ ID NO 1430
<211> LENGTH: 21
<212> TYPE: RNA
<213> ORGANISM: artificial
<220> FEATURE:
<223> OTHER INFORMATION: RNA Oligomer

<400> SEQUENCE: 1430
agacagguga auuucuccca a                                              21

<210> SEQ ID NO 1431
<211> LENGTH: 21
<212> TYPE: RNA
<213> ORGANISM: artificial
<220> FEATURE:
<223> OTHER INFORMATION: RNA Oligomer

<400> SEQUENCE: 1431
ucgcucaguu acaacuagau g                                              21

<210> SEQ ID NO 1432
<211> LENGTH: 21
<212> TYPE: RNA
<213> ORGANISM: artificial
<220> FEATURE:
<223> OTHER INFORMATION: RNA Oligomer

<400> SEQUENCE: 1432
```
ccagauguua agaaaaacua g                                              21

<210> SEQ ID NO 1433
<211> LENGTH: 21
<212> TYPE: RNA
<213> ORGANISM: artificial
<220> FEATURE:
<223> OTHER INFORMATION: RNA Oligomer

<400> SEQUENCE: 1433
agccagaugu uaagaaaaac u                                              21

<210> SEQ ID NO 1434
<211> LENGTH: 21
<212> TYPE: RNA
<213> ORGANISM: artificial
<220> FEATURE:
<223> OTHER INFORMATION: RNA Oligomer

<400> SEQUENCE: 1434
auggcaaugu uuccuuguu c                                               21

<210> SEQ ID NO 1435
<211> LENGTH: 21
<212> TYPE: RNA
<213> ORGANISM: artificial
<220> FEATURE:
<223> OTHER INFORMATION: RNA Oligomer

<400> SEQUENCE: 1435
agagauggca auguuuccu u                                               21

<210> SEQ ID NO 1436
<211> LENGTH: 21
<212> TYPE: RNA
<213> ORGANISM: artificial
<220> FEATURE:
<223> OTHER INFORMATION: RNA Oligomer

<400> SEQUENCE: 1436
gaacaacucc aaaaggagca a                                              21

<210> SEQ ID NO 1437
<211> LENGTH: 21
<212> TYPE: RNA
<213> ORGANISM: artificial
<220> FEATURE:
<223> OTHER INFORMATION: RNA Oligomer

<400> SEQUENCE: 1437
gggcaaaagc ucuccauauc c                                              21

<210> SEQ ID NO 1438
<211> LENGTH: 21
<212> TYPE: RNA
<213> ORGANISM: artificial
<220> FEATURE:
<223> OTHER INFORMATION: RNA Oligomer

<400> SEQUENCE: 1438
aucggaaaac cccauucaca a                                              21

<210> SEQ ID NO 1439
<211> LENGTH: 21
<212> TYPE: RNA
<213> ORGANISM: artificial -continued

```
<220> FEATURE:
<223> OTHER INFORMATION: RNA Oligomer

<400> SEQUENCE: 1439
acgugcauga ugcccaaugu g                                              21

<210> SEQ ID NO 1440
<211> LENGTH: 21
<212> TYPE: RNA
<213> ORGANISM: artificial
<220> FEATURE:
<223> OTHER INFORMATION: RNA Oligomer

<400> SEQUENCE: 1440
gguccuaaaa caccaguaca u                                              21

<210> SEQ ID NO 1441
<211> LENGTH: 21
<212> TYPE: RNA
<213> ORGANISM: artificial
<220> FEATURE:
<223> OTHER INFORMATION: RNA Oligomer

<400> SEQUENCE: 1441
cagucagcga cggaaagagu a                                              21

<210> SEQ ID NO 1442
<211> LENGTH: 21
<212> TYPE: RNA
<213> ORGANISM: artificial
<220> FEATURE:
<223> OTHER INFORMATION: RNA Oligomer

<400> SEQUENCE: 1442
cuccggcauu ucacuaaaca c                                              21

<210> SEQ ID NO 1443
<211> LENGTH: 21
<212> TYPE: RNA
<213> ORGANISM: artificial
<220> FEATURE:
<223> OTHER INFORMATION: RNA Oligomer

<400> SEQUENCE: 1443
gacuucaguc agcgacggaa a                                              21

<210> SEQ ID NO 1444
<211> LENGTH: 21
<212> TYPE: RNA
<213> ORGANISM: artificial
<220> FEATURE:
<223> OTHER INFORMATION: RNA Oligomer

<400> SEQUENCE: 1444
aagccauuca cucucugaac u                                              21

<210> SEQ ID NO 1445
<211> LENGTH: 21
<212> TYPE: RNA
<213> ORGANISM: artificial
<220> FEATURE:
<223> OTHER INFORMATION: RNA Oligomer

<400> SEQUENCE: 1445
cugagcccag uaucagcaac a                                              21
```

```
<210> SEQ ID NO 1446
<211> LENGTH: 21
<212> TYPE: RNA
<213> ORGANISM: artificial
<220> FEATURE:
<223> OTHER INFORMATION: RNA Oligomer

<400> SEQUENCE: 1446
gacagugaac ucauuaaauu c                                              21

<210> SEQ ID NO 1447
<211> LENGTH: 21
<212> TYPE: RNA
<213> ORGANISM: artificial
<220> FEATURE:
<223> OTHER INFORMATION: RNA Oligomer

<400> SEQUENCE: 1447
gaagacccca accaguugac a                                              21

<210> SEQ ID NO 1448
<211> LENGTH: 21
<212> TYPE: RNA
<213> ORGANISM: artificial
<220> FEATURE:
<223> OTHER INFORMATION: RNA Oligomer

<400> SEQUENCE: 1448
agccaaacug acagaaguug a                                              21

<210> SEQ ID NO 1449
<211> LENGTH: 21
<212> TYPE: RNA
<213> ORGANISM: artificial
<220> FEATURE:
<223> OTHER INFORMATION: RNA Oligomer

<400> SEQUENCE: 1449
aagcugguug agacuaccau g                                              21

<210> SEQ ID NO 1450
<211> LENGTH: 21
<212> TYPE: RNA
<213> ORGANISM: artificial
<220> FEATURE:
<223> OTHER INFORMATION: RNA Oligomer

<400> SEQUENCE: 1450
gaggagcuau uauccauucc u                                              21

<210> SEQ ID NO 1451
<211> LENGTH: 21
<212> TYPE: RNA
<213> ORGANISM: artificial
<220> FEATURE:
<223> OTHER INFORMATION: RNA Oligomer

<400> SEQUENCE: 1451
gguccacagc ucaucaugau g                                              21

<210> SEQ ID NO 1452
<211> LENGTH: 21
<212> TYPE: RNA
<213> ORGANISM: artificial
<220> FEATURE:
<223> OTHER INFORMATION: RNA Oligomer

<400> SEQUENCE: 1452
```
gcuacuaauc aggcucaguc a                                              21

<210> SEQ ID NO 1453
<211> LENGTH: 21
<212> TYPE: RNA
<213> ORGANISM: artificial
<220> FEATURE:
<223> OTHER INFORMATION: RNA Oligomer

<400> SEQUENCE: 1453
cccagucuuc auugcuacua a                                              21

<210> SEQ ID NO 1454
<211> LENGTH: 21
<212> TYPE: RNA
<213> ORGANISM: artificial
<220> FEATURE:
<223> OTHER INFORMATION: RNA Oligomer

<400> SEQUENCE: 1454
ugaugacugc augcagcuuu u                                              21

<210> SEQ ID NO 1455
<211> LENGTH: 21
<212> TYPE: RNA
<213> ORGANISM: artificial
<220> FEATURE:
<223> OTHER INFORMATION: RNA Oligomer

<400> SEQUENCE: 1455
gagacaggug aauuucuccc a                                              21

<210> SEQ ID NO 1456
<211> LENGTH: 21
<212> TYPE: RNA
<213> ORGANISM: artificial
<220> FEATURE:
<223> OTHER INFORMATION: RNA Oligomer

<400> SEQUENCE: 1456
uuucgcucag uuacaacuag a                                              21

<210> SEQ ID NO 1457
<211> LENGTH: 21
<212> TYPE: RNA
<213> ORGANISM: artificial
<220> FEATURE:
<223> OTHER INFORMATION: RNA Oligomer

<400> SEQUENCE: 1457
augauaugac aucuggcuaa a                                              21

<210> SEQ ID NO 1458
<211> LENGTH: 21
<212> TYPE: RNA
<213> ORGANISM: artificial
<220> FEATURE:
<223> OTHER INFORMATION: RNA Oligomer

<400> SEQUENCE: 1458
ggacaccauu ugggcuaguu u                                              21

<210> SEQ ID NO 1459
<211> LENGTH: 21
<212> TYPE: RNA
<213> ORGANISM: artificial

```
<220> FEATURE:
<223> OTHER INFORMATION: RNA Oligomer

<400> SEQUENCE: 1459
ucauagccaa aacuaguaua g                                              21

<210> SEQ ID NO 1460
<211> LENGTH: 21
<212> TYPE: RNA
<213> ORGANISM: artificial
<220> FEATURE:
<223> OTHER INFORMATION: RNA Oligomer

<400> SEQUENCE: 1460
ucugagcuag uuuuuugua c                                               21

<210> SEQ ID NO 1461
<211> LENGTH: 21
<212> TYPE: RNA
<213> ORGANISM: artificial
<220> FEATURE:
<223> OTHER INFORMATION: RNA Oligomer

<400> SEQUENCE: 1461
gagauggcaa uguuuuccuu g                                              21

<210> SEQ ID NO 1462
<211> LENGTH: 21
<212> TYPE: RNA
<213> ORGANISM: artificial
<220> FEATURE:
<223> OTHER INFORMATION: RNA Oligomer

<400> SEQUENCE: 1462
gugaauacuc ccugcagcaa a                                              21

<210> SEQ ID NO 1463
<211> LENGTH: 21
<212> TYPE: RNA
<213> ORGANISM: artificial
<220> FEATURE:
<223> OTHER INFORMATION: RNA Oligomer

<400> SEQUENCE: 1463
aaccuuauuc uccagugaa u                                               21

<210> SEQ ID NO 1464
<211> LENGTH: 21
<212> TYPE: RNA
<213> ORGANISM: artificial
<220> FEATURE:
<223> OTHER INFORMATION: RNA Oligomer

<400> SEQUENCE: 1464
ggaaaaccuu auucuccuag u                                              21

<210> SEQ ID NO 1465
<211> LENGTH: 21
<212> TYPE: RNA
<213> ORGANISM: artificial
<220> FEATURE:
<223> OTHER INFORMATION: RNA Oligomer

<400> SEQUENCE: 1465
gccuucaccu acugaaaaaa c                                              21
```

<210> SEQ ID NO 1466
<211> LENGTH: 21
<212> TYPE: RNA
<213> ORGANISM: artificial
<220> FEATURE:
<223> OTHER INFORMATION: RNA Oligomer

<400> SEQUENCE: 1466
ugcucagaau ugcagaaaaa g                                          21

<210> SEQ ID NO 1467
<211> LENGTH: 21
<212> TYPE: RNA
<213> ORGANISM: artificial
<220> FEATURE:
<223> OTHER INFORMATION: RNA Oligomer

<400> SEQUENCE: 1467
gaguaugagc uggaaaaaca g                                          21

<210> SEQ ID NO 1468
<211> LENGTH: 21
<212> TYPE: RNA
<213> ORGANISM: artificial
<220> FEATURE:
<223> OTHER INFORMATION: RNA Oligomer

<400> SEQUENCE: 1468
augguccuaa aacaccagua c                                          21

<210> SEQ ID NO 1469
<211> LENGTH: 21
<212> TYPE: RNA
<213> ORGANISM: artificial
<220> FEATURE:
<223> OTHER INFORMATION: RNA Oligomer

<400> SEQUENCE: 1469
acacacuacu uggccucagu g                                          21

<210> SEQ ID NO 1470
<211> LENGTH: 21
<212> TYPE: RNA
<213> ORGANISM: artificial
<220> FEATURE:
<223> OTHER INFORMATION: RNA Oligomer

<400> SEQUENCE: 1470
gagacacacu acuuggccuc a                                          21

<210> SEQ ID NO 1471
<211> LENGTH: 21
<212> TYPE: RNA
<213> ORGANISM: artificial
<220> FEATURE:
<223> OTHER INFORMATION: RNA Oligomer

<400> SEQUENCE: 1471
auggagacac acuacuuggc c                                          21

<210> SEQ ID NO 1472
<211> LENGTH: 21
<212> TYPE: RNA
<213> ORGANISM: artificial
<220> FEATURE:
<223> OTHER INFORMATION: RNA Oligomer

<400> SEQUENCE: 1472
agcuauggag acacacuacu u                                           21

<210> SEQ ID NO 1473
<211> LENGTH: 21
<212> TYPE: RNA
<213> ORGANISM: artificial
<220> FEATURE:
<223> OTHER INFORMATION: RNA Oligomer

<400> SEQUENCE: 1473
gcauuucacu aaacacaagu c                                           21

<210> SEQ ID NO 1474
<211> LENGTH: 21
<212> TYPE: RNA
<213> ORGANISM: artificial
<220> FEATURE:
<223> OTHER INFORMATION: RNA Oligomer

<400> SEQUENCE: 1474
ucagucagcg acggaaagag u                                           21

<210> SEQ ID NO 1475
<211> LENGTH: 21
<212> TYPE: RNA
<213> ORGANISM: artificial
<220> FEATURE:
<223> OTHER INFORMATION: RNA Oligomer

<400> SEQUENCE: 1475
auucacucuc ugaacuucua a                                           21

<210> SEQ ID NO 1476
<211> LENGTH: 21
<212> TYPE: RNA
<213> ORGANISM: artificial
<220> FEATURE:
<223> OTHER INFORMATION: RNA Oligomer

<400> SEQUENCE: 1476
aacacagauu uuggugauga a                                           21

<210> SEQ ID NO 1477
<211> LENGTH: 21
<212> TYPE: RNA
<213> ORGANISM: artificial
<220> FEATURE:
<223> OTHER INFORMATION: RNA Oligomer

<400> SEQUENCE: 1477
gucaacacag auuuuggguga u                                          21

<210> SEQ ID NO 1478
<211> LENGTH: 21
<212> TYPE: RNA
<213> ORGANISM: artificial
<220> FEATURE:
<223> OTHER INFORMATION: RNA Oligomer

<400> SEQUENCE: 1478
gaacucauua aauucagaug c                                           21

<210> SEQ ID NO 1479
<211> LENGTH: 21
<212> TYPE: RNA
<213> ORGANISM: artificial

```
<220> FEATURE:
<223> OTHER INFORMATION: RNA Oligomer

<400> SEQUENCE: 1479
accaguugac agugaacuca u                                              21

<210> SEQ ID NO 1480
<211> LENGTH: 21
<212> TYPE: RNA
<213> ORGANISM: artificial
<220> FEATURE:
<223> OTHER INFORMATION: RNA Oligomer

<400> SEQUENCE: 1480
agguaacugu aguccacauu u                                              21

<210> SEQ ID NO 1481
<211> LENGTH: 21
<212> TYPE: RNA
<213> ORGANISM: artificial
<220> FEATURE:
<223> OTHER INFORMATION: RNA Oligomer

<400> SEQUENCE: 1481
uauacccuca auggaaaaag a                                              21

<210> SEQ ID NO 1482
<211> LENGTH: 21
<212> TYPE: RNA
<213> ORGANISM: artificial
<220> FEATURE:
<223> OTHER INFORMATION: RNA Oligomer

<400> SEQUENCE: 1482
uccauuccug aguuacagug u                                              21

<210> SEQ ID NO 1483
<211> LENGTH: 21
<212> TYPE: RNA
<213> ORGANISM: artificial
<220> FEATURE:
<223> OTHER INFORMATION: RNA Oligomer

<400> SEQUENCE: 1483
ggagcuauua uccauuccug a                                              21

<210> SEQ ID NO 1484
<211> LENGTH: 21
<212> TYPE: RNA
<213> ORGANISM: artificial
<220> FEATURE:
<223> OTHER INFORMATION: RNA Oligomer

<400> SEQUENCE: 1484
acgguaugca acaggacauu g                                              21

<210> SEQ ID NO 1485
<211> LENGTH: 21
<212> TYPE: RNA
<213> ORGANISM: artificial
<220> FEATURE:
<223> OTHER INFORMATION: RNA Oligomer

<400> SEQUENCE: 1485
cccuguugau uuagacggua u                                              21
```

-continued

```
<210> SEQ ID NO 1486
<211> LENGTH: 21
<212> TYPE: RNA
<213> ORGANISM: artificial
<220> FEATURE:
<223> OTHER INFORMATION: RNA Oligomer

<400> SEQUENCE: 1486
guagccccug uugauuuaga c                                              21

<210> SEQ ID NO 1487
<211> LENGTH: 21
<212> TYPE: RNA
<213> ORGANISM: artificial
<220> FEATURE:
<223> OTHER INFORMATION: RNA Oligomer

<400> SEQUENCE: 1487
gaaacuucug uugcucaggu a                                              21

<210> SEQ ID NO 1488
<211> LENGTH: 21
<212> TYPE: RNA
<213> ORGANISM: artificial
<220> FEATURE:
<223> OTHER INFORMATION: RNA Oligomer

<400> SEQUENCE: 1488
gagagcccag ucuucauugc u                                              21

<210> SEQ ID NO 1489
<211> LENGTH: 21
<212> TYPE: RNA
<213> ORGANISM: artificial
<220> FEATURE:
<223> OTHER INFORMATION: RNA Oligomer

<400> SEQUENCE: 1489
aaaccagugg aucugccaac u                                              21

<210> SEQ ID NO 1490
<211> LENGTH: 21
<212> TYPE: RNA
<213> ORGANISM: artificial
<220> FEATURE:
<223> OTHER INFORMATION: RNA Oligomer

<400> SEQUENCE: 1490
uuaggaggau uugaccuuuu c                                              21

<210> SEQ ID NO 1491
<211> LENGTH: 21
<212> TYPE: RNA
<213> ORGANISM: artificial
<220> FEATURE:
<223> OTHER INFORMATION: RNA Oligomer

<400> SEQUENCE: 1491
aagccagaug uuaagaaaaa c                                              21

<210> SEQ ID NO 1492
<211> LENGTH: 21
<212> TYPE: RNA
<213> ORGANISM: artificial
<220> FEATURE:
<223> OTHER INFORMATION: RNA Oligomer

<400> SEQUENCE: 1492
```

```
uucccaaaag uaagaagcca g                                    21

<210> SEQ ID NO 1493
<211> LENGTH: 21
<212> TYPE: RNA
<213> ORGANISM: artificial
<220> FEATURE:
<223> OTHER INFORMATION: RNA Oligomer

<400> SEQUENCE: 1493
ggagcaagag aaagccuuuu u                                    21

<210> SEQ ID NO 1494
<211> LENGTH: 21
<212> TYPE: RNA
<213> ORGANISM: artificial
<220> FEATURE:
<223> OTHER INFORMATION: RNA Oligomer

<400> SEQUENCE: 1494
gauggcaaug uuuuccuugu u                                    21

<210> SEQ ID NO 1495
<211> LENGTH: 21
<212> TYPE: RNA
<213> ORGANISM: artificial
<220> FEATURE:
<223> OTHER INFORMATION: RNA Oligomer

<400> SEQUENCE: 1495
aaggagcaag agaaagccuu u                                    21

<210> SEQ ID NO 1496
<211> LENGTH: 21
<212> TYPE: RNA
<213> ORGANISM: artificial
<220> FEATURE:
<223> OTHER INFORMATION: RNA Oligomer

<400> SEQUENCE: 1496
aagccuucac cuacugaaaa a                                    21

<210> SEQ ID NO 1497
<211> LENGTH: 21
<212> TYPE: RNA
<213> ORGANISM: artificial
<220> FEATURE:
<223> OTHER INFORMATION: RNA Oligomer

<400> SEQUENCE: 1497
ugaagcucaa cuugcauuaa u                                    21

<210> SEQ ID NO 1498
<211> LENGTH: 21
<212> TYPE: RNA
<213> ORGANISM: artificial
<220> FEATURE:
<223> OTHER INFORMATION: RNA Oligomer

<400> SEQUENCE: 1498
augaagcuca acuugcauua a                                    21

<210> SEQ ID NO 1499
<211> LENGTH: 21
<212> TYPE: RNA
<213> ORGANISM: artificial
```

```
<220> FEATURE:
<223> OTHER INFORMATION: RNA Oligomer

<400> SEQUENCE: 1499
cccauucccu guagaaaaaa u                                              21

<210> SEQ ID NO 1500
<211> LENGTH: 21
<212> TYPE: RNA
<213> ORGANISM: artificial
<220> FEATURE:
<223> OTHER INFORMATION: RNA Oligomer

<400> SEQUENCE: 1500
uuggaggcuc aucucacaag a                                              21

<210> SEQ ID NO 1501
<211> LENGTH: 21
<212> TYPE: RNA
<213> ORGANISM: artificial
<220> FEATURE:
<223> OTHER INFORMATION: RNA Oligomer

<400> SEQUENCE: 1501
agcuggaaaa acagaaaaaa c                                              21

<210> SEQ ID NO 1502
<211> LENGTH: 21
<212> TYPE: RNA
<213> ORGANISM: artificial
<220> FEATURE:
<223> OTHER INFORMATION: RNA Oligomer

<400> SEQUENCE: 1502
gugcaugaug cccaauguga g                                              21

<210> SEQ ID NO 1503
<211> LENGTH: 21
<212> TYPE: RNA
<213> ORGANISM: artificial
<220> FEATURE:
<223> OTHER INFORMATION: RNA Oligomer

<400> SEQUENCE: 1503
cacgugcaug augcccaaug u                                              21

<210> SEQ ID NO 1504
<211> LENGTH: 21
<212> TYPE: RNA
<213> ORGANISM: artificial
<220> FEATURE:
<223> OTHER INFORMATION: RNA Oligomer

<400> SEQUENCE: 1504
acaccaguac auucuucugg g                                              21

<210> SEQ ID NO 1505
<211> LENGTH: 21
<212> TYPE: RNA
<213> ORGANISM: artificial
<220> FEATURE:
<223> OTHER INFORMATION: RNA Oligomer

<400> SEQUENCE: 1505
guccuaaaac accaguacau u                                              21
```

-continued

```
<210> SEQ ID NO 1506
<211> LENGTH: 21
<212> TYPE: RNA
<213> ORGANISM: artificial
<220> FEATURE:
<223> OTHER INFORMATION: RNA Oligomer

<400> SEQUENCE: 1506
uggagacaca cuacuuggcc u                                            21

<210> SEQ ID NO 1507
<211> LENGTH: 21
<212> TYPE: RNA
<213> ORGANISM: artificial
<220> FEATURE:
<223> OTHER INFORMATION: RNA Oligomer

<400> SEQUENCE: 1507
acuuuauucu uaccccuccu a                                            21

<210> SEQ ID NO 1508
<211> LENGTH: 21
<212> TYPE: RNA
<213> ORGANISM: artificial
<220> FEATURE:
<223> OTHER INFORMATION: RNA Oligomer

<400> SEQUENCE: 1508
agccacuuua uucuuacccc u                                            21

<210> SEQ ID NO 1509
<211> LENGTH: 21
<212> TYPE: RNA
<213> ORGANISM: artificial
<220> FEATURE:
<223> OTHER INFORMATION: RNA Oligomer

<400> SEQUENCE: 1509
uuucuuaaca ucuggcuucu u                                            21

<210> SEQ ID NO 1510
<211> LENGTH: 21
<212> TYPE: RNA
<213> ORGANISM: artificial
<220> FEATURE:
<223> OTHER INFORMATION: RNA Oligomer

<400> SEQUENCE: 1510
gcuuuuguca uuucucccuu u                                            21

<210> SEQ ID NO 1511
<211> LENGTH: 21
<212> TYPE: RNA
<213> ORGANISM: artificial
<220> FEATURE:
<223> OTHER INFORMATION: RNA Oligomer

<400> SEQUENCE: 1511
gccacuuuau ucuuacccu c                                             21

<210> SEQ ID NO 1512
<211> LENGTH: 21
<212> TYPE: RNA
<213> ORGANISM: artificial
<220> FEATURE:
<223> OTHER INFORMATION: RNA Oligomer

<400> SEQUENCE: 1512
```
cuuuauucuu accccuccua c            21

<210> SEQ ID NO 1513
<211> LENGTH: 21
<212> TYPE: RNA
<213> ORGANISM: artificial
<220> FEATURE:
<223> OTHER INFORMATION: RNA Oligomer

<400> SEQUENCE: 1513
aauucugagc agccacuuua u            21

<210> SEQ ID NO 1514
<211> LENGTH: 21
<212> TYPE: RNA
<213> ORGANISM: artificial
<220> FEATURE:
<223> OTHER INFORMATION: RNA Oligomer

<400> SEQUENCE: 1514
cacuuuauuc uuaccccucc u            21

<210> SEQ ID NO 1515
<211> LENGTH: 21
<212> TYPE: RNA
<213> ORGANISM: artificial
<220> FEATURE:
<223> OTHER INFORMATION: RNA Oligomer

<400> SEQUENCE: 1515
acuuacaggc aauucuuucu c            21

<210> SEQ ID NO 1516
<211> LENGTH: 21
<212> TYPE: RNA
<213> ORGANISM: artificial
<220> FEATURE:
<223> OTHER INFORMATION: RNA Oligomer

<400> SEQUENCE: 1516
auuuagaagu ucagagagug a            21

<210> SEQ ID NO 1517
<211> LENGTH: 21
<212> TYPE: RNA
<213> ORGANISM: artificial
<220> FEATURE:
<223> OTHER INFORMATION: RNA Oligomer

<400> SEQUENCE: 1517
ucaucuacaa acgggaaugu c            21

<210> SEQ ID NO 1518
<211> LENGTH: 21
<212> TYPE: RNA
<213> ORGANISM: artificial
<220> FEATURE:
<223> OTHER INFORMATION: RNA Oligomer

<400> SEQUENCE: 1518
uuuucuuaac aucuggcuuc u            21

<210> SEQ ID NO 1519
<211> LENGTH: 21
<212> TYPE: RNA
<213> ORGANISM: artificial

```
<220> FEATURE:
<223> OTHER INFORMATION: RNA Oligomer

<400> SEQUENCE: 1519
uucuuuuucu gcaauucuga g                                      21

<210> SEQ ID NO 1520
<211> LENGTH: 21
<212> TYPE: RNA
<213> ORGANISM: artificial
<220> FEATURE:
<223> OTHER INFORMATION: RNA Oligomer

<400> SEQUENCE: 1520
cugagcagcc acuuuauucu u                                      21

<210> SEQ ID NO 1521
<211> LENGTH: 21
<212> TYPE: RNA
<213> ORGANISM: artificial
<220> FEATURE:
<223> OTHER INFORMATION: RNA Oligomer

<400> SEQUENCE: 1521
gcagccacuu uauucuuacc c                                      21

<210> SEQ ID NO 1522
<211> LENGTH: 21
<212> TYPE: RNA
<213> ORGANISM: artificial
<220> FEATURE:
<223> OTHER INFORMATION: RNA Oligomer

<400> SEQUENCE: 1522
uguucuuguc uuuccuuuuc a                                      21

<210> SEQ ID NO 1523
<211> LENGTH: 21
<212> TYPE: RNA
<213> ORGANISM: artificial
<220> FEATURE:
<223> OTHER INFORMATION: RNA Oligomer

<400> SEQUENCE: 1523
cuuaaaguag caggugaggg c                                      21

<210> SEQ ID NO 1524
<211> LENGTH: 21
<212> TYPE: RNA
<213> ORGANISM: artificial
<220> FEATURE:
<223> OTHER INFORMATION: RNA Oligomer

<400> SEQUENCE: 1524
agaaaccuca uugucaucua c                                      21

<210> SEQ ID NO 1525
<211> LENGTH: 21
<212> TYPE: RNA
<213> ORGANISM: artificial
<220> FEATURE:
<223> OTHER INFORMATION: RNA Oligomer

<400> SEQUENCE: 1525
ucuuaacauc uggcuucuua c                                      21
```

```
<210> SEQ ID NO 1526
<211> LENGTH: 21
<212> TYPE: RNA
<213> ORGANISM: artificial
<220> FEATURE:
<223> OTHER INFORMATION: RNA Oligomer

<400> SEQUENCE: 1526
uuaacaucug gcuucuuacu u                                              21

<210> SEQ ID NO 1527
<211> LENGTH: 21
<212> TYPE: RNA
<213> ORGANISM: artificial
<220> FEATURE:
<223> OTHER INFORMATION: RNA Oligomer

<400> SEQUENCE: 1527
cagccacuuu auucuuaccc c                                              21

<210> SEQ ID NO 1528
<211> LENGTH: 21
<212> TYPE: RNA
<213> ORGANISM: artificial
<220> FEATURE:
<223> OTHER INFORMATION: RNA Oligomer

<400> SEQUENCE: 1528
cuuacaggca auucuuucuc u                                              21

<210> SEQ ID NO 1529
<211> LENGTH: 21
<212> TYPE: RNA
<213> ORGANISM: artificial
<220> FEATURE:
<223> OTHER INFORMATION: RNA Oligomer

<400> SEQUENCE: 1529
cccauuuaga aguucagaga g                                              21

<210> SEQ ID NO 1530
<211> LENGTH: 21
<212> TYPE: RNA
<213> ORGANISM: artificial
<220> FEATURE:
<223> OTHER INFORMATION: RNA Oligomer

<400> SEQUENCE: 1530
auugagggua uagaugagua a                                              21

<210> SEQ ID NO 1531
<211> LENGTH: 21
<212> TYPE: RNA
<213> ORGANISM: artificial
<220> FEATURE:
<223> OTHER INFORMATION: RNA Oligomer

<400> SEQUENCE: 1531
auuaguagca augaagacug g                                              21

<210> SEQ ID NO 1532
<211> LENGTH: 21
<212> TYPE: RNA
<213> ORGANISM: artificial
<220> FEATURE:
<223> OTHER INFORMATION: RNA Oligomer

<400> SEQUENCE: 1532
```
aagaaaccuc auugucaucu a                                          21

<210> SEQ ID NO 1533
<211> LENGTH: 21
<212> TYPE: RNA
<213> ORGANISM: artificial
<220> FEATURE:
<223> OTHER INFORMATION: RNA Oligomer

<400> SEQUENCE: 1533
gucaucuaca aacgggaaug u                                          21

<210> SEQ ID NO 1534
<211> LENGTH: 21
<212> TYPE: RNA
<213> ORGANISM: artificial
<220> FEATURE:
<223> OTHER INFORMATION: RNA Oligomer

<400> SEQUENCE: 1534
guacauagug guuaguuuug c                                          21

<210> SEQ ID NO 1535
<211> LENGTH: 21
<212> TYPE: RNA
<213> ORGANISM: artificial
<220> FEATURE:
<223> OTHER INFORMATION: RNA Oligomer

<400> SEQUENCE: 1535
aacaucuggc uucuuacuuu u                                          21

<210> SEQ ID NO 1536
<211> LENGTH: 21
<212> TYPE: RNA
<213> ORGANISM: artificial
<220> FEATURE:
<223> OTHER INFORMATION: RNA Oligomer

<400> SEQUENCE: 1536
aucuggcuuc uuacuuuugg g                                          21

<210> SEQ ID NO 1537
<211> LENGTH: 21
<212> TYPE: RNA
<213> ORGANISM: artificial
<220> FEATURE:
<223> OTHER INFORMATION: RNA Oligomer

<400> SEQUENCE: 1537
uucuccuuuu ucuuugagca a                                          21

<210> SEQ ID NO 1538
<211> LENGTH: 21
<212> TYPE: RNA
<213> ORGANISM: artificial
<220> FEATURE:
<223> OTHER INFORMATION: RNA Oligomer

<400> SEQUENCE: 1538
aucuaaaucu ugcucuaguu c                                          21

<210> SEQ ID NO 1539
<211> LENGTH: 21
<212> TYPE: RNA
<213> ORGANISM: artificial

```
<220> FEATURE:
<223> OTHER INFORMATION: RNA Oligomer

<400> SEQUENCE: 1539 ucuuuucug caauucugag c                                          21

<210> SEQ ID NO 1540
<211> LENGTH: 21
<212> TYPE: RNA
<213> ORGANISM: artificial
<220> FEATURE:
<223> OTHER INFORMATION: RNA Oligomer

<400> SEQUENCE: 1540
guucuugucu uuccuuuuca a                                         21

<210> SEQ ID NO 1541
<211> LENGTH: 21
<212> TYPE: RNA
<213> ORGANISM: artificial
<220> FEATURE:
<223> OTHER INFORMATION: RNA Oligomer

<400> SEQUENCE: 1541
auucuuucuc uggguguuc u                                          21

<210> SEQ ID NO 1542
<211> LENGTH: 21
<212> TYPE: RNA
<213> ORGANISM: artificial
<220> FEATURE:
<223> OTHER INFORMATION: RNA Oligomer

<400> SEQUENCE: 1542
agaagaaugu acgguguuu u                                          21

<210> SEQ ID NO 1543
<211> LENGTH: 21
<212> TYPE: RNA
<213> ORGANISM: artificial
<220> FEATURE:
<223> OTHER INFORMATION: RNA Oligomer

<400> SEQUENCE: 1543
uuuaggacca uucuguuuga c                                         21

<210> SEQ ID NO 1544
<211> LENGTH: 21
<212> TYPE: RNA
<213> ORGANISM: artificial
<220> FEATURE:
<223> OTHER INFORMATION: RNA Oligomer

<400> SEQUENCE: 1544
gcuuucaggg ugguuuuggu u                                         21

<210> SEQ ID NO 1545
<211> LENGTH: 21
<212> TYPE: RNA
<213> ORGANISM: artificial
<220> FEATURE:
<223> OTHER INFORMATION: RNA Oligomer

<400> SEQUENCE: 1545
uucagggugg uuuugguuga a                                         21
```

```
<210> SEQ ID NO 1546
<211> LENGTH: 21
<212> TYPE: RNA
<213> ORGANISM: artificial
<220> FEATURE:
<223> OTHER INFORMATION: RNA Oligomer

<400> SEQUENCE: 1546
cauuuagaag uucagagagu g                                               21

<210> SEQ ID NO 1547
<211> LENGTH: 21
<212> TYPE: RNA
<213> ORGANISM: artificial
<220> FEATURE:
<223> OTHER INFORMATION: RNA Oligomer

<400> SEQUENCE: 1547
caaauacuuc ucgacuuacu c                                               21

<210> SEQ ID NO 1548
<211> LENGTH: 21
<212> TYPE: RNA
<213> ORGANISM: artificial
<220> FEATURE:
<223> OTHER INFORMATION: RNA Oligomer

<400> SEQUENCE: 1548
agccgaagaa accucauugu c                                               21

<210> SEQ ID NO 1549
<211> LENGTH: 21
<212> TYPE: RNA
<213> ORGANISM: artificial
<220> FEATURE:
<223> OTHER INFORMATION: RNA Oligomer

<400> SEQUENCE: 1549
aucaaaguac aaagcaucug a                                               21

<210> SEQ ID NO 1550
<211> LENGTH: 21
<212> TYPE: RNA
<213> ORGANISM: artificial
<220> FEATURE:
<223> OTHER INFORMATION: RNA Oligomer

<400> SEQUENCE: 1550
auuucuuuuu agccagaugu c                                               21

<210> SEQ ID NO 1551
<211> LENGTH: 21
<212> TYPE: RNA
<213> ORGANISM: artificial
<220> FEATURE:
<223> OTHER INFORMATION: RNA Oligomer

<400> SEQUENCE: 1551
uuuuucuuaa caucuggcuu c                                               21

<210> SEQ ID NO 1552
<211> LENGTH: 21
<212> TYPE: RNA
<213> ORGANISM: artificial
<220> FEATURE:
<223> OTHER INFORMATION: RNA Oligomer

<400> SEQUENCE: 1552
```

-continued acaucuggcu ucuuacuuuu g                                              21

<210> SEQ ID NO 1553
<211> LENGTH: 21
<212> TYPE: RNA
<213> ORGANISM: artificial
<220> FEATURE:
<223> OTHER INFORMATION: RNA Oligomer

<400> SEQUENCE: 1553
ucacuaggag aauaagguuu u                                              21

<210> SEQ ID NO 1554
<211> LENGTH: 21
<212> TYPE: RNA
<213> ORGANISM: artificial
<220> FEATURE:
<223> OTHER INFORMATION: RNA Oligomer

<400> SEQUENCE: 1554
uuauucuuac cccuccuacg u                                              21

<210> SEQ ID NO 1555
<211> LENGTH: 21
<212> TYPE: RNA
<213> ORGANISM: artificial
<220> FEATURE:
<223> OTHER INFORMATION: RNA Oligomer

<400> SEQUENCE: 1555
gaguuguucu ugucuuuccu u                                              21

<210> SEQ ID NO 1556
<211> LENGTH: 21
<212> TYPE: RNA
<213> ORGANISM: artificial
<220> FEATURE:
<223> OTHER INFORMATION: RNA Oligomer

<400> SEQUENCE: 1556
cuugaauguu ugucuuuugu g                                              21

<210> SEQ ID NO 1557
<211> LENGTH: 21
<212> TYPE: RNA
<213> ORGANISM: artificial
<220> FEATURE:
<223> OTHER INFORMATION: RNA Oligomer

<400> SEQUENCE: 1557
uguuugucuu uugugaaugg g                                              21

<210> SEQ ID NO 1558
<211> LENGTH: 21
<212> TYPE: RNA
<213> ORGANISM: artificial
<220> FEATURE:
<223> OTHER INFORMATION: RNA Oligomer

<400> SEQUENCE: 1558
uugucuuuug ugaauggggu u                                              21

<210> SEQ ID NO 1559
<211> LENGTH: 21
<212> TYPE: RNA
<213> ORGANISM: artificial

```
<220> FEATURE:
<223> OTHER INFORMATION: RNA Oligomer

<400> SEQUENCE: 1559
aggcaauucu uucucuggug u                                               21

<210> SEQ ID NO 1560
<211> LENGTH: 21
<212> TYPE: RNA
<213> ORGANISM: artificial
<220> FEATURE:
<223> OTHER INFORMATION: RNA Oligomer

<400> SEQUENCE: 1560
caauucuuuc ucggugugu u                                                21

<210> SEQ ID NO 1561
<211> LENGTH: 21
<212> TYPE: RNA
<213> ORGANISM: artificial
<220> FEATURE:
<223> OTHER INFORMATION: RNA Oligomer

<400> SEQUENCE: 1561
uuuuaggacc auucuguuug a                                               21

<210> SEQ ID NO 1562
<211> LENGTH: 21
<212> TYPE: RNA
<213> ORGANISM: artificial
<220> FEATURE:
<223> OTHER INFORMATION: RNA Oligomer

<400> SEQUENCE: 1562
ucauacucuu uccgucgcug a                                               21

<210> SEQ ID NO 1563
<211> LENGTH: 21
<212> TYPE: RNA
<213> ORGANISM: artificial
<220> FEATURE:
<223> OTHER INFORMATION: RNA Oligomer

<400> SEQUENCE: 1563
aaucauugaa uucugcugug c                                               21

<210> SEQ ID NO 1564
<211> LENGTH: 21
<212> TYPE: RNA
<213> ORGANISM: artificial
<220> FEATURE:
<223> OTHER INFORMATION: RNA Oligomer

<400> SEQUENCE: 1564
agggugguuu ugguugaaag c                                               21

<210> SEQ ID NO 1565
<211> LENGTH: 21
<212> TYPE: RNA
<213> ORGANISM: artificial
<220> FEATURE:
<223> OTHER INFORMATION: RNA Oligomer

<400> SEQUENCE: 1565
aaaaucugug uugacugugg c                                               21
```

-continued

<210> SEQ ID NO 1566
<211> LENGTH: 21
<212> TYPE: RNA
<213> ORGANISM: artificial
<220> FEATURE:
<223> OTHER INFORMATION: RNA Oligomer

<400> SEQUENCE: 1566
ggcaucugaa uuuaaugagu u                                              21

<210> SEQ ID NO 1567
<211> LENGTH: 21
<212> TYPE: RNA
<213> ORGANISM: artificial
<220> FEATURE:
<223> OTHER INFORMATION: RNA Oligomer

<400> SEQUENCE: 1567
uuuaaugagu ucacugucaa c                                              21

<210> SEQ ID NO 1568
<211> LENGTH: 21
<212> TYPE: RNA
<213> ORGANISM: artificial
<220> FEATURE:
<223> OTHER INFORMATION: RNA Oligomer

<400> SEQUENCE: 1568
aacucaggaa uggauaauag c                                              21

<210> SEQ ID NO 1569
<211> LENGTH: 21
<212> TYPE: RNA
<213> ORGANISM: artificial
<220> FEATURE:
<223> OTHER INFORMATION: RNA Oligomer

<400> SEQUENCE: 1569
auaauagcuc cucccaaacu u                                              21

<210> SEQ ID NO 1570
<211> LENGTH: 21
<212> TYPE: RNA
<213> ORGANISM: artificial
<220> FEATURE:
<223> OTHER INFORMATION: RNA Oligomer

<400> SEQUENCE: 1570
uaauagcucc ucccaaacuu g                                              21

<210> SEQ ID NO 1571
<211> LENGTH: 21
<212> TYPE: RNA
<213> ORGANISM: artificial
<220> FEATURE:
<223> OTHER INFORMATION: RNA Oligomer

<400> SEQUENCE: 1571
cugauuagua gcaaugaaga c                                              21

<210> SEQ ID NO 1572
<211> LENGTH: 21
<212> TYPE: RNA
<213> ORGANISM: artificial
<220> FEATURE:
<223> OTHER INFORMATION: RNA Oligomer

<400> SEQUENCE: 1572
cgaagaaacc ucauugucau c                                              21

<210> SEQ ID NO 1573
<211> LENGTH: 21
<212> TYPE: RNA
<213> ORGANISM: artificial
<220> FEATURE:
<223> OTHER INFORMATION: RNA Oligomer

<400> SEQUENCE: 1573
ucaaaguaca aagcaucuga u                                              21

<210> SEQ ID NO 1574
<211> LENGTH: 21
<212> TYPE: RNA
<213> ORGANISM: artificial
<220> FEATURE:
<223> OTHER INFORMATION: RNA Oligomer

<400> SEQUENCE: 1574
aucugauuug ggaauguggg c                                              21

<210> SEQ ID NO 1575
<211> LENGTH: 21
<212> TYPE: RNA
<213> ORGANISM: artificial
<220> FEATURE:
<223> OTHER INFORMATION: RNA Oligomer

<400> SEQUENCE: 1575
aguaugagca uuucacauca c                                              21

<210> SEQ ID NO 1576
<211> LENGTH: 21
<212> TYPE: RNA
<213> ORGANISM: artificial
<220> FEATURE:
<223> OTHER INFORMATION: RNA Oligomer

<400> SEQUENCE: 1576
uucacaucac aguaggagcu u                                              21

<210> SEQ ID NO 1577
<211> LENGTH: 21
<212> TYPE: RNA
<213> ORGANISM: artificial
<220> FEATURE:
<223> OTHER INFORMATION: RNA Oligomer

<400> SEQUENCE: 1577
uuuuccaucu ucaucacgua g                                              21

<210> SEQ ID NO 1578
<211> LENGTH: 21
<212> TYPE: RNA
<213> ORGANISM: artificial
<220> FEATURE:
<223> OTHER INFORMATION: RNA Oligomer

<400> SEQUENCE: 1578
uccaucuuca ucacguagca u                                              21

<210> SEQ ID NO 1579
<211> LENGTH: 21
<212> TYPE: RNA
<213> ORGANISM: artificial

```
<220> FEATURE:
<223> OTHER INFORMATION: RNA Oligomer

<400> SEQUENCE: 1579
aggugcugag uuguuuuuc a                                              21

<210> SEQ ID NO 1580
<211> LENGTH: 21
<212> TYPE: RNA
<213> ORGANISM: artificial
<220> FEATURE:
<223> OTHER INFORMATION: RNA Oligomer

<400> SEQUENCE: 1580
aguuguuuuu ucaguaggug a                                             21

<210> SEQ ID NO 1581
<211> LENGTH: 21
<212> TYPE: RNA
<213> ORGANISM: artificial
<220> FEATURE:
<223> OTHER INFORMATION: RNA Oligomer

<400> SEQUENCE: 1581
uaaaucuugc ucuaguucua c                                             21

<210> SEQ ID NO 1582
<211> LENGTH: 21
<212> TYPE: RNA
<213> ORGANISM: artificial
<220> FEATURE:
<223> OTHER INFORMATION: RNA Oligomer

<400> SEQUENCE: 1582
ucccgaauua augcaaguug a                                             21

<210> SEQ ID NO 1583
<211> LENGTH: 21
<212> TYPE: RNA
<213> ORGANISM: artificial
<220> FEATURE:
<223> OTHER INFORMATION: RNA Oligomer

<400> SEQUENCE: 1583
aguuguucuu gucuuuccuu u                                             21

<210> SEQ ID NO 1584
<211> LENGTH: 21
<212> TYPE: RNA
<213> ORGANISM: artificial
<220> FEATURE:
<223> OTHER INFORMATION: RNA Oligomer

<400> SEQUENCE: 1584
auguuugucu uuugugaaug g                                             21

<210> SEQ ID NO 1585
<211> LENGTH: 21
<212> TYPE: RNA
<213> ORGANISM: artificial
<220> FEATURE:
<223> OTHER INFORMATION: RNA Oligomer

<400> SEQUENCE: 1585
ggcaauucuu ucucggugu g                                              21
```

```
<210> SEQ ID NO 1586
<211> LENGTH: 21
<212> TYPE: RNA
<213> ORGANISM: artificial
<220> FEATURE:
<223> OTHER INFORMATION: RNA Oligomer

<400> SEQUENCE: 1586
guguuuuagg accauucugu u                                              21

<210> SEQ ID NO 1587
<211> LENGTH: 21
<212> TYPE: RNA
<213> ORGANISM: artificial
<220> FEATURE:
<223> OTHER INFORMATION: RNA Oligomer

<400> SEQUENCE: 1587
uuuccagcuc auacucuuuc c                                              21

<210> SEQ ID NO 1588
<211> LENGTH: 21
<212> TYPE: RNA
<213> ORGANISM: artificial
<220> FEATURE:
<223> OTHER INFORMATION: RNA Oligomer

<400> SEQUENCE: 1588
uaaugaguuc acugucaacu g                                              21

<210> SEQ ID NO 1589
<211> LENGTH: 21
<212> TYPE: RNA
<213> ORGANISM: artificial
<220> FEATURE:
<223> OTHER INFORMATION: RNA Oligomer

<400> SEQUENCE: 1589
aaauacuucu cgacuuacuc c                                              21

<210> SEQ ID NO 1590
<211> LENGTH: 21
<212> TYPE: RNA
<213> ORGANISM: artificial
<220> FEATURE:
<223> OTHER INFORMATION: RNA Oligomer

<400> SEQUENCE: 1590
aauacuucuc gacuuacucc a                                              21

<210> SEQ ID NO 1591
<211> LENGTH: 21
<212> TYPE: RNA
<213> ORGANISM: artificial
<220> FEATURE:
<223> OTHER INFORMATION: RNA Oligomer

<400> SEQUENCE: 1591
auacuucucg acuuacucca a                                              21

<210> SEQ ID NO 1592
<211> LENGTH: 21
<212> TYPE: RNA
<213> ORGANISM: artificial
<220> FEATURE:
<223> OTHER INFORMATION: RNA Oligomer

<400> SEQUENCE: 1592
```
uaacucagga auggauaaua g 21

<210> SEQ ID NO 1593
<211> LENGTH: 21
<212> TYPE: RNA
<213> ORGANISM: artificial
<220> FEATURE:
<223> OTHER INFORMATION: RNA Oligomer

<400> SEQUENCE: 1593
acuugcucaa uguccuguug c 21

<210> SEQ ID NO 1594
<211> LENGTH: 21
<212> TYPE: RNA
<213> ORGANISM: artificial
<220> FEATURE:
<223> OTHER INFORMATION: RNA Oligomer

<400> SEQUENCE: 1594
uugcauaccg ucuaaaucaa c 21

<210> SEQ ID NO 1595
<211> LENGTH: 21
<212> TYPE: RNA
<213> ORGANISM: artificial
<220> FEATURE:
<223> OTHER INFORMATION: RNA Oligomer

<400> SEQUENCE: 1595
gauuaguagc aaugaagacu g 21

<210> SEQ ID NO 1596
<211> LENGTH: 21
<212> TYPE: RNA
<213> ORGANISM: artificial
<220> FEATURE:
<223> OTHER INFORMATION: RNA Oligomer

<400> SEQUENCE: 1596
aagacugggc ucucgaugug a 21

<210> SEQ ID NO 1597
<211> LENGTH: 21
<212> TYPE: RNA
<213> ORGANISM: artificial
<220> FEATURE:
<223> OTHER INFORMATION: RNA Oligomer

<400> SEQUENCE: 1597
ugucaaucaa auccaugucc u 21

<210> SEQ ID NO 1598
<211> LENGTH: 21
<212> TYPE: RNA
<213> ORGANISM: artificial
<220> FEATURE:
<223> OTHER INFORMATION: RNA Oligomer

<400> SEQUENCE: 1598
ucugauuugg gaaugugggc a 21

<210> SEQ ID NO 1599
<211> LENGTH: 21
<212> TYPE: RNA
<213> ORGANISM: artificial

```
<220> FEATURE:
<223> OTHER INFORMATION: RNA Oligomer

<400> SEQUENCE: 1599 aauguggca accugggagu a                                               21

<210> SEQ ID NO 1600
<211> LENGTH: 21
<212> TYPE: RNA
<213> ORGANISM: artificial
<220> FEATURE:
<223> OTHER INFORMATION: RNA Oligomer

<400> SEQUENCE: 1600
ccuuuauuag uaccagcucu u                                              21

<210> SEQ ID NO 1601
<211> LENGTH: 21
<212> TYPE: RNA
<213> ORGANISM: artificial
<220> FEATURE:
<223> OTHER INFORMATION: RNA Oligomer

<400> SEQUENCE: 1601
cuuuauuagu accagcucuu a                                              21

<210> SEQ ID NO 1602
<211> LENGTH: 21
<212> TYPE: RNA
<213> ORGANISM: artificial
<220> FEATURE:
<223> OTHER INFORMATION: RNA Oligomer

<400> SEQUENCE: 1602
ugccauuuuu uguccauaca g                                              21

<210> SEQ ID NO 1603
<211> LENGTH: 21
<212> TYPE: RNA
<213> ORGANISM: artificial
<220> FEATURE:
<223> OTHER INFORMATION: RNA Oligomer

<400> SEQUENCE: 1603
agcucagaaa aggucaaauc c                                              21

<210> SEQ ID NO 1604
<211> LENGTH: 21
<212> TYPE: RNA
<213> ORGANISM: artificial
<220> FEATURE:
<223> OTHER INFORMATION: RNA Oligomer

<400> SEQUENCE: 1604
uucacuagga gaauaagguu u                                              21

<210> SEQ ID NO 1605
<211> LENGTH: 21
<212> TYPE: RNA
<213> ORGANISM: artificial
<220> FEATURE:
<223> OTHER INFORMATION: RNA Oligomer

<400> SEQUENCE: 1605
uaaggugcug aguuguuuu u                                               21
```

```
<210> SEQ ID NO 1606
<211> LENGTH: 21
<212> TYPE: RNA
<213> ORGANISM: artificial
<220> FEATURE:
<223> OTHER INFORMATION: RNA Oligomer

<400> SEQUENCE: 1606
augaucuaaa ucuugcucua g                                              21

<210> SEQ ID NO 1607
<211> LENGTH: 21
<212> TYPE: RNA
<213> ORGANISM: artificial
<220> FEATURE:
<223> OTHER INFORMATION: RNA Oligomer

<400> SEQUENCE: 1607
uuuccaguuu ucuuuuucug c                                              21

<210> SEQ ID NO 1608
<211> LENGTH: 21
<212> TYPE: RNA
<213> ORGANISM: artificial
<220> FEATURE:
<223> OTHER INFORMATION: RNA Oligomer

<400> SEQUENCE: 1608
uaucccgaau uaaugcaagu u                                              21

<210> SEQ ID NO 1609
<211> LENGTH: 21
<212> TYPE: RNA
<213> ORGANISM: artificial
<220> FEATURE:
<223> OTHER INFORMATION: RNA Oligomer

<400> SEQUENCE: 1609
aucccgaauu aaugcaaguu g                                              21

<210> SEQ ID NO 1610
<211> LENGTH: 21
<212> TYPE: RNA
<213> ORGANISM: artificial
<220> FEATURE:
<223> OTHER INFORMATION: RNA Oligomer

<400> SEQUENCE: 1610
ucuacaggga augggauaug g                                              21

<210> SEQ ID NO 1611
<211> LENGTH: 21
<212> TYPE: RNA
<213> ORGANISM: artificial
<220> FEATURE:
<223> OTHER INFORMATION: RNA Oligomer

<400> SEQUENCE: 1611
gcuugaaugu uugucuuuug u                                              21

<210> SEQ ID NO 1612
<211> LENGTH: 21
<212> TYPE: RNA
<213> ORGANISM: artificial
<220> FEATURE:
<223> OTHER INFORMATION: RNA Oligomer

<400> SEQUENCE: 1612
```
uuugucuuuu gugaaugggg u     21

<210> SEQ ID NO 1613
<211> LENGTH: 21
<212> TYPE: RNA
<213> ORGANISM: artificial
<220> FEATURE:
<223> OTHER INFORMATION: RNA Oligomer

<400> SEQUENCE: 1613
caggacuuac aggcaauucu u     21

<210> SEQ ID NO 1614
<211> LENGTH: 21
<212> TYPE: RNA
<213> ORGANISM: artificial
<220> FEATURE:
<223> OTHER INFORMATION: RNA Oligomer

<400> SEQUENCE: 1614
aggacuuaca ggcaauucuu u     21

<210> SEQ ID NO 1615
<211> LENGTH: 21
<212> TYPE: RNA
<213> ORGANISM: artificial
<220> FEATURE:
<223> OTHER INFORMATION: RNA Oligomer

<400> SEQUENCE: 1615
aauucuuucu cugguguguu c     21

<210> SEQ ID NO 1616
<211> LENGTH: 21
<212> TYPE: RNA
<213> ORGANISM: artificial
<220> FEATURE:
<223> OTHER INFORMATION: RNA Oligomer

<400> SEQUENCE: 1616
uguuuuucca gcucauacuc u     21

<210> SEQ ID NO 1617
<211> LENGTH: 21
<212> TYPE: RNA
<213> ORGANISM: artificial
<220> FEATURE:
<223> OTHER INFORMATION: RNA Oligomer

<400> SEQUENCE: 1617
cauuaagaaa auggacua c     21

<210> SEQ ID NO 1618
<211> LENGTH: 21
<212> TYPE: RNA
<213> ORGANISM: artificial
<220> FEATURE:
<223> OTHER INFORMATION: RNA Oligomer

<400> SEQUENCE: 1618
cauugagggu auagaugagu a     21

<210> SEQ ID NO 1619
<211> LENGTH: 21
<212> TYPE: RNA
<213> ORGANISM: artificial -continued

```
<220> FEATURE:
<223> OTHER INFORMATION: RNA Oligomer

<400> SEQUENCE: 1619
ccaaacuugc ucaauguccu g                                              21

<210> SEQ ID NO 1620
<211> LENGTH: 21
<212> TYPE: RNA
<213> ORGANISM: artificial
<220> FEATURE:
<223> OTHER INFORMATION: RNA Oligomer

<400> SEQUENCE: 1620
agugacugaa acguagccga a                                              21

<210> SEQ ID NO 1621
<211> LENGTH: 21
<212> TYPE: RNA
<213> ORGANISM: artificial
<220> FEATURE:
<223> OTHER INFORMATION: RNA Oligomer

<400> SEQUENCE: 1621
uagccgaaga aaccucauug u                                              21

<210> SEQ ID NO 1622
<211> LENGTH: 21
<212> TYPE: RNA
<213> ORGANISM: artificial
<220> FEATURE:
<223> OTHER INFORMATION: RNA Oligomer

<400> SEQUENCE: 1622
augucaauca aauccauguc c                                              21

<210> SEQ ID NO 1623
<211> LENGTH: 21
<212> TYPE: RNA
<213> ORGANISM: artificial
<220> FEATURE:
<223> OTHER INFORMATION: RNA Oligomer

<400> SEQUENCE: 1623
ccauuuuuug uccauacagu a                                              21

<210> SEQ ID NO 1624
<211> LENGTH: 21
<212> TYPE: RNA
<213> ORGANISM: artificial
<220> FEATURE:
<223> OTHER INFORMATION: RNA Oligomer

<400> SEQUENCE: 1624
aggguguccu aagaaauugu u                                              21

<210> SEQ ID NO 1625
<211> LENGTH: 21
<212> TYPE: RNA
<213> ORGANISM: artificial
<220> FEATURE:
<223> OTHER INFORMATION: RNA Oligomer

<400> SEQUENCE: 1625
guccuaagaa auuguuuaca g                                              21
```

```
<210> SEQ ID NO 1626
<211> LENGTH: 21
<212> TYPE: RNA
<213> ORGANISM: artificial
<220> FEATURE:
<223> OTHER INFORMATION: RNA Oligomer

<400> SEQUENCE: 1626
agaauaaggu uuccaucuu c                                              21

<210> SEQ ID NO 1627
<211> LENGTH: 21
<212> TYPE: RNA
<213> ORGANISM: artificial
<220> FEATURE:
<223> OTHER INFORMATION: RNA Oligomer

<400> SEQUENCE: 1627 guuuccauc uucaucacgu a                                              21

<210> SEQ ID NO 1628
<211> LENGTH: 21
<212> TYPE: RNA
<213> ORGANISM: artificial
<220> FEATURE:
<223> OTHER INFORMATION: RNA Oligomer

<400> SEQUENCE: 1628
aacuucgaga uauaaggugc u                                             21

<210> SEQ ID NO 1629
<211> LENGTH: 21
<212> TYPE: RNA
<213> ORGANISM: artificial
<220> FEATURE:
<223> OTHER INFORMATION: RNA Oligomer

<400> SEQUENCE: 1629
uauaaggugc ugaguuguuu u                                             21

<210> SEQ ID NO 1630
<211> LENGTH: 21
<212> TYPE: RNA
<213> ORGANISM: artificial
<220> FEATURE:
<223> OTHER INFORMATION: RNA Oligomer

<400> SEQUENCE: 1630
caaaugaucu aaaucuugcu c                                             21

<210> SEQ ID NO 1631
<211> LENGTH: 21
<212> TYPE: RNA
<213> ORGANISM: artificial
<220> FEATURE:
<223> OTHER INFORMATION: RNA Oligomer

<400> SEQUENCE: 1631
ucuaaaucuu gcucuaguuc u                                             21

<210> SEQ ID NO 1632
<211> LENGTH: 21
<212> TYPE: RNA
<213> ORGANISM: artificial
<220> FEATURE:
<223> OTHER INFORMATION: RNA Oligomer

<400> SEQUENCE: 1632
```
uccaguuuuc uuuuucugca a                                             21

<210> SEQ ID NO 1633
<211> LENGTH: 21
<212> TYPE: RNA
<213> ORGANISM: artificial
<220> FEATURE:
<223> OTHER INFORMATION: RNA Oligomer

<400> SEQUENCE: 1633
cuacagggaa ugggauaugg a                                             21

<210> SEQ ID NO 1634
<211> LENGTH: 21
<212> TYPE: RNA
<213> ORGANISM: artificial
<220> FEATURE:
<223> OTHER INFORMATION: RNA Oligomer

<400> SEQUENCE: 1634
guuugucuuu ugugaauggg g                                             21

<210> SEQ ID NO 1635
<211> LENGTH: 21
<212> TYPE: RNA
<213> ORGANISM: artificial
<220> FEATURE:
<223> OTHER INFORMATION: RNA Oligomer

<400> SEQUENCE: 1635
uucuuucucu gguguguucu c                                             21

<210> SEQ ID NO 1636
<211> LENGTH: 21
<212> TYPE: RNA
<213> ORGANISM: artificial
<220> FEATURE:
<223> OTHER INFORMATION: RNA Oligomer

<400> SEQUENCE: 1636 uaucccaga agaauguacu g                                              21

<210> SEQ ID NO 1637
<211> LENGTH: 21
<212> TYPE: RNA
<213> ORGANISM: artificial
<220> FEATURE:
<223> OTHER INFORMATION: RNA Oligomer

<400> SEQUENCE: 1637
uccagcucau acucuuuccg u                                             21

<210> SEQ ID NO 1638
<211> LENGTH: 21
<212> TYPE: RNA
<213> ORGANISM: artificial
<220> FEATURE:
<223> OTHER INFORMATION: RNA Oligomer

<400> SEQUENCE: 1638
uuagugaaau gccggaguca g                                             21

<210> SEQ ID NO 1639
<211> LENGTH: 21
<212> TYPE: RNA
<213> ORGANISM: artificial
<220> FEATURE:
<223> OTHER INFORMATION: RNA Oligomer

<400> SEQUENCE: 1639
aucauugaau ucugcugugc u                                          21

<210> SEQ ID NO 1640
<211> LENGTH: 21
<212> TYPE: RNA
<213> ORGANISM: artificial
<220> FEATURE:
<223> OTHER INFORMATION: RNA Oligomer

<400> SEQUENCE: 1640
ugacuguggc aucugaauuu a                                          21

<210> SEQ ID NO 1641
<211> LENGTH: 21
<212> TYPE: RNA
<213> ORGANISM: artificial
<220> FEATURE:
<223> OTHER INFORMATION: RNA Oligomer

<400> SEQUENCE: 1641
guggcaucug aauuuaauga g                                          21

<210> SEQ ID NO 1642
<211> LENGTH: 21
<212> TYPE: RNA
<213> ORGANISM: artificial
<220> FEATURE:
<223> OTHER INFORMATION: RNA Oligomer

<400> SEQUENCE: 1642
uaagaaaaug uggacuacag u                                          21

<210> SEQ ID NO 1643
<211> LENGTH: 21
<212> TYPE: RNA
<213> ORGANISM: artificial
<220> FEATURE:
<223> OTHER INFORMATION: RNA Oligomer

<400> SEQUENCE: 1643
accuacuucu uuuccauug a                                           21

<210> SEQ ID NO 1644
<211> LENGTH: 21
<212> TYPE: RNA
<213> ORGANISM: artificial
<220> FEATURE:
<223> OTHER INFORMATION: RNA Oligomer

<400> SEQUENCE: 1644
cucaggaaug gauaauagcu c                                          21

<210> SEQ ID NO 1645
<211> LENGTH: 21
<212> TYPE: RNA
<213> ORGANISM: artificial
<220> FEATURE:
<223> OTHER INFORMATION: RNA Oligomer

<400> SEQUENCE: 1645
aaacuugcuc aauguccugu u                                          21

```
<210> SEQ ID NO 1646
<211> LENGTH: 21
<212> TYPE: RNA
<213> ORGANISM: artificial
<220> FEATURE:
<223> OTHER INFORMATION: RNA Oligomer

<400> SEQUENCE: 1646
guccuguugc auaccgucua a                                          21

<210> SEQ ID NO 1647
<211> LENGTH: 21
<212> TYPE: RNA
<213> ORGANISM: artificial
<220> FEATURE:
<223> OTHER INFORMATION: RNA Oligomer

<400> SEQUENCE: 1647
uccuguugca uaccgucuaa a                                          21

<210> SEQ ID NO 1648
<211> LENGTH: 21
<212> TYPE: RNA
<213> ORGANISM: artificial
<220> FEATURE:
<223> OTHER INFORMATION: RNA Oligomer

<400> SEQUENCE: 1648
aacguagccg aagaaaccuc a                                          21

<210> SEQ ID NO 1649
<211> LENGTH: 21
<212> TYPE: RNA
<213> ORGANISM: artificial
<220> FEATURE:
<223> OTHER INFORMATION: RNA Oligomer

<400> SEQUENCE: 1649
acguagccga agaaaccuca u                                          21

<210> SEQ ID NO 1650
<211> LENGTH: 21
<212> TYPE: RNA
<213> ORGANISM: artificial
<220> FEATURE:
<223> OTHER INFORMATION: RNA Oligomer

<400> SEQUENCE: 1650
cagucaucaa aguacaaagc a                                          21

<210> SEQ ID NO 1651
<211> LENGTH: 21
<212> TYPE: RNA
<213> ORGANISM: artificial
<220> FEATURE:
<223> OTHER INFORMATION: RNA Oligomer

<400> SEQUENCE: 1651
ucaucaaagu acaaagcauc u                                          21

<210> SEQ ID NO 1652
<211> LENGTH: 21
<212> TYPE: RNA
<213> ORGANISM: artificial
<220> FEATURE:
<223> OTHER INFORMATION: RNA Oligomer

<400> SEQUENCE: 1652
```
aaucaaaucc auguccugcu g                                          21

<210> SEQ ID NO 1653
<211> LENGTH: 21
<212> TYPE: RNA
<213> ORGANISM: artificial
<220> FEATURE:
<223> OTHER INFORMATION: RNA Oligomer

<400> SEQUENCE: 1653
ugucucuuca ucuaguugua a                                          21

<210> SEQ ID NO 1654
<211> LENGTH: 21
<212> TYPE: RNA
<213> ORGANISM: artificial
<220> FEATURE:
<223> OTHER INFORMATION: RNA Oligomer

<400> SEQUENCE: 1654
uccuuuauua guaccagcuc u                                          21

<210> SEQ ID NO 1655
<211> LENGTH: 21
<212> TYPE: RNA
<213> ORGANISM: artificial
<220> FEATURE:
<223> OTHER INFORMATION: RNA Oligomer

<400> SEQUENCE: 1655
uuucuuuuua gccagauguc a                                          21

<210> SEQ ID NO 1656
<211> LENGTH: 21
<212> TYPE: RNA
<213> ORGANISM: artificial
<220> FEATURE:
<223> OTHER INFORMATION: RNA Oligomer

<400> SEQUENCE: 1656
uuacacuuac acagaaacua g                                          21

<210> SEQ ID NO 1657
<211> LENGTH: 21
<212> TYPE: RNA
<213> ORGANISM: artificial
<220> FEATURE:
<223> OTHER INFORMATION: RNA Oligomer

<400> SEQUENCE: 1657
acacuuacac agaaacuagc c                                          21

<210> SEQ ID NO 1658
<211> LENGTH: 21
<212> TYPE: RNA
<213> ORGANISM: artificial
<220> FEATURE:
<223> OTHER INFORMATION: RNA Oligomer

<400> SEQUENCE: 1658
acuuacacag aaacuagccc a                                          21

<210> SEQ ID NO 1659
<211> LENGTH: 21
<212> TYPE: RNA
<213> ORGANISM: artificial

```
<220> FEATURE:
<223> OTHER INFORMATION: RNA Oligomer

<400> SEQUENCE: 1659
ugguguccua agaaauuguu u                                              21

<210> SEQ ID NO 1660
<211> LENGTH: 21
<212> TYPE: RNA
<213> ORGANISM: artificial
<220> FEATURE:
<223> OTHER INFORMATION: RNA Oligomer

<400> SEQUENCE: 1660
ugauucaaca uacugacacu c                                              21

<210> SEQ ID NO 1661
<211> LENGTH: 21
<212> TYPE: RNA
<213> ORGANISM: artificial
<220> FEATURE:
<223> OTHER INFORMATION: RNA Oligomer

<400> SEQUENCE: 1661
ucacaguagg agcuuuuagu a                                              21

<210> SEQ ID NO 1662
<211> LENGTH: 21
<212> TYPE: RNA
<213> ORGANISM: artificial
<220> FEATURE:
<223> OTHER INFORMATION: RNA Oligomer

<400> SEQUENCE: 1662
uuccaucuuc aucacguagc a                                              21

<210> SEQ ID NO 1663
<211> LENGTH: 21
<212> TYPE: RNA
<213> ORGANISM: artificial
<220> FEATURE:
<223> OTHER INFORMATION: RNA Oligomer

<400> SEQUENCE: 1663
aaacuucgag auauaaggug c                                              21

<210> SEQ ID NO 1664
<211> LENGTH: 21
<212> TYPE: RNA
<213> ORGANISM: artificial
<220> FEATURE:
<223> OTHER INFORMATION: RNA Oligomer

<400> SEQUENCE: 1664
acuucgagau auaaggugcu g                                              21

<210> SEQ ID NO 1665
<211> LENGTH: 21
<212> TYPE: RNA
<213> ORGANISM: artificial
<220> FEATURE:
<223> OTHER INFORMATION: RNA Oligomer

<400> SEQUENCE: 1665
gaguuguuuu uucaguaggu g                                              21
```

```
<210> SEQ ID NO 1666
<211> LENGTH: 21
<212> TYPE: RNA
<213> ORGANISM: artificial
<220> FEATURE:
<223> OTHER INFORMATION: RNA Oligomer

<400> SEQUENCE: 1666
gaucuaaauc uugcucuagu u                                              21

<210> SEQ ID NO 1667
<211> LENGTH: 21
<212> TYPE: RNA
<213> ORGANISM: artificial
<220> FEATURE:
<223> OTHER INFORMATION: RNA Oligomer

<400> SEQUENCE: 1667
aaucuugcuc uaguucuacu a                                              21

<210> SEQ ID NO 1668
<211> LENGTH: 21
<212> TYPE: RNA
<213> ORGANISM: artificial
<220> FEATURE:
<223> OTHER INFORMATION: RNA Oligomer

<400> SEQUENCE: 1668
uaccccuccu acguauaucc c                                              21

<210> SEQ ID NO 1669
<211> LENGTH: 21
<212> TYPE: RNA
<213> ORGANISM: artificial
<220> FEATURE:
<223> OTHER INFORMATION: RNA Oligomer

<400> SEQUENCE: 1669
ucuuucucug guguguucuc a                                              21

<210> SEQ ID NO 1670
<211> LENGTH: 21
<212> TYPE: RNA
<213> ORGANISM: artificial
<220> FEATURE:
<223> OTHER INFORMATION: RNA Oligomer

<400> SEQUENCE: 1670
uuuuuccagc ucauacucuu u                                              21

<210> SEQ ID NO 1671
<211> LENGTH: 21
<212> TYPE: RNA
<213> ORGANISM: artificial
<220> FEATURE:
<223> OTHER INFORMATION: RNA Oligomer

<400> SEQUENCE: 1671
uuccagcuca uacucuuucc g                                              21

<210> SEQ ID NO 1672
<211> LENGTH: 21
<212> TYPE: RNA
<213> ORGANISM: artificial
<220> FEATURE:
<223> OTHER INFORMATION: RNA Oligomer

<400> SEQUENCE: 1672
```
uguuugacac uuccaggggc a                            21

<210> SEQ ID NO 1673
<211> LENGTH: 21
<212> TYPE: RNA
<213> ORGANISM: artificial
<220> FEATURE:
<223> OTHER INFORMATION: RNA Oligomer

<400> SEQUENCE: 1673
ugacacuucc agggcacua u                             21

<210> SEQ ID NO 1674
<211> LENGTH: 21
<212> TYPE: RNA
<213> ORGANISM: artificial
<220> FEATURE:
<223> OTHER INFORMATION: RNA Oligomer

<400> SEQUENCE: 1674
gcucauacuc uuccgucgc u                             21

<210> SEQ ID NO 1675
<211> LENGTH: 21
<212> TYPE: RNA
<213> ORGANISM: artificial
<220> FEATURE:
<223> OTHER INFORMATION: RNA Oligomer

<400> SEQUENCE: 1675
cucauacucu uuccgucgcu g                            21

<210> SEQ ID NO 1676
<211> LENGTH: 21
<212> TYPE: RNA
<213> ORGANISM: artificial
<220> FEATURE:
<223> OTHER INFORMATION: RNA Oligomer

<400> SEQUENCE: 1676
aucagaaaca ucaaugggcc c                            21

<210> SEQ ID NO 1677
<211> LENGTH: 21
<212> TYPE: RNA
<213> ORGANISM: artificial
<220> FEATURE:
<223> OTHER INFORMATION: RNA Oligomer

<400> SEQUENCE: 1677
uuaagaaaau guggacuaca g                            21

<210> SEQ ID NO 1678
<211> LENGTH: 21
<212> TYPE: RNA
<213> ORGANISM: artificial
<220> FEATURE:
<223> OTHER INFORMATION: RNA Oligomer

<400> SEQUENCE: 1678
ccuacuucuu uuccauuga g                             21

<210> SEQ ID NO 1679
<211> LENGTH: 21
<212> TYPE: RNA
<213> ORGANISM: artificial

```
<220> FEATURE:
<223> OTHER INFORMATION: RNA Oligomer

<400> SEQUENCE: 1679
uucucgacuu acuccaagau c                                              21

<210> SEQ ID NO 1680
<211> LENGTH: 21
<212> TYPE: RNA
<213> ORGANISM: artificial
<220> FEATURE:
<223> OTHER INFORMATION: RNA Oligomer

<400> SEQUENCE: 1680
aucuauaucu ugccuccaaa g                                              21

<210> SEQ ID NO 1681
<211> LENGTH: 21
<212> TYPE: RNA
<213> ORGANISM: artificial
<220> FEATURE:
<223> OTHER INFORMATION: RNA Oligomer

<400> SEQUENCE: 1681
cucccaaacu ugcucaaugu c                                              21

<210> SEQ ID NO 1682
<211> LENGTH: 21
<212> TYPE: RNA
<213> ORGANISM: artificial
<220> FEATURE:
<223> OTHER INFORMATION: RNA Oligomer

<400> SEQUENCE: 1682
ucccaaacuu gcucaauguc c                                              21

<210> SEQ ID NO 1683
<211> LENGTH: 21
<212> TYPE: RNA
<213> ORGANISM: artificial
<220> FEATURE:
<223> OTHER INFORMATION: RNA Oligomer

<400> SEQUENCE: 1683
gcaacagaag uuucagguga c                                              21

<210> SEQ ID NO 1684
<211> LENGTH: 21
<212> TYPE: RNA
<213> ORGANISM: artificial
<220> FEATURE:
<223> OTHER INFORMATION: RNA Oligomer

<400> SEQUENCE: 1684
uaguagcaau gaagacuggg c                                              21

<210> SEQ ID NO 1685
<211> LENGTH: 21
<212> TYPE: RNA
<213> ORGANISM: artificial
<220> FEATURE:
<223> OTHER INFORMATION: RNA Oligomer

<400> SEQUENCE: 1685
caaugaagac ugggcucucg a                                              21
```

```
<210> SEQ ID NO 1686
<211> LENGTH: 21
<212> TYPE: RNA
<213> ORGANISM: artificial
<220> FEATURE:
<223> OTHER INFORMATION: RNA Oligomer

<400> SEQUENCE: 1686
aagugacuga aacguagccg a                                              21

<210> SEQ ID NO 1687
<211> LENGTH: 21
<212> TYPE: RNA
<213> ORGANISM: artificial
<220> FEATURE:
<223> OTHER INFORMATION: RNA Oligomer

<400> SEQUENCE: 1687
aaacguagcc gaagaaaccu c                                              21

<210> SEQ ID NO 1688
<211> LENGTH: 21
<212> TYPE: RNA
<213> ORGANISM: artificial
<220> FEATURE:
<223> OTHER INFORMATION: RNA Oligomer

<400> SEQUENCE: 1688
caugcaguca ucaaaguaca a                                              21

<210> SEQ ID NO 1689
<211> LENGTH: 21
<212> TYPE: RNA
<213> ORGANISM: artificial
<220> FEATURE:
<223> OTHER INFORMATION: RNA Oligomer

<400> SEQUENCE: 1689
agucaucaaa guacaaagca u                                              21

<210> SEQ ID NO 1690
<211> LENGTH: 21
<212> TYPE: RNA
<213> ORGANISM: artificial
<220> FEATURE:
<223> OTHER INFORMATION: RNA Oligomer

<400> SEQUENCE: 1690
gucaucaaag uacaaagcau c                                              21

<210> SEQ ID NO 1691
<211> LENGTH: 21
<212> TYPE: RNA
<213> ORGANISM: artificial
<220> FEATURE:
<223> OTHER INFORMATION: RNA Oligomer

<400> SEQUENCE: 1691
uucaccuguc ucuucaucua g                                              21

<210> SEQ ID NO 1692
<211> LENGTH: 21
<212> TYPE: RNA
<213> ORGANISM: artificial
<220> FEATURE:
<223> OTHER INFORMATION: RNA Oligomer

<400> SEQUENCE: 1692
```
aaugccauuu uuguccaua c 21

<210> SEQ ID NO 1693
<211> LENGTH: 21
<212> TYPE: RNA
<213> ORGANISM: artificial
<220> FEATURE:
<223> OTHER INFORMATION: RNA Oligomer

<400> SEQUENCE: 1693
augccauuuu uuguccauac a 21

<210> SEQ ID NO 1694
<211> LENGTH: 21
<212> TYPE: RNA
<213> ORGANISM: artificial
<220> FEATURE:
<223> OTHER INFORMATION: RNA Oligomer

<400> SEQUENCE: 1694
aauggugucc uaagaaauug u 21

<210> SEQ ID NO 1695
<211> LENGTH: 21
<212> TYPE: RNA
<213> ORGANISM: artificial
<220> FEATURE:
<223> OTHER INFORMATION: RNA Oligomer

<400> SEQUENCE: 1695
aaguaugagc auuucacauc a 21

<210> SEQ ID NO 1696
<211> LENGTH: 21
<212> TYPE: RNA
<213> ORGANISM: artificial
<220> FEATURE:
<223> OTHER INFORMATION: RNA Oligomer

<400> SEQUENCE: 1696
gcauuucaca ucacaguagg a 21

<210> SEQ ID NO 1697
<211> LENGTH: 21
<212> TYPE: RNA
<213> ORGANISM: artificial
<220> FEATURE:
<223> OTHER INFORMATION: RNA Oligomer

<400> SEQUENCE: 1697
ugcagggagu auucacuagg a 21

<210> SEQ ID NO 1698
<211> LENGTH: 21
<212> TYPE: RNA
<213> ORGANISM: artificial
<220> FEATURE:
<223> OTHER INFORMATION: RNA Oligomer

<400> SEQUENCE: 1698
augaugagcu guggaccgug u 21

<210> SEQ ID NO 1699
<211> LENGTH: 21
<212> TYPE: RNA
<213> ORGANISM: artificial

```
<220> FEATURE:
<223> OTHER INFORMATION: RNA Oligomer

<400> SEQUENCE: 1699
gaccauucug uuugacacuu c                                         21

<210> SEQ ID NO 1700
<211> LENGTH: 21
<212> TYPE: RNA
<213> ORGANISM: artificial
<220> FEATURE:
<223> OTHER INFORMATION: RNA Oligomer

<400> SEQUENCE: 1700
ccauucuguu ugacacuucc a                                         21

<210> SEQ ID NO 1701
<211> LENGTH: 21
<212> TYPE: RNA
<213> ORGANISM: artificial
<220> FEATURE:
<223> OTHER INFORMATION: RNA Oligomer

<400> SEQUENCE: 1701
gcucuuccac uucagaauca c                                         21

<210> SEQ ID NO 1702
<211> LENGTH: 21
<212> TYPE: RNA
<213> ORGANISM: artificial
<220> FEATURE:
<223> OTHER INFORMATION: RNA Oligomer

<400> SEQUENCE: 1702
auugaauucu gcugugcuuu c                                         21

<210> SEQ ID NO 1703
<211> LENGTH: 21
<212> TYPE: RNA
<213> ORGANISM: artificial
<220> FEATURE:
<223> OTHER INFORMATION: RNA Oligomer

<400> SEQUENCE: 1703
ccaaaaucug uguugacugu g                                         21

<210> SEQ ID NO 1704
<211> LENGTH: 21
<212> TYPE: RNA
<213> ORGANISM: artificial
<220> FEATURE:
<223> OTHER INFORMATION: RNA Oligomer

<400> SEQUENCE: 1704
cuucugucag uuuggcuucu g                                         21

<210> SEQ ID NO 1705
<211> LENGTH: 21
<212> TYPE: RNA
<213> ORGANISM: artificial
<220> FEATURE:
<223> OTHER INFORMATION: RNA Oligomer

<400> SEQUENCE: 1705
ugagcaacag aaguuucagg u                                         21
```

```
<210> SEQ ID NO 1706
<211> LENGTH: 21
<212> TYPE: RNA
<213> ORGANISM: artificial
<220> FEATURE:
<223> OTHER INFORMATION: RNA Oligomer

<400> SEQUENCE: 1706
cuugccucca aaguauguca a                                              21

<210> SEQ ID NO 1707
<211> LENGTH: 21
<212> TYPE: RNA
<213> ORGANISM: artificial
<220> FEATURE:
<223> OTHER INFORMATION: RNA Oligomer

<400> SEQUENCE: 1707
ccuccaaagu augucaauca a                                              21

<210> SEQ ID NO 1708
<211> LENGTH: 21
<212> TYPE: RNA
<213> ORGANISM: artificial
<220> FEATURE:
<223> OTHER INFORMATION: RNA Oligomer

<400> SEQUENCE: 1708
ggaauaucag gaacaaguga c                                              21

<210> SEQ ID NO 1709
<211> LENGTH: 21
<212> TYPE: RNA
<213> ORGANISM: artificial
<220> FEATURE:
<223> OTHER INFORMATION: RNA Oligomer

<400> SEQUENCE: 1709
gcagucauca aaguacaaag c                                              21

<210> SEQ ID NO 1710
<211> LENGTH: 21
<212> TYPE: RNA
<213> ORGANISM: artificial
<220> FEATURE:
<223> OTHER INFORMATION: RNA Oligomer

<400> SEQUENCE: 1710
gucaaucaaa uccauguccu g                                              21

<210> SEQ ID NO 1711
<211> LENGTH: 21
<212> TYPE: RNA
<213> ORGANISM: artificial
<220> FEATURE:
<223> OTHER INFORMATION: RNA Oligomer

<400> SEQUENCE: 1711
cucuucaucu aguuguaacu g                                              21

<210> SEQ ID NO 1712
<211> LENGTH: 21
<212> TYPE: RNA
<213> ORGANISM: artificial
<220> FEATURE:
<223> OTHER INFORMATION: RNA Oligomer

<400> SEQUENCE: 1712
```
uuuuuagcca gaugucauau c                                              21

<210> SEQ ID NO 1713
<211> LENGTH: 21
<212> TYPE: RNA
<213> ORGANISM: artificial
<220> FEATURE:
<223> OTHER INFORMATION: RNA Oligomer

<400> SEQUENCE: 1713
aacuacugau ucaacauacu g                                              21

<210> SEQ ID NO 1714
<211> LENGTH: 21
<212> TYPE: RNA
<213> ORGANISM: artificial
<220> FEATURE:
<223> OTHER INFORMATION: RNA Oligomer

<400> SEQUENCE: 1714
acauacugac acuccaaugc u                                              21

<210> SEQ ID NO 1715
<211> LENGTH: 21
<212> TYPE: RNA
<213> ORGANISM: artificial
<220> FEATURE:
<223> OTHER INFORMATION: RNA Oligomer

<400> SEQUENCE: 1715
auacugacac uccaaugcuu u                                              21

<210> SEQ ID NO 1716
<211> LENGTH: 21
<212> TYPE: RNA
<213> ORGANISM: artificial
<220> FEATURE:
<223> OTHER INFORMATION: RNA Oligomer

<400> SEQUENCE: 1716
agcauuucac aucacaguag g                                              21

<210> SEQ ID NO 1717
<211> LENGTH: 21
<212> TYPE: RNA
<213> ORGANISM: artificial
<220> FEATURE:
<223> OTHER INFORMATION: RNA Oligomer

<400> SEQUENCE: 1717
aaacuagcuc agaaaagguc a                                              21

<210> SEQ ID NO 1718
<211> LENGTH: 21
<212> TYPE: RNA
<213> ORGANISM: artificial
<220> FEATURE:
<223> OTHER INFORMATION: RNA Oligomer

<400> SEQUENCE: 1718
uagcucagaa aaggucaaau c                                              21

<210> SEQ ID NO 1719
<211> LENGTH: 21
<212> TYPE: RNA
<213> ORGANISM: artificial

```
<220> FEATURE:
<223> OTHER INFORMATION: RNA Oligomer

<400> SEQUENCE: 1719
ucuucaucac guagcaugcu g                                          21

<210> SEQ ID NO 1720
<211> LENGTH: 21
<212> TYPE: RNA
<213> ORGANISM: artificial
<220> FEATURE:
<223> OTHER INFORMATION: RNA Oligomer

<400> SEQUENCE: 1720
aaaacuucga gauauaaggu g                                          21

<210> SEQ ID NO 1721
<211> LENGTH: 21
<212> TYPE: RNA
<213> ORGANISM: artificial
<220> FEATURE:
<223> OTHER INFORMATION: RNA Oligomer

<400> SEQUENCE: 1721
cuucgagaua uaaggugcug a                                          21

<210> SEQ ID NO 1722
<211> LENGTH: 21
<212> TYPE: RNA
<213> ORGANISM: artificial
<220> FEATURE:
<223> OTHER INFORMATION: RNA Oligomer

<400> SEQUENCE: 1722
ucgagauaua aggugcugag u                                          21

<210> SEQ ID NO 1723
<211> LENGTH: 21
<212> TYPE: RNA
<213> ORGANISM: artificial
<220> FEATURE:
<223> OTHER INFORMATION: RNA Oligomer

<400> SEQUENCE: 1723
aucuugcucu aguucuacua u                                          21

<210> SEQ ID NO 1724
<211> LENGTH: 21
<212> TYPE: RNA
<213> ORGANISM: artificial
<220> FEATURE:
<223> OTHER INFORMATION: RNA Oligomer

<400> SEQUENCE: 1724
uuaccccucc uacguauauc c                                          21

<210> SEQ ID NO 1725
<211> LENGTH: 21
<212> TYPE: RNA
<213> ORGANISM: artificial
<220> FEATURE:
<223> OTHER INFORMATION: RNA Oligomer

<400> SEQUENCE: 1725
gaaugggaua uggagagcuu u                                          21
```

<210> SEQ ID NO 1726
<211> LENGTH: 21
<212> TYPE: RNA
<213> ORGANISM: artificial
<220> FEATURE:
<223> OTHER INFORMATION: RNA Oligomer

<400> SEQUENCE: 1726
ugggauaugg agagcuuuug c                                              21

<210> SEQ ID NO 1727
<211> LENGTH: 21
<212> TYPE: RNA
<213> ORGANISM: artificial
<220> FEATURE:
<223> OTHER INFORMATION: RNA Oligomer

<400> SEQUENCE: 1727
uuuugcccua aguucaucuc u                                              21

<210> SEQ ID NO 1728
<211> LENGTH: 21
<212> TYPE: RNA
<213> ORGANISM: artificial
<220> FEATURE:
<223> OTHER INFORMATION: RNA Oligomer

<400> SEQUENCE: 1728
uugcccuaag uucaucucuu g                                              21

<210> SEQ ID NO 1729
<211> LENGTH: 21
<212> TYPE: RNA
<213> ORGANISM: artificial
<220> FEATURE:
<223> OTHER INFORMATION: RNA Oligomer

<400> SEQUENCE: 1729
cccuaaguuc aucucuugug a                                              21

<210> SEQ ID NO 1730
<211> LENGTH: 21
<212> TYPE: RNA
<213> ORGANISM: artificial
<220> FEATURE:
<223> OTHER INFORMATION: RNA Oligomer

<400> SEQUENCE: 1730
accauucugu uugacacuuc c                                              21

<210> SEQ ID NO 1731
<211> LENGTH: 21
<212> TYPE: RNA
<213> ORGANISM: artificial
<220> FEATURE:
<223> OTHER INFORMATION: RNA Oligomer

<400> SEQUENCE: 1731
auucuguuug acacuuccag g                                              21

<210> SEQ ID NO 1732
<211> LENGTH: 21
<212> TYPE: RNA
<213> ORGANISM: artificial
<220> FEATURE:
<223> OTHER INFORMATION: RNA Oligomer

<400> SEQUENCE: 1732

-continued uagcucuucc acuucagaau c            21

<210> SEQ ID NO 1733
<211> LENGTH: 21
<212> TYPE: RNA
<213> ORGANISM: artificial
<220> FEATURE:
<223> OTHER INFORMATION: RNA Oligomer

<400> SEQUENCE: 1733
agcucauacu cuuccgucg c            21

<210> SEQ ID NO 1734
<211> LENGTH: 21
<212> TYPE: RNA
<213> ORGANISM: artificial
<220> FEATURE:
<223> OTHER INFORMATION: RNA Oligomer

<400> SEQUENCE: 1734
uugcaaagug auagaucaga a            21

<210> SEQ ID NO 1735
<211> LENGTH: 21
<212> TYPE: RNA
<213> ORGANISM: artificial
<220> FEATURE:
<223> OTHER INFORMATION: RNA Oligomer

<400> SEQUENCE: 1735
cuucucgacu uacuccaaga u            21

<210> SEQ ID NO 1736
<211> LENGTH: 21
<212> TYPE: RNA
<213> ORGANISM: artificial
<220> FEATURE:
<223> OTHER INFORMATION: RNA Oligomer

<400> SEQUENCE: 1736
aacuugcuca auguccuguu g            21

<210> SEQ ID NO 1737
<211> LENGTH: 21
<212> TYPE: RNA
<213> ORGANISM: artificial
<220> FEATURE:
<223> OTHER INFORMATION: RNA Oligomer

<400> SEQUENCE: 1737
agcaacagaa guuucaggug a            21

<210> SEQ ID NO 1738
<211> LENGTH: 21
<212> TYPE: RNA
<213> ORGANISM: artificial
<220> FEATURE:
<223> OTHER INFORMATION: RNA Oligomer

<400> SEQUENCE: 1738
aaugaagacu gggcucucga u            21

<210> SEQ ID NO 1739
<211> LENGTH: 21
<212> TYPE: RNA
<213> ORGANISM: artificial

```
<220> FEATURE:
<223> OTHER INFORMATION: RNA Oligomer

<400> SEQUENCE: 1739
ggaacaagug acugaaacgu a                                              21

<210> SEQ ID NO 1740
<211> LENGTH: 21
<212> TYPE: RNA
<213> ORGANISM: artificial
<220> FEATURE:
<223> OTHER INFORMATION: RNA Oligomer

<400> SEQUENCE: 1740
aacaagugac ugaaacguag c                                              21

<210> SEQ ID NO 1741
<211> LENGTH: 21
<212> TYPE: RNA
<213> ORGANISM: artificial
<220> FEATURE:
<223> OTHER INFORMATION: RNA Oligomer

<400> SEQUENCE: 1741
acaagugacu gaaacguagc c                                              21

<210> SEQ ID NO 1742
<211> LENGTH: 21
<212> TYPE: RNA
<213> ORGANISM: artificial
<220> FEATURE:
<223> OTHER INFORMATION: RNA Oligomer

<400> SEQUENCE: 1742
caagugacug aaacguagcc g                                              21

<210> SEQ ID NO 1743
<211> LENGTH: 21
<212> TYPE: RNA
<213> ORGANISM: artificial
<220> FEATURE:
<223> OTHER INFORMATION: RNA Oligomer

<400> SEQUENCE: 1743
acugaaacgu agccgaagaa a                                              21

<210> SEQ ID NO 1744
<211> LENGTH: 21
<212> TYPE: RNA
<213> ORGANISM: artificial
<220> FEATURE:
<223> OTHER INFORMATION: RNA Oligomer

<400> SEQUENCE: 1744
uaugucaauc aaauccaugu c                                              21

<210> SEQ ID NO 1745
<211> LENGTH: 21
<212> TYPE: RNA
<213> ORGANISM: artificial
<220> FEATURE:
<223> OTHER INFORMATION: RNA Oligomer

<400> SEQUENCE: 1745
cuuuuuagcc agaugucaua u                                              21
```

```
<210> SEQ ID NO 1746
<211> LENGTH: 21
<212> TYPE: RNA
<213> ORGANISM: artificial
<220> FEATURE:
<223> OTHER INFORMATION: RNA Oligomer

<400> SEQUENCE: 1746
cuuacacaga aacuagccca a                                           21

<210> SEQ ID NO 1747
<211> LENGTH: 21
<212> TYPE: RNA
<213> ORGANISM: artificial
<220> FEATURE:
<223> OTHER INFORMATION: RNA Oligomer

<400> SEQUENCE: 1747
cuacugauuc aacauacuga c                                           21

<210> SEQ ID NO 1748
<211> LENGTH: 21
<212> TYPE: RNA
<213> ORGANISM: artificial
<220> FEATURE:
<223> OTHER INFORMATION: RNA Oligomer

<400> SEQUENCE: 1748
uacugauuca acauacugac a                                           21

<210> SEQ ID NO 1749
<211> LENGTH: 21
<212> TYPE: RNA
<213> ORGANISM: artificial
<220> FEATURE:
<223> OTHER INFORMATION: RNA Oligomer

<400> SEQUENCE: 1749
acugauucaa cauacugaca c                                           21

<210> SEQ ID NO 1750
<211> LENGTH: 21
<212> TYPE: RNA
<213> ORGANISM: artificial
<220> FEATURE:
<223> OTHER INFORMATION: RNA Oligomer

<400> SEQUENCE: 1750
uucaacauac ugacacucca a                                           21

<210> SEQ ID NO 1751
<211> LENGTH: 21
<212> TYPE: RNA
<213> ORGANISM: artificial
<220> FEATURE:
<223> OTHER INFORMATION: RNA Oligomer

<400> SEQUENCE: 1751
ugagcauuuc acaucacagu a                                           21

<210> SEQ ID NO 1752
<211> LENGTH: 21
<212> TYPE: RNA
<213> ORGANISM: artificial
<220> FEATURE:
<223> OTHER INFORMATION: RNA Oligomer

<400> SEQUENCE: 1752
```
aaaaacuagc ucagaaaagg u                    21

<210> SEQ ID NO 1753
<211> LENGTH: 21
<212> TYPE: RNA
<213> ORGANISM: artificial
<220> FEATURE:
<223> OTHER INFORMATION: RNA Oligomer

<400> SEQUENCE: 1753
acuagcucag aaaaggucaa a                    21

<210> SEQ ID NO 1754
<211> LENGTH: 21
<212> TYPE: RNA
<213> ORGANISM: artificial
<220> FEATURE:
<223> OTHER INFORMATION: RNA Oligomer

<400> SEQUENCE: 1754
ugccaucucu uguuugcugc a                    21

<210> SEQ ID NO 1755
<211> LENGTH: 21
<212> TYPE: RNA
<213> ORGANISM: artificial
<220> FEATURE:
<223> OTHER INFORMATION: RNA Oligomer

<400> SEQUENCE: 1755
gcagggagua uucacuagga g                    21

<210> SEQ ID NO 1756
<211> LENGTH: 21
<212> TYPE: RNA
<213> ORGANISM: artificial
<220> FEATURE:
<223> OTHER INFORMATION: RNA Oligomer

<400> SEQUENCE: 1756
caucuucauc acguagcaug c                    21

<210> SEQ ID NO 1757
<211> LENGTH: 21
<212> TYPE: RNA
<213> ORGANISM: artificial
<220> FEATURE:
<223> OTHER INFORMATION: RNA Oligomer

<400> SEQUENCE: 1757
gaaaacuucg agauauaagg u                    21

<210> SEQ ID NO 1758
<211> LENGTH: 21
<212> TYPE: RNA
<213> ORGANISM: artificial
<220> FEATURE:
<223> OTHER INFORMATION: RNA Oligomer

<400> SEQUENCE: 1758
ccuacguaua ucccgaauua a                    21

<210> SEQ ID NO 1759
<211> LENGTH: 21
<212> TYPE: RNA
<213> ORGANISM: artificial

```
<220> FEATURE:
<223> OTHER INFORMATION: RNA Oligomer

<400> SEQUENCE: 1759
ucuuuggaca ucauuucguu g                                      21

<210> SEQ ID NO 1760
<211> LENGTH: 21
<212> TYPE: RNA
<213> ORGANISM: artificial
<220> FEATURE:
<223> OTHER INFORMATION: RNA Oligomer

<400> SEQUENCE: 1760
gaagucaaca acagggaggu u                                      21

<210> SEQ ID NO 1761
<211> LENGTH: 21
<212> TYPE: RNA
<213> ORGANISM: artificial
<220> FEATURE:
<223> OTHER INFORMATION: RNA Oligomer

<400> SEQUENCE: 1761 cuuugcccu aaguucaucu c                                       21

<210> SEQ ID NO 1762
<211> LENGTH: 21
<212> TYPE: RNA
<213> ORGANISM: artificial
<220> FEATURE:
<223> OTHER INFORMATION: RNA Oligomer

<400> SEQUENCE: 1762
ugcccuaagu ucaucucuug u                                      21

<210> SEQ ID NO 1763
<211> LENGTH: 21
<212> TYPE: RNA
<213> ORGANISM: artificial
<220> FEATURE:
<223> OTHER INFORMATION: RNA Oligomer

<400> SEQUENCE: 1763
cauugaauuc ugcugugcuu u                                      21

<210> SEQ ID NO 1764
<211> LENGTH: 21
<212> TYPE: RNA
<213> ORGANISM: artificial
<220> FEATURE:
<223> OTHER INFORMATION: RNA Oligomer

<400> SEQUENCE: 1764
aagugauaga ucagaaacau c                                      21

<210> SEQ ID NO 1765
<211> LENGTH: 21
<212> TYPE: RNA
<213> ORGANISM: artificial
<220> FEATURE:
<223> OTHER INFORMATION: RNA Oligomer

<400> SEQUENCE: 1765
accaaaaucu guguugacug u                                      21
```

<210> SEQ ID NO 1766
<211> LENGTH: 21
<212> TYPE: RNA
<213> ORGANISM: artificial
<220> FEATURE:
<223> OTHER INFORMATION: RNA Oligomer

<400> SEQUENCE: 1766
augcugcuga aggaauccuc a                                             21

<210> SEQ ID NO 1767
<211> LENGTH: 21
<212> TYPE: RNA
<213> ORGANISM: artificial
<220> FEATURE:
<223> OTHER INFORMATION: RNA Oligomer

<400> SEQUENCE: 1767
ucuugccucc aaaguauguc a                                             21

<210> SEQ ID NO 1768
<211> LENGTH: 21
<212> TYPE: RNA
<213> ORGANISM: artificial
<220> FEATURE:
<223> OTHER INFORMATION: RNA Oligomer

<400> SEQUENCE: 1768
aguaugucaa ucaaauccau g                                             21

<210> SEQ ID NO 1769
<211> LENGTH: 21
<212> TYPE: RNA
<213> ORGANISM: artificial
<220> FEATURE:
<223> OTHER INFORMATION: RNA Oligomer

<400> SEQUENCE: 1769
ucaaucaaau ccauguccug c                                             21

<210> SEQ ID NO 1770
<211> LENGTH: 21
<212> TYPE: RNA
<213> ORGANISM: artificial
<220> FEATURE:
<223> OTHER INFORMATION: RNA Oligomer

<400> SEQUENCE: 1770
gaaauucacc ugucucuuca u                                             21

<210> SEQ ID NO 1771
<211> LENGTH: 21
<212> TYPE: RNA
<213> ORGANISM: artificial
<220> FEATURE:
<223> OTHER INFORMATION: RNA Oligomer

<400> SEQUENCE: 1771
aauucaccug ucucuucauc u                                             21

<210> SEQ ID NO 1772
<211> LENGTH: 21
<212> TYPE: RNA
<213> ORGANISM: artificial
<220> FEATURE:
<223> OTHER INFORMATION: RNA Oligomer

<400> SEQUENCE: 1772
acauaguggu uaguuuugca a    21

<210> SEQ ID NO 1773
<211> LENGTH: 21
<212> TYPE: RNA
<213> ORGANISM: artificial
<220> FEATURE:
<223> OTHER INFORMATION: RNA Oligomer

<400> SEQUENCE: 1773
uucuuuuuag ccagauguca u    21

<210> SEQ ID NO 1774
<211> LENGTH: 21
<212> TYPE: RNA
<213> ORGANISM: artificial
<220> FEATURE:
<223> OTHER INFORMATION: RNA Oligomer

<400> SEQUENCE: 1774
cacuuacaca gaaacuagcc c    21

<210> SEQ ID NO 1775
<211> LENGTH: 21
<212> TYPE: RNA
<213> ORGANISM: artificial
<220> FEATURE:
<223> OTHER INFORMATION: RNA Oligomer

<400> SEQUENCE: 1775
uuacacagaa acuagcccaa a    21

<210> SEQ ID NO 1776
<211> LENGTH: 21
<212> TYPE: RNA
<213> ORGANISM: artificial
<220> FEATURE:
<223> OTHER INFORMATION: RNA Oligomer

<400> SEQUENCE: 1776
gauucaacau acugacacuc c    21

<210> SEQ ID NO 1777
<211> LENGTH: 21
<212> TYPE: RNA
<213> ORGANISM: artificial
<220> FEATURE:
<223> OTHER INFORMATION: RNA Oligomer

<400> SEQUENCE: 1777
guaugagcau uucacaucac a    21

<210> SEQ ID NO 1778
<211> LENGTH: 21
<212> TYPE: RNA
<213> ORGANISM: artificial
<220> FEATURE:
<223> OTHER INFORMATION: RNA Oligomer

<400> SEQUENCE: 1778
uucgagauau aaggugcuga g    21

<210> SEQ ID NO 1779
<211> LENGTH: 21
<212> TYPE: RNA
<213> ORGANISM: artificial

```
<220> FEATURE:
<223> OTHER INFORMATION: RNA Oligomer

<400> SEQUENCE: 1779
uccuacguau aucccgaauu a                                        21

<210> SEQ ID NO 1780
<211> LENGTH: 21
<212> TYPE: RNA
<213> ORGANISM: artificial
<220> FEATURE:
<223> OTHER INFORMATION: RNA Oligomer

<400> SEQUENCE: 1780
uuuggaguug uucuugucuu u                                        21

<210> SEQ ID NO 1781
<211> LENGTH: 21
<212> TYPE: RNA
<213> ORGANISM: artificial
<220> FEATURE:
<223> OTHER INFORMATION: RNA Oligomer

<400> SEQUENCE: 1781
uuggaguugu ucuugucuuu c                                        21

<210> SEQ ID NO 1782
<211> LENGTH: 21
<212> TYPE: RNA
<213> ORGANISM: artificial
<220> FEATURE:
<223> OTHER INFORMATION: RNA Oligomer

<400> SEQUENCE: 1782
ugcucuuugg acaucauuuc g                                        21

<210> SEQ ID NO 1783
<211> LENGTH: 21
<212> TYPE: RNA
<213> ORGANISM: artificial
<220> FEATURE:
<223> OTHER INFORMATION: RNA Oligomer

<400> SEQUENCE: 1783
cucuuuggac aucauuucgu u                                        21

<210> SEQ ID NO 1784
<211> LENGTH: 21
<212> TYPE: RNA
<213> ORGANISM: artificial
<220> FEATURE:
<223> OTHER INFORMATION: RNA Oligomer

<400> SEQUENCE: 1784
ugaagucaac aacagggagg u                                        21

<210> SEQ ID NO 1785
<211> LENGTH: 21
<212> TYPE: RNA
<213> ORGANISM: artificial
<220> FEATURE:
<223> OTHER INFORMATION: RNA Oligomer

<400> SEQUENCE: 1785
aacaacaggg agguuaauga u                                        21
```

```
<210> SEQ ID NO 1786
<211> LENGTH: 21
<212> TYPE: RNA
<213> ORGANISM: artificial
<220> FEATURE:
<223> OTHER INFORMATION: RNA Oligomer

<400> SEQUENCE: 1786
ugcaaaguga uagaucagaa a                                          21

<210> SEQ ID NO 1787
<211> LENGTH: 21
<212> TYPE: RNA
<213> ORGANISM: artificial
<220> FEATURE:
<223> OTHER INFORMATION: RNA Oligomer

<400> SEQUENCE: 1787
cgggaauauc aggaacaagu g                                          21

<210> SEQ ID NO 1788
<211> LENGTH: 21
<212> TYPE: RNA
<213> ORGANISM: artificial
<220> FEATURE:
<223> OTHER INFORMATION: RNA Oligomer

<400> SEQUENCE: 1788
ccaaaguaug ucaaucaaau c                                          21

<210> SEQ ID NO 1789
<211> LENGTH: 21
<212> TYPE: RNA
<213> ORGANISM: artificial
<220> FEATURE:
<223> OTHER INFORMATION: RNA Oligomer

<400> SEQUENCE: 1789
aggaacaagu gacugaaacg u                                          21

<210> SEQ ID NO 1790
<211> LENGTH: 21
<212> TYPE: RNA
<213> ORGANISM: artificial
<220> FEATURE:
<223> OTHER INFORMATION: RNA Oligomer

<400> SEQUENCE: 1790
aauugggaga aauucaccug u                                          21

<210> SEQ ID NO 1791
<211> LENGTH: 21
<212> TYPE: RNA
<213> ORGANISM: artificial
<220> FEATURE:
<223> OTHER INFORMATION: RNA Oligomer

<400> SEQUENCE: 1791
auccuuuauu aguaccagcu c                                          21

<210> SEQ ID NO 1792
<211> LENGTH: 21
<212> TYPE: RNA
<213> ORGANISM: artificial
<220> FEATURE:
<223> OTHER INFORMATION: RNA Oligomer

<400> SEQUENCE: 1792
```

```
uaugagcauu ucacaucaca g                                              21

<210> SEQ ID NO 1793
<211> LENGTH: 21
<212> TYPE: RNA
<213> ORGANISM: artificial
<220> FEATURE:
<223> OTHER INFORMATION: RNA Oligomer

<400> SEQUENCE: 1793
uccuccuaaa ucuaguuuuu c                                              21

<210> SEQ ID NO 1794
<211> LENGTH: 21
<212> TYPE: RNA
<213> ORGANISM: artificial
<220> FEATURE:
<223> OTHER INFORMATION: RNA Oligomer

<400> SEQUENCE: 1794
uuuucuccuu uuucuuugag c                                              21

<210> SEQ ID NO 1795
<211> LENGTH: 21
<212> TYPE: RNA
<213> ORGANISM: artificial
<220> FEATURE:
<223> OTHER INFORMATION: RNA Oligomer

<400> SEQUENCE: 1795
cuuuuggagu uguucuuguc u                                              21

<210> SEQ ID NO 1796
<211> LENGTH: 21
<212> TYPE: RNA
<213> ORGANISM: artificial
<220> FEATURE:
<223> OTHER INFORMATION: RNA Oligomer

<400> SEQUENCE: 1796
cccuccuacg uauaucccga a                                              21

<210> SEQ ID NO 1797
<211> LENGTH: 21
<212> TYPE: RNA
<213> ORGANISM: artificial
<220> FEATURE:
<223> OTHER INFORMATION: RNA Oligomer

<400> SEQUENCE: 1797
auugaacugc ucuuuggaca u                                              21

<210> SEQ ID NO 1798
<211> LENGTH: 21
<212> TYPE: RNA
<213> ORGANISM: artificial
<220> FEATURE:
<223> OTHER INFORMATION: RNA Oligomer

<400> SEQUENCE: 1798
ugaacugcuc uuuggacauc a                                              21

<210> SEQ ID NO 1799
<211> LENGTH: 21
<212> TYPE: RNA
<213> ORGANISM: artificial
```

```
<220> FEATURE:
<223> OTHER INFORMATION: RNA Oligomer

<400> SEQUENCE: 1799
uuuuuucugu uuuuccagcu c                                              21

<210> SEQ ID NO 1800
<211> LENGTH: 21
<212> TYPE: RNA
<213> ORGANISM: artificial
<220> FEATURE:
<223> OTHER INFORMATION: RNA Oligomer

<400> SEQUENCE: 1800
uuguguuuag ugaaaugccg g                                              21

<210> SEQ ID NO 1801
<211> LENGTH: 21
<212> TYPE: RNA
<213> ORGANISM: artificial
<220> FEATURE:
<223> OTHER INFORMATION: RNA Oligomer

<400> SEQUENCE: 1801
gugauagauc agaaacauca a                                              21

<210> SEQ ID NO 1802
<211> LENGTH: 21
<212> TYPE: RNA
<213> ORGANISM: artificial
<220> FEATURE:
<223> OTHER INFORMATION: RNA Oligomer

<400> SEQUENCE: 1802
auagaucaga aacaucaaug g                                              21

<210> SEQ ID NO 1803
<211> LENGTH: 21
<212> TYPE: RNA
<213> ORGANISM: artificial
<220> FEATURE:
<223> OTHER INFORMATION: RNA Oligomer

<400> SEQUENCE: 1803
uagaucagaa acaucaaugg g                                              21

<210> SEQ ID NO 1804
<211> LENGTH: 21
<212> TYPE: RNA
<213> ORGANISM: artificial
<220> FEATURE:
<223> OTHER INFORMATION: RNA Oligomer

<400> SEQUENCE: 1804
gaucagaaac aucaaugggc c                                              21

<210> SEQ ID NO 1805
<211> LENGTH: 21
<212> TYPE: RNA
<213> ORGANISM: artificial
<220> FEATURE:
<223> OTHER INFORMATION: RNA Oligomer

<400> SEQUENCE: 1805
gacuacaguu accuacuucu u                                              21
```

```
<210> SEQ ID NO 1806
<211> LENGTH: 21
<212> TYPE: RNA
<213> ORGANISM: artificial
<220> FEATURE:
<223> OTHER INFORMATION: RNA Oligomer

<400> SEQUENCE: 1806
aaaacuagcu cagaaaaggu c                                              21

<210> SEQ ID NO 1807
<211> LENGTH: 21
<212> TYPE: RNA
<213> ORGANISM: artificial
<220> FEATURE:
<223> OTHER INFORMATION: RNA Oligomer

<400> SEQUENCE: 1807
gcaugcugaa aacuucgaga u                                              21

<210> SEQ ID NO 1808
<211> LENGTH: 21
<212> TYPE: RNA
<213> ORGANISM: artificial
<220> FEATURE:
<223> OTHER INFORMATION: RNA Oligomer

<400> SEQUENCE: 1808
uuuuggaguu guucuugucu u                                              21

<210> SEQ ID NO 1809
<211> LENGTH: 21
<212> TYPE: RNA
<213> ORGANISM: artificial
<220> FEATURE:
<223> OTHER INFORMATION: RNA Oligomer

<400> SEQUENCE: 1809
ucuuuuguga auggggguuuu c                                             21

<210> SEQ ID NO 1810
<211> LENGTH: 21
<212> TYPE: RNA
<213> ORGANISM: artificial
<220> FEATURE:
<223> OTHER INFORMATION: RNA Oligomer

<400> SEQUENCE: 1810
ugacaagggu uguaccauau c                                              21

<210> SEQ ID NO 1811
<211> LENGTH: 21
<212> TYPE: RNA
<213> ORGANISM: artificial
<220> FEATURE:
<223> OTHER INFORMATION: RNA Oligomer

<400> SEQUENCE: 1811
acuaucuagc ucuuccacuu c                                              21

<210> SEQ ID NO 1812
<211> LENGTH: 21
<212> TYPE: RNA
<213> ORGANISM: artificial
<220> FEATURE:
<223> OTHER INFORMATION: RNA Oligomer

<400> SEQUENCE: 1812
```

```
gcaaagugau agaucagaaa c                                              21

<210> SEQ ID NO 1813
<211> LENGTH: 21
<212> TYPE: RNA
<213> ORGANISM: artificial
<220> FEATURE:
<223> OTHER INFORMATION: RNA Oligomer

<400> SEQUENCE: 1813
agaucagaaa caucaauggg c                                              21

<210> SEQ ID NO 1814
<211> LENGTH: 21
<212> TYPE: RNA
<213> ORGANISM: artificial
<220> FEATURE:
<223> OTHER INFORMATION: RNA Oligomer

<400> SEQUENCE: 1814
cugauuuggg aauguggca a                                               21

<210> SEQ ID NO 1815
<211> LENGTH: 21
<212> TYPE: RNA
<213> ORGANISM: artificial
<220> FEATURE:
<223> OTHER INFORMATION: RNA Oligomer

<400> SEQUENCE: 1815
ugauuuggga auggggcaa c                                               21

<210> SEQ ID NO 1816
<211> LENGTH: 21
<212> TYPE: RNA
<213> ORGANISM: artificial
<220> FEATURE:
<223> OTHER INFORMATION: RNA Oligomer

<400> SEQUENCE: 1816
uugccaucuc uuguuugcug c                                              21

<210> SEQ ID NO 1817
<211> LENGTH: 21
<212> TYPE: RNA
<213> ORGANISM: artificial
<220> FEATURE:
<223> OTHER INFORMATION: RNA Oligomer

<400> SEQUENCE: 1817
uuucuccuuu uucuuugagc a                                              21

<210> SEQ ID NO 1818
<211> LENGTH: 21
<212> TYPE: RNA
<213> ORGANISM: artificial
<220> FEATURE:
<223> OTHER INFORMATION: RNA Oligomer

<400> SEQUENCE: 1818
aauuaaugca aguugagcuu c                                              21

<210> SEQ ID NO 1819
<211> LENGTH: 21
<212> TYPE: RNA
<213> ORGANISM: artificial
```

```
<220> FEATURE:
<223> OTHER INFORMATION: RNA Oligomer

<400> SEQUENCE: 1819
gcuucauuga acugcucuuu g                                              21

<210> SEQ ID NO 1820
<211> LENGTH: 21
<212> TYPE: RNA
<213> ORGANISM: artificial
<220> FEATURE:
<223> OTHER INFORMATION: RNA Oligomer

<400> SEQUENCE: 1820
cuuuugugaa uggggguuuuc c                                             21

<210> SEQ ID NO 1821
<211> LENGTH: 21
<212> TYPE: RNA
<213> ORGANISM: artificial
<220> FEATURE:
<223> OTHER INFORMATION: RNA Oligomer

<400> SEQUENCE: 1821
uuuuucuguu uuuccagcuc a                                              21

<210> SEQ ID NO 1822
<211> LENGTH: 21
<212> TYPE: RNA
<213> ORGANISM: artificial
<220> FEATURE:
<223> OTHER INFORMATION: RNA Oligomer

<400> SEQUENCE: 1822
augcuguugc ugauacuggg c                                              21

<210> SEQ ID NO 1823
<211> LENGTH: 21
<212> TYPE: RNA
<213> ORGANISM: artificial
<220> FEATURE:
<223> OTHER INFORMATION: RNA Oligomer

<400> SEQUENCE: 1823
aauguggacu acaguuaccu a                                              21

<210> SEQ ID NO 1824
<211> LENGTH: 21
<212> TYPE: RNA
<213> ORGANISM: artificial
<220> FEATURE:
<223> OTHER INFORMATION: RNA Oligomer

<400> SEQUENCE: 1824
agacacugua acucaggaau g                                              21

<210> SEQ ID NO 1825
<211> LENGTH: 21
<212> TYPE: RNA
<213> ORGANISM: artificial
<220> FEATURE:
<223> OTHER INFORMATION: RNA Oligomer

<400> SEQUENCE: 1825
cucauuguca ucuacaaacg g                                              21
```

```
<210> SEQ ID NO 1826
<211> LENGTH: 21
<212> TYPE: RNA
<213> ORGANISM: artificial
<220> FEATURE:
<223> OTHER INFORMATION: RNA Oligomer

<400> SEQUENCE: 1826
uaauccuuua uuaguaccag c                                              21

<210> SEQ ID NO 1827
<211> LENGTH: 21
<212> TYPE: RNA
<213> ORGANISM: artificial
<220> FEATURE:
<223> OTHER INFORMATION: RNA Oligomer

<400> SEQUENCE: 1827
aacuagccca aaugugucc u                                               21

<210> SEQ ID NO 1828
<211> LENGTH: 21
<212> TYPE: RNA
<213> ORGANISM: artificial
<220> FEATURE:
<223> OTHER INFORMATION: RNA Oligomer

<400> SEQUENCE: 1828
agggaauggg auauggagag c                                              21

<210> SEQ ID NO 1829
<211> LENGTH: 21
<212> TYPE: RNA
<213> ORGANISM: artificial
<220> FEATURE:
<223> OTHER INFORMATION: RNA Oligomer

<400> SEQUENCE: 1829
ucagaaacau caaugggccc a                                              21

<210> SEQ ID NO 1830
<211> LENGTH: 21
<212> TYPE: RNA
<213> ORGANISM: artificial
<220> FEATURE:
<223> OTHER INFORMATION: RNA Oligomer

<400> SEQUENCE: 1830
agagagugaa uggcuuaaag u                                              21

<210> SEQ ID NO 1831
<211> LENGTH: 21
<212> TYPE: RNA
<213> ORGANISM: artificial
<220> FEATURE:
<223> OTHER INFORMATION: RNA Oligomer

<400> SEQUENCE: 1831
aauggcuuaa aguagcaggu g                                              21

<210> SEQ ID NO 1832
<211> LENGTH: 21
<212> TYPE: RNA
<213> ORGANISM: artificial
<220> FEATURE:
<223> OTHER INFORMATION: RNA Oligomer

<400> SEQUENCE: 1832
```

-continued uggcuuaaag uagcagguga g    21

<210> SEQ ID NO 1833
<211> LENGTH: 21
<212> TYPE: RNA
<213> ORGANISM: artificial
<220> FEATURE:
<223> OTHER INFORMATION: RNA Oligomer

<400> SEQUENCE: 1833
ucaaccagcu ugucauuuuc a    21

<210> SEQ ID NO 1834
<211> LENGTH: 21
<212> TYPE: RNA
<213> ORGANISM: artificial
<220> FEATURE:
<223> OTHER INFORMATION: RNA Oligomer

<400> SEQUENCE: 1834
aauccuuuau uaguaccagc u    21

<210> SEQ ID NO 1835
<211> LENGTH: 21
<212> TYPE: RNA
<213> ORGANISM: artificial
<220> FEATURE:
<223> OTHER INFORMATION: RNA Oligomer

<400> SEQUENCE: 1835
guuuuggcua ugauuuugca u    21

<210> SEQ ID NO 1836
<211> LENGTH: 21
<212> TYPE: RNA
<213> ORGANISM: artificial
<220> FEATURE:
<223> OTHER INFORMATION: RNA Oligomer

<400> SEQUENCE: 1836
aacauugcca ucucuuguuu g    21

<210> SEQ ID NO 1837
<211> LENGTH: 21
<212> TYPE: RNA
<213> ORGANISM: artificial
<220> FEATURE:
<223> OTHER INFORMATION: RNA Oligomer

<400> SEQUENCE: 1837
gugaaggcuu uugucauuuu c    21

<210> SEQ ID NO 1838
<211> LENGTH: 21
<212> TYPE: RNA
<213> ORGANISM: artificial
<220> FEATURE:
<223> OTHER INFORMATION: RNA Oligomer

<400> SEQUENCE: 1838
gucuuuugug aaugggguuu u    21

<210> SEQ ID NO 1839
<211> LENGTH: 21
<212> TYPE: RNA
<213> ORGANISM: artificial

```
<220> FEATURE:
<223> OTHER INFORMATION: RNA Oligomer

<400> SEQUENCE: 1839
uuuucuguuu uuccagcuca u                                              21

<210> SEQ ID NO 1840
<211> LENGTH: 21
<212> TYPE: RNA
<213> ORGANISM: artificial
<220> FEATURE:
<223> OTHER INFORMATION: RNA Oligomer

<400> SEQUENCE: 1840
uaucuagcuc uuccacuuca g                                              21

<210> SEQ ID NO 1841
<211> LENGTH: 21
<212> TYPE: RNA
<213> ORGANISM: artificial
<220> FEATURE:
<223> OTHER INFORMATION: RNA Oligomer

<400> SEQUENCE: 1841
uguuuaguga aaugccggag u                                              21

<210> SEQ ID NO 1842
<211> LENGTH: 21
<212> TYPE: RNA
<213> ORGANISM: artificial
<220> FEATURE:
<223> OTHER INFORMATION: RNA Oligomer

<400> SEQUENCE: 1842
agaaguucag agagugaaug g                                              21

<210> SEQ ID NO 1843
<211> LENGTH: 21
<212> TYPE: RNA
<213> ORGANISM: artificial
<220> FEATURE:
<223> OTHER INFORMATION: RNA Oligomer

<400> SEQUENCE: 1843
aaguucagag agugaauggc u                                              21

<210> SEQ ID NO 1844
<211> LENGTH: 21
<212> TYPE: RNA
<213> ORGANISM: artificial
<220> FEATURE:
<223> OTHER INFORMATION: RNA Oligomer

<400> SEQUENCE: 1844
gugaauggcu uaaaguagca g                                              21

<210> SEQ ID NO 1845
<211> LENGTH: 21
<212> TYPE: RNA
<213> ORGANISM: artificial
<220> FEATURE:
<223> OTHER INFORMATION: RNA Oligomer

<400> SEQUENCE: 1845
auggcuuaaa guagcaggug a                                              21
```

```
<210> SEQ ID NO 1846
<211> LENGTH: 21
<212> TYPE: RNA
<213> ORGANISM: artificial
<220> FEATURE:
<223> OTHER INFORMATION: RNA Oligomer

<400> SEQUENCE: 1846
uuaaaguagc aggugagggc a                                              21

<210> SEQ ID NO 1847
<211> LENGTH: 21
<212> TYPE: RNA
<213> ORGANISM: artificial
<220> FEATURE:
<223> OTHER INFORMATION: RNA Oligomer

<400> SEQUENCE: 1847
uaaaguagca ggugagggca u                                              21

<210> SEQ ID NO 1848
<211> LENGTH: 21
<212> TYPE: RNA
<213> ORGANISM: artificial
<220> FEATURE:
<223> OTHER INFORMATION: RNA Oligomer

<400> SEQUENCE: 1848
guuaccuacu ucuuuuucca u                                              21

<210> SEQ ID NO 1849
<211> LENGTH: 21
<212> TYPE: RNA
<213> ORGANISM: artificial
<220> FEATURE:
<223> OTHER INFORMATION: RNA Oligomer

<400> SEQUENCE: 1849
aacuucuguc aguuuggcuu c                                              21

<210> SEQ ID NO 1850
<211> LENGTH: 21
<212> TYPE: RNA
<213> ORGANISM: artificial
<220> FEATURE:
<223> OTHER INFORMATION: RNA Oligomer

<400> SEQUENCE: 1850
ugacacucca augcuuuuua a                                              21

<210> SEQ ID NO 1851
<211> LENGTH: 21
<212> TYPE: RNA
<213> ORGANISM: artificial
<220> FEATURE:
<223> OTHER INFORMATION: RNA Oligomer

<400> SEQUENCE: 1851
gggaacaagg aaaacauugc c                                              21

<210> SEQ ID NO 1852
<211> LENGTH: 21
<212> TYPE: RNA
<213> ORGANISM: artificial
<220> FEATURE:
<223> OTHER INFORMATION: RNA Oligomer

<400> SEQUENCE: 1852
```
agauauaagg ugcugaguug u                                          21

<210> SEQ ID NO 1853
<211> LENGTH: 21
<212> TYPE: RNA
<213> ORGANISM: artificial
<220> FEATURE:
<223> OTHER INFORMATION: RNA Oligomer

<400> SEQUENCE: 1853
uuucugcaau ucugagcagc c                                          21

<210> SEQ ID NO 1854
<211> LENGTH: 21
<212> TYPE: RNA
<213> ORGANISM: artificial
<220> FEATURE:
<223> OTHER INFORMATION: RNA Oligomer

<400> SEQUENCE: 1854
gggaauggga uauggagagc u                                          21

<210> SEQ ID NO 1855
<211> LENGTH: 21
<212> TYPE: RNA
<213> ORGANISM: artificial
<220> FEATURE:
<223> OTHER INFORMATION: RNA Oligomer

<400> SEQUENCE: 1855
ggaaugggau auggagagcu u                                          21

<210> SEQ ID NO 1856
<211> LENGTH: 21
<212> TYPE: RNA
<213> ORGANISM: artificial
<220> FEATURE:
<223> OTHER INFORMATION: RNA Oligomer

<400> SEQUENCE: 1856
agcggcuuga auguuugucu u                                          21

<210> SEQ ID NO 1857
<211> LENGTH: 21
<212> TYPE: RNA
<213> ORGANISM: artificial
<220> FEATURE:
<223> OTHER INFORMATION: RNA Oligomer

<400> SEQUENCE: 1857
ugucuuuugu gaaugggguu u                                          21

<210> SEQ ID NO 1858
<211> LENGTH: 21
<212> TYPE: RNA
<213> ORGANISM: artificial
<220> FEATURE:
<223> OTHER INFORMATION: RNA Oligomer

<400> SEQUENCE: 1858
cuuguguuua gugaaaugcc g                                          21

<210> SEQ ID NO 1859
<211> LENGTH: 21
<212> TYPE: RNA
<213> ORGANISM: artificial

```
<220> FEATURE:
<223> OTHER INFORMATION: RNA Oligomer

<400> SEQUENCE: 1859
ucauugucau cuacaaacgg g                                              21

<210> SEQ ID NO 1860
<211> LENGTH: 21
<212> TYPE: RNA
<213> ORGANISM: artificial
<220> FEATURE:
<223> OTHER INFORMATION: RNA Oligomer

<400> SEQUENCE: 1860
cauugucauc uacaaacggg a                                              21

<210> SEQ ID NO 1861
<211> LENGTH: 21
<212> TYPE: RNA
<213> ORGANISM: artificial
<220> FEATURE:
<223> OTHER INFORMATION: RNA Oligomer

<400> SEQUENCE: 1861
accugggagu aguuggcaga u                                              21

<210> SEQ ID NO 1862
<211> LENGTH: 21
<212> TYPE: RNA
<213> ORGANISM: artificial
<220> FEATURE:
<223> OTHER INFORMATION: RNA Oligomer

<400> SEQUENCE: 1862 uaguuuucu uaacaucugg c                                               21

<210> SEQ ID NO 1863
<211> LENGTH: 21
<212> TYPE: RNA
<213> ORGANISM: artificial
<220> FEATURE:
<223> OTHER INFORMATION: RNA Oligomer

<400> SEQUENCE: 1863
aggugaaggc uuuugucauu u                                              21

<210> SEQ ID NO 1864
<211> LENGTH: 21
<212> TYPE: RNA
<213> ORGANISM: artificial
<220> FEATURE:
<223> OTHER INFORMATION: RNA Oligomer

<400> SEQUENCE: 1864
uuuuucugca auucugagca g                                              21

<210> SEQ ID NO 1865
<211> LENGTH: 21
<212> TYPE: RNA
<213> ORGANISM: artificial
<220> FEATURE:
<223> OTHER INFORMATION: RNA Oligomer

<400> SEQUENCE: 1865
gaauuaaugc aaguugagcu u                                              21
```

```
<210> SEQ ID NO 1866
<211> LENGTH: 21
<212> TYPE: RNA
<213> ORGANISM: artificial
<220> FEATURE:
<223> OTHER INFORMATION: RNA Oligomer

<400> SEQUENCE: 1866
ugaauggggu uuuccgauga c                                              21

<210> SEQ ID NO 1867
<211> LENGTH: 21
<212> TYPE: RNA
<213> ORGANISM: artificial
<220> FEATURE:
<223> OTHER INFORMATION: RNA Oligomer

<400> SEQUENCE: 1867
uucacuguca acugguuggg g                                              21

<210> SEQ ID NO 1868
<211> LENGTH: 21
<212> TYPE: RNA
<213> ORGANISM: artificial
<220> FEATURE:
<223> OTHER INFORMATION: RNA Oligomer

<400> SEQUENCE: 1868
acaguuaccu acuucuuuuu c                                              21

<210> SEQ ID NO 1869
<211> LENGTH: 21
<212> TYPE: RNA
<213> ORGANISM: artificial
<220> FEATURE:
<223> OTHER INFORMATION: RNA Oligomer

<400> SEQUENCE: 1869
aguuaccuac uucuuuuucc a                                              21

<210> SEQ ID NO 1870
<211> LENGTH: 21
<212> TYPE: RNA
<213> ORGANISM: artificial
<220> FEATURE:
<223> OTHER INFORMATION: RNA Oligomer

<400> SEQUENCE: 1870
ucaguuuggc uucuggacuu g                                              21

<210> SEQ ID NO 1871
<211> LENGTH: 21
<212> TYPE: RNA
<213> ORGANISM: artificial
<220> FEATURE:
<223> OTHER INFORMATION: RNA Oligomer

<400> SEQUENCE: 1871
aauggauaau agcuccuccc a                                              21

<210> SEQ ID NO 1872
<211> LENGTH: 21
<212> TYPE: RNA
<213> ORGANISM: artificial
<220> FEATURE:
<223> OTHER INFORMATION: RNA Oligomer

<400> SEQUENCE: 1872
```
uacauagugg uuaguuugc a                                              21

<210> SEQ ID NO 1873
<211> LENGTH: 21
<212> TYPE: RNA
<213> ORGANISM: artificial
<220> FEATURE:
<223> OTHER INFORMATION: RNA Oligomer

<400> SEQUENCE: 1873
uaggagaaua agguuuucca u                                             21

<210> SEQ ID NO 1874
<211> LENGTH: 21
<212> TYPE: RNA
<213> ORGANISM: artificial
<220> FEATURE:
<223> OTHER INFORMATION: RNA Oligomer

<400> SEQUENCE: 1874
uuuuuucagu aggugaaggc u                                             21

<210> SEQ ID NO 1875
<211> LENGTH: 21
<212> TYPE: RNA
<213> ORGANISM: artificial
<220> FEATURE:
<223> OTHER INFORMATION: RNA Oligomer

<400> SEQUENCE: 1875
ggcuuuuguc auuuucuccu u                                             21

<210> SEQ ID NO 1876
<211> LENGTH: 21
<212> TYPE: RNA
<213> ORGANISM: artificial
<220> FEATURE:
<223> OTHER INFORMATION: RNA Oligomer

<400> SEQUENCE: 1876
gcggcuugaa uguuugucuu u                                             21

<210> SEQ ID NO 1877
<211> LENGTH: 21
<212> TYPE: RNA
<213> ORGANISM: artificial
<220> FEATURE:
<223> OTHER INFORMATION: RNA Oligomer

<400> SEQUENCE: 1877
uuuuccgaug accaggacuu a                                             21

<210> SEQ ID NO 1878
<211> LENGTH: 21
<212> TYPE: RNA
<213> ORGANISM: artificial
<220> FEATURE:
<223> OTHER INFORMATION: RNA Oligomer

<400> SEQUENCE: 1878
uuucuguuuu uccagcucau a                                             21

<210> SEQ ID NO 1879
<211> LENGTH: 21
<212> TYPE: RNA
<213> ORGANISM: artificial

```
<220> FEATURE:
<223> OTHER INFORMATION: RNA Oligomer

<400> SEQUENCE: 1879
ugagauggug acaaggguug u                                              21

<210> SEQ ID NO 1880
<211> LENGTH: 21
<212> TYPE: RNA
<213> ORGANISM: artificial
<220> FEATURE:
<223> OTHER INFORMATION: RNA Oligomer

<400> SEQUENCE: 1880
agauggugac aaggguugua c                                              21

<210> SEQ ID NO 1881
<211> LENGTH: 21
<212> TYPE: RNA
<213> ORGANISM: artificial
<220> FEATURE:
<223> OTHER INFORMATION: RNA Oligomer

<400> SEQUENCE: 1881
acugaggcca aguagugugu c                                              21

<210> SEQ ID NO 1882
<211> LENGTH: 21
<212> TYPE: RNA
<213> ORGANISM: artificial
<220> FEATURE:
<223> OTHER INFORMATION: RNA Oligomer

<400> SEQUENCE: 1882
cuuugcaaag ugauagauca g                                              21

<210> SEQ ID NO 1883
<211> LENGTH: 21
<212> TYPE: RNA
<213> ORGANISM: artificial
<220> FEATURE:
<223> OTHER INFORMATION: RNA Oligomer

<400> SEQUENCE: 1883
ugaauggcuu aaaguagcag g                                              21

<210> SEQ ID NO 1884
<211> LENGTH: 21
<212> TYPE: RNA
<213> ORGANISM: artificial
<220> FEATURE:
<223> OTHER INFORMATION: RNA Oligomer

<400> SEQUENCE: 1884
acugaaguca aauacuucuc g                                              21

<210> SEQ ID NO 1885
<211> LENGTH: 21
<212> TYPE: RNA
<213> ORGANISM: artificial
<220> FEATURE:
<223> OTHER INFORMATION: RNA Oligomer

<400> SEQUENCE: 1885
auugucaucu acaaacggga a                                              21
```

-continued

<210> SEQ ID NO 1886
<211> LENGTH: 21
<212> TYPE: RNA
<213> ORGANISM: artificial
<220> FEATURE:
<223> OTHER INFORMATION: RNA Oligomer

<400> SEQUENCE: 1886
uacaaacggg aaugucugcg c                                      21

<210> SEQ ID NO 1887
<211> LENGTH: 21
<212> TYPE: RNA
<213> ORGANISM: artificial
<220> FEATURE:
<223> OTHER INFORMATION: RNA Oligomer

<400> SEQUENCE: 1887
ugggaguagu uggcagaucc a                                      21

<210> SEQ ID NO 1888
<211> LENGTH: 21
<212> TYPE: RNA
<213> ORGANISM: artificial
<220> FEATURE:
<223> OTHER INFORMATION: RNA Oligomer

<400> SEQUENCE: 1888
uucaucuagu uguaacugag c                                      21

<210> SEQ ID NO 1889
<211> LENGTH: 21
<212> TYPE: RNA
<213> ORGANISM: artificial
<220> FEATURE:
<223> OTHER INFORMATION: RNA Oligomer

<400> SEQUENCE: 1889
uaguuuuggc uaugauuuug c                                      21

<210> SEQ ID NO 1890
<211> LENGTH: 21
<212> TYPE: RNA
<213> ORGANISM: artificial
<220> FEATURE:
<223> OTHER INFORMATION: RNA Oligomer

<400> SEQUENCE: 1890
aguacaaaaa aacuagcuca g                                      21

<210> SEQ ID NO 1891
<211> LENGTH: 21
<212> TYPE: RNA
<213> ORGANISM: artificial
<220> FEATURE:
<223> OTHER INFORMATION: RNA Oligomer

<400> SEQUENCE: 1891
ucagaaaagg ucaaauccuc c                                      21

<210> SEQ ID NO 1892
<211> LENGTH: 21
<212> TYPE: RNA
<213> ORGANISM: artificial
<220> FEATURE:
<223> OTHER INFORMATION: RNA Oligomer

<400> SEQUENCE: 1892

```
agaaaagguc aaauccuccu a                                              21

<210> SEQ ID NO 1893
<211> LENGTH: 21
<212> TYPE: RNA
<213> ORGANISM: artificial
<220> FEATURE:
<223> OTHER INFORMATION: RNA Oligomer

<400> SEQUENCE: 1893
uuuucugcaa uucugagcag c                                              21

<210> SEQ ID NO 1894
<211> LENGTH: 21
<212> TYPE: RNA
<213> ORGANISM: artificial
<220> FEATURE:
<223> OTHER INFORMATION: RNA Oligomer

<400> SEQUENCE: 1894
ucugcaauuc ugagcagcca c                                              21

<210> SEQ ID NO 1895
<211> LENGTH: 21
<212> TYPE: RNA
<213> ORGANISM: artificial
<220> FEATURE:
<223> OTHER INFORMATION: RNA Oligomer

<400> SEQUENCE: 1895
ugcaauucug agcagccacu u                                              21

<210> SEQ ID NO 1896
<211> LENGTH: 21
<212> TYPE: RNA
<213> ORGANISM: artificial
<220> FEATURE:
<223> OTHER INFORMATION: RNA Oligomer

<400> SEQUENCE: 1896
uguacuggug uuuuaggacc a                                              21

<210> SEQ ID NO 1897
<211> LENGTH: 21
<212> TYPE: RNA
<213> ORGANISM: artificial
<220> FEATURE:
<223> OTHER INFORMATION: RNA Oligomer

<400> SEQUENCE: 1897
acugguguuu uaggaccauu c                                              21

<210> SEQ ID NO 1898
<211> LENGTH: 21
<212> TYPE: RNA
<213> ORGANISM: artificial
<220> FEATURE:
<223> OTHER INFORMATION: RNA Oligomer

<400> SEQUENCE: 1898
cacuucagaa ucacugaggc c                                              21

<210> SEQ ID NO 1899
<211> LENGTH: 21
<212> TYPE: RNA
<213> ORGANISM: artificial
```

```
<220> FEATURE:
<223> OTHER INFORMATION: RNA Oligomer

<400> SEQUENCE: 1899
ugugucucca uagcuggaag a                                              21

<210> SEQ ID NO 1900
<211> LENGTH: 21
<212> TYPE: RNA
<213> ORGANISM: artificial
<220> FEATURE:
<223> OTHER INFORMATION: RNA Oligomer

<400> SEQUENCE: 1900
acuuguguuu agugaaaugc c                                              21

<210> SEQ ID NO 1901
<211> LENGTH: 21
<212> TYPE: RNA
<213> ORGANISM: artificial
<220> FEATURE:
<223> OTHER INFORMATION: RNA Oligomer

<400> SEQUENCE: 1901
guuuagugaa augccggagu c                                              21

<210> SEQ ID NO 1902
<211> LENGTH: 21
<212> TYPE: RNA
<213> ORGANISM: artificial
<220> FEATURE:
<223> OTHER INFORMATION: RNA Oligomer

<400> SEQUENCE: 1902
agugaauggc uuaaaguagc a                                              21

<210> SEQ ID NO 1903
<211> LENGTH: 21
<212> TYPE: RNA
<213> ORGANISM: artificial
<220> FEATURE:
<223> OTHER INFORMATION: RNA Oligomer

<400> SEQUENCE: 1903
ucgcugacug aagucaaaua c                                              21

<210> SEQ ID NO 1904
<211> LENGTH: 21
<212> TYPE: RNA
<213> ORGANISM: artificial
<220> FEATURE:
<223> OTHER INFORMATION: RNA Oligomer

<400> SEQUENCE: 1904
cuguugcuga uacugggcuc a                                              21

<210> SEQ ID NO 1905
<211> LENGTH: 21
<212> TYPE: RNA
<213> ORGANISM: artificial
<220> FEATURE:
<223> OTHER INFORMATION: RNA Oligomer

<400> SEQUENCE: 1905
gacugaaguc aaauacuucu c                                              21
```

```
<210> SEQ ID NO 1906
<211> LENGTH: 21
<212> TYPE: RNA
<213> ORGANISM: artificial
<220> FEATURE:
<223> OTHER INFORMATION: RNA Oligomer

<400> SEQUENCE: 1906
cugaagucaa auacuucucg a                                              21

<210> SEQ ID NO 1907
<211> LENGTH: 21
<212> TYPE: RNA
<213> ORGANISM: artificial
<220> FEATURE:
<223> OTHER INFORMATION: RNA Oligomer

<400> SEQUENCE: 1907
cugaauuuaa ugaguucacu g                                              21

<210> SEQ ID NO 1908
<211> LENGTH: 21
<212> TYPE: RNA
<213> ORGANISM: artificial
<220> FEATURE:
<223> OTHER INFORMATION: RNA Oligomer

<400> SEQUENCE: 1908
acuucuguca guuuggcuuc u                                              21

<210> SEQ ID NO 1909
<211> LENGTH: 21
<212> TYPE: RNA
<213> ORGANISM: artificial
<220> FEATURE:
<223> OTHER INFORMATION: RNA Oligomer

<400> SEQUENCE: 1909
gaauggauaa uagcuccucc c                                              21

<210> SEQ ID NO 1910
<211> LENGTH: 21
<212> TYPE: RNA
<213> ORGANISM: artificial
<220> FEATURE:
<223> OTHER INFORMATION: RNA Oligomer

<400> SEQUENCE: 1910
auggauaaua gcuccuccca a                                              21

<210> SEQ ID NO 1911
<211> LENGTH: 21
<212> TYPE: RNA
<213> ORGANISM: artificial
<220> FEATURE:
<223> OTHER INFORMATION: RNA Oligomer

<400> SEQUENCE: 1911
accgucuaaa ucaacagggg c                                              21

<210> SEQ ID NO 1912
<211> LENGTH: 21
<212> TYPE: RNA
<213> ORGANISM: artificial
<220> FEATURE:
<223> OTHER INFORMATION: RNA Oligomer

<400> SEQUENCE: 1912
```
auugggagaa auucaccugu c					21

<210> SEQ ID NO 1913
<211> LENGTH: 21
<212> TYPE: RNA
<213> ORGANISM: artificial
<220> FEATURE:
<223> OTHER INFORMATION: RNA Oligomer

<400> SEQUENCE: 1913
aguuuuggcu augauuugc a					21

<210> SEQ ID NO 1914
<211> LENGTH: 21
<212> TYPE: RNA
<213> ORGANISM: artificial
<220> FEATURE:
<223> OTHER INFORMATION: RNA Oligomer

<400> SEQUENCE: 1914
ucuggcuucu uacuuuggg a					21

<210> SEQ ID NO 1915
<211> LENGTH: 21
<212> TYPE: RNA
<213> ORGANISM: artificial
<220> FEATURE:
<223> OTHER INFORMATION: RNA Oligomer

<400> SEQUENCE: 1915
gcuucuuacu uugggaaca a					21

<210> SEQ ID NO 1916
<211> LENGTH: 21
<212> TYPE: RNA
<213> ORGANISM: artificial
<220> FEATURE:
<223> OTHER INFORMATION: RNA Oligomer

<400> SEQUENCE: 1916
ucuugcuccu uuuggaguug u					21

<210> SEQ ID NO 1917
<211> LENGTH: 21
<212> TYPE: RNA
<213> ORGANISM: artificial
<220> FEATURE:
<223> OTHER INFORMATION: RNA Oligomer

<400> SEQUENCE: 1917
uuuuuucuac agggaauggg a					21

<210> SEQ ID NO 1918
<211> LENGTH: 21
<212> TYPE: RNA
<213> ORGANISM: artificial
<220> FEATURE:
<223> OTHER INFORMATION: RNA Oligomer

<400> SEQUENCE: 1918
gugaaugggg uuuuccgaug a					21

<210> SEQ ID NO 1919
<211> LENGTH: 21
<212> TYPE: RNA
<213> ORGANISM: artificial

```
<220> FEATURE:
<223> OTHER INFORMATION: RNA Oligomer

<400> SEQUENCE: 1919
uuacaggcaa uucuuucucu g                                              21

<210> SEQ ID NO 1920
<211> LENGTH: 21
<212> TYPE: RNA
<213> ORGANISM: artificial
<220> FEATURE:
<223> OTHER INFORMATION: RNA Oligomer

<400> SEQUENCE: 1920
aucaugcacg ugagugcucu g                                              21

<210> SEQ ID NO 1921
<211> LENGTH: 21
<212> TYPE: RNA
<213> ORGANISM: artificial
<220> FEATURE:
<223> OTHER INFORMATION: RNA Oligomer

<400> SEQUENCE: 1921
ccccagaaga auguacuggu g                                              21

<210> SEQ ID NO 1922
<211> LENGTH: 21
<212> TYPE: RNA
<213> ORGANISM: artificial
<220> FEATURE:
<223> OTHER INFORMATION: RNA Oligomer

<400> SEQUENCE: 1922
uguguuuagu gaaaugccgg a                                              21

<210> SEQ ID NO 1923
<211> LENGTH: 21
<212> TYPE: RNA
<213> ORGANISM: artificial
<220> FEATURE:
<223> OTHER INFORMATION: RNA Oligomer

<400> SEQUENCE: 1923
uuuagugaaa ugccggaguc a                                              21

<210> SEQ ID NO 1924
<211> LENGTH: 21
<212> TYPE: RNA
<213> ORGANISM: artificial
<220> FEATURE:
<223> OTHER INFORMATION: RNA Oligomer

<400> SEQUENCE: 1924
gcuuaaagua gcaggugagg g                                              21

<210> SEQ ID NO 1925
<211> LENGTH: 21
<212> TYPE: RNA
<213> ORGANISM: artificial
<220> FEATURE:
<223> OTHER INFORMATION: RNA Oligomer

<400> SEQUENCE: 1925
cugucaguuu ggcuucugga c                                              21
```

-continued

<210> SEQ ID NO 1926
<211> LENGTH: 21
<212> TYPE: RNA
<213> ORGANISM: artificial
<220> FEATURE:
<223> OTHER INFORMATION: RNA Oligomer

<400> SEQUENCE: 1926
accaugguag ucucaaccag c                                              21

<210> SEQ ID NO 1927
<211> LENGTH: 21
<212> TYPE: RNA
<213> ORGANISM: artificial
<220> FEATURE:
<223> OTHER INFORMATION: RNA Oligomer

<400> SEQUENCE: 1927
uaagacacug uaacucagga a                                              21

<210> SEQ ID NO 1928
<211> LENGTH: 21
<212> TYPE: RNA
<213> ORGANISM: artificial
<220> FEATURE:
<223> OTHER INFORMATION: RNA Oligomer

<400> SEQUENCE: 1928
uaccgucuaa aucaacaggg g                                              21

<210> SEQ ID NO 1929
<211> LENGTH: 21
<212> TYPE: RNA
<213> ORGANISM: artificial
<220> FEATURE:
<223> OTHER INFORMATION: RNA Oligomer

<400> SEQUENCE: 1929
aguaguuggc agauccacug g                                              21

<210> SEQ ID NO 1930
<211> LENGTH: 21
<212> TYPE: RNA
<213> ORGANISM: artificial
<220> FEATURE:
<223> OTHER INFORMATION: RNA Oligomer

<400> SEQUENCE: 1930
uugggagaaa uucaccuguc u                                              21

<210> SEQ ID NO 1931
<211> LENGTH: 21
<212> TYPE: RNA
<213> ORGANISM: artificial
<220> FEATURE:
<223> OTHER INFORMATION: RNA Oligomer

<400> SEQUENCE: 1931
caucuaguug uaacugagcg a                                              21

<210> SEQ ID NO 1932
<211> LENGTH: 21
<212> TYPE: RNA
<213> ORGANISM: artificial
<220> FEATURE:
<223> OTHER INFORMATION: RNA Oligomer

<400> SEQUENCE: 1932

-continued cuaguuuuuc uuaacaucug g          21

<210> SEQ ID NO 1933
<211> LENGTH: 21
<212> TYPE: RNA
<213> ORGANISM: artificial
<220> FEATURE:
<223> OTHER INFORMATION: RNA Oligomer

<400> SEQUENCE: 1933
aguuuuucuu aacaucuggc u          21

<210> SEQ ID NO 1934
<211> LENGTH: 21
<212> TYPE: RNA
<213> ORGANISM: artificial
<220> FEATURE:
<223> OTHER INFORMATION: RNA Oligomer

<400> SEQUENCE: 1934
gaacaaggaa aacauugcca u          21

<210> SEQ ID NO 1935
<211> LENGTH: 21
<212> TYPE: RNA
<213> ORGANISM: artificial
<220> FEATURE:
<223> OTHER INFORMATION: RNA Oligomer

<400> SEQUENCE: 1935
aaggaaaaca uugccaucuc u          21

<210> SEQ ID NO 1936
<211> LENGTH: 21
<212> TYPE: RNA
<213> ORGANISM: artificial
<220> FEATURE:
<223> OTHER INFORMATION: RNA Oligomer

<400> SEQUENCE: 1936
uugcuccuuu uggaguuguu c          21

<210> SEQ ID NO 1937
<211> LENGTH: 21
<212> TYPE: RNA
<213> ORGANISM: artificial
<220> FEATURE:
<223> OTHER INFORMATION: RNA Oligomer

<400> SEQUENCE: 1937
ggauauggag agcuuuugcc c          21

<210> SEQ ID NO 1938
<211> LENGTH: 21
<212> TYPE: RNA
<213> ORGANISM: artificial
<220> FEATURE:
<223> OTHER INFORMATION: RNA Oligomer

<400> SEQUENCE: 1938
uugugaaugg gguuuuccga u          21

<210> SEQ ID NO 1939
<211> LENGTH: 21
<212> TYPE: RNA
<213> ORGANISM: artificial

```
<220> FEATURE:
<223> OTHER INFORMATION: RNA Oligomer

<400> SEQUENCE: 1939
cacauugggc aucaugcacg u                                              21

<210> SEQ ID NO 1940
<211> LENGTH: 21
<212> TYPE: RNA
<213> ORGANISM: artificial
<220> FEATURE:
<223> OTHER INFORMATION: RNA Oligomer

<400> SEQUENCE: 1940
auguacuggu guuuuaggac c                                              21

<210> SEQ ID NO 1941
<211> LENGTH: 21
<212> TYPE: RNA
<213> ORGANISM: artificial
<220> FEATURE:
<223> OTHER INFORMATION: RNA Oligomer

<400> SEQUENCE: 1941
uacucuuucc gucgcugacu g                                              21

<210> SEQ ID NO 1942
<211> LENGTH: 21
<212> TYPE: RNA
<213> ORGANISM: artificial
<220> FEATURE:
<223> OTHER INFORMATION: RNA Oligomer

<400> SEQUENCE: 1942
guguuuagug aaaugccgga g                                              21

<210> SEQ ID NO 1943
<211> LENGTH: 21
<212> TYPE: RNA
<213> ORGANISM: artificial
<220> FEATURE:
<223> OTHER INFORMATION: RNA Oligomer

<400> SEQUENCE: 1943
uuuccgucgc ugacugaagu c                                              21

<210> SEQ ID NO 1944
<211> LENGTH: 21
<212> TYPE: RNA
<213> ORGANISM: artificial
<220> FEATURE:
<223> OTHER INFORMATION: RNA Oligomer

<400> SEQUENCE: 1944
aguucagaga gugaauggcu u                                              21

<210> SEQ ID NO 1945
<211> LENGTH: 21
<212> TYPE: RNA
<213> ORGANISM: artificial
<220> FEATURE:
<223> OTHER INFORMATION: RNA Oligomer

<400> SEQUENCE: 1945
uguugcugau acugggcuca g                                              21
```

```
<210> SEQ ID NO 1946
<211> LENGTH: 21
<212> TYPE: RNA
<213> ORGANISM: artificial
<220> FEATURE:
<223> OTHER INFORMATION: RNA Oligomer

<400> SEQUENCE: 1946
gaauuuaaug aguucacugu c                                              21

<210> SEQ ID NO 1947
<211> LENGTH: 21
<212> TYPE: RNA
<213> ORGANISM: artificial
<220> FEATURE:
<223> OTHER INFORMATION: RNA Oligomer

<400> SEQUENCE: 1947
ugucaacugg uugggucuu c                                               21

<210> SEQ ID NO 1948
<211> LENGTH: 21
<212> TYPE: RNA
<213> ORGANISM: artificial
<220> FEATURE:
<223> OTHER INFORMATION: RNA Oligomer

<400> SEQUENCE: 1948
ucaacuucug ucaguuuggc u                                              21

<210> SEQ ID NO 1949
<211> LENGTH: 21
<212> TYPE: RNA
<213> ORGANISM: artificial
<220> FEATURE:
<223> OTHER INFORMATION: RNA Oligomer

<400> SEQUENCE: 1949
caugguaguc ucaaccagcu u                                              21

<210> SEQ ID NO 1950
<211> LENGTH: 21
<212> TYPE: RNA
<213> ORGANISM: artificial
<220> FEATURE:
<223> OTHER INFORMATION: RNA Oligomer

<400> SEQUENCE: 1950
aggaauggau aauagcuccu c                                              21

<210> SEQ ID NO 1951
<211> LENGTH: 21
<212> TYPE: RNA
<213> ORGANISM: artificial
<220> FEATURE:
<223> OTHER INFORMATION: RNA Oligomer

<400> SEQUENCE: 1951
caucaugaug agcuguggac c                                              21

<210> SEQ ID NO 1952
<211> LENGTH: 21
<212> TYPE: RNA
<213> ORGANISM: artificial
<220> FEATURE:
<223> OTHER INFORMATION: RNA Oligomer

<400> SEQUENCE: 1952
```
ugacugagcc ugauuaguag c                                              21

<210> SEQ ID NO 1953
<211> LENGTH: 21
<212> TYPE: RNA
<213> ORGANISM: artificial
<220> FEATURE:
<223> OTHER INFORMATION: RNA Oligomer

<400> SEQUENCE: 1953
uuaguagcaa ugaagacugg g                                              21

<210> SEQ ID NO 1954
<211> LENGTH: 21
<212> TYPE: RNA
<213> ORGANISM: artificial
<220> FEATURE:
<223> OTHER INFORMATION: RNA Oligomer

<400> SEQUENCE: 1954
aaaagcugca ugcagucauc a                                              21

<210> SEQ ID NO 1955
<211> LENGTH: 21
<212> TYPE: RNA
<213> ORGANISM: artificial
<220> FEATURE:
<223> OTHER INFORMATION: RNA Oligomer

<400> SEQUENCE: 1955
ugggagaaau ucaccugucu c                                              21

<210> SEQ ID NO 1956
<211> LENGTH: 21
<212> TYPE: RNA
<213> ORGANISM: artificial
<220> FEATURE:
<223> OTHER INFORMATION: RNA Oligomer

<400> SEQUENCE: 1956
ucuaguugua acugagcgaa a                                              21

<210> SEQ ID NO 1957
<211> LENGTH: 21
<212> TYPE: RNA
<213> ORGANISM: artificial
<220> FEATURE:
<223> OTHER INFORMATION: RNA Oligomer

<400> SEQUENCE: 1957
uuuagccaga ugucauauca u                                              21

<210> SEQ ID NO 1958
<211> LENGTH: 21
<212> TYPE: RNA
<213> ORGANISM: artificial
<220> FEATURE:
<223> OTHER INFORMATION: RNA Oligomer

<400> SEQUENCE: 1958
aaacuagccc aaauggguguc c                                             21

<210> SEQ ID NO 1959
<211> LENGTH: 21
<212> TYPE: RNA
<213> ORGANISM: artificial

```
<220> FEATURE:
<223> OTHER INFORMATION: RNA Oligomer

<400> SEQUENCE: 1959
cuauacuagu uuuggcuaug a                                              21

<210> SEQ ID NO 1960
<211> LENGTH: 21
<212> TYPE: RNA
<213> ORGANISM: artificial
<220> FEATURE:
<223> OTHER INFORMATION: RNA Oligomer

<400> SEQUENCE: 1960
guacaaaaaa acuagcucag a                                              21

<210> SEQ ID NO 1961
<211> LENGTH: 21
<212> TYPE: RNA
<213> ORGANISM: artificial
<220> FEATURE:
<223> OTHER INFORMATION: RNA Oligomer

<400> SEQUENCE: 1961
caaggaaaac auugccaucu c                                              21

<210> SEQ ID NO 1962
<211> LENGTH: 21
<212> TYPE: RNA
<213> ORGANISM: artificial
<220> FEATURE:
<223> OTHER INFORMATION: RNA Oligomer

<400> SEQUENCE: 1962
uuugcugcag ggaguauuca c                                              21

<210> SEQ ID NO 1963
<211> LENGTH: 21
<212> TYPE: RNA
<213> ORGANISM: artificial
<220> FEATURE:
<223> OTHER INFORMATION: RNA Oligomer

<400> SEQUENCE: 1963
auucacuagg agaauaaggu u                                              21

<210> SEQ ID NO 1964
<211> LENGTH: 21
<212> TYPE: RNA
<213> ORGANISM: artificial
<220> FEATURE:
<223> OTHER INFORMATION: RNA Oligomer

<400> SEQUENCE: 1964
acuaggagaa uaagguuuuc c                                              21

<210> SEQ ID NO 1965
<211> LENGTH: 21
<212> TYPE: RNA
<213> ORGANISM: artificial
<220> FEATURE:
<223> OTHER INFORMATION: RNA Oligomer

<400> SEQUENCE: 1965 guuuuucag uaggugaagg c                                               21
```

```
<210> SEQ ID NO 1966
<211> LENGTH: 21
<212> TYPE: RNA
<213> ORGANISM: artificial
<220> FEATURE:
<223> OTHER INFORMATION: RNA Oligomer

<400> SEQUENCE: 1966
cuuuuucugc aauucugagc a                                              21

<210> SEQ ID NO 1967
<211> LENGTH: 21
<212> TYPE: RNA
<213> ORGANISM: artificial
<220> FEATURE:
<223> OTHER INFORMATION: RNA Oligomer

<400> SEQUENCE: 1967
cuguuuuucc agcucauacu c                                              21

<210> SEQ ID NO 1968
<211> LENGTH: 21
<212> TYPE: RNA
<213> ORGANISM: artificial
<220> FEATURE:
<223> OTHER INFORMATION: RNA Oligomer

<400> SEQUENCE: 1968
guacuggugu uuuaggacca u                                              21

<210> SEQ ID NO 1969
<211> LENGTH: 21
<212> TYPE: RNA
<213> ORGANISM: artificial
<220> FEATURE:
<223> OTHER INFORMATION: RNA Oligomer

<400> SEQUENCE: 1969
cacugaggcc aaguagugug u                                              21

<210> SEQ ID NO 1970
<211> LENGTH: 21
<212> TYPE: RNA
<213> ORGANISM: artificial
<220> FEATURE:
<223> OTHER INFORMATION: RNA Oligomer

<400> SEQUENCE: 1970
ugaggccaag uagugugucu c                                              21

<210> SEQ ID NO 1971
<211> LENGTH: 21
<212> TYPE: RNA
<213> ORGANISM: artificial
<220> FEATURE:
<223> OTHER INFORMATION: RNA Oligomer

<400> SEQUENCE: 1971
ggccaaguag ugugucucca u                                              21

<210> SEQ ID NO 1972
<211> LENGTH: 21
<212> TYPE: RNA
<213> ORGANISM: artificial
<220> FEATURE:
<223> OTHER INFORMATION: RNA Oligomer

<400> SEQUENCE: 1972
```
aaguagugug ucuccauagc u                                    21

<210> SEQ ID NO 1973
<211> LENGTH: 21
<212> TYPE: RNA
<213> ORGANISM: artificial
<220> FEATURE:
<223> OTHER INFORMATION: RNA Oligomer

<400> SEQUENCE: 1973
gacuuguguu uagugaaaug c                                    21

<210> SEQ ID NO 1974
<211> LENGTH: 21
<212> TYPE: RNA
<213> ORGANISM: artificial
<220> FEATURE:
<223> OTHER INFORMATION: RNA Oligomer

<400> SEQUENCE: 1974
acucuuuccg ucgcugacug a                                    21

<210> SEQ ID NO 1975
<211> LENGTH: 21
<212> TYPE: RNA
<213> ORGANISM: artificial
<220> FEATURE:
<223> OTHER INFORMATION: RNA Oligomer

<400> SEQUENCE: 1975
uuagaaguuc agagagugaa u                                    21

<210> SEQ ID NO 1976
<211> LENGTH: 21
<212> TYPE: RNA
<213> ORGANISM: artificial
<220> FEATURE:
<223> OTHER INFORMATION: RNA Oligomer

<400> SEQUENCE: 1976
uucaucacca aaaucugugu u                                    21

<210> SEQ ID NO 1977
<211> LENGTH: 21
<212> TYPE: RNA
<213> ORGANISM: artificial
<220> FEATURE:
<223> OTHER INFORMATION: RNA Oligomer

<400> SEQUENCE: 1977
aucaccaaaa ucuguguuga c                                    21

<210> SEQ ID NO 1978
<211> LENGTH: 21
<212> TYPE: RNA
<213> ORGANISM: artificial
<220> FEATURE:
<223> OTHER INFORMATION: RNA Oligomer

<400> SEQUENCE: 1978
gcaucugaau uuaaugaguu c                                    21

<210> SEQ ID NO 1979
<211> LENGTH: 21
<212> TYPE: RNA
<213> ORGANISM: artificial -continued
<220> FEATURE:
<223> OTHER INFORMATION: RNA Oligomer

<400> SEQUENCE: 1979
augaguucac ugucaacugg u                                              21

<210> SEQ ID NO 1980
<211> LENGTH: 21
<212> TYPE: RNA
<213> ORGANISM: artificial
<220> FEATURE:
<223> OTHER INFORMATION: RNA Oligomer

<400> SEQUENCE: 1980
aaauguggac uacaguuacc u                                              21

<210> SEQ ID NO 1981
<211> LENGTH: 21
<212> TYPE: RNA
<213> ORGANISM: artificial
<220> FEATURE:
<223> OTHER INFORMATION: RNA Oligomer

<400> SEQUENCE: 1981
ucuuuuucca uugaggguau a                                              21

<210> SEQ ID NO 1982
<211> LENGTH: 21
<212> TYPE: RNA
<213> ORGANISM: artificial
<220> FEATURE:
<223> OTHER INFORMATION: RNA Oligomer

<400> SEQUENCE: 1982
acacuguaac ucaggaaugg a                                              21

<210> SEQ ID NO 1983
<211> LENGTH: 21
<212> TYPE: RNA
<213> ORGANISM: artificial
<220> FEATURE:
<223> OTHER INFORMATION: RNA Oligomer

<400> SEQUENCE: 1983
ucaggaaugg auaauagcuc c                                              21

<210> SEQ ID NO 1984
<211> LENGTH: 21
<212> TYPE: RNA
<213> ORGANISM: artificial
<220> FEATURE:
<223> OTHER INFORMATION: RNA Oligomer

<400> SEQUENCE: 1984
caauguccug uugcauaccg u                                              21

<210> SEQ ID NO 1985
<211> LENGTH: 21
<212> TYPE: RNA
<213> ORGANISM: artificial
<220> FEATURE:
<223> OTHER INFORMATION: RNA Oligomer

<400> SEQUENCE: 1985
auaccgucua aaucaacagg g                                              21

```
<210> SEQ ID NO 1986
<211> LENGTH: 21
<212> TYPE: RNA
<213> ORGANISM: artificial
<220> FEATURE:
<223> OTHER INFORMATION: RNA Oligomer

<400> SEQUENCE: 1986
gucuaaauca acaggggcua c                                              21

<210> SEQ ID NO 1987
<211> LENGTH: 21
<212> TYPE: RNA
<213> ORGANISM: artificial
<220> FEATURE:
<223> OTHER INFORMATION: RNA Oligomer

<400> SEQUENCE: 1987
uaccugagca acagaaguuu c                                              21

<210> SEQ ID NO 1988
<211> LENGTH: 21
<212> TYPE: RNA
<213> ORGANISM: artificial
<220> FEATURE:
<223> OTHER INFORMATION: RNA Oligomer

<400> SEQUENCE: 1988
agcaaugaag acugggcucu c                                              21

<210> SEQ ID NO 1989
<211> LENGTH: 21
<212> TYPE: RNA
<213> ORGANISM: artificial
<220> FEATURE:
<223> OTHER INFORMATION: RNA Oligomer

<400> SEQUENCE: 1989
aguuggcaga uccacugguu u                                              21

<210> SEQ ID NO 1990
<211> LENGTH: 21
<212> TYPE: RNA
<213> ORGANISM: artificial
<220> FEATURE:
<223> OTHER INFORMATION: RNA Oligomer

<400> SEQUENCE: 1990
gaaaagguca aauccuccua a                                              21

<210> SEQ ID NO 1991
<211> LENGTH: 21
<212> TYPE: RNA
<213> ORGANISM: artificial
<220> FEATURE:
<223> OTHER INFORMATION: RNA Oligomer

<400> SEQUENCE: 1991
guuuuucuua acaucuggcu u                                              21

<210> SEQ ID NO 1992
<211> LENGTH: 21
<212> TYPE: RNA
<213> ORGANISM: artificial
<220> FEATURE:
<223> OTHER INFORMATION: RNA Oligomer

<400> SEQUENCE: 1992
```
cuggcuucuu acuuuggga a                                           21

<210> SEQ ID NO 1993
<211> LENGTH: 21
<212> TYPE: RNA
<213> ORGANISM: artificial
<220> FEATURE:
<223> OTHER INFORMATION: RNA Oligomer

<400> SEQUENCE: 1993
aaaaaggcuu ucucuugcuc c                                          21

<210> SEQ ID NO 1994
<211> LENGTH: 21
<212> TYPE: RNA
<213> ORGANISM: artificial
<220> FEATURE:
<223> OTHER INFORMATION: RNA Oligomer

<400> SEQUENCE: 1994
aacaaggaaa acauugccau c                                          21

<210> SEQ ID NO 1995
<211> LENGTH: 21
<212> TYPE: RNA
<213> ORGANISM: artificial
<220> FEATURE:
<223> OTHER INFORMATION: RNA Oligomer

<400> SEQUENCE: 1995
aaaggcuuuc ucuugcuccu u                                          21

<210> SEQ ID NO 1996
<211> LENGTH: 21
<212> TYPE: RNA
<213> ORGANISM: artificial
<220> FEATURE:
<223> OTHER INFORMATION: RNA Oligomer

<400> SEQUENCE: 1996
uuuuucagua ggugaaggcu u                                          21

<210> SEQ ID NO 1997
<211> LENGTH: 21
<212> TYPE: RNA
<213> ORGANISM: artificial
<220> FEATURE:
<223> OTHER INFORMATION: RNA Oligomer

<400> SEQUENCE: 1997
auuaaugcaa guugagcuuc a                                          21

<210> SEQ ID NO 1998
<211> LENGTH: 21
<212> TYPE: RNA
<213> ORGANISM: artificial
<220> FEATURE:
<223> OTHER INFORMATION: RNA Oligomer

<400> SEQUENCE: 1998
uuaaugcaag uugagcuuca u                                              21

<210> SEQ ID NO 1999
<211> LENGTH: 21
<212> TYPE: RNA
<213> ORGANISM: artificial
<220> FEATURE:
<223> OTHER INFORMATION: RNA Oligomer

<400> SEQUENCE: 1999
auuuuuucua cagggaaugg g                                              21

<210> SEQ ID NO 2000
<211> LENGTH: 21
<212> TYPE: RNA
<213> ORGANISM: artificial
<220> FEATURE:
<223> OTHER INFORMATION: RNA Oligomer

<400> SEQUENCE: 2000
ucuugugaga ugagccucca a                                              21

<210> SEQ ID NO 2001
<211> LENGTH: 21
<212> TYPE: RNA
<213> ORGANISM: artificial
<220> FEATURE:
<223> OTHER INFORMATION: RNA Oligomer

<400> SEQUENCE: 2001
guuuuuucug uuuuuccagc u                                              21

<210> SEQ ID NO 2002
<211> LENGTH: 21
<212> TYPE: RNA
<213> ORGANISM: artificial
<220> FEATURE:
<223> OTHER INFORMATION: RNA Oligomer

<400> SEQUENCE: 2002
cucacauugg gcaucaugca c                                              21

<210> SEQ ID NO 2003
<211> LENGTH: 21
<212> TYPE: RNA
<213> ORGANISM: artificial
<220> FEATURE:
<223> OTHER INFORMATION: RNA Oligomer -continued

<400> SEQUENCE: 2003
acauugggca ucaugcacgu g                                              21

<210> SEQ ID NO 2004
<211> LENGTH: 21
<212> TYPE: RNA
<213> ORGANISM: artificial
<220> FEATURE:
<223> OTHER INFORMATION: RNA Oligomer

<400> SEQUENCE: 2004
cccagaagaa uguacuggug u                                              21

<210> SEQ ID NO 2005
<211> LENGTH: 21
<212> TYPE: RNA
<213> ORGANISM: artificial
<220> FEATURE:
<223> OTHER INFORMATION: RNA Oligomer

<400> SEQUENCE: 2005
aauguacugg uguuuuagga c                                              21

<210> SEQ ID NO 2006
<211> LENGTH: 21
<212> TYPE: RNA
<213> ORGANISM: artificial
<220> FEATURE:
<223> OTHER INFORMATION: RNA Oligomer

<400> SEQUENCE: 2006
aggccaagua gugugucucc a                                              21

<210> SEQ ID NO 2007
<211> LENGTH: 21
<212> TYPE: RNA
<213> ORGANISM: Artificial
<220> FEATURE:
<223> OTHER INFORMATION: RNA Oligomer

<400> SEQUENCE: 2007
ggcuacgucc aggagcgcac c                                              21

<210> SEQ ID NO 2008
<211> LENGTH: 21
<212> TYPE: RNA
<213> ORGANISM: Artificial
<220> FEATURE:
<223> OTHER INFORMATION: RNA Oligomer

<400> SEQUENCE: 2008
ggugcgcucc uggacguagc c                                              21

OLIGORIBONUCLEOTIDE INHIBITORS OF NRF2 AND METHODS OF USE THEREOF FOR TREATMENT OF CANCER

This application is a divisional of U.S. Ser. No. 12/077,414 filed Mar. 19, 2008, now U.S. Pat. No. 7,812,002, issued Oct. 12, 2010, which claims the benefit of U.S. Provisional Application No. 60/937,135, filed Jun. 26, 2007 and of U.S. Provisional Application No. 60/919,413, filed Mar. 22, 2007, which contents of all of which are hereby incorporated by reference into this application.

Throughout this application various patent and scientific publications are cited. The disclosures for these publications in their entireties are hereby incorporated by reference into this application to more fully describe the state of the art to which this invention pertains.

This application contains nucleotide and/or amino acid sequences which are present in the file named "20120603_77688_AZ_SubstituteSequenceListing.txt," which is 348 KB in size, and was created on Jun. 3, 2012 in the IBM-PCT machine format and has an operating system compatibility with MS-Windows, which is contained in the text file filed Jun. 13, 2012 as part of this application.

BACKGROUND OF THE INVENTION siRNAs and RNA Interference

RNA interference (RNAi) is a phenomenon involving double-stranded (ds) RNA-dependent gene specific posttranscriptional silencing. Originally, attempts to study this phenomenon and to manipulate mammalian cells experimentally were frustrated by an active, non-specific antiviral defense mechanism which was activated in response to long dsRNA molecules; see Gil et al. 2000, Apoptosis, 5:107-114. Later it was discovered that synthetic duplexes of 21 nucleotide RNAs could mediate gene specific RNAi in mammalian cells, without the stimulation of the generic antiviral defense mechanisms (see Elbashir et al. Nature 2001, 411:494-498 and Caplen et al. Proc Natl Acad Sci 2001, 98:9742-9747). As a result, small interfering RNAs (siRNAs), which are short double-stranded RNAs, have become powerful tools in attempting to understand gene function.

Thus, RNA interference (RNAi) refers to the process of sequence-specific post-transcriptional gene silencing in mammals mediated by small interfering RNAs (siRNAs) (Fire et al, 1998, Nature 391, 806) or microRNAs (miRNAs) (Ambros V. Nature 431:7006, 350-355 (2004); and Bartel D P. Cell. 2004 Jan. 23; 116(2): 281-97 *MicroRNAs: genomics, biogenesis, mechanism, and function*). The corresponding process in plants is commonly referred to as specific post-transcriptional gene silencing or RNA silencing and is also referred to as quelling in fungi. An siRNA is a double-stranded RNA molecule which down-regulates or silences (prevents) the expression of a gene/mRNA of its endogenous (cellular) counterpart. RNA interference is based on the ability of dsRNA species to enter a specific protein complex, where it is then targeted to the complementary cellular RNA and specifically degrades it. Thus, the RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al 2001, Genes Dev., 15, 188). In more detail, longer dsRNAs are digested into short (17-29 bp) dsRNA fragments (also referred to as short inhibitory RNAs—"siRNAs") by type III RNAses (DICER, DROSHA, etc., Bernstein et al., Nature, 2001, v. 409, p. 363-6; Lee et al., Nature, 2003, 425, p. 415-9). The RISC protein complex recognizes these fragments and complementary mRNA. The whole process is culminated by endonuclease cleavage of target mRNA (McManus & Sharp, Nature Rev Genet, 2002, v. 3, p. 737-47; Paddison & Hannon, Curr Opin Mol. Ther. 2003 June; 5(3): 217-24). For information on these terms and proposed mechanisms, see Bernstein E., Denli A M. Hannon G J: 2001 *The rest is silence. RNA. I;* 7(11): 1509-21; Nishikura K.: 2001 *A short primer on RNAi: RNA-directed RNA polymerase acts as a key catalyst*. Cell. 116; 107(4): 415-8 and PCT publication WO 01/36646 (Glover et al).

The selection and synthesis of siRNA corresponding to known genes has been widely reported; see for example Chalk A M, Wahlestedt C, Sonnhammner E L. 2004 Improved and automated prediction of effective siRNA Biochem. Biophys. Res. Commun. June 18; 319(1): 264-74; Sioud M, Leirdal M., 2004, *Potential design rules and enzymatic synthesis of siRNAs*, Methods Mol. Biol.; 252:457-69; Levenkova N, Gu Q, Rux J J. 2004, *Gene specific siRNA selector* Bioinformatics. 112; 20(3): 430-2. and Ui-Tei K, Naito Y, Takahashi F, Haraguchi T, Ohki-Hamazaki H, Juni A, Ueda R, Saigo K., *Guidelines for the selection of highly effective siRNA sequences for mammalian and chick RNA interference Nucleic Acids* Res. 2004 I 9; 32(3):936-48. See also Liu Y, Braasch D A, Nulf C J, Corey D R. *Efficient and isoform-selective inhibition of cellular gene expression by peptide nucleic acids*, Biochemistry, 2004 I 24; 43(7):1921-7. See also PCT publications WO 2004/015107 (Atugen) and WO 02/44321 (Tuschl et al), and also Chiu Y L, Rana T M. *siRNA function in RNAi: a chemical modification analysis*, RNA 2003 September; 9(9):1034-48 and I U.S. Pat. Nos. 5,898,031 and 6107094 (Crooke) for production of modified/more stable siRNAs.

Several groups have described the development of DNA-based vectors capable of generating siRNA within cells. The method generally involves transcription of short hairpin RNAs that are efficiently processed to form siRNAs within cells. Paddison et al. *PNAS* 2002, 99:1443-1448; Paddison et al. *Genes & Dev* 2002, 16:948-958; Sui et al. *PNAS* 2002, 8:5515-5520; and Brummelkamp et al. *Science* 2002, 296: 550-553. These reports describe methods to generate siRNAs capable of specifically targeting numerous endogenously and exogenously expressed genes.

Several studies have revealed that siRNA therapeutics are effective in viva in both mammals and in humans. Bitko et al., have shown that specific siRNA molecules directed against the respiratory syncytial virus (RSV) nucleocapsid N gene are effective in treating mice when administered intranasally (Bitko et al., Nat. Med. 2005, 11(1):50-55). For reviews of therapeutic applications of siRNAs see for example, Batik (Mol. Med. 2005, 83: 764-773); Chakraborty (Current Drug Targets 2007 8(3):469-82) and Dykxhoom, et al (Gene Therapy 2006, 13, 541-552). Furthermore, a phase I clinical study with short siRNA molecule that targets the VEGFR1 receptor for the treatment of Age-Related Macular Degeneration (AMD) has been conducted in human patients. In studies such siRNA administered by intravitreal (intraocular) injection was found effective and safe in 14 patients tested (Kaiser, Am J Ophthalmol. 2006 142(4):660-8).

The Nrf2 Gene and Polypeptide (gi|166295208|ref|NM_006164.3| *Homo sapiens* Nuclear Factor (Erythroid-Derived 2)-like 2 (NFE2L2):

Nuclear factor erythroid-2 related factor 2 (Nrf2), a cap-and-collar basic leucine zipper transcription factor, positively regulates a transcriptional program that maintains cellular redox homeostasis and protects cells from oxidative insult, including insult from chemotherapeutic agents (Rangasamy T, et al. J Clin Invest 114, 1248 (2004)). Nrf2 activates transcription of its target genes through binding specifically to the antioxidant-response element (ARE) found in those gene promoters. The Nrf2-regulated transcriptional program includes a broad spectrum of genes, including antioxidants such as heme oxygenase-1, superoxide dismutase, glutathione reductase (GSR), glutathione peroxidase, thioredoxin, thioredoxin reductase, peroxiredoxins (PRDX).

Lung Cancer:

Lung cancer is a cancer that forms in tissues of the lung, usually in the cells lining air passages. The two main types are small cell lung cancer and non-small cell lung cancer. These types are diagnosed based on the morphology of the cells under a microscope. It is the most lethal of all cancers worldwide, responsible for up to 3 million deaths annually. In non-small cell lung cancer (NSCLC), results of standard treatment are poor except for the most localized cancers. Surgery is the most potentially curative therapeutic option for this disease; radiation therapy can produce a cure in a small number of patients and can provide palliation in most patients. Adjuvant chemotherapy may provide an additional benefit to patients with resected NSCLC. In advanced-stage disease, chemotherapy offers modest improvements in median survival, though overall survival is poor. Chemotherapy has produced short-term improvement in disease-related symptoms.

WO 2006/128041 discloses specific siRNA molecules for Nrf2 and its use for treating any cancer, preferably lung and kidney cancers. US20020164576 discloses a method of inhibiting tumor growth (preferably a lymphoma cancer) using antisense molecules directed to Nrf2 or specific antibodies. US20070042418 discloses the use of siRNA molecules for Nrf2 for treating cancer.

Despite the evident progress, there remains a continued need for improved molecules in particular improved siRNA compounds able to treat cancerous diseases, particularly lung cancers.

SUMMARY OF THE INVENTION

The invention provides novel double stranded oligoribonucleotides that inhibit the Nrf2 gene. The invention also provides a pharmaceutical composition comprising one or more such oligoribonucleotides, and a vector capable of expressing the oligoribonucleotide. The present invention also relates to methods and compositions for treating or preventing the incidence or severity of a cancerous disease, particularly various lung cancers. The methods and compositions involve administering to a mammal in need of such treatment a prophylactically or therapeutically effective amount of one or more compounds which down-regulate expression of the Nrf2 gene, particularly novel small interfering RNAs (siRNAs), small molecule inhibitors of Nrf2 as described herein or antibodies to Nrf2 polypeptide.

In certain embodiments the present invention provides a compound having the structure:

wherein each of N and N' is a ribonucleotide which may be independently modified or unmodified in its sugar residue; wherein each of $(N)_x$ and $(N')_y$ is an oligomer in which each consecutive N or N' is joined to the next N or N' by a covalent bond;

wherein each of x and y is an integer between 19 and 40;

wherein each of Z and Z' may be present or absent, but if present is 1-5 consecutive nucleotides covalently attached at the 3' terminus of the strand in which it is present; and wherein the sequence of $(N)_x$ is set forth as any one of SEQ ID NOS 504 to 1006 or 1507 to 2006, and the sequence of $(N')_y$ is set forth as the complementary sequence. The sequence of $(N')_y$ is a complementary sequence set forth as SEQ ID NOS: 1 to 503 or 1007 to 1506, respectively.

In some embodiments the covalent bond joining each consecutive N or N' is a phosphodiester bond. In various embodiments all the covalent bonds are phosphodiester bonds.

In various embodiments the compound comprises ribonucleotides wherein x=y and each of x and y is 19, 20, 21, 22 or 23. In some embodiments x=y=23. In other embodiments x=y=19.

In some embodiments the compound is blunt ended, for example wherein both Z and Z' are absent. In an alternative embodiment, the compound comprises at least one 3' overhang, wherein at least one of Z or Z' is present. Z and Z' can independently comprise one or more covalently linked modified or non-modified nucleotides, for example inverted dT or dA; dT, LNA, mirror nucleotide and the like. In some embodiments each of Z and V are independently selected from dT and dTdT.

In some embodiments N or N' comprises a modification in the sugar residue of one or more ribonucleotides. In other embodiments the compound comprises at least one ribonucleotide modified in the sugar residue. In some embodiments the compound comprises a modification at the 2' position of the sugar residue. In some embodiments the modification in the 2' position comprises the presence of an amino, a fluoro, an alkoxy or an alkyl moiety. In certain embodiments the 2' modification comprises a methoxy moiety. A presently preferred modification is a 2' methoxy of the sugar residue (2'-O-methyl; 2-O-Me; 2'-O—CH$_3$).

In some embodiments the compound comprises modified alternating ribonucleotides in one or both of the antisense and the sense strands. In certain embodiments the compound comprises modified alternating ribonucleotides in the antisense and the sense strands. In other embodiments the compound comprises modified alternating ribonucleotides in the antisense strand only. In certain embodiments the middle ribonucleotide of the antisense strand is not modified; e.g. ribonucleotide in position 10 in a 19-mer strand or position 12 in a 23-mer strand.

In additional embodiments the compound comprises modified ribonucleotides in alternating positions wherein each N at the 5' and 3' termini of $(N)_x$ are modified in their sugar residues, and each N' at the 5' and 3' termini of $(N')_y$ are unmodified in their sugar residues. In some embodiments, neither $(N)_x$ nor $(N')_y$ are phosphorylated at the 3' and 5' termini. In other embodiments either or both $(N)_x$ and $(N')_y$ are phosphorylated at the 3' termini. Preferably the siRNA molecule is either phosphorylated at the 3' termini of both sense and anti-sense strands, or non-phosphorylated at all; similar results are obtained for both siRNAs. The siRNA molecules used in the in vitro experiments were phosphorylated at the 3' termini of both sense and anti-sense strands while the siRNA molecules used in the in vivo experiments were non-phosphorylated at all.

More specifically, the present invention provides methods and compositions for treating a patient suffering from a cancerous disease, (e.g. lung cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer). In a particular embodiment, the cancer is lung cancer such as non-small-cell lung carcinoma (NSCLC) or small-cell lung carcinoma. The methods of the invention comprising administering to the patient one or more compounds which down-regulate expression of the Nrf2 gene, particularly siRNAs that inhibit Nrf2, typically as a pharmaceutical composition, in a therapeutically effective dose so as to thereby treat the patient.

Still further, the invention relates to a method for treating or preventing the incidence or severity of a cancerous disease, particularly a lung disease in a patient comprising administering to the patient a composition comprising an effective amount of naked siRNA molecules. Preferably, the naked siRNA molecules are applied directly to lung for example via aerosol delivery which has the potential for delivering high concentrations of the therapeutic molecule to the inner lung.

Still further, the invention relates to the use of a therapeutically effective dose of an oligonucleotide for the preparation of a composition for treating a subject suffering from a cancerous disease, preferably lung cancer, wherein the oligonucleotide is set forth as any one of SEQ ID NOS:1-2006.

DETAILED DESCRIPTION OF THE INVENTION

Figure 1:
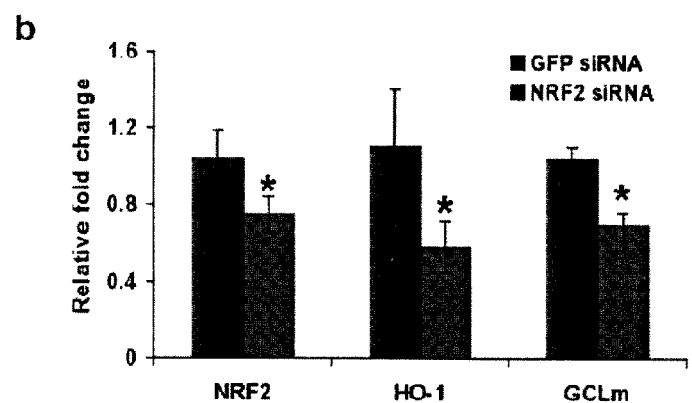
FIG. 1: A549-C8 luciferase cells were transfected with non-targeting luciferase siRNA or Nrf2 siRNA-1 (sense strand SEQ ID NO: 10) at 20 nM concentration. Seventy two hours post transfection, cells were harvested and total RNA was isolated. Nrf2 knockdown as well as expression of two Nrf2 dependent target genes (GCLM and HO-1) were analyzed by real time RT-PCR.

The present invention relates generally to compounds which down-regulate expression of the Nrf2 gene particularly to novel small interfering RNAs (siRNAs), and to the use of these novel siRNAs in the treatment of various diseases and medical conditions in particular various forms of cancerous diseases. Such preferred siRNA compounds comprise sequences set forth as any one of SEQ ID NOS: 1 to 2006.

The inventors of the present invention have provided novel siRNAs to Nrf2 in order to treat any of the above diseases or disorders. Methods, molecules and compositions which inhibit Nrf2 are discussed herein at length, and any of said molecules and/or compositions may be beneficially employed in the treatment of a patient suffering from any of said conditions.

The present invention provides methods and compositions for inhibiting expression of a target Nrf2 gene in vivo. In general, the method includes administering oligoribonucleotides, such as small interfering RNAs (i.e., siRNAs) that are targeted to a particular Nrf2 mRNA and hybridize to, or interact with, the mRNAs under biological conditions (within the cell), or a nucleic acid material that can produce siRNA in a cell, in an amount sufficient to down-regulate expression of a target gene by an RNA interference mechanism. In particular, the subject method can be used to inhibit expression of the Nrf2 gene for treatment of a disease.

In accordance with the present invention, the siRNA molecules or inhibitors of the Nrf2 gene may be used as drugs to treat various pathologies accompanied by an elevated level of Nrf2 polypeptide.

The present invention provides double-stranded oligoribonucleotides (siRNAs), which down-regulate the expression of the Nrf2 gene. An siRNA of the invention is a duplex oligoribonucleotide in which the sense strand is derived from the mRNA sequence of the Nrf2 gene, and the antisense strand is complementary to the sense strand. In general, some deviation from the target mRNA sequence is tolerated without compromising the siRNA activity (see e.g. Czauderna et al 2003 Nucleic Acids Research 31(11), 2705-2716). An siRNA of the invention inhibits gene expression on a post-transcriptional level with or without destroying the mRNA. Without being bound by theory, siRNA may target the mRNA for specific cleavage and degradation and/or may inhibit translation from the targeted message.

As used herein, the term "Nrf2", or "Nrf2 polypeptide" (gi|166295208|ref|NM_006164.3| *Homo sapiens* nuclear factor (erythroid-derived 2)-like 2 (NFE2L2) is defined as any homolog of the Nrf2 polypeptide having preferably 90% homology, more preferably 95% homology, and even more preferably 98% homology to the Nrf2 gene, as either full-length or a fragment or a domain thereof, as a mutant or the polypeptide encoded by a spliced variant nucleic acid sequence, as a chimera with other polypeptides, provided that any of the above has the same or substantially the same biological function as the Nrf2 polypeptide.

Generally, the siRNAs used in the present invention comprise a ribonucleic acid comprising a double stranded structure, whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides and whereby said second stretch is at least partially identical to a target nucleic acid, whereby said first strand and/or said second strand comprises a plurality of groups of modified nucleotides having a modification at the 2'-position whereby within the strand each group of modified nucleotides is flanked on one or both sides by a flanking group of nucleotides whereby the flanking nucleotides forming the flanking group of nucleotides is either an unmodified nucleotide or a nucleotide having a modification different from the modification of the modified nucleotides. Further, said first strand and/or said second strand may comprise said plurality of modified nucleotides and may comprises said plurality of groups of modified nucleotides.

The group of modified nucleotides and/or the group of flanking nucleotides may comprise a number of nucleotides whereby the number is selected from the group comprising one nucleotide to 10 nucleotides. In connection with any ranges specified herein it is to be understood that each range discloses any individual integer between the respective figures used to define the range including said two figures defining said range. In the present case the group thus comprises one nucleotide, two nucleotides, three nucleotides, four nucleotides, five nucleotides, six nucleotides, seven nucleotides, eight nucleotides, nine nucleotides and ten nucleotides.

The pattern of modified nucleotides of said first strand may be shifted by one or more nucleotides relative to the pattern of modified nucleotides of the second strand.

The modifications discussed above may be selected from the group comprising amino, fluoro, methoxy alkoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O—, S—, or N-alkyl; O-, S-, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1.

The double stranded structure of the siRNA may be blunt ended, on one or both sides. More specifically, the double stranded structure may be blunt ended on the double stranded structure's side which is defined by the 5'-end of the first strand and the 3'-end of the second strand, or the double stranded structure may be blunt ended on the double stranded structure's side which is defined by at the 3'-end of the first strand and the 5'-end of the second strand.

Additionally, at least one of the two strands may have an overhang of at least one nucleotide at the 5'-end; the overhang may consist of at least one deoxyribonucleotide. At least one of the strands may also optionally have an overhang of at least one nucleotide at the 3'-end.

The length of the double-stranded structure of the siRNA is typically from about 17 to 21 and more preferably 18 or 19 bases. Further, the length of said first strand and/or the length of said second strand may independently from each other be selected from the group comprising the ranges of from about 15 to about 23 bases, 17 to 21 bases and 18 or 19 bases.

Additionally, the complementarily between said first strand and the target nucleic acid may be perfect, or the duplex formed between the first strand and the target nucleic acid may comprise at least 15 nucleotides wherein there is one mismatch or two mismatches between said first strand and the target nucleic acid forming said double-stranded structure.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, compared to another sequence.

In some cases both the first strand and the second strand each comprise at least one group of modified nucleotides and at least one flanking group of nucleotides, whereby each group of modified nucleotides comprises at least one nucleotide and whereby each flanking group of nucleotides comprising at least one nucleotide with each group of modified nucleotides of the first strand being aligned with a flanking group of nucleotides on the second strand, whereby the most terminal 5' nucleotide of the first strand is a nucleotide of the group of modified nucleotides, and the most terminal 3' nucleotide of the second strand is a nucleotide of the flanking group of nucleotides. Each group of modified nucleotides may consist of a single nucleotide and/or each flanking group of nucleotides may consist of a single nucleotide.

Additionally, it is possible that on the first strand the nucleotide forming the flanking group of nucleotides is an unmodified nucleotide which is arranged in a 3' direction relative to the nucleotide forming the group of modified nucleotides, and on the second strand the nucleotide forming the group of modified nucleotides is a modified nucleotide which is arranged in 5' direction relative to the nucleotide forming the flanking group of nucleotides.

Further the first strand of the siRNA may comprise eight to twelve, preferably nine to eleven, groups of modified nucleotides, and the second strand may comprise seven to eleven, preferably eight to ten, groups of modified nucleotides.

The first strand and the second strand may be linked by a loop structure, which may be comprised of a non-nucleic acid polymer such as, inter alia, polyethylene glycol. Alternatively, the loop structure may be comprised of a nucleic acid.

Further, the 5'-terminus of the first strand of the siRNA may be linked to the 3'-terminus of the second strand, or the 3'-end of the first strand may be linked to the 5'-terminus of the second strand, said linkage being via a nucleic acid linker typically having a length between 10-2000 nucleobases.

In particular, the invention provides a compound having structure A:

wherein each N and N' is a ribonucleotide which may independently be modified or unmodified in its sugar residue and each of $(N)_x$ and $(N')_y$ is oligomer in which each consecutive N or N' is joined to the next N or N' by a covalent bond;

wherein each of x and y is an integer between 19 and 40;

wherein each of Z and Z' may be present or absent, but if present is dTdT and is covalently attached at the 3' terminus of the strand in which it is present;

and wherein the sequence of $(N)_x$ is set forth as any one of SEQ ID NOS 504 to 1006 or 1507 to 2006, and the sequence of $(N')_y$ is set forth as the complementary sequence. The sequence of $(N')_y$ is a complementary sequence set forth as SEQ ID NOS: 1 to 503 or 1007 to 1506, respectively.

It will be readily understood by those skilled in the art that the compounds of the present invention consist of a plurality of nucleotides, which are linked through covalent linkages. Each such covalent linkage may be a phosphodiester linkage, a phosphothioate linkage, or a combination of both, along the length of the nucleotide sequence of the individual strand.

Other possible backbone modifications are described inter alia in U.S. Pat. Nos. 5,587,361; 6,242,589; 6,277,967; 6,326,358; 5,399,676; 5,489,677; and 5,596,086.

In particular embodiments, x and y are preferably an integer between about 19 to about 27, most preferably from about 19 to about 23. In a particular embodiment of the compound of the invention, x may be equal to y (viz., x=y) and in preferred embodiments x=y=19 or x=y=21. In a particularly preferred embodiment x=y=19.

In one embodiment of the compound of the invention, Z and Z' are both absent; in another embodiment one of Z or Z' is present.

In one embodiment of the compound of the invention, all of the ribonucleotides of the compound are unmodified in their sugar residues.

In preferred embodiments of the compound of the invention, at least one ribonucleotide is modified in its sugar residue, preferably a modification at the 2' position. The modification at the 2' position results in the presence of a moiety which is preferably selected from the group comprising amino, fluoro, methoxy, alkoxy and alkyl groups. In a presently most preferred embodiment the moiety at the 2' position is methoxy (2'-O-methyl).

In preferred embodiments of the invention, alternating ribonucleotides are modified in both the antisense and the sense strands of the compound. In particular the siRNA used in the Examples has been such modified such that a 2' O-Me group was present on the first, third, fifth, seventh, ninth, eleventh, thirteenth, fifteenth, seventeenth and nineteenth nucleotide of the antisense strand, whereby the very same modification, i.e. a 2'-O-Me group was present at the second, fourth, sixth, eighth, tenth, twelfth, fourteenth, sixteenth and eighteenth nucleotide of the sense strand. Additionally, it is to be noted that the in case of these particular nucleic acids according to the present invention the first stretch is identical to the first strand and the second stretch is identical to the second strand and these nucleic acids are also blunt ended.

According to one preferred embodiment of the invention, the antisense and the sense strands of the siRNA molecule are both phosphorylated only at the 3'-terminus and not at the 5'-terminus. According to another preferred embodiment of the invention, the antisense and the sense strands are both non-phosphorylated both at the 3'-terminus and also at the 5'-terminus. According to yet another preferred embodiment of the invention, the $1^{st}$ nucleotide in the 5' position in the sense strand is specifically modified to abolish any possibility of in vivo 5'-phosphorylation.

In another embodiment of the compound of the invention, the ribonucleotides at the 5' and 3' termini of the antisense strand are modified in their sugar residues, and the ribonucleotides at the 5' and 3' termini of the sense strand are unmodified in their sugar residues.

The invention further provides a vector capable of expressing any of the aforementioned oligoribonucleotides in unmodified form in a cell after which appropriate modification may be made.

The invention also provides a composition comprising one or more of the compounds of the invention in a carrier, preferably a pharmaceutically acceptable carrier. This composition may comprise a mixture of two or more different siRNAs.

The invention also provides a composition which comprises the above compound of the invention covalently or non-covalently bound to one or more compounds of the invention in an amount effective to inhibit Nrf2 and a carrier. This composition may be processed intracellularly by endogenous cellular complexes to produce one or more oligoribonucleotides of the invention.

The invention also provides a composition comprising a carrier and one or more of the compounds of the invention in an amount effective to down-regulate expression in a cell of Nrf2, which compound comprises a sequence substantially complementary to the sequence of $(N)_x$.

Additionally the invention provides a method of down-regulating the expression of Nrf2 by at least 50% as compared to a control comprising contacting an mRNA transcript of Nrf2 with one or more of the compounds of the invention.

In one embodiment the oligoribonucleotide is down-regulating Nrf2, whereby the down-regulation of Nrf2 is selected from the group comprising down-regulation of gene function, down-regulation of polypeptide and down-regulation of mRNA expression.

In one embodiment the compound is down-regulating the Nrf2 polypeptide, whereby the down-regulation is selected from the group comprising down-regulation of function (which may be examined by an enzymatic assay or a binding assay with a known interactor of the native gene/polypeptide, inter alia), down-regulation of protein (which may be examined by Western blotting, ELISA or immuno-precipitation, inter alia) and down-regulation of mRNA expression (which may be examined by Northern blotting, quantitative RT-PCR, in-situ hybridisation or microarray hybridisation, inter alia).

The invention also provides a method of treating a patient suffering from a disease accompanied by an elevated level of Nrf2, the method comprising administering to the patient a composition of the invention in a therapeutically effective dose thereby treating the patient.

More particularly, the invention provides an oligoribonucleotide wherein one strand comprises consecutive nucleotides having, from 5' to 3', the sequence set forth in Table A (19mer siRNA molecules, SEQ ID NOS: 1-1006) or in Table B (21mer siRNA molecules, SEQ ID NOS: 1007-2006), or a homolog thereof wherein in up to 2 of the nucleotides in each terminal region a base is altered. Preferred 19mer siRNA molecules comprise the sense and corresponding antisense sequences listed in Table C. More preferred siRNA comprises SEQ ID NO: 10 (sense sequence) and SEQ ID NO: 513 (antisense sequence).

The terminal region of the oligonucleotide refers to bases 1-4 and/or 16-19 in the 19-mer sequence and to bases 1-4 and/or 18-21 in the 21-mer sequence.

The presently most preferred compound of the invention is a blunt-ended 19-mer oligonucleotide, i.e. x=y=19 and Z and Z' are both absent. The oligonucleotide molecule is either phosphorylated at 3' termini of both sense and anti-sense strands, or non-phosphorylated at all; or having 1" nucleotide in the 5' position on the sense strand specifically modified to abolish any possibility of in vivo 5'-phosphorylation. The alternating ribonucleotides are modified at the 2' position in both the antisense and the sense strands, wherein the moiety at the 2' position is methoxy (2'-O-methyl) and wherein the ribonucleotides at the 5' and 3' termini of the antisense strand are modified in their sugar residues, and the ribonucleotides at the 5' and 3' termini of the sense strand are unmodified in their sugar residues.

In certain embodiments the present invention provides a compound having the structure

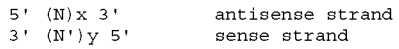

```
5'  (N)x 3'        antisense strand
3'  (N')y 5'       sense strand
``` wherein each of x and y=19 and $(N)_x$ and $(N')_y$ are fully complementary;
wherein alternating ribonucleotides in (N)x and (N')y are modified to result in a 2'-O-methyl modification in the sugar residue of the ribonucleotides;
wherein each N at the 5' and 3' termini of $(N)_x$ are modified;
wherein each N' at the 5' and 3' termini of $(N')_y$ are unmodified;
wherein each of $(N)_x$ and $(N')_y$ is selected from the group of oligomers set forth in any one of Tables A and B (SEQ ID NOS: 1-2006).
$(N)_x$ and $(N')_y$ may be phosphorylated or non-phosphorylated at the 3' and 5' termini.

In certain embodiments of the invention, alternating ribonucleotides are modified in the 2' position of the sugar residue in both the antisense and the sense strands of the compound. In particular the siRNAs may be modified such that a 2'-O-methyl (Me) group is present on the first, third, fifth, seventh, ninth, eleventh, thirteenth, fifteenth, seventeenth and nineteenth nucleotide of the antisense strand, whereby the very same modification, i.e. a 2'-O-Me group, is present at the second, fourth, sixth, eighth, tenth, twelfth, fourteenth, sixteenth and eighteenth nucleotide of the sense strand. These particular siRNA compounds may also be blunt ended.

In certain embodiments of the compounds of the invention having alternating ribonucleotides modified in one or both of the antisense and the sense strands of the compound; for 19-mers and 23-mers the ribonucleotides at the 5' and 3' termini of the antisense strand are modified in their sugar residues, and the ribonucleotides at the 5' and 3' termini of the sense strand are unmodified in their sugar residues. For 21-mers the ribonucleotides at the 5' and 3' termini of the sense strand are modified in their sugar residues, and the ribonucleotides at the 5' and 3' termini of the antisense strand are unmodified in their sugar residues. As mentioned above, it is preferred that the middle nucleotide of the antisense strand is unmodified.

In some preferred embodiments the middle ribonucleotide in the first strand (antisense) is an unmodified nucleotide. For example, in a 19-oligomer antisense strand, ribonucleotide number 10 is unmodified; in a 21-oligomer antisense strand, ribonucleotide number 11 is unmodified; and in a 23-oligomer antisense strand, ribonucleotide number 12 is unmodified. The modifications or pattern of modification, if any, of the siRNA must be planned to allow for this.

Delivery:

The siRNA molecules of the present invention may be delivered to the target tissue (such as the lung) by direct application of the naked molecules admixed with a carrier or a diluent using an aerosol.

For administration via the upper respiratory tract, the composition is formulated into a solution, e.g., water or isotonic saline, buffered or unbuffered, or as a suspension, at an appropriate concentration for oro-nasal administration as an aerosol. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's Pharmaceutical Sciences 16th edition, Ed. Arthur Osol, page 1445 (1980)). One skilled in the art can readily determine a suitable saline content and pH for an innocuous aqueous solution for nasal and/or upper respiratory administration.

Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compositions may contain minor amounts of polymers, surfactants, or other excipients well known to those of the art. In this context, "minor amounts" means no auxiliary agents or substances are present that might affect or mediate uptake of nucleic acid in the cells of the lungs.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6:273-313, 1990; and in Moren, "Aerosol dosage forms and formulations," in: Aerosols in Medicine, Principles, Diagnosis and Therapy, Moren, et al., Eds. Elsevier, Amsterdam, 1985. The term aerosol as used herein refers to any preparation of a fine mist of particles, which can be in solution or a suspension, whether or not it is produced using a propellant. Aerosols can be produced using standard techniques, such as ultrasonication or high pressure treatment.

Various suitable devices and methods of inhalation which can be used to administer particles to a patient's respiratory tract are known in the art. Nebulizers create a fine mist from a solution or suspension, which is inhaled by the patient. The devices described in U.S. Pat. No. 5,709,202 to Lloyd, et al., can be used. An MDI typically includes a pressurized canister having a meter valve, wherein the canister is filled with the solution or suspension and a propellant. The solvent itself may function as the propellant, or the composition may be combined with a propellant, such as freon. The composition is a fine mist when released from the canister due to the release in pressure. The propellant and solvent may wholly or partially evaporate due to the decrease in pressure.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA". However, the siRNA molecules of the invention can also be delivered in liposome formulations and lipofectin formulations and the like and can be prepared by methods well known to those skilled in the art. Such methods are described, for example, in U.S. Pat. Nos. 5,593,972, 5,589, 466, and 5,580,859, which are herein incorporated by reference.

Delivery systems aimed specifically at the enhanced and improved delivery of siRNA into mammalian cells have been developed, see, for example, Shen et al (FEBS letters 539: 111-114 (2003)), Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details see Tolentino et al., Retina 24(1) February 2004 I 132-138. Respiratory formulations for siRNA are described in U.S. patent application No. 2004/0063654 of Davis et al. Cholesterol-conjugated siRNAs (and other steroid and lipid conjugated siRNAs) can been used for delivery see Soutschek et al Nature 432: 173-177 (2004); and Lorenz et al. Bioorg. Med. Chemistry. Lett. 14:4975-4977 (2004).

The siRNAs or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art. The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres.

Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations are particularly preferred.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer.

The term "treatment" as used herein refers to administration of a therapeutic substance effective to ameliorate symptoms associated with a disease, to lessen the severity or cure the disease, or to prevent the disease from occurring. Thus "treatment" refers to both therapeutic treatment and prophylactic or preventative measures, wherein the object is to prevent or slow down (lessen) a disease in particular a cancerous disease such as lung cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer. In a particular embodiment, the cancer is lung cancer such as non-small-cell lung carcinoma (NSCLC) or small-cell lung carcinoma In another aspect of the invention a pharmaceutical composition is provided which comprises any of the above oligoribonucleotides or vectors and a pharmaceutically acceptable carrier. Another aspect of the invention is the use of a therapeutically effective amount of any of the above oligoribonucleotides or vectors for the preparation of a medicament for treating a patient suffering from a cancer disease.

By "cancerous disease" is meant any disease that is caused by or results in inappropriately high levels of cell division, inappropriately low levels of apoptosis, or both. Examples of cancerous diseases include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangio sarcoma, lymphangioendotheliosarcoma, synovioma, mesothelioma, Ewing's tumor, leiomyo sarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, crailiopharyngioma, ependymoma, pinealoma, hemangioblastoma, acoustic neuroma, oligodenroglioma, schwamioma, meningioma, melanoma, neuroblastoma, and retinoblastoma).

In one embodiment, the present invention provides a pharmaceutical composition comprising an Nrf2 inhibitory molecule, preferable an siRNA molecule that decreases the expression of the Nrf2 gene in combination with a chemotherapeutic agent. Without being bound by theory, since Nrf2 positively regulates drug detoxification enzymes, targeting this molecule may have a broad effect on all anticancer drugs. In various embodiments, the Nrf2 inhibitory molecule is administered prior to, concurrently with, or following administration of a chemotherapeutic. Without wishing to be bound by theory, administration of an Nrf2 inhibitory molecule likely enhances the accumulation or efficacy of a chemotherapeutic agent.

Compositions and methods of the invention may be used in combination with any conventional therapy known in the art. In one embodiment, the Nrf2 inhibitory molecules of the invention may be used in combination with one or more anti-cancerous therapy known in the art. Thus the Nrf2 inhibitors may be used before, during or following anti-cancerous therapy Exemplary anti-cancerous therapies include, for example, chemotherapy, cryotherapy, hormone therapy, growth factor inhibitors, radiotherapy, and surgery. Chemotherapeutics typically used in the treatment of a cancerous disease are for example abiraterone acetate, altretamine, anhydrovinbiastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chiorambucil, cyclophosphamide, 3',4'-didehydro-4'-deoxy-8'-norvincaleukoblastine, docetaxol, doxetaxel, cyclophosphamide, carboplatin, carmustine (BCNTJ), cisplatin, cryptophycin, cyclophosphamide, cytarabine, dacarbazine (DTIC), dactinomycin, daunorubicin, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), mechlorethamine (nitrogen mustard), melphalan, mivobulin isethionate, rhizoxin, sertenef, streptozocin, mitomycin, methotrexate, 5-fluorouracil, nilutamide, onapristone, oxaliplatin paclitaxel, prednimustine, procarbazine, RPR1 09881, satrapaltin, stramustine phosphate, tamoxifen, tasonermin, taxol, tretinoin, vinbiastine, vincristine, vindesine sulfate, and vinflunine. Other examples of chemotherapeutic agents can be found in Cancer Principles and Practice of Oncology by V. T. Devita and S. Heliman (editors), 6th edition (Fel. 15, 2001), Lippincott Williams & Wilkins Publishers. A preferred combination according to the present invention is an siRNA molecule targeting Nrf2 with platinum drugs, more preferably an siRNA molecule set forth in Table C with a platinum drug, preferably carboplatin. Without being bound by theory, the Nrf2 siRNA inhibitors of the invention are found to be efficient promoters for the antineoplastic potential of platinum drugs, causing additive/synergistic effects in cancer cells. Platinum drugs include carboplatin, cisplatin, oxaliplatin and satrapaltin inter alia; see Kelland and Farrell, *Platinum-based drugs in cancer therapy* (Cancer drug discovery & development) Lavoisier 2000 which is hereby incorporated by reference.

The compounds which reduce or prevent the cancerous disease such as lung cancer, eg the novel siRNAs inter alia are preferably administered directly to the inner lung as naked siRNA in a vehicle such as PBS or other physiological solutions, but may alternatively be administered with a delivery vehicle as described above.

The present invention also provides for a process of preparing a pharmaceutical composition, which comprises:
  obtaining one or more double stranded compound of the invention; and
  admixing said compound with a pharmaceutically acceptable carrier.

The present invention also provides for a process of preparing a pharmaceutical composition, which comprises admixing one or more compounds of the present invention with a pharmaceutically acceptable carrier.

In a preferred embodiment, the compound used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

Modifications or analogs of nucleotides can be introduced to improve the therapeutic properties of the nucleotides. Improved properties include increased nuclease resistance and/or increased ability to permeate cell membranes.

Accordingly, the present invention also includes all analogs of, or modifications to, a oligonucleotide of the invention that does not substantially affect the function of the polynucleotide or oligonucleotide. In a preferred embodiment such modification is related to the base moiety of the nucleotide, to the sugar moiety of the nucleotide and/or to the phosphate moiety of the nucleotide.

In embodiments of the invention, the nucleotides can be selected from naturally occurring or synthetically modified bases. Naturally occurring bases include adenine, guanine, cytosine, thymine and uracil. Modified bases of the oligonucleotides include inosine, xanthine, hypoxanthine, 2-aminoadenine, 6-methyl-, 2-propyl- and other alkyl-adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thiolalkyl adenine, 8-hydroxyl adenine and other 8-substituted adenines, 8-halo guanine, 8-amino guanine, 8-thiol guanine, 8-thioalkyl guanine, 8-hydroxyl guanine and other substituted guanines, other aza and deaza adenines, other aza and deaza guanines, 5-trifluoromethyl uracil and 5-trifluoro cytosine.

In addition, analogs of nucleotides can be prepared wherein the structures of the nucleotides are fundamentally altered and are better suited as therapeutic or experimental reagents. An example of a nucleotide analog is a peptide nucleic acid (PNA) wherein the deoxyribose (or ribose) phosphate backbone in DNA (or RNA) is replaced with a polyamide backbone similar to that found in peptides. PNA analogs have been shown to be resistant to degradation by enzymes and to have extended lives in vivo and in vitro. Further, PNAs have been shown to bind more strongly to a complementary DNA sequence than to a DNA molecule. This observation is attributed to the lack of charge repulsion between the PNA strand and the DNA strand. Other modifications that can be made to oligonucleotides include polymer backbones, cyclic backbones, or acyclic backbones.

In one embodiment the modification is a modification of the phosphate moiety, whereby the modified phosphate moiety is selected from the group comprising phosphothioate.

The compounds of the present invention can be synthesized by any of the methods that are well-known in the art for synthesis of ribonucleic (or deoxyribonucleic) oligonucleotides. Such synthesis is, among others, described in Beaucage S. L. and Iyer R. P., Tetrahedron 1992; 48: 2223-2311, Beaucage S. L. and Iyer R. P., Tetrahedron 1993; 49: 6123-6194 and Caruthers M. H. et. al., Methods Enzymol. 1987; 154: 287-313; the synthesis of thioates is, among others, described in Eckstein F., Annu. Rev. Biochem. 1985; 54: 367-402, the synthesis of RNA molecules is described in Sproat B., in Humana Press 2005 edited by Herdewijn P.; Kap. 2: 17-31 and respective downstream processes are, among others, described in Pingoud A. et. al., in IRL Press 1989 edited by Oliver R. W. A.; Kap. 7: 183-208 and Sproat B., in Humana Press 2005 edited by Herdewijn P.; Kap. 2: 17-31 (supra).

Other synthetic procedures are known in the art e.g. the procedures as described in Usman et al., 1987, *J. Am. Chem. Soc.*, 109, 7845; Scaringe et al., 1990, *Nucleic Acids Res.*, 18, 5433; Wincott et al., 1995, *Nucleic Acids Res.* 23, 2677-2684; and Wincott et al., 1997, *Methods Mol. Bio.*, 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., 1992, Science 256, 9923; Draper et al., International PCT publication No. WO93/23569; Shabarova et al., 1991, Nucleic Acids Research 19, 4247; Bellon et al., 1997, *Nucleosides & Nucleotides*, 16, 951; Bellon et al., 1997, *Bioconjugate Chem.* 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via a tandem synthesis methodology, as described in US patent application publication No. US2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the siRNA molecules are comprised of a double-stranded nucleic acid structure as described herein, wherein the two siRNA sequences are selected from Tables A or B.

In another embodiment, the siRNA molecules are comprised of a double-stranded nucleic acid structure, wherein the first siRNA sequence is selected from Tables A or B, and the second siRNA molecule targets another anti-cancer gene, thereby providing beneficial activity. The tandem double-stranded structure which comprises two or more siRNA sequences is processed intracellularly to form two or more different siRNAs. Such second siRNA molecule is preferably an siRNA molecule that targets a anti-cancer gene. Preferred anti-cancer genes are for example gene encoding growth factors such as insulin-like growth factor (IGF), epidermal growth factor (EGF), fibroblast growth factor (FGF) and platelet derived growth factor (PDGF).

The siRNA molecules are covalently or non-covalently bound or joined by a linker to form a tandem siRNA molecule. Such tandem siRNA molecules comprising two siRNA sequences are typically of 38-150 nucleotides in length, more preferably 38 or 40-60 nucleotides in length, and longer accordingly if more than two siRNA sequences are included in the tandem molecule. A longer tandem molecule comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention.

siRNA molecules that target Nrf2 may be the main active component in a pharmaceutical composition, or may be one active component of a pharmaceutical composition containing two or more siRNAs (or molecules which encode or endogenously produce two or more siRNAs, be it a mixture of molecules or one or more tandem molecules which encode two or more siRNAs), said pharmaceutical composition further being comprised of one or more additional siRNA molecule which targets one or more additional gene. Simultaneous inhibition of Nrf2 and said additional gene(s) will likely have an additive or synergistic effect for treatment of the diseases disclosed herein.

In a preferred embodiment, the one or more additional siRNA molecules target an anti-cancer gene, thus having an additive or synergistic effect with the Nrf2 siRNA. The additional siRNA molecules may target one or more of the anti-cancer genes defined above.

As disclosed herein, aptamers may also be used in the present invention alone or in combination with the novel siRNAs disclosed herein for targeting NRF2 and for the treatment of any one of the conditions disclosed herein. For example, an aptamer can be used with any one of the siRNAs disclosed herein in combination therapy for the treatment of any one of the conditions disclosed herein. The novel pharmaceutical composition employed for such a combination therapy, which is also part of the present invention, may comprise an siRNA of the present invention covalently or non-covalently attached to an aptamer. Aptamers are RNA or DNA single-strand or double-strand oligonucleic acids which bind to a target protein and do not generally exhibit non-specific effects. Aptamers can be modified for stability or other desired qualities in accordance with any nucleic acid modifications disclosed herein and/or known to one of skill in the art. Modifications to aptamers can be introduced any-where in the molecule, such as the 5' or 3' termini, or at any internally defined modification site. For example, RNA aptamers can be stabilized with 2'-fluoro or 2'-amino modified pyrimidines. Aptamers can also be linked to reporter molecules or linker chemistries and can be attached to beads or other solid support if necessary (e.g., 5' or 3' amino, thiol ester or biotin groups). Thioaptamers are aptamers which contain sulfur modifications at specific internucleoside phosphoryl sites, and may possess enhanced stability, nuclease resistance, target affinity and/or selectivity. Examples of thio-aptamers include phosphoromonothioate (S-ODN) and phosphorodithioate (S2-ODN) oligodeoxy thioaptamers. For further information on aptamers and thioaptamers see U.S. Pat. Nos. 5,218,088 and 6,423,493.

Additionally, the siRNA disclosed herein or any nucleic acid molecule comprising or encoding such siRNA can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with a Nrf2 siRNA molecule. In another example, an aptamer which can act like a ligand/antibody may be combined (covalently or non-covalently) with a Nrf2 siRNA molecule.

The term "Covalent bonding" as used herein refers to chemical bonding that is characterized by the sharing of pairs of electrons between atoms.

The term "Noncovalent bonding" as used herein refers to a variety of interactions that are not covalent in nature between molecules or parts of molecules that provide force to hold the molecules or parts of molecules together, usually in a specific orientation or conformation. These noncovalent interactions include: ionic bonds, hydrophobic interactions, hydrogen bonds, Van der Waals forces anddipole-dipole bonds.

The compounds of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

It is also envisaged that a long oligonucleotide (typically 25-500 nucleotides in length) comprising one or more stem and loop structures, where stern regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of an NRF2 gene. In particular, it is envisaged that this oligonucleotide comprises sense and antisense siRNA sequences as depicted as any one of SEQ ID NO: 1-2006.

As used herein, the term "inhibition" of the Nrf2 gene means inhibition of the gene expression (transcription or translation) or polypeptide activity.

Although the inhibitor may be an siRNA molecule, other inhibitors contemplated to be used in the methods of the invention to inhibit the Nrf2 gene and to treat the diseases and conditions described herein are inter alia antibodies, preferably neutralizing antibodies or fragments thereof, including single chain antibodies, antisense oligonucleotides, antisense DNA or RNA molecules, aptamers, proteins, polypeptides and peptides including peptidomimetics and dominant negatives, and also expression vectors expressing all the above. Additional inhibitors may be small chemical molecules, which generally have a molecular weight of less than 2000 daltons, more preferably less than 1000 daltons, even more preferably less than 500 daltons. These inhibitors may act as follows: small molecules may affect expression and/or activity; antibodies may affect activity; all kinds of antisense may affect the gene expression; and dominant negative polypeptides and peptidomimetics may affect activity; expression vectors may be used inter alia for delivery of antisense or dominant-negative polypeptides or antibodies.

The term "antibody" refers to IgG, IgM, IgD, IgA, and IgE antibody, inter alia. The definition includes polyclonal antibodies or monoclonal antibodies. This term refers to whole antibodies or fragments of antibodies comprising an antigen-binding domain, e.g. antibodies without the Fc portion, single chain antibodies, miniantibodies, fragments consisting of essentially only the variable, antigen-binding domain of the antibody, etc. The term "antibody" may also refer to antibodies against polynucleotide sequences obtained by cDNA vaccination. The term also encompasses antibody fragments which retain the ability to selectively bind with their antigen or receptor and are exemplified as follows, inter alia:
(1) Fab, the fragment which contains a monovalent antigen-binding fragment of an antibody molecule which can be produced by digestion of whole antibody with the enzyme papain to yield a light chain and a portion of the heavy chain;
(2) (Fab')$_2$, the fragment of the antibody that can be obtained by treating whole antibody with the enzyme pepsin without subsequent reduction; F(ab'$_2$) is a dimer of two Fab fragments held together by two disulfide bonds;
(3) Fv, defined as a genetically engineered fragment containing the variable region of the light chain and the variable region of the heavy chain expressed as two chains; and
(4) Single chain antibody (SCA), defined as a genetically engineered molecule containing the variable region of the light chain and the variable region of the heavy chain linked by a suitable polypeptide linker as a genetically fused single chain molecule.

Antisense Molecules

By the term "antisense" (AS) or "antisense fragment" is meant a polynucleotide fragment (comprising either deoxyribonucleotides, ribonucleotides or a mixture of both) having inhibitory antisense activity, said activity causing a decrease in the expression of the endogenous genomic copy of the corresponding gene. An AS polynucleotide is a polynucleotide which comprises consecutive nucleotides having a sequence of sufficient length and homology to a sequence present within the sequence of the target gene to permit hybridization of the AS to the gene. Many reviews have covered the main aspects of antisense (AS) technology and its enormous therapeutic potential (Aboul-Fadl T., Curr Med. Chem. 2005; 12(19):2193-214; Crooke S T, Curr Mol. Med. 2004 August; 4(5):465-87; Crooke S T, Annu Rev Med. 2004; 55:61-95; Vacek M et al., Cell Mol Life Sci. 2003 May; 60(5):825-33; Cho-Chung Y S, Arch Pharm Res. 2003 March; 26(3):183-91. There are further reviews on the chemical (Crooke, 1995; Uhlmann et al, 1990), cellular (Wagner, 1994) and therapeutic (Hanania, et al, 1995; Scanlon, et al, 1995; Gewirtz, 1993) aspects of this technology. Antisense intervention in the expression of specific genes can be achieved by the use of synthetic AS oligonucleotide sequences (for recent reports see Lefebvre-d'Hellencourt et al, 1995; Agrawal, 1996; LevLehman et al, 1997).

AS oligonucleotide sequences may be short sequences of DNA, typically 15-30 mer but may be as small as 7 mer (Wagner et al, 1996), designed to complement a target mRNA of interest and form an RNA:AS duplex. This duplex formation can prevent processing, splicing, transport or translation of the relevant in RNA. Moreover, certain AS nucleotide sequences can elicit cellular RNase H activity when hybridized with their target mRNA, resulting in mRNA degradation (Calabretta et al, 1996 Semin Oncol. 23(1):78-87). In that case, RNase H will cleave the RNA component of the duplex and can potentially release the AS to further hybridize with additional molecules of the target RNA. An additional mode of action results from the interaction of AS with genomic DNA to form a triple helix which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation [Anazodo et al., 19961. For example, the computer program OLIGO (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analogue substitution do not substantially affect function.

Phosphorothioate antisense oligonucleotides do not normally show significant toxicity at concentrations that are effective and exhibit sufficient pharmacodynamic half-lives in animals (Agarwal et al., 1996) and are nuclease resistant. Antisense induced loss-of-function phenotypes related with cellular development were shown for the glial fibrillary acidic protein (GFAP), for the establishment of tectal plate formation in chick (Galileo et al., 1991) and for the N-myc protein, responsible for the maintenance of cellular heterogeneity in neuroectodermal cultures (ephithelial vs. neuroblastic cells, which differ in their colony forming abilities, tumorigenicity and adherence) (Rosolen et al., 1990; Whitesell et al, 1991). Antisense oligonucleotide inhibition of basic fibroblast growth factor (bFgF), having mitogenic and angiogenic properties, suppressed 80% of growth in glioma cells (Morrison, 1991) in a saturable and specific manner. Being hydrophobic, antisense oligonucleotides interact well with phospholipid membranes (Akhter et al., 1991). Following their interaction with the cellular plasma membrane, they are actively (or passively) transported into living cells (Loke et al., 1989), in a saturable mechanism predicted to involve specific receptors (Yakubov et al., 1989).

Ribozymes

A "ribozyme" is an RNA molecule that possesses RNA catalytic ability (see Cech for review) and cleaves a specific site in a target RNA. In accordance with the present invention, ribozymes which cleave mRNA may be utilized as inhibitors. This may be necessary in cases where antisense therapy is limited by stoichiometric considerations (Sarver et al., 1990, *Gene Regulation and Aids*, pp. 305-325). Ribozymes can then be used that will target the a gene associated with a bone marrow disease. The number of RNA molecules that are cleaved by a ribozyme is greater than the number predicted by stochiochemistry. (Hampel and Tritz, 1989; Uhlenbeck, 1987).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). In general the ribozyme has a length of from about 30-100 nucleotides. Delivery of ribozymes is similar to that of AS fragments and/or siRNA molecules.

Screening of Inactivation Compounds for Nrf2:

Some of the compounds and compositions of the present invention may be used in a screening assay for identifying and isolating compounds that modulate the activity of the NRF2 gene, in particular compounds that modulate a disorder accompanied by an elevated level of NRF2. The compounds to be screened comprise inter alia substances such as small chemical molecules and antisense oligonucleotides.

The inhibitory activity of the compounds of the present invention on Nrf2 expression may be used to determine the interaction of an additional compound with the target polypeptide, e.g., if the additional compound competes with the oligonucleotides of the present invention for inhibition of Nrf2, or if the additional compound rescues said inhibition. The inhibition or activation can be tested by various means, such as, inter alia, assaying for the product of the activity of the Nrf2 polypeptide or displacement of binding compound from the Nrf2 polypeptide in radioactive or fluorescent competition assays.

The present invention is illustrated in detail below with reference to the Examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry can be used for detection of cells containing specific DNA and mRNA sequences (Testoni et al., 1996, Blood 87:3822.) Methods of performing RT-PCR are also well known in the art.

Example 1

Generation of Sequences for Active siRNA Compounds

Using proprietary algorithms and the known sequence of Nrf2 (gi2014957), the sequences of many potential siRNAs were generated. Table A shows a list of 19-mers siRNAs specific to Nrf2 which are either human-specific, or human and cross-species with other species. Table B shows a list of 21-mers siRNAs specific to Nrf2 which are either human-specific, or human and cross-species with other species. All siRNAs are depicted in 5' to 3' orientation, and the sense and complementary antisense sequences are depicted on the same line in the Table. The sense siRNAs in Table A have SEQ ID NOS: 1-503 and the antisense siRNAs in Table A have SEQ ID NOS: 504-1006. The sense siRNAs in Table B have SEQ ID NOS: 1007-1506 and the antisense siRNAs in Table B have SEQ ID NOS: 1507-2006.

TABLE A

| 19-mers siRNAs specific to Nrf2 (SEQ ID NOS: 1-1006) | | | | |
|---|---|---|---|---|
| SEQ ID NO. | Sense siRNA | SEQ ID NO. | Antisense siRNA | Human-20149575 |
| 1 | GGGGUAAGAAUAAAGUGGC | 504 | GCCACUUUAUUCUUACCCC | [1624-1642](19/19) |
| 2 | GGAGGGGUAAGAAUAAAGU | 505 | ACUUUAUUCUUACCCCUCC | [1621-1639](19/19) |
| 3 | GCAAAACUAACCACUAUGU | 506 | ACAUAGUGGUUAGUUUUGC | [2270-2288](19/19) |
| 4 | AAGGAGAAAAUGACAAAAG | 507 | CUUUUGUCAUUUUCUCCUU | [1741-1759](19/19) |
| 5 | CAGAAUUGCAGAAAAGAA | 508 | UUCUUUUUCUGCAAUUCUG | [1647-1665](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 6 | GGGUAAGAAUAAAGUGGCU | 509 | AGCCACUUUAUUCUUACCC | [1625-1643](19/19) |
| 7 | GCCCUCACCUGCUACUUUA | 510 | UAAAGUAGCAGGUGAGGGC | [1010-1028](19/19) |
| 8 | AGGGGUAAGAAUAAAGUGG | 511 | CCACUUUAUUCUUACCCCU | [1623-1641](19/19) |
| 9 | AGGAGGGGUAAGAAUAAAG | 512 | CUUUAUUCUUACCCCUCCU | [1620-1638](19/19) |
| 10 | UCCCGUUUGUAGAUGACAA | 513 | UUGUCAUCUACAAACGGGA | [493-511](19/19) |
| 11 | AGGAGAAAAUGACAAAAGC | 514 | GCUUUUGUCAUUUUCUCCU | [1742-1760](19/19) |
| 12 | GCUCAGAAUUGCAGAAAAA | 515 | UUUUUCUGCAAUUCUGAGC | [1644-1662](19/19) |
| 13 | GAGAAAGAAUUGCCUGUAA | 516 | UUACAGGCAAUUCUUUCUC | [1392-1410](19/19) |
| 14 | UCCGGCAUUUCACUAAACA | 517 | UGUUUAGUGAAAUGCCGGA | [1143-1161](19/19) |
| 15 | GAGUUACAGUGUCUUAAUA | 518 | UAUUAAGACACUGUAACUC | [699-717](19/19) |
| 16 | GCCAAAACUAGUAUAGAAA | 519 | UUUCUAUACUAGUUUUGGC | [2044-2062](19/19) |
| 17 | AGCCAGAUGUUAAGAAAAA | 520 | UUUUUCUUAACAUCUGGCU | [1909-1927](19/19) |
| 18 | GAAGCCAGAUGUUAAGAAA | 521 | UUUCUUAACAUCUGGCUUC | [1907-1925](19/19) |
| 19 | AGAAGCCAGAUGUUAAGAA | 522 | UUCUUAACAUCUGGCUUCU | [1906-1924](19/19) |
| 20 | UCAGAAUUGCAGAAAAAGA | 523 | UCUUUUUCUGCAAUUCUGA | [1646-1664](19/19) |
| 21 | UAGGAGGGGUAAGAAUAAA | 524 | UUUAUUCUUACCCCUCCUA | [1619-1637](19/19) |
| 22 | CACUCUCUGAACUUCUAAA | 525 | UUUAGAAGUUCAGAGAGUG | [1036-1054](19/19) |
| 23 | UAGCCCCUGUUGAUUUAGA | 526 | UCUAAAUCAACAGGGGCUA | [628-646](19/19) |
| 24 | GAUCUGCCAACUACUCCCA | 527 | UGGGAGUAGUUGGCAGAUC | [406-424](19/19) |
| 25 | GCAAAUCAUAGCCAAAAC | 528 | GUUUUGGCUAUGAUUUGC | [2033-2051](19/19) |
| 26 | GUAAGAAGCCAGAUGUUAA | 529 | UUAACAUCUGGCUUCUUAC | [1903-1921](19/19) |
| 27 | UAAAGUGGCUGCUCAGAAU | 530 | AUUCUGAGCAGCCACUUUA | [1634-1652](19/19) |
| 28 | AGAAUAAAGUGGCUGCUCA | 531 | UGAGCAGCCACUUUAUUCU | [1630-1648](19/19) |
| 29 | AGGAAAGACAAGAACAACU | 532 | AGUUGUUCUUGUCUUUCCU | [280-298](19/19) |
| 30 | AAAGGAAAGACAAGAACAA | 533 | UUGUUCUUGUCUUUCCUUU | [278-296](19/19) |
| 31 | AACUUGAAAAGGAAAGACA | 534 | UGUCUUUCCUUUUCAAGUU | [271-289](19/19) |
| 32 | GACAAACAUUCAAGCCGCU | 535 | AGCGGCUUGAAUGUUUGUC | [1443-1461](19/19) |
| 33 | GACUCCGGCAUUUCACUAA | 536 | UUAGUGAAAUGCCGGAGUC | [1140-1158](19/19) |
| 34 | ACCAAAACCACCCUGAAAG | 537 | CUUUCAGGGUGGUUUUGGU | [1099-1117](19/19) |
| 35 | ACUCUCUGAACUUCUAAAU | 538 | AUUUAGAAGUUCAGAGAGU | [1037-1055](19/19) |
| 36 | GACAGUGAACUCAUUAAAU | 539 | AUUUAAUGAGUUCACUGUC | [911-929](19/19) |
| 37 | AAGUUUGGGAGGAGCUAUU | 540 | AAUAGCUCCUCCCAAACUU | [670-688](19/19) |
| 38 | UUGUAGAUGACAAUGAGGU | 541 | ACCUCAUUGUCAUCUACAA | [499-517](19/19) |
| 39 | AAACUAACCACUAUGUACU | 542 | AGUACAUAGUGGUUAGUUU | [2273-2291](19/19) |
| 40 | CAAAAUCAUAGCCAAAACU | 543 | AGUUUUGGCUAUGAUUUUG | [2034-2052](19/19) |
| 41 | UAAGAAGCCAGAUGUUAAG | 544 | CUUAACAUCUGGCUUCUUA | [1904-1922](19/19) |
| 42 | ACGUGAUGAAGAUGGAAAA | 545 | UUUUCCAUCUUCAUCACGU | [1817-1835](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 43 | CUGGAAAAUAUAGUAGAAC | 546 | GUUCUACUAUAUUUUCCAG | [1668-1686](19/19) |
| 44 | GAAAAGGAAAGACAAGAAC | 547 | GUUCUUGUCUUUCCUUUUC | [276-294](19/19) |
| 45 | UGAAAAGGAAAGACAAGAA | 548 | UUCUUGUCUUUCCUUUUCA | [275-293](19/19) |
| 46 | UGGAGACACACUACUUGGC | 549 | GCCAAGUAGUGUGUCUCCA | [1211-1229](19/19) |
| 47 | UCAACCAAAACCACCCUGA | 550 | UCAGGGUGGUUUUGGUUGA | [1096-1114](19/19) |
| 48 | CCCUCACCUGCUACUUUAA | 551 | UUAAAGUAGCAGGUGAGGG | [1011-1029](19/19) |
| 49 | UGACAGUGAACUCAUUAAA | 552 | UUUAAUGAGUUCACUGUCA | [910-928](19/19) |
| 50 | UUGGAGGCAAGAUAUAGAU | 553 | AUCUAUAUCUUGCCUCCAA | [182-200](19/19) |
| 51 | GAGCUAUUAUCCAUUCCUG | 554 | CAGGAAUGGAUAAUAGCUC | [681-699](19/19) |
| 52 | UAGAUGACAAUGAGGUUUC | 555 | GAAACCUCAUUGUCAUCUA | [502-520](19/19) |
| 53 | UGCCCACAUUCCCAAAUCA | 556 | UGAUUUGGGAAUGUGGGCA | [428-446](19/19) |
| 54 | AGCCAAAACUAGUAUAGAA | 557 | UUCUAUACUAGUUUUGGCU | [2043-2061](19/19) |
| 55 | AAAGUAAGAAGCCAGAUGU | 558 | ACAUCUGGCUUCUUACUUU | [1900-1918](19/19) |
| 56 | CCAAAAGUAAGAAGCCAGA | 559 | UCUGGCUUCUUACUUUUGG | [1897-1915](19/19) |
| 57 | CCCAAAAGUAAGAAGCCAG | 560 | CUGGCUUCUUACUUUUGGG | [1896-1914](19/19) |
| 58 | UACGUGAUGAAGAUGGAAA | 561 | UUUCCAUCUUCAUCACGUA | [1816-1834](19/19) |
| 59 | GCUCAAAGAAAAAGGAGAA | 562 | UUCUCCUUUUUCUUUGAGC | [1730-1748](19/19) |
| 60 | AACUAGAGCAAGAUUUAGA | 563 | UCUAAAUCUUGCUCUAGUU | [1684-1702](19/19) |
| 61 | AAGUGGCUGCUCAGAAUUG | 564 | CAAUUCUGAGCAGCCACUU | [1636-1654](19/19) |
| 62 | GUAGGAGGGGUAAGAAUAA | 565 | UUAUUCUUACCCCUCCUAC | [1618-1636](19/19) |
| 63 | UCAACUUGCAUUAAUUCGG | 566 | CCGAAUUAAUGCAAGUUGA | [1592-1610](19/19) |
| 64 | AAAGACAAGAACAACUCCA | 567 | UGGAGUUGUUCUUGUCUUU | [283-301](19/19) |
| 65 | AGAAAGAAUUGCCUGUAAG | 568 | CUUACAGGCAAUUCUUUCU | [1393-1411](19/19) |
| 66 | ACACACCAGAGAAAGAAUU | 569 | AAUUCUUUCUCUGGUGUGU | [1384-1402](19/19) |
| 67 | AACACCAGUACAUUCUUCU | 570 | AGAAGAAUGUACUGGUGUU | [1295-1313](19/19) |
| 68 | AAACACCAGUACAUUCUUC | 571 | GAAGAAUGUACUGGUGUUU | [1294-1312](19/19) |
| 69 | ACAGAAUGGUCCUAAAACA | 572 | UGUUUUAGGACCAUUCUGU | [1280-1298](19/19) |
| 70 | AAACCACCCUGAAAGCACA | 573 | UGUGCUUUCAGGGUGGUUU | [1103-1121](19/19) |
| 71 | AACCAAAACCACCCUGAAA | 574 | UUUCAGGGUGGUUUUGGUU | [1098-1116](19/19) |
| 72 | UCUCUGAACUUCUAAAUGG | 575 | CCAUUUAGAAGUUCAGAGA | [1039-1057](19/19) |
| 73 | UUCACUCUCUGAACUUCUA | 576 | UAGAAGUUCAGAGAGUGAA | [1034-1052](19/19) |
| 74 | GUAGUCCACAUUUUCUUAA | 577 | UUAAGAAAAUGUGGACUAC | [838-856](19/19) |
| 75 | UUGAAAAUGACAAGCUGGU | 578 | ACCAGCUUGUCAUUUUCAA | [718-736](19/19) |
| 76 | CAGUCUUCAUUGCUACUAA | 579 | UUAGUAGCAAUGAAGACUG | [574-592](19/19) |
| 77 | AUGACAAUGAGGUUUCUUC | 580 | GAAGAAACCUCAUUGUCAU | [505-523](19/19) |
| 78 | AGAUGACAAUGAGGUUUCU | 581 | AGAAACCUCAUUGUCAUCU | [503-521](19/19) |
| 79 | GUAGAUGACAAUGAGGUUU | 582 | AAACCUCAUUGUCAUCUAC | [501-519](19/19) |
| 80 | UGCCAACUACUCCCAGGUU | 583 | AACCUGGGAGUAGUUGGCA | [410-428](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 81 | AAGCCAGAUGUUAAGAAAA | 584 | UUUUCUUAACAUCUGGCUU | [1908-1926](19/19) |
| 82 | ACCUUAUUCUCCUAGUGAA | 585 | UUCACUAGGAGAAUAAGGU | [1835-1853](19/19) |
| 83 | ACCUACUGAAAAACAACU | 586 | AGUUGUUUUUCAGUAGGU | [1765-1783](19/19) |
| 84 | ACAAAAGCCUUCACCUACU | 587 | AGUAGGUGAAGGCUUUUGU | [1753-1771](19/19) |
| 85 | UGCUCAAAGAAAAGGAGA | 588 | UCUCCUUUUCUUUGAGCA | [1729-1747](19/19) |
| 86 | CAACUUGCAUUAAUUCGGG | 589 | CCCGAAUUAAUGCAAGUUG | [1593-1611](19/19) |
| 87 | GGAAAGACAAGAACAACUC | 590 | GAGUUGUUCUUGUCUUUCC | [281-299](19/19) |
| 88 | UUGAAAAGGAAAGACAAGA | 591 | UCUUGUCUUUCCUUUUCAA | [274-292](19/19) |
| 89 | CAAAAGACAAACAUUCAAG | 592 | CUUGAAUGUUUGUCUUUUG | [1438-1456](19/19) |
| 90 | UCACAAAAGACAAACAUUC | 593 | GAAUGUUUGUCUUUUGUGA | [1435-1453](19/19) |
| 91 | ACCCCAUUCACAAAAGACA | 594 | UGUCUUUUGUGAAUGGGGU | [1428-1446](19/19) |
| 92 | AGAAUUGCCUGUAAGUCCU | 595 | AGGACUUACAGGCAAUUCU | [1397-1415](19/19) |
| 93 | AGCGACGGAAAGAGUAUGA | 596 | UCAUACUCUUUCCGUCGCU | [235-253](19/19) |
| 94 | AAGCACAGCAGAAUUCAAU | 597 | AUUGAAUUCUGCUGUGCUU | [1115-1133](19/19) |
| 95 | CUCUGAACUUCUAAAUGGG | 598 | CCCAUUUAGAAGUUCAGAG | [1040-1058](19/19) |
| 96 | UUGACAGUGAACUCAUUAA | 599 | UUAAUGAGUUCACUGUCAA | [909-927](19/19) |
| 97 | UAAGUCGAGAAGUAUUUGA | 600 | UCAAAUACUUCUCGACUUA | [208-226](19/19) |
| 98 | UGGAGUAAGUCGAGAAGUA | 601 | UACUUCUCGACUUACUCCA | [203-221](19/19) |
| 99 | UACUCAUCUAUACCCUCAA | 602 | UUGAGGGUAUAGAUGAGUA | [798-816](19/19) |
| 100 | UCCAAGUCCAGAAGCCAAA | 603 | UUUGGCUUCUGGACUUGGA | [752-770](19/19) |
| 101 | CUGUUGAUUUAGACGGUAU | 604 | AUACCGUCUAAAUCAACAG | [634-652](19/19) |
| 102 | UUGCUACUAAUCAGGCUCA | 605 | UGAGCCUGAUUAGUAGCAA | [583-601](19/19) |
| 103 | GCCCAGUCUUCAUUGCUAC | 606 | GUAGCAAUGAAGACUGGGC | [571-589](19/19) |
| 104 | CAUUCCCGUUUGUAGAUGA | 607 | UCAUCUACAAACGGGAAUG | [490-508](19/19) |
| 105 | AUGCUUUGUACUUUGAUGA | 608 | UCAUCAAAGUACAAAGCAU | [448-466](19/19) |
| 106 | CAGAUGCUUUGUACUUUGA | 609 | UCAAAGUACAAAGCAUCUG | [445-463](19/19) |
| 107 | AAGAGCUGGUACUAAUAAA | 610 | UUUAUUAGUACCAGCUCUU | [2370-2388](19/19) |
| 108 | GGACAAAAAAUGGCAUUUU | 611 | AAAAUGCCAUUUUUUGUCC | [2310-2328](19/19) |
| 109 | GUGAAAUGCUCAUACUUUA | 612 | UAAAGUAUGAGCAUUUCAC | [2001-2019](19/19) |
| 110 | AACCUUAUUCUCCUAGUGA | 613 | UCACUAGGAGAAUAAGGUU | [1834-1852](19/19) |
| 111 | AAAACCUUAUUCUCCUAGU | 614 | ACUAGGAGAAUAAGGUUUU | [1832-1850](19/19) |
| 112 | AAACAACUCAGCACCUUAU | 615 | AUAAGGUGCUGAGUUGUUU | [1776-1794](19/19) |
| 113 | CACCUACUGAAAAACAAC | 616 | GUUGUUUUUCAGUAGGUG | [1764-1782](19/19) |
| 114 | UUCACCUACUGAAAAACA | 617 | UGUUUUUCAGUAGGUGAA | [1762-1780](19/19) |
| 115 | ACAAGAACAACUCCAAAAG | 618 | CUUUUGGAGUUGUUCUUGU | [287-305](19/19) |
| 116 | UUGCAUUAAUUCGGGAUAU | 619 | AUAUCCCGAAUUAAUGCAA | [1597-1615](19/19) |
| 117 | AACUUGCAUUAAUUCGGGA | 620 | UCCCGAAUUAAUGCAAGUU | [1594-1612](19/19) |

TABLE A-continued

19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 118 | CACAAAAGACAAACAUUCA | 621 | UGAAUGUUUGUCUUUUGUG | [1436-1454](19/19) |
| 119 | CCCAUUCACAAAAGACAAA | 622 | UUUGUCUUUUGUGAAUGGG | [1430-1448](19/19) |
| 120 | GAACACACCAGAGAAAGAA | 623 | UUCUUUCUCUGGUGUGUUC | [1382-1400](19/19) |
| 121 | ACGGUCCACAGCUCAUCAU | 624 | AUGAUGAGCUGUGGACCGU | [97-115](19/19) |
| 122 | UGAGAACACACCAGAGAAA | 625 | UUUCUCUGGUGUGUUCUCA | [1379-1397](19/19) |
| 123 | GUGAUUCUGAAGUGGAAGA | 626 | UCUUCCACUUCAGAAUCAC | [1234-1252](19/19) |
| 124 | ACAGCAGAAUUCAAUGAUU | 627 | AAUCAUUGAAUUCUGCUGU | [1119-1137](19/19) |
| 125 | GCACAGCAGAAUUCAAUGA | 628 | UCAUUGAAUUCUGCUGUGC | [1117-1135](19/19) |
| 126 | CUCAUUAAAUUCAGAUGCC | 629 | GGCAUCUGAAUUUAAUGAG | [920-938](19/19) |
| 127 | ACUCAUUAAAUUCAGAUGC | 630 | GCAUCUGAAUUUAAUGAGU | [919-937](19/19) |
| 128 | AACCAGUUGACAGUGAACU | 631 | AGUUCACUGUCAACUGGUU | [903-921](19/19) |
| 129 | UCCUUCAGCAGCAUCCUCU | 632 | AGAGGAUGCUGCUGAAGGA | [870-888](19/19) |
| 130 | GAGGAUUCCUUCAGCAGCA | 633 | UGCUGCUGAAGGAAUCCUC | [864-882](19/19) |
| 131 | AGUAAGUCGAGAAGUAUUU | 634 | AAAUACUUCUCGACUUACU | [206-224](19/19) |
| 132 | GAGUAAGUCGAGAAGUAUU | 635 | AAUACUUCUCGACUUACUC | [205-223](19/19) |
| 133 | ACUCAUCUAUACCCUCAAU | 636 | AUUGAGGGUAUAGAUGAGU | [799-817](19/19) |
| 134 | UUACUCAUCUAUACCCUCA | 637 | UGAGGGUAUAGAUGAGUAA | [797-815](19/19) |
| 135 | UGAGUUACAGUGUCUUAAU | 638 | AUUAAGACACUGUAACUCA | [698-716](19/19) |
| 136 | UUUGGAGGCAAGAUAUAGA | 639 | UCUAUAUCUUGCCUCCAAA | [181-199](19/19) |
| 137 | AGGACAUUGAGCAAGUUUG | 640 | CAAACUUGCUCAAUGUCCU | [658-676](19/19) |
| 138 | UAGACGGUAUGCAACAGGA | 641 | UCCUGUUGCAUACCGUCUA | [643-661](19/19) |
| 139 | UUGAUUUAGACGGUAUGCA | 642 | UGCAUACCGUCUAAAUCAA | [637-655](19/19) |
| 140 | UUCAUUGCUACUAAUCAGG | 643 | CCUGAUUAGUAGCAAUGAA | [579-597](19/19) |
| 141 | AGUCUUCAUUGCUACUAAU | 644 | AUUAGUAGCAAUGAAGACU | [575-593](19/19) |
| 142 | CGGCUACGUUUCAGUCACU | 645 | AGUGACUGAAACGUAGCCG | [523-541](19/19) |
| 143 | AGGACAUGGAUUUGAUUGA | 646 | UCAAUCAAAUCCAUGUCCU | [157-175](19/19) |
| 144 | GCCCACAUUCCCAAAUCAG | 647 | CUGAUUUGGGAAUGUGGGC | [429-447](19/19) |
| 145 | AGCAGGACAUGGAUUUGAU | 648 | AUCAAAUCCAUGUCCUGCU | [154-172](19/19) |
| 146 | AGCUGGUACUAAUAAAGGA | 649 | UCCUUUAUUAGUACCAGCU | [2373-2391](19/19) |
| 147 | GAGCUGGUACUAAUAAAGG | 650 | CCUUUAUUAGUACCAGCUC | [2372-2390](19/19) |
| 148 | AGAGCUGGUACUAAUAAAG | 651 | CUUUAUUAGUACCAGCUCU | [2371-2389](19/19) |
| 149 | CUAACCACUAUGUACUUUU | 652 | AAAAGUACAUAGUGGUUAG | [2276-2294](19/19) |
| 150 | ACAUCGGCUAAAAGAAA | 653 | UUUCUUUUAGCCAGAUGU | [2246-2264](19/19) |
| 151 | CUGUUCUUAUGUCAUUUGU | 654 | ACAAAUGACAUAAGAACAG | [2199-2217](19/19) |
| 152 | UGGGCUAGUUUCUGUGUAA | 655 | UUACACAGAAACUAGCCCA | [2152-2170](19/19) |
| 153 | GUAAACAAUUUCUUAGGAC | 656 | GUCCUAAGAAAUUGUUUAC | [2127-2145](19/19) |
| 154 | CUGUAAACAAUUUCUUAGG | 657 | CCUAAGAAAUUGUUUACAG | [2125-2143](19/19) |
| 155 | GUCAGUAUGUUGAAUCAGU | 658 | ACUGAUUCAACAUACUGAC | [2093-2111](19/19) |

TABLE A-continued

19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 156 | GGCAAUGUUUUCCUUGUUC | 659 | GAACAAGGAAAACAUUGCC | [1878-1896](19/19) |
| 157 | GCACCUUAUAUCUCGAAGU | 660 | ACUUCGAGAUAUAAGGUGC | [1786-1804](19/19) |
| 158 | GAAAAAACAACUCAGCACC | 661 | GGUGCUGAGUUGUUUUUUC | [1772-1790](19/19) |
| 159 | AGAGCAAGAUUUAGAUCAU | 662 | AUGAUCUAAAUCUUGCUCU | [1688-1706](19/19) |
| 160 | UAGAGCAAGAUUUAGAUCA | 663 | UGAUCUAAAUCUUGCUCUA | [1687-1705](19/19) |
| 161 | UAGAACUAGAGCAAGAUUU | 664 | AAAUCUUGCUCUAGUUCUA | [1681-1699](19/19) |
| 162 | ACGUAGGAGGGGUAAGAAU | 665 | AUUCUUACCCCUCCUACGU | [1616-1634](19/19) |
| 163 | UCCCUGUUGUUGACUUCAA | 666 | UUGAAGUCAACAACAGGGA | [1540-1558](19/19) |
| 164 | UCCCUGUAGAAAAAAUCAU | 667 | AUGAUUUUUUCUACAGGGA | [1516-1534](19/19) |
| 165 | UCACAAGAGAUGAACUUAG | 668 | CUAAGUUCAUCUCUUGUGA | [1474-1492](19/19) |
| 166 | AGAGAAAGAAUUGCCUGUA | 669 | UACAGGCAAUUCUUUCUCU | [1391-1409](19/19) |
| 167 | ACCAGAGAAAGAAUUGCCU | 670 | AGGCAAUUCUUUCUCUGGU | [1388-1406](19/19) |
| 168 | CACCAGAGAAAGAAUUGCC | 671 | GGCAAUUCUUUCUCUGGUG | [1387-1405](19/19) |
| 169 | AGUAUGAGCUGGAAAAACA | 672 | UGUUUUUCCAGCUCAUACU | [247-265](19/19) |
| 170 | GUACAUUCUUCUGGGGAUA | 673 | UAUCCCCAGAAGAAUGUAC | [1302-1320](19/19) |
| 171 | CAAACAGAAUGGUCCUAAA | 674 | UUUAGGACCAUUCUGUUUG | [1277-1295](19/19) |
| 172 | CUGGAAGUGUCAAACAGAA | 675 | UUCUGUUUGACACUUCCAG | [1267-1285](19/19) |
| 173 | GGAAAGAGUAUGAGCUGGA | 676 | UCCAGCUCAUACUCUUUCC | [241-259](19/19) |
| 174 | CAGUGAUUCUGAAGUGGAA | 677 | UUCCACUUCAGAAUCACUG | [1232-1250](19/19) |
| 175 | GACGGAAAGAGUAUGAGCU | 678 | AGCUCAUACUCUUUCCGUC | [238-256](19/19) |
| 176 | CACAGCAGAAUUCAAUGAU | 679 | AUCAUUGAAUUCUGCUGUG | [1118-1136](19/19) |
| 177 | GCCACAGUCAACACAGAUU | 680 | AAUCUGUGUUGACUGUGGC | [936-954](19/19) |
| 178 | UAAAUUCAGAUGCCACAGU | 681 | ACUGUGGCAUCUGAAUUUA | [925-943](19/19) |
| 179 | CCAGUUGACAGUGAACUCA | 682 | UGAGUUCACUGUCAACUGG | [905-923](19/19) |
| 180 | GUCGAGAAGUAUUUGACUU | 683 | AAGUCAAAUACUUCUCGAC | [211-229](19/19) |
| 181 | CUGUAGUCCACAUUUUCUU | 684 | AAGAAAAUGUGGACUACAG | [836-854](19/19) |
| 182 | GGAGUAAGUCGAGAAGUAU | 685 | AUACUUCUCGACUUACUCC | [204-222](19/19) |
| 183 | GACAGAAGUUGACAAUUAU | 686 | AUAAUUGUCAACUUCUGUC | [773-791](19/19) |
| 184 | GAGACUACCAUGGUUCCAA | 687 | UUGGAACCAUGGUAGUCUC | [738-756](19/19) |
| 185 | CUAUUAUCCAUUCCUGAGU | 688 | ACUCAGGAAUGGAUAAUAG | [684-702](19/19) |
| 186 | GACGGUAUGCAACAGGACA | 689 | UGUCCUGUUGCAUACCGUC | [645-663](19/19) |
| 187 | CGAGAGCCCAGUCUUCAUU | 690 | AAUGAAGACUGGGCUCUCG | [566-584](19/19) |
| 188 | UUGAUUGACAUACUUUGGA | 691 | UCCAAAGUAUGUCAAUCAA | [168-186](19/19) |
| 189 | GUCACUUGUUCCUGAUAUU | 692 | AAUAUCAGGAACAAGUGAC | [536-554](19/19) |
| 190 | UCGGCUACGUUUCAGUCAC | 693 | GUGACUGAAACGUAGCCGA | [522-540](19/19) |
| 191 | GAGGUUUCUUCGGCUACGU | 694 | ACGUAGCCGAAGAAACCUC | [513-531](19/19) |
| 192 | GACAUUCCCGUUUGUAGAU | 695 | AUCUACAAACGGGAAUGUC | [488-506](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 193 | GACAUGGAUUUGAUUGACA | 696 | UGUCAAUCAAAUCCAUGUC | [159-177](19/19) |
| 194 | UCAGAUGCUUUGUACUUUG | 697 | CAAAGUACAAAGCAUCUGA | [444-462](19/19) |
| 195 | CAGCAGGACAUGGAUUUGA | 698 | UCAAAUCCAUGUCCUGCUG | [153-171](19/19) |
| 196 | AUGGACAAAAAAUGGCAUU | 699 | AAUGCCAUUUUUUGUCCAU | [2308-2326](19/19) |
| 197 | GUAUGGACAAAAAAUGGCA | 700 | UGCCAUUUUUUGUCCAUAC | [2306-2324](19/19) |
| 198 | CAUCUGGCUAAAAGAAAU | 701 | AUUUCUUUUAGCCAGAUG | [2247-2265](19/19) |
| 199 | GACAUCUGGCUAAAAGAA | 702 | UUCUUUUAGCCAGAUGUC | [2245-2263](19/19) |
| 200 | GAGCUAGUUUUUUGUACU | 703 | AGUACAAAAAACUAGCUC | [1956-1974](19/19) |
| 201 | GAAGAUGGAAAACCUUAUU | 704 | AAUAAGGUUUUCCAUCUUC | [1824-1842](19/19) |
| 202 | GCUACGUGAUGAAGAUGGA | 705 | UCCAUCUUCAUCACGUAGC | [1814-1832](19/19) |
| 203 | UGCUACGUGAUGAAGAUGG | 706 | CCAUCUUCAUCACGUAGCA | [1813-1831](19/19) |
| 204 | GAGCAAGAUUUAGAUCAUU | 707 | AAUGAUCUAAAUCUUGCUC | [1689-1707](19/19) |
| 205 | ACUAGAGCAAGAUUUAGAU | 708 | AUCUAAAUCUUGCUCUAGU | [1685-1703](19/19) |
| 206 | UAGUAGAACUAGAGCAAGA | 709 | UCUUGCUCUAGUUCUACUA | [1678-1696](19/19) |
| 207 | AUAUCCCAUUCCCUGUAGA | 710 | UCUACAGGGAAUGGGAUAU | [1507-1525](19/19) |
| 208 | CCAUAUCCCAUUCCCUGUA | 711 | UACAGGGAAUGGGAUAUGG | [1505-1523](19/19) |
| 209 | CCCCAUUCACAAAAGACAA | 712 | UUGUCUUUUGUGAAUGGGG | [1429-1447](19/19) |
| 210 | ACACCAGAGAAAGAAUUGC | 713 | GCAAUUCUUUCUCUGGUGU | [1386-1404](19/19) |
| 211 | UCAAACAGAAUGGUCCUAA | 714 | UUAGGACCAUUCUGUUUGA | [1276-1294](19/19) |
| 212 | AAGAGUAUGAGCUGGAAAA | 715 | UUUUCCAGCUCAUACUCUU | [244-262](19/19) |
| 213 | UGCCCCUGGAAGUGUCAAA | 716 | UUUGACACUUCCAGGGGCA | [1262-1280](19/19) |
| 214 | GCGACGGAAAGAGUAUGAG | 717 | CUCAUACUCUUUCCGUCGC | [236-254](19/19) |
| 215 | CUGAACUUCUAAAUGGGCC | 718 | GGCCCAUUUAGAAGUUCAG | [1042-1060](19/19) |
| 216 | CCACAGUCAACACAGAUUU | 719 | AAAUCUGUGUUGACUGUGG | [937-955](19/19) |
| 217 | AUGCUUUUGAGGAUUCCUU | 720 | AAGGAAUCCUCAAAAGCAU | [856-874](19/19) |
| 218 | CUCAAUGGAAAAAGAAGUA | 721 | UACUUCUUUUUCCAUUGAG | [812-830](19/19) |
| 219 | CUCAUCUAUACCCUCAAUG | 722 | CAUUGAGGGUAUAGAUGAG | [800-818](19/19) |
| 220 | ACAUUGAGCAAGUUUGGGA | 723 | UCCCAAACUUGCUCAAUGU | [661-679](19/19) |
| 221 | AACAGGACAUUGAGCAAGU | 724 | ACUUGCUCAAUGUCCUGUU | [655-673](19/19) |
| 222 | UUAGACGGUAUGCAACAGG | 725 | CCUGUUGCAUACCGUCUAA | [642-660](19/19) |
| 223 | ACCUGAAACUUCUGUUGCU | 726 | AGCAACAGAAGUUUCAGGU | [605-623](19/19) |
| 224 | CCAGUCUUCAUUGCUACUA | 727 | UAGUAGCAAUGAAGACUGG | [573-591](19/19) |
| 225 | AGAGCCCAGUCUUCAUUGC | 728 | GCAAUGAAGACUGGGCUCU | [568-586](19/19) |
| 226 | AGUCACUUGUUCCUGAUAU | 729 | AUAUCAGGAACAAGUGACU | [535-553](19/19) |
| 227 | UGGAUUUGAUUGACAUACU | 730 | AGUAUGUCAAUCAAAUCCA | [163-181](19/19) |
| 228 | CAAUGAGGUUUCUUCGGCU | 731 | AGCCGAAGAAACCUCAUUG | [509-527](19/19) |
| 229 | ACAAUGAGGUUUCUUCGGC | 732 | GCCGAAGAAACCUCAUUGU | [508-526](19/19) |
| 230 | AGACAUUCCCGUUUGUAGA | 733 | UCUACAAACGGGAAUGUCU | [487-505](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 231 | GCUUUGUACUUUGAUGACU | 734 | AGUCAUCAAAGUACAAAGC | [450-468](19/19) |
| 232 | CCCACAUUCCCAAAUCAGA | 735 | UCUGAUUUGGGAAUGUGGG | [430-448](19/19) |
| 233 | ACAACUAGAUGAAGAGACA | 736 | UGUCUCUUCAUCUAGUUGU | [335-353](19/19) |
| 234 | UACAACUAGAUGAAGAGAC | 737 | GUCUCUUCAUCUAGUUGUA | [334-352](19/19) |
| 235 | UUUAAGAGCUGGUACUAAU | 738 | AUUAGUACCAGCUCUUAAA | [2367-2385](19/19) |
| 236 | UGGACAAAAAUGGCAUUU | 739 | AAAUGCCAUUUUUGUCCA | [2309-2327](19/19) |
| 237 | GGGCUAGUUUCUGUGUAAG | 740 | CUUACACAGAAACUAGCCC | [2153-2171](19/19) |
| 238 | UUGGGCUAGUUUCUGUGUA | 741 | UACACAGAAACUAGCCCAA | [2151-2169](19/19) |
| 239 | GUGUCAGUAUGUUGAAUCA | 742 | UGAUUCAACAUACUGACAC | [2091-2109](19/19) |
| 240 | GAUGUGAAAUGCUCAUACU | 743 | AGUAUGAGCAUUUCACAUC | [1998-2016](19/19) |
| 241 | CUCCUACUGUGAUGUGAAA | 744 | UUUCACAUCACAGUAGGAG | [1988-2006](19/19) |
| 242 | AGAUUUAGGAGGAUUUGAC | 745 | GUCAAAUCCUCCUAAAUCU | [1930-1948](19/19) |
| 243 | GCAAUGUUUCCUUGUUCC | 746 | GGAACAAGGAAACAUUGC | [1879-1897](19/19) |
| 244 | AACAAGAGAUGGCAAUGUU | 747 | AACAUUGCCAUCUCUUGUU | [1868-1886](19/19) |
| 245 | GCAGCAAACAAGAGAUGGC | 748 | GCCAUCUCUUGUUUGCUGC | [1862-1880](19/19) |
| 246 | CUCCUAGUGAAUACUCCCU | 749 | AGGGAGUAUUCACUAGGAG | [1843-1861](19/19) |
| 247 | CAGCACCUUAUAUCUCGAA | 750 | UUCGAGAUAUAAGGUGCUG | [1784-1802](19/19) |
| 248 | UCACCUACUGAAAAACAA | 751 | UUGUUUUUCAGUAGGUGA | [1763-1781](19/19) |
| 249 | GCAAGAUUUAGAUCAUUUG | 752 | CAAAUGAUCUAAAUCUUGC | [1691-1709](19/19) |
| 250 | CAGAAAAGAAAACUGGAA | 753 | UUCCAGUUUUCUUUUUCUG | [1655-1673](19/19) |
| 251 | AUACGUAGGAGGGGUAAGA | 754 | UCUUACCCCUCCUACGUAU | [1614-1632](19/19) |
| 252 | UGCAUUAAUUCGGGAUAUA | 755 | UAUAUCCCGAAUUAAUGCA | [1598-1616](19/19) |
| 253 | AAGCUCUCCAUAUCCCAUU | 756 | AAUGGGAUAUGGAGAGCUU | [1498-1516](19/19) |
| 254 | CAUUCACAAAAGACAAACA | 757 | UGUUUGUCUUUUGUGAAUG | [1432-1450](19/19) |
| 255 | GAGUAUGAGCUGGAAAAAC | 758 | GUUUUUCCAGCUCAUACUC | [246-264](19/19) |
| 256 | CAGAAUGGUCCUAAAACAC | 759 | GUGUUUUAGGACCAUUCUG | [1281-1299](19/19) |
| 257 | GUGUCAAACAGAAUGGUCC | 760 | GGACCAUUCUGUUUGACAC | [1273-1291](19/19) |
| 258 | GAAGUGUCAAACAGAAUGG | 761 | CCAUUCUGUUUGACACUUC | [1270-1288](19/19) |
| 259 | CUGAAGUGGAAGAGCUAGA | 762 | UCUAGCUCUUCCACUUCAG | [1240-1258](19/19) |
| 260 | CCAGAACACUCAGUGGAAU | 763 | AUUCCACUGAGUGUUCUGG | [1182-1200](19/19) |
| 261 | UUCUGACUCCGGCAUUUCA | 764 | UGAAAUGCCGGAGUCAGAA | [1136-1154](19/19) |
| 262 | AUGAUUCUGACUCCGGCAU | 765 | AUGCCGGAGUCAGAAUCAU | [1132-1150](19/19) |
| 263 | GGCCCAUUGAUGUUUCUGA | 766 | UCAGAAACAUCAAUGGGCC | [1057-1075](19/19) |
| 264 | CACAGAUUUUGGUGAUGAA | 767 | UUCAUCACCAAAAUCUGUG | [947-965](19/19) |
| 265 | CAGUUGACAGUGAACUCAU | 768 | AUGAGUUCACUGUCAACUG | [906-924](19/19) |
| 266 | UUAAUGCUUUUGAGGAUUC | 769 | GAAUCCUCAAAAGCAUUAA | [853-871](19/19) |
| 267 | UCUUAAUGCUUUUGAGGAU | 770 | AUCCUCAAAAGCAUUAAGA | [851-869](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 268 | AGUCCACAUUUUCUUAAUG | 771 | CAUUAAGAAAAUGUGGACU | [840-858](19/19) |
| 269 | UGACAGAAGUUGACAAUUA | 772 | UAAUUGUCAACUUCUGUCA | [772-790](19/19) |
| 270 | CCAAACUGACAGAAGUUGA | 773 | UCAACUUCUGUCAGUUUGG | [766-784](19/19) |
| 271 | GUUGAGACUACCAUGGUUC | 774 | GAACCAUGGUAGUCUCAAC | [735-753](19/19) |
| 272 | ACAAGCUGGUUGAGACUAC | 775 | GUAGUCUCAACCAGCUUGU | [727-745](19/19) |
| 273 | AUACUUUGGAGGCAAGAUA | 776 | UAUCUUGCCUCCAAAGUAU | [177-195](19/19) |
| 274 | GACAUACUUUGGAGGCAAG | 777 | CUUGCCUCCAAAGUAUGUC | [174-192](19/19) |
| 275 | GUCACCUGAAACUUCUGUU | 778 | AACAGAAGUUUCAGGUGAC | [602-620](19/19) |
| 276 | UCGAGAGCCCAGUCUUCAU | 779 | AUGAAGACUGGGCUCUCGA | [565-583](19/19) |
| 277 | GUACUUUGAUGACUGCAUG | 780 | CAUGCAGUCAUCAAAGUAC | [455-473](19/19) |
| 278 | UGUACUUUGAUGACUGCAU | 781 | AUGCAGUCAUCAAAGUACA | [454-472](19/19) |
| 279 | GGACAUGGAUUUGAUUGAC | 782 | GUCAAUCAAAUCCAUGUCC | [158-176](19/19) |
| 280 | GAUGCUUUGUACUUUGAUG | 783 | CAUCAAAGUACAAAGCAUC | [447-465](19/19) |
| 281 | AUCAGAUGCUUUGUACUUU | 784 | AAAGUACAAAGCAUCUGAU | [443-461](19/19) |
| 282 | UUCCCAAAUCAGAUGCUUU | 785 | AAAGCAUCUGAUUUGGGAA | [436-454](19/19) |
| 283 | CAUUCCCAAAUCAGAUGCU | 786 | AGCAUCUGAUUUGGGAAUG | [434-452](19/19) |
| 284 | CCACAUUCCCAAAUCAGAU | 787 | AUCUGAUUUGGGAAUGUGG | [431-449](19/19) |
| 285 | AGUUACAACUAGAUGAAGA | 788 | UCUUCAUCUAGUUGUAACU | [331-349](19/19) |
| 286 | UAUGGACAAAAAAUGGCAU | 789 | AUGCCAUUUUUUGUCCAUA | [2307-2325](19/19) |
| 287 | ACUGUAUGGACAAAAAAUG | 790 | CAUUUUUUGUCCAUACAGU | [2303-2321](19/19) |
| 288 | UAUGACAUCUGGCUAAAAA | 791 | UUUUUAGCCAGAUGUCAUA | [2242-2260](19/19) |
| 289 | ACUGUUCUUAUGUCAUUUG | 792 | CAAAUGACAUAAGAACAGU | [2198-2216](19/19) |
| 290 | UAGUUUCUGUGUAAGUGUA | 793 | UACACUUACACAGAAACUA | [2157-2175](19/19) |
| 291 | GGCUAGUUUCUGUGUAAGU | 794 | ACUUACACAGAAACUAGCC | [2154-2172](19/19) |
| 292 | CAAUUUCUUAGGACACCAU | 795 | AUGGUGUCCUAAGAAAUUG | [2132-2150](19/19) |
| 293 | GUAUGUUGAAUCAGUAGUU | 796 | AACUACUGAUUCAACAUAC | [2097-2115](19/19) |
| 294 | UCAGUAUGUUGAAUCAGUA | 797 | UACUGAUUCAACAUACUGA | [2094-2112](19/19) |
| 295 | UGAUGUGAAAUGCUCAUAC | 798 | GUAUGAGCAUUUCACAUCA | [1997-2015](19/19) |
| 296 | AAAGCUCCUACUGUGAUGU | 799 | ACAUCACAGUAGGAGCUUU | [1984-2002](19/19) |
| 297 | UACUAAAAGCUCCUACUGU | 800 | ACAGUAGGAGCUUUUAGUA | [1979-1997](19/19) |
| 298 | GGAUUUGACCUUUUCUGAG | 801 | CUCAGAAAAGGUCAAAUCC | [1940-1958](19/19) |
| 299 | AGAGAUGGCAAUGUUUUCC | 802 | GGAAAACAUUGCCAUCUCU | [1872-1890](19/19) |
| 300 | AAACAAGAGAUGGCAAUGU | 803 | ACAUUGCCAUCUCUUGUUU | [1867-1885](19/19) |
| 301 | CAGCAAACAAGAGAUGGCA | 804 | UGCCAUCUCUUGUUUGCUG | [1863-1881](19/19) |
| 302 | CUAGUGAAUACUCCCUGCA | 805 | UGCAGGGAGUAUUCACUAG | [1846-1864](19/19) |
| 303 | AAGAUGGAAAACCUUAUUC | 806 | GAAUAAGGUUUUCCAUCUU | [1825-1843](19/19) |
| 304 | CAGCAUGCUACGUGAUGAA | 807 | UUCAUCACGUAGCAUGCUG | [1808-1826](19/19) |
| 305 | CACCUUAUAUCUCGAAGUU | 808 | AACUUCGAGAUAUAAGGUG | [1787-1805](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 306 | UCAGCACCUUAUAUCUCGA | 809 | UCGAGAUAUAAGGUGCUGA | [1783-1801](19/19) |
| 307 | AUAUAGUAGAACUAGAGCA | 810 | UGCUCUAGUUCUACUAUAU | [1675-1693](19/19) |
| 308 | UUGCAGAAAAAGAAAACUG | 811 | CAGUUUUCUUUUUCUGCAA | [1652-1670](19/19) |
| 309 | ACGAAAUGAUGUCCAAAGA | 812 | UCUUUGGACAUCAUUUCGU | [1558-1576](19/19) |
| 310 | ACCUCCCUGUUGUUGACUU | 813 | AAGUCAACAACAGGGAGGU | [1537-1555](19/19) |
| 311 | CCCUGUAGAAAAAUCAUU | 814 | AAUGAUUUUUCUACAGGG | [1517-1535](19/19) |
| 312 | GAGAUGAACUUAGGGCAAA | 815 | UUUGCCCUAAGUUCAUCUC | [1480-1498](19/19) |
| 313 | CACAAGAGAUGAACUUAGG | 816 | CCUAAGUUCAUCUCUUGUG | [1475-1493](19/19) |
| 314 | AACCCCAUUCACAAAAGAC | 817 | GUCUUUUGUGAAUGGGGUU | [1427-1445](19/19) |
| 315 | AGAACACACCAGAGAAAGA | 818 | UCUUUCUCUGGUGUGUUCU | [1381-1399](19/19) |
| 316 | GUCAAACAGAAUGGUCCUA | 819 | UAGGACCAUUCUGUUUGAC | [1275-1293](19/19) |
| 317 | GGAAGUGUCAAACAGAAUG | 820 | CAUUCUGUUUGACACUUCC | [1269-1287](19/19) |
| 318 | UGGAAGUGUCAAACAGAAU | 821 | AUUCUGUUUGACACUUCCA | [1268-1286](19/19) |
| 319 | CCCUGGAAGUGUCAAACAG | 822 | CUGUUUGACACUUCCAGGG | [1265-1283](19/19) |
| 320 | GUGGAAGAGCUAGAUAGUG | 823 | CACUAUCUAGCUCUUCCAC | [1245-1263](19/19) |
| 321 | ACCAGAACACUCAGUGGAA | 824 | UUCCACUGAGUGUUCUGGU | [1181-1199](19/19) |
| 322 | CAGCGACGGAAAGAGUAUG | 825 | CAUACUCUUUCCGUCGCUG | [234-252](19/19) |
| 323 | UGAUCUAUCACUUUGCAAA | 826 | UUUGCAAAGUGAUAGAUCA | [1073-1091](19/19) |
| 324 | GCCCAUUGAUGUUUCUGAU | 827 | AUCAGAAACAUCAAUGGGC | [1058-1076](19/19) |
| 325 | AGUCAACACAGAUUUUGGU | 828 | ACCAAAAUCUGUGUUGACU | [941-959](19/19) |
| 326 | AGUUGACAGUGAACUCAUU | 829 | AAUGAGUUCACUGUCAACU | [907-925](19/19) |
| 327 | ACUGUAGUCCACAUUUUCU | 830 | AGAAAAUGUGGACUACAGU | [835-853](19/19) |
| 328 | CAAUGGAAAAAGAAGUAGG | 831 | CCUACUUCUUUUUCCAUUG | [814-832](19/19) |
| 329 | CAAACUGACAGAAGUUGAC | 832 | GUCAACUUCUGUCAGUUUG | [767-785](19/19) |
| 330 | AGACUACCAUGGUUCCAAG | 833 | CUUGGAACCAUGGUAGUCU | [739-757](19/19) |
| 331 | ACAGGACAUUGAGCAAGUU | 834 | AACUUGCUCAAUGUCCUGU | [656-674](19/19) |
| 332 | UGACAUACUUUGGAGGCAA | 835 | UUGCCUCCAAAGUAUGUCA | [173-191](19/19) |
| 333 | ACGUUCAGUCACUUGUUC | 836 | GAACAAGUGACUGAAACGU | [528-546](19/19) |
| 334 | CUACGUUUCAGUCACUUGU | 837 | ACAAGUGACUGAAACGUAG | [526-544](19/19) |
| 335 | GGCUACGUUUCAGUCACUU | 838 | AAGUGACUGAAACGUAGCC | [524-542](19/19) |
| 336 | GGAUUUGAUUGACAUACUU | 839 | AAGUAUGUCAAUCAAAUCC | [164-182](19/19) |
| 337 | UCUUCGGCUACGUUUCAGU | 840 | ACUGAAACGUAGCCGAAGA | [519-537](19/19) |
| 338 | CAGUCAGAAACCAGUGGAU | 841 | AUCCACUGGUUUCUGACUG | [390-408](19/19) |
| 339 | UGAAGAGACAGGUGAAUUU | 842 | AAAUUCACCUGUCUCUUCA | [344-362](19/19) |
| 340 | UAGAUGAAGAGACAGGUGA | 843 | UCACCUGUCUCUUCAUCUA | [340-358](19/19) |
| 341 | UAAGAGCUGGUACUAAUAA | 844 | UUAUUAGUACCAGCUCUUA | [2369-2387](19/19) |
| 342 | CUGUAUGGACAAAAAUGG | 845 | CCAUUUUUUGUCCAUACAG | [2304-2322](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 343 | UGGAGUGUCAGUAUGUUGA | 846 | UCAACAUACUGACACUCCA | [2087-2105](19/19) |
| 344 | UGUGAAAUGCUCAUACUUU | 847 | AAAGUAUGAGCAUUUCACA | [2000-2018](19/19) |
| 345 | GUGAUGUGAAAUGCUCAUA | 848 | UAUGAGCAUUUCACAUCAC | [1996-2014](19/19) |
| 346 | AGCUCCUACUGUGAUGUGA | 849 | UCACAUCACAGUAGGAGCU | [1986-2004](19/19) |
| 347 | UCCUAGUGAAUACUCCCUG | 850 | CAGGGAGUAUUCACUAGGA | [1844-1862](19/19) |
| 348 | UUCUCCUAGUGAAUACUCC | 851 | GGAGUAUUCACUAGGAGAA | [1841-1859](19/19) |
| 349 | CAUGCUACGUGAUGAAGAU | 852 | AUCUUCAUCACGUAGCAUG | [1811-1829](19/19) |
| 350 | GCAUGCUACGUGAUGAAGA | 853 | UCUUCAUCACGUAGCAUGC | [1810-1828](19/19) |
| 351 | AGCACCUUAUAUCUCGAAG | 854 | CUUCGAGAUAUAAGGUGCU | [1785-1803](19/19) |
| 352 | AGAAAAGGAGAAAAUGAC | 855 | GUCAUUUUCUCCUUUUUCU | [1736-1754](19/19) |
| 353 | UGCAGAAAAAGAAAACUGG | 856 | CCAGUUUUCUUUUUCUGCA | [1653-1671](19/19) |
| 354 | UCAUUAACCUCCCUGUUGU | 857 | ACAACAGGGAGGUUAAUGA | [1531-1549](19/19) |
| 355 | AAGUGUCAAACAGAAUGGU | 858 | ACCAUUCUGUUUGACACUU | [1271-1289](19/19) |
| 356 | GAAAGAGUAUGAGCUGGAA | 859 | UUCCAGCUCAUACUCUUUC | [242-260](19/19) |
| 357 | AAAGCACAGCAGAAUUCAA | 860 | UUGAAUUCUGCUGUGCUUU | [1114-1132](19/19) |
| 358 | AUGUUUCUGAUCUAUCACU | 861 | AGUGAUAGAUCAGAAACAU | [1066-1084](19/19) |
| 359 | UGGGCCCAUUGAUGUUUCU | 862 | AGAAACAUCAAUGGGCCCA | [1055-1073](19/19) |
| 360 | CAGUCAACACAGAUUUUGG | 863 | CCAAAAUCUGUGUUGACUG | [940-958](19/19) |
| 361 | ACAGUCAACACAGAUUUUG | 864 | CAAAAUCUGUGUUGACUGU | [939-957](19/19) |
| 362 | CACAGUCAACACAGAUUUU | 865 | AAAAUCUGUGUUGACUGUG | [938-956](19/19) |
| 363 | ACAGAAGACCCCAACCAGU | 866 | ACUGGUUGGGGUCUUCUGU | [891-909](19/19) |
| 364 | AGGAUUCCUUCAGCAGCAU | 867 | AUGCUGCUGAAGGAAUCCU | [865-883](19/19) |
| 365 | AAUGGAAAAGAAGUAGGU | 868 | ACCUACUUCUUUUUCCAUU | [815-833](19/19) |
| 366 | AUGACAAGCUGGUUGAGAC | 869 | GUCUCAACCAGCUUGUCAU | [724-742](19/19) |
| 367 | UUGAGCAAGUUUGGGAGGA | 870 | UCCUCCCAAACUUGCUCAA | [664-682](19/19) |
| 368 | CUGAAACUUCUGUUGCUCA | 871 | UGAGCAACAGAAGUUUCAG | [607-625](19/19) |
| 369 | UCACCUGAAACUUCUGUUG | 872 | CAACAGAAGUUUCAGGUGA | [603-621](19/19) |
| 370 | UUGACAUACUUUGGAGGCA | 873 | UGCCUCCAAAGUAUGUCAA | [172-190](19/19) |
| 371 | UGAUUGACAUACUUUGGAG | 874 | CUCCAAAGUAUGUCAAUCA | [169-187](19/19) |
| 372 | AGGUUUCUUCGGCUACGUU | 875 | AACGUAGCCGAAGAAACCU | [514-532](19/19) |
| 373 | AUGGAUUUGAUUGACAUAC | 876 | GUAUGUCAAUCAAAUCCAU | [162-180](19/19) |
| 374 | ACAUGGAUUUGAUUGACAU | 877 | AUGUCAAUCAAAUCCAUGU | [160-178](19/19) |
| 375 | UUCUCCCAAUUCAGCCAGC | 878 | GCUGGCUGAAUUGGGAGAA | [361-379](19/19) |
| 376 | AAGAGACAGGUGAAUUUCU | 879 | AGAAAUUCACCUGUCUCUU | [346-364](19/19) |
| 377 | GAUGAAGAGACAGGUGAAU | 880 | AUUCACCUGUCUCUUCAUC | [342-360](19/19) |
| 378 | AACUAGAUGAAGAGACAGG | 881 | CCUGUCUCUUCAUCUAGUU | [337-355](19/19) |
| 379 | UUGCAAAACUAACCACUAU | 882 | AUAGUGGUUAGUUUUGCAA | [2268-2286](19/19) |
| 380 | UGACAUCUGGCUAAAAAGA | 883 | UCUUUUUAGCCAGAUGUCA | [2244-2262](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 381 | GAGUGUCAGUAUGUUGAAU | 884 | AUUCAACAUACUGACACUC | [2089-2107](19/19) |
| 382 | AAGCAUUGGAGUGUCAGUA | 885 | UACUGACACUCCAAUGCUU | [2081-2099](19/19) |
| 383 | GCUCCUACUGUGAUGUGAA | 886 | UUCACAUCACAGUAGGAGC | [1987-2005](19/19) |
| 384 | GACCUUUUCUGAGCUAGUU | 887 | AACUAGCUCAGAAAAGGUC | [1946-1964](19/19) |
| 385 | UGACCUUUUCUGAGCUAGU | 888 | ACUAGCUCAGAAAAGGUCA | [1945-1963](19/19) |
| 386 | UCAUGAUGGACUUGGAGCU | 889 | AGCUCCAAGUCCAUCAUGA | [112-130](19/19) |
| 387 | CCUUAUAUCUCGAAGUUUU | 890 | AAAACUUCGAGAUAUAAGG | [1789-1807](19/19) |
| 388 | CUCAGCACCUUAUAUCUCG | 891 | CGAGAUAUAAGGUGCUGAG | [1782-1800](19/19) |
| 389 | GACAAGAACAACUCCAAAA | 892 | UUUUGGAGUUGUUCUUGUC | [286-304](19/19) |
| 390 | UCGGGAUAUACGUAGGAGG | 893 | CCUCCUACGUAUAUCCCGA | [1607-1625](19/19) |
| 391 | UAAUUCGGGAUAUACGUAG | 894 | CUACGUAUAUCCCGAAUUA | [1603-1621](19/19) |
| 392 | GAAAUGAUGUCCAAAGAGC | 895 | GCUCUUUGGACAUCAUUUC | [1560-1578](19/19) |
| 393 | AACGAAAUGAUGUCCAAAG | 896 | CUUUGGACAUCAUUUCGUU | [1557-1575](19/19) |
| 394 | GAAAAAUCAUUAACCUCC | 897 | GGAGGUUAAUGAUUUUUC | [1524-1542](19/19) |
| 395 | AGCUCUCCAUAUCCCAUUC | 898 | GAAUGGGAUAUGGAGAGCU | [1499-1517](19/19) |
| 396 | GCAAAGCUCUCCAUAUCC | 899 | GGAUAUGGAGAGCUUUUGC | [1494-1512](19/19) |
| 397 | AAGAGAUGAACUUAGGGCA | 900 | UGCCCUAAGUUCAUCUCUU | [1478-1496](19/19) |
| 398 | CUGGAAAAACAGAAAAAAC | 901 | GUUUUUUCUGUUUUUCCAG | [255-273](19/19) |
| 399 | GAGCUGGAAAACAGAAAA | 902 | UUUUCUGUUUUUCCAGCUC | [252-270](19/19) |
| 400 | CCCCUGGAAGUGUCAAACA | 903 | UGUUUGACACUUCCAGGGG | [1264-1282](19/19) |
| 401 | AUUCUGAAGUGGAAGAGCU | 904 | AGCUCUUCCACUUCAGAAU | [1237-1255](19/19) |
| 402 | CAUCACCAGAACACUCAGU | 905 | ACUGAGUGUUCUGGUGAUG | [1177-1195](19/19) |
| 403 | CUGAUCUAUCACUUUGCAA | 906 | UUGCAAAGUGAUAGAUCAG | [1072-1090](19/19) |
| 404 | UCUGAUCUAUCACUUUGCA | 907 | UGCAAAGUGAUAGAUCAGA | [1071-1089](19/19) |
| 405 | UUCUGAUCUAUCACUUUGC | 908 | GCAAAGUGAUAGAUCAGAA | [1070-1088](19/19) |
| 406 | GAGCCCAGUAUCAGCAACA | 909 | UGUUGCUGAUACUGGGCUC | [987-1005](19/19) |
| 407 | GAAGUAGGUAACUGUAGUC | 910 | GACUACAGUUACCUACUUC | [825-843](19/19) |
| 408 | AGAAGUAGGUAACUGUAGU | 911 | ACUACAGUUACCUACUUCU | [824-842](19/19) |
| 409 | AAAAGAAGUAGGUAACUGU | 912 | ACAGUUACCUACUUCUUUU | [821-839](19/19) |
| 410 | GCAACAGGACAUUGAGCAA | 913 | UUGCUCAAUGUCCUGUUGC | [653-671](19/19) |
| 411 | CACUUGUUCCUGAUAUUCC | 914 | GGAAUAUCAGGAACAAGUG | [538-556](19/19) |
| 412 | GCAGGACAUGGAUUUGAUU | 915 | AAUCAAAUCCAUGUCCUGC | [155-173](19/19) |
| 413 | GUUUCUGUGUAAGUGUAAA | 916 | UUUACACUUACACAGAAAC | [2159-2177](19/19) |
| 414 | GCAUUGGAGUGUCAGUAUG | 917 | CAUACUGACACUCCAAUGC | [2083-2101](19/19) |
| 415 | UGUGAUGUGAAAUGCUCAU | 918 | AUGAGCAUUUCACAUCACA | [1995-2013](19/19) |
| 416 | ACUAGAUUUAGGAGGAUUU | 919 | AAAUCCUCCUAAAUCUAGU | [1927-1945](19/19) |
| 417 | CUCGAAGUUUUCAGCAUGC | 920 | GCAUGCUGAAAACUUCGAG | [1797-1815](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 418 | AUCUCGAAGUUUUCAGCAU | 921 | AUGCUGAAAACUUCGAGAU | [1795-1813](19/19) |
| 419 | GCAGAAAAGAAAACUGGA | 922 | UCCAGUUUUCUUUUUCUGC | [1654-1672](19/19) |
| 420 | GGAUAUACGUAGGAGGGGU | 923 | ACCCCUCCUACGUAUAUCC | [1610-1628](19/19) |
| 421 | AAGACAAGAACAACUCCAA | 924 | UUGGAGUUGUUCUUGUCUU | [284-302](19/19) |
| 422 | AAAGAGCAGUUCAAUGAAG | 925 | CUUCAUUGAACUGCUCUUU | [1572-1590](19/19) |
| 423 | UCAACGAAAUGAUGUCCAA | 926 | UUGGACAUCAUUUCGUUGA | [1555-1573](19/19) |
| 424 | UAACCUCCCUGUUGUUGAC | 927 | GUCAACAACAGGGAGGUUA | [1535-1553](19/19) |
| 425 | CAAAAGCUCUCCAUAUCCC | 928 | GGGAUAUGGAGAGCUUUUG | [1495-1513](19/19) |
| 426 | AGAUGAACUUAGGGCAAAA | 929 | UUUUGCCCUAAGUUCAUCU | [1481-1499](19/19) |
| 427 | AGAGAUGAACUUAGGGCAA | 930 | UUGCCCUAAGUUCAUCUCU | [1479-1497](19/19) |
| 428 | AGCUGGAAAAACAGAAAAA | 931 | UUUUUCUGUUUUUCCAGCU | [253-271](19/19) |
| 429 | UCCUAAAACACCAGUACAU | 932 | AUGUACUGGUGUUUUAGGA | [1289-1307](19/19) |
| 430 | UGAUGUUUCUGAUCUAUCA | 933 | UGAUAGAUCAGAAACAUCA | [1064-1082](19/19) |
| 431 | CCAUUGAUGUUUCUGAUCU | 934 | AGAUCAGAAACAUCAAUGG | [1060-1078](19/19) |
| 432 | AGUAUGUUGAAUCAGUAGU | 935 | ACUACUGAUUCAACAUACU | [2096-2114](19/19) |
| 433 | UUCUGAGCUAGUUUUUUUG | 936 | CAAAAAACUAGCUCAGAA | [1952-1970](19/19) |
| 434 | UCGAAGUUUUCAGCAUGCU | 937 | AGCAUGCUGAAAACUUCGA | [1798-1816](19/19) |
| 435 | AUUCGGGAUAUACGUAGGA | 938 | UCCUACGUAUAUCCCGAAU | [1605-1623](19/19) |
| 436 | UGUCCAAAGAGCAGUUCAA | 939 | UUGAACUGCUCUUUGGACA | [1567-1585](19/19) |
| 437 | UUCUGGGGAUAUGGUACAA | 940 | UUGUACCAUAUCCCCAGAA | [1310-1328](19/19) |
| 438 | CUUCUGGGGAUAUGGUACA | 941 | UGUACCAUAUCCCCAGAAG | [1309-1327](19/19) |
| 439 | UGUUUCUGAUCUAUCACUU | 942 | AAGUGAUAGAUCAGAAACA | [1067-1085](19/19) |
| 440 | ACCUGCUACUUUAAGCCAU | 943 | AUGGCUUAAAGUAGCAGGU | [1016-1034](19/19) |
| 441 | GUUUCAGUCACUUGUUCCU | 944 | AGGAACAAGUGACUGAAAC | [530-548](19/19) |
| 442 | CACAUCCAGUCAGAAACCA | 945 | UGGUUUCUGACUGGAUGUG | [384-402](19/19) |
| 443 | CUGGUACUAAUAAAGGAUU | 946 | AAUCCUUUAUUAGUACCAG | [2375-2393](19/19) |
| 444 | AGUGUCAGUAUGUUGAAUC | 947 | GAUUCAACAUACUGACACU | [2090-2108](19/19) |
| 445 | AAACUAGAUUUAGGAGGAU | 948 | AUCCUCCUAAAUCUAGUUU | [1925-1943](19/19) |
| 446 | AAAACUAGAUUUAGGAGGA | 949 | UCCUCCUAAAUCUAGUUUU | [1924-1942](19/19) |
| 447 | AGCUCAACUUGCAUUAAUU | 950 | AAUUAAUGCAAGUUGAGCU | [1589-1607](19/19) |
| 448 | AAGAGCAGUUCAAUGAAGC | 951 | GCUUCAUUGAACUGCUCUU | [1573-1591](19/19) |
| 449 | UGAUGUCCAAAGAGCAGUU | 952 | AACUGCUCUUUGGACAUCA | [1564-1582](19/19) |
| 450 | GAAAACCCCAUUCACAAAA | 953 | UUUUGUGAAUGGGGUUUUC | [1424-1442](19/19) |
| 451 | UGAGCUGGAAAAACAGAAA | 954 | UUUCUGUUUUUCCAGCUCA | [251-269](19/19) |
| 452 | UUGAUGUUUCUGAUCUAUC | 955 | GAUAGAUCAGAAACAUCAA | [1063-1081](19/19) |
| 453 | UUGCCCACAUUCCCAAAUC | 956 | GAUUUGGGAAUGUGGGCAA | [427-445](19/19) |
| 454 | GCACAUCCAGUCAGAAACC | 957 | GGUUUCUGACUGGAUGUGC | [383-401](19/19) |
| 455 | GCUGGUACUAAUAAAGGAU | 958 | AUCCUUUAUUAGUACCAGC | [2374-2392](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 456 | GGAGUGUCAGUAUGUUGAA | 959 | UUCAACAUACUGACACUCC | [2088-2106](19/19) |
| 457 | CCUUUUCUGAGCUAGUUUU | 960 | AAAACUAGCUCAGAAAAGG | [1948-1966](19/19) |
| 458 | CUCAAAGAAAAGGAGAAA | 961 | UUUCUCCUUUUUCUUUGAG | [1731-1749](19/19) |
| 459 | AGACAAGAACAACUCCAAA | 962 | UUUGGAGUUGUUCUUGUCU | [285-303](19/19) |
| 460 | AUGAUGUCCAAAGAGCAGU | 963 | ACUGCUCUUUGGACAUCAU | [1563-1581](19/19) |
| 461 | AUGAGCUGGAAAAACAGAA | 964 | UUCUGUUUUUCCAGCUCAU | [250-268](19/19) |
| 462 | GUCCUAAAACACCAGUACA | 965 | UGUACUGGUGUUUUAGGAC | [1288-1306](19/19) |
| 463 | AUCAGCAACAGCAUGCCCU | 966 | AGGGCAUGCUGUUGCUGAU | [996-1014](19/19) |
| 464 | AAGCCAAACUGACAGAAGU | 967 | ACUUCUGUCAGUUUGGCUU | [763-781](19/19) |
| 465 | CGUUUGUAGAUGACAAUGA | 968 | UCAUUGUCAUCUACAAACG | [496-514](19/19) |
| 466 | GUUGCCCACAUUCCCAAAU | 969 | AUUUGGGAAUGUGGGCAAC | [426-444](19/19) |
| 467 | GCAAACAAGAGAUGGCAAU | 970 | AUUGCCAUCUCUUGUUUGC | [1865-1883](19/19) |
| 468 | AUUGCUCAAAGAAAAAGGA | 971 | UCCUUUUUCUUUGAGCAAU | [1727-1745](19/19) |
| 469 | AAACCCCAUUCACAAAAGA | 972 | UCUUUUGUGAAUGGGGUUU | [1426-1444](19/19) |
| 470 | AAGUGGAAGAGCUAGAUAG | 973 | CUAUCUAGCUCUUCCACUU | [1243-1261](19/19) |
| 471 | UCACUAAACACAAGUCCCA | 974 | UGGGACUUGUGUUUAGUGA | [1152-1170](19/19) |
| 472 | CGGCAUUUCACUAAACACA | 975 | UGUGUUUAGUGAAAUGCCG | [1145-1163](19/19) |
| 473 | UUUAAGCCAUUCACUCUCU | 976 | AGAGAGUGAAUGGCUUAAA | [1025-1043](19/19) |
| 474 | CACCUGCUACUUUAAGCCA | 977 | UGGCUUAAAGUAGCAGGUG | [1015-1033](19/19) |
| 475 | GGAGGAGCUAUUAUCCAUU | 978 | AAUGGAUAAUAGCUCCUCC | [677-695](19/19) |
| 476 | GGGAGGAGCUAUUAUCCAU | 979 | AUGGAUAAUAGCUCCUCCC | [676-694](19/19) |
| 477 | UCGCUCAGUUACAACUAGA | 980 | UCUAGUUGUAACUGAGCGA | [325-343](19/19) |
| 478 | UGAAGAUGGAAAACCUUAU | 981 | AUAAGGUUUUCCAUCUUCA | [1823-1841](19/19) |
| 479 | AAGCUCAACUUGCAUUAAU | 982 | AUUAAUGCAAGUUGAGCUU | [1588-1606](19/19) |
| 480 | AAAACCCCAUUCACAAAAG | 983 | CUUUUGUGAAUGGGGUUUU | [1425-1443](19/19) |
| 481 | GCUAUGGAGACACACUACU | 984 | AGUAGUGUGUCUCCAUAGC | [1207-1225](19/19) |
| 482 | GUAUUUGACUUCAGUCAGC | 985 | GCUGACUGAAGUCAAAUAC | [219-237](19/19) |
| 483 | CCUGCUACUUUAAGCCAUU | 986 | AAUGGCUUAAAGUAGCAGG | [1017-1035](19/19) |
| 484 | UGAGCCCAGUAUCAGCAAC | 987 | GUUGCUGAUACUGGGCUCA | [986-1004](19/19) |
| 485 | GAGAAGUAUUUGACUUCAG | 988 | CUGAAGUCAAAUACUUCUC | [214-232](19/19) |
| 486 | UGGAAAAGAAGUAGGUAA | 989 | UUACCUACUUCUUUUUCCA | [817-835](19/19) |
| 487 | GAAGCCAAACUGACAGAAG | 990 | CUUCUGUCAGUUUGGCUUC | [762-780](19/19) |
| 488 | CAGAAGCCAAACUGACAGA | 991 | UCUGUCAGUUUGGCUUCUG | [760-778](19/19) |
| 489 | GAAAAUGACAAGCUGGUUG | 992 | CAACCAGCUUGUCAUUUUC | [720-738](19/19) |
| 490 | AAAAGCAUUGGAGUGUCA | 993 | UGACACUCCAAUGCUUUUU | [2078-2096](19/19) |
| 491 | UAGGAGGAUUUGACCUUUU | 994 | AAAAGGUCAAAUCCUCCUA | [1935-1953](19/19) |
| 492 | AGAUGGAAAACCUUAUUCU | 995 | AGAAUAAGGUUUUCCAUCU | [1826-1844](19/19) |

TABLE A-continued 19-mers siRNAs specific to Nrf2 (SEQ ID NOS: 1-1006)

| SEQ ID NO. | Sense siRNA | SEQ ID NO. | Antisense siRNA | Human-20149575 |
|---|---|---|---|---|
| 493 | GAAGCUCAACUUGCAUUAA | 996 | UUAAUGCAAGUUGAGCUUC | [1587-1605](1919) |
| 494 | GCUCUCCAUAUCCCAUUCC | 997 | GGAAUGGGAUAUGGAGAGC | [1500-1518](19/19) |
| 495 | GGAAAACCCCAUUCACAAA | 998 | UUUGUGAAUGGGGUUUUCC | [1423-1441](19/19) |
| 496 | AGAGCACUCACGUGCAUGA | 999 | UCAUGCACGUGAGUGCUCU | [1351-1369](19/19) |
| 497 | ACCCUUGUCACCAUCUCAG | 1000 | CUGAGAUGGUGACAAGGGU | [1328-1346](19/19) |
| 498 | CUACUUGGCCUCAGUGAUU | 1001 | AAUCACUGAGGCCAAGUAG | [1221-1239](19/19) |
| 499 | GUGAACUCAUUAAAUUCAG | 1002 | CUGAAUUUAAUGAGUUCAC | [915-933](19/19) |
| 500 | GGAAAAGAAGUAGGUAAC | 1003 | GUUACCUACUUCUUUUUCC | [818-836](19/19) |
| 501 | CCCUGUCGAAAAAUCAUU | 1004 | AAUGAUUUUUCGACAGGG | |
| 502 | UCCCUGUCGAAAAAUCAU | 1005 | AUGAUUUUUCGACAGGGA | |
| 503 | CCUGUCGAAAAAUCAUUA | 1006 | UAAUGAUUUUUCGACAGG | |

TABLE B 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1007 | UAGGAGGGGUAAGAAUAAAGU | 1507 | ACUUUAUUCUUACCCCUCCUA | [1619-1639](21/21) |
| 1008 | AGGGGUAAGAAUAAAGUGGCU | 1508 | AGCCACUUUAUUCUUACCCCU | [1623-1643](21/21) |
| 1009 | AAGAAGCCAGAUGUUAAGAAA | 1509 | UUUCUUAACAUCUGGCUUCUU | [1905-1925](21/21) |
| 1010 | AAAGGAGAAAUGACAAAAGC | 1510 | GCUUUUGUCAUUUCUCCUUU | [1740-1760](21/21) |
| 1011 | GAGGGGUAAGAAUAAAGUGGC | 1511 | GCCACUUUAUUCUUACCCCUC | [1622-1642](21/21) |
| 1012 | GUAGGAGGGGUAAGAAUAAAG | 1512 | CUUUAUUCUUACCCCUCCUAC | [1618-1638](21/21) |
| 1013 | AUAAAGUGGCUGCUCAGAAUU | 1513 | AAUUCUGAGCAGCCACUUUAU | [1633-1653](21/21) |
| 1014 | AGGAGGGGUAAGAAUAAAGUG | 1514 | CACUUUAUUCUUACCCCUCCU | [1620-1640](21/21) |
| 1015 | GAGAAAGAAUUGCCUGUAAGU | 1515 | ACUUACAGGCAAUUCUUUCUC | [1392-1412](21/21) |
| 1016 | UCACUCUCUGAACUUCUAAAU | 1516 | AUUUAGAAGUUCAGAGAGUGA | [1035-1055](21/21) |
| 1017 | GACAUUCCCGUUUGUAGAUGA | 1517 | UCAUCUACAAACGGGAAUGUC | [488-508](21/21) |
| 1018 | AGAAGCCAGAUGUUAAGAAAA | 1518 | UUUUCUUAACAUCUGGCUUCU | [1906-1926](21/21) |
| 1019 | CUCAGAAUUGCAGAAAAAGAA | 1519 | UUCUUUUUCUGCAAUUCUGAG | [1645-1665](21/21) |
| 1020 | AAGAAUAAAGUGGCUGCUCAG | 1520 | CUGAGCAGCCACUUUAUUCUU | [1629-1649](21/21) |
| 1021 | GGGUAAGAAUAAAGUGGCUGC | 1521 | GCAGCCACUUUAUUCUUACCC | [1625-1645](21/21) |
| 1022 | UGAAAAGGAAAGACAAGAACA | 1522 | UGUUCUUGUCUUUCCUUUUCA | [275-295](21/21) |
| 1023 | GCCCUCACCUGCUACUUUAAG | 1523 | CUUAAAGUAGCAGGUGAGGGC | [1010-1030](21/21) |
| 1024 | GUAGAUGACAAUGAGGUUUCU | 1524 | AGAAACCUCAUUGUCAUCUAC | [501-521](21/21) |
| 1025 | GUAAGAAGCCAGAUGUUAAGA | 1525 | UCUUAACAUCUGGCUUCUUAC | [1903-1923](21/21) |
| 1026 | AAGUAAGAAGCCAGAUGUUAA | 1526 | UUAACAUCUGGCUUCUUACUU | [1901-1921](21/21) |
| 1027 | GGGGUAAGAAUAAAGUGGCUG | 1527 | CAGCCACUUUAUUCUUACCCC | [1624-1644](21/21) |
| 1028 | AGAGAAAGAAUUGCCUGUAAG | 1528 | CUUACAGGCAAUUCUUUCUCU | [1391-1411](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1029 | CUCUCUGAACUUCUAAAUGGG | 1529 | CCCAUUUAGAAGUUCAGAGAG | [1038-1058](21/21) |
| 1030 | UUACUCAUCUAUACCCUCAAU | 1530 | AUUGAGGGUAUAGAUGAGUAA | [797-817](21/21) |
| 1031 | CCAGUCUUCAUUGCUACUAAU | 1531 | AUUAGUAGCAAUGAAGACUGG | [573-593](21/21) |
| 1032 | UAGAUGACAAUGAGGUUUCUU | 1532 | AAGAAACCUCAUUGUCAUCUA | [502-522](21/21) |
| 1033 | ACAUUCCCGUUUGUAGAUGAC | 1533 | GUCAUCUACAAACGGGAAUGU | [489-509](21/21) |
| 1034 | GCAAACUAACCACUAUGUAC | 1534 | GUACAUAGUGGUUAGUUUUGC | [2270-2290](21/21) |
| 1035 | AAAAGUAAGAAGCCAGAUGUU | 1535 | AACAUCUGGCUUCUUACUUUU | [1899-1919](21/21) |
| 1036 | CCCAAAAGUAAGAAGCCAGAU | 1536 | AUCUGGCUUCUUACUUUUGGG | [1896-1916](21/21) |
| 1037 | UUGCUCAAAGAAAAGGAGAA | 1537 | UUCUCCUUUUCUUUGAGCAA | [1728-1748](21/21) |
| 1038 | GAACUAGAGCAAGAUUUAGAU | 1538 | AUCUAAAUCUUGCUCUAGUUC | [1683-1703](21/21) |
| 1039 | GCUCAGAAUUGCAGAAAAAGA | 1539 | UCUUUUUCUGCAAUUCUGAGC | [1644-1664](21/21) |
| 1040 | UUGAAAGGAAAGACAAGAAC | 1540 | GUUCUUGUCUUUCCUUUUCAA | [274-294](21/21) |
| 1041 | AGAACACACCAGAGAAAGAAU | 1541 | AUUCUUUCUCUGGUGUGUUCU | [1381-1401](21/21) |
| 1042 | AAAACACCAGUACAUUCUUCU | 1542 | AGAAGAAUGUACUGGUGUUUU | [1293-1313](21/21) |
| 1043 | GUCAAACAGAAUGGUCCUAAA | 1543 | UUUAGGACCAUUCUGUUUGAC | [1275-1295](21/21) |
| 1044 | AACCAAAACCACCCUGAAAGC | 1544 | GCUUUCAGGGUGGUUUUGGUU | [1098-1118](21/21) |
| 1045 | UUCAACCAAAACCACCCUGAA | 1545 | UUCAGGGUGGUUUUGGUUGAA | [1095-1115](21/21) |
| 1046 | CACUCUCUGAACUUCUAAAUG | 1546 | CAUUUAGAAGUUCAGAGAGUG | [1036-1056](21/21) |
| 1047 | GAGUAAGUCGAGAAGUAUUUG | 1547 | CAAAUACUUCUCGACUUACUC | [205-225](21/21) |
| 1048 | GACAAUGAGGUUUCUUCGGCU | 1548 | AGCCGAAGAAACCUCAUUGUC | [507-527](21/21) |
| 1049 | UCAGAUGCUUUGUACUUUGAU | 1549 | AUCAAAGUACAAAGCAUCUGA | [444-464](21/21) |
| 1050 | GACAUCUGGCUAAAAGAAAU | 1550 | AUUUCUUUUAGCCAGAUGUC | [2245-2265](21/21) |
| 1051 | GAAGCCAGAUGUUAAGAAAAA | 1551 | UUUUUCUUAACAUCUGGCUUC | [1907-1927](21/21) |
| 1052 | CAAAAGUAAGAAGCCAGAUGU | 1552 | ACAUCUGGCUUCUUACUUUUG | [1898-1918](21/21) |
| 1053 | AAAACCUUAUUCUCCUAGUGA | 1553 | UCACUAGGAGAAUAAGGUUUU | [1832-1852](21/21) |
| 1054 | ACGUAGGAGGGGUAAGAAUAA | 1554 | UUAUUCUUACCCCUCCUACGU | [1616-1636](21/21) |
| 1055 | AAGGAAAGACAAGAACAACUC | 1555 | GAGUUGUUCUUGUCUUUCCUU | [279-299](21/21) |
| 1056 | CACAAAGACAAACAUUCAAG | 1556 | CUUGAAUGUUUGUCUUUUGUG | [1436-1456](21/21) |
| 1057 | CCCAUUCACAAAAGACAAACA | 1557 | UGUUUGUCUUUUGUGAAUGGG | [1430-1450](21/21) |
| 1058 | AACCCAUUCACAAAAGACAA | 1558 | UUGUCUUUUGUGAAUGGGUU | [1427-1447](21/21) |
| 1059 | ACACCAGAGAAAGAAUUGCCU | 1559 | AGGCAAUUCUUUCUCUGGUGU | [1386-1406](21/21) |
| 1060 | AACACACCAGAGAAAGAAUUG | 1560 | CAAUUCUUUCUCUGGUGUGUU | [1383-1403](21/21) |
| 1061 | UCAAACAGAAUGGUCCUAAAA | 1561 | UUUUAGGACCAUUCUGUUUGA | [1276-1296](21/21) |
| 1062 | UCAGCGACGAAAGAGUAUGA | 1562 | UCAUACUCUUUCCGUCGCUGA | [233-253](21/21) |
| 1063 | GCACAGCAGAAUUCAAUGAUU | 1563 | AAUCAUUGAAUUCUGCUGUGC | [1117-1137](21/21) |
| 1064 | GCUUUCAACCAAAACCACCCU | 1564 | AGGGUGGUUUUGGUUGAAAGC | [1092-1112](21/21) |
| 1065 | GCCACAGUCAACACAGAUUUU | 1565 | AAAAUCUGUGUUGACUGUGGC | [936-956](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1066 | AACUCAUUAAAUUCAGAUGCC | 1566 | GGCAUCUGAAUUUAAUGAGUU | [918-938](21/21) |
| 1067 | GUUGACAGUGAACUCAUUAAA | 1567 | UUUAAUGAGUUCACUGUCAAC | [908-928](21/21) |
| 1068 | GCUAUUAUCCAUUCCUGAGUU | 1568 | AACUCAGGAAUGGAUAAUAGC | [683-703](21/21) |
| 1069 | AAGUUUGGGAGGAGCUAUUAU | 1569 | AUAAUAGCUCCUCCCAAACUU | [670-690](21/21) |
| 1070 | CAAGUUUGGGAGGAGCUAUUA | 1570 | UAAUAGCUCCUCCCAAACUUG | [669-689](21/21) |
| 1071 | GUCUUCAUUGCUACUAAUCAG | 1571 | CUGAUUAGUAGCAAUGAAGAC | [576-596](21/21) |
| 1072 | GAUGACAAUGAGGUUUCUUCG | 1572 | CGAAGAAACCUCAUUGUCAUC | [504-524](21/21) |
| 1073 | AUCAGAUGCUUUGUACUUUGA | 1573 | UCAAAGUACAAAGCAUCUGAU | [443-463](21/21) |
| 1074 | GCCCACAUUCCCAAAUCAGAU | 1574 | AUCUGAUUUGGGAAUGUGGGC | [429-449](21/21) |
| 1075 | GUGAUGUGAAAUGCUCAUACU | 1575 | AGUAUGAGCAUUUCACAUCAC | [1996-2016](21/21) |
| 1076 | AAGCUCCUACUGUGAUGUGAA | 1576 | UUCACAUCACAGUAGGAGCUU | [1985-2005](21/21) |
| 1077 | CUACGUGAUGAAGAUGGAAAA | 1577 | UUUUCCAUCUUCAUCACGUAG | [1815-1835](21/21) |
| 1078 | AUGCUACGUGAUGAAGAUGGA | 1578 | UCCAUCUUCAUCACGUAGCAU | [1812-1832](21/21) |
| 1079 | UGAAAAACAACUCAGCACCU | 1579 | AGGUGCUGAGUUGUUUUUUCA | [1771-1791](21/21) |
| 1080 | UCACCUACUGAAAAACAACU | 1580 | AGUUGUUUUUCAGUAGGUGA | [1763-1783](21/21) |
| 1081 | GUAGAACUAGAGCAAGAUUUA | 1581 | UAAAUCUUGCUCUAGUUCUAC | [1680-1700](21/21) |
| 1082 | UCAACUUGCAUUAAUUCGGGA | 1582 | UCCCGAAUUAAUGCAAGUUGA | [1592-1612](21/21) |
| 1083 | AAAGGAAAGACAAGAACAACU | 1583 | AGUUGUUCUUGUCUUUCCUUU | [278-298](21/21) |
| 1084 | CCAUUCACAAAAGACAAACAU | 1584 | AUGUUUGUCUUUUGUGAAUGG | [1431-1451](21/21) |
| 1085 | CACACCAGAGAAAGAAUUGCC | 1585 | GGCAAUUCUUUCUCUGGUGUG | [1385-1405](21/21) |
| 1086 | AACAGAAUGGUCCUAAAACAC | 1586 | GUGUUUUAGGACCAUUCUGUU | [1279-1299](21/21) |
| 1087 | GGAAAGAGUAUGAGCUGGAAA | 1587 | UUUCCAGCUCAUACUCUUUCC | [241-261](21/21) |
| 1088 | CAGUUGACAGUGAACUCAUUA | 1588 | UAAUGAGUUCACUGUCAACUG | [906-926](21/21) |
| 1089 | GGAGUAAGUCGAGAAGUAUUU | 1589 | AAAUACUUCUCGACUUACUCC | [204-224](21/21) |
| 1090 | UGGAGUAAGUCGAGAAGUAUU | 1590 | AAUACUUCUCGACUUACUCCA | [203-223](21/21) |
| 1091 | UUGGAGUAAGUCGAGAAGUAU | 1591 | AUACUUCUCGACUUACUCCAA | [202-222](21/21) |
| 1092 | CUAUUAUCCAUUCCUGAGUUA | 1592 | UAACUCAGGAAUGGAUAAUAG | [684-704](21/21) |
| 1093 | GCAACAGGACAUUGAGCAAGU | 1593 | ACUUGCUCAAUGUCCUGUUGC | [653-673](21/21) |
| 1094 | GUUGAUUUAGACGGUAUGCAA | 1594 | UUGCAUACCGUCUAAAUCAAC | [636-656](21/21) |
| 1095 | CAGUCUUCAUUGCUACUAAUC | 1595 | GAUUAGUAGCAAUGAAGACUG | [574-594](21/21) |
| 1096 | UCACAUCGAGAGCCCAGUCUU | 1596 | AAGACUGGGCUCUCGAUGUGA | [560-580](21/21) |
| 1097 | AGGACAUGGAUUUGAUUGACA | 1597 | UGUCAAUCAAAUCCAUGUCCU | [157-177](21/21) |
| 1098 | UGCCCACAUUCCCAAAUCAGA | 1598 | UCUGAUUUGGGAAUGUGGGCA | [428-448](21/21) |
| 1099 | UACUCCCAGGUUGCCCACAUU | 1599 | AAUGUGGGCAACCUGGGAGUA | [417-437](21/21) |
| 1100 | AAGAGCUGGUACUAAUAAAGG | 1600 | CCUUUAUUAGUACCAGCUCUU | [2370-2390](21/21) |
| 1101 | UAAGAGCUGGUACUAAUAAAG | 1601 | CUUUAUUAGUACCAGCUCUUA | [2369-2389](21/21) |
| 1102 | CUGUAUGGACAAAAAUGGCA | 1602 | UGCCAUUUUUGUCCAUACAG | [2304-2324](21/21) |
| 1103 | GGAUUUGACCUUUUCUGAGCU | 1603 | AGCUCAGAAAAGGUCAAAUCC | [1940-1960](21/21) |

TABLE B-continued

21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1104 | AAACCUUAUUCUCCUAGUGAA | 1604 | UUCACUAGGAGAAUAAGGUUU | [1833-1853](21/21) |
| 1105 | AAAAAACAACUCAGCACCUUA | 1605 | UAAGGUGCUGAGUUGUUUUUU | [1773-1793](21/21) |
| 1106 | CUAGAGCAAGAUUUAGAUCAU | 1606 | AUGAUCUAAAUCUUGCUCUAG | [1686-1706](21/21) |
| 1107 | GCAGAAAAGAAAACUGGAAA | 1607 | UUUCCAGUUUUCUUUUUCUGC | [1654-1674](21/21) |
| 1108 | AACUUGCAUUAAUUCGGAUA | 1608 | UAUCCCGAAUUAAUGCAAGUU | [1594-1614](21/21) |
| 1109 | CAACUUGCAUUAAUUCGGAU | 1609 | AUCCCGAAUUAAUGCAAGUUG | [1593-1613](21/21) |
| 1110 | CCAUAUCCCAUUCCCUGUAGA | 1610 | UCUACAGGGAAUGGGAUAUGG | [1505-1525](21/21) |
| 1111 | ACAAAGACAAACAUUCAAGC | 1611 | GCUUGAAUGUUUGUCUUUUGU | [1437-1457](21/21) |
| 1112 | ACCCCAUUCACAAAAGACAAA | 1612 | UUUGUCUUUUGUGAAUGGGGU | [1428-1448](21/21) |
| 1113 | AAGAAUUGCCUGUAAGUCCUG | 1613 | CAGGACUUACAGGCAAUUCUU | [1396-1416](21/21) |
| 1114 | AAAGAAUUGCCUGUAAGUCCU | 1614 | AGGACUUACAGGCAAUUCUUU | [1395-1415](21/21) |
| 1115 | GAACACACCAGAGAAAGAAUU | 1615 | AAUUCUUUCUCUGGUGUGUUC | [1382-1402](21/21) |
| 1116 | AGAGUAUGAGCUGGAAAAACA | 1616 | UGUUUUUCCAGCUCAUACUCU | [245-265](21/21) |
| 1117 | GUAGUCCACAUUUUCUUAAUG | 1617 | CAUUAAGAAAAUGUGGACUAC | [838-858](21/21) |
| 1118 | UACUCAUCUAUACCCUCAAUG | 1618 | CAUUGAGGGUAUAGAUGAGUA | [798-818](21/21) |
| 1119 | CAGGACAUUGAGCAAGUUUGG | 1619 | CCAAACUUGCUCAAUGUCCUG | [657-677](21/21) |
| 1120 | UUCGGCUACGUUUCAGUCACU | 1620 | AGUGACUGAAACGUAGCCGAA | [521-541](21/21) |
| 1121 | ACAAUGAGGUUUCUUCGGCUA | 1621 | UAGCCGAAGAAACCUCAUUGU | [508-528](21/21) |
| 1122 | GGACAUGGAUUUGAUUGACAU | 1622 | AUGUCAAUCAAAUCCAUGUCC | [158-178](21/21) |
| 1123 | UACUGUAUGGACAAAAAAUGG | 1623 | CCAUUUUUUGUCCAUACAGUA | [2302-2322](21/21) |
| 1124 | AACAAUUUCUUAGGACACCAU | 1624 | AUGGUGUCCUAAGAAAUUGUU | [2130-2150](21/21) |
| 1125 | CUGUAAACAAUUUCUUAGGAC | 1625 | GUCCUAAGAAAUUGUUUACAG | [2125-2145](21/21) |
| 1126 | GAAGAUGGAAAACCUUAUUCU | 1626 | AGAAUAAGGUUUUCCAUCUUC | [1824-1844](21/21) |
| 1127 | UACGUGAUGAAGAUGGAAAAC | 1627 | GUUUUCCAUCUUCAUCACGUA | [1816-1836](21/21) |
| 1128 | AGCACCUUAUAUCUCGAAGUU | 1628 | AACUUCGAGAUAUAAGGUGCU | [1785-1805](21/21) |
| 1129 | AAAACAACUCAGCACCUUAUA | 1629 | UAUAAGGUGCUGAGUUGUUUU | [1775-1795](21/21) |
| 1130 | GAGCAAGAUUUAGAUCAUUUG | 1630 | CAAAUGAUCUAAAUCUUGCUC | [1689-1709](21/21) |
| 1131 | AGAACUAGAGCAAGAUUUAGA | 1631 | UCUAAAUCUUGCUCUAGUUCU | [1682-1702](21/21) |
| 1132 | UUGCAGAAAAGAAAACUGGA | 1632 | UCCAGUUUUCUUUUUCUGCAA | [1652-1672](21/21) |
| 1133 | UCCAUAUCCCAUUCCCUGUAG | 1633 | CUACAGGGAAUGGGAUAUGGA | [1504-1524](21/21) |
| 1134 | CCCCAUUCACAAAAGACAAAC | 1634 | GUUUGUCUUUUGUGAAUGGGG | [1429-1449](21/21) |
| 1135 | GAGAACACACCAGAGAAAGAA | 1635 | UUCUUUCUCUGGUGUGUUCUC | [1380-1400](21/21) |
| 1136 | CAGUACAUUCUUCUGGGGAUA | 1636 | UAUCCCCAGAAGAAUGUACUG | [1300-1320](21/21) |
| 1137 | ACGGAAAGAGUAUGAGCUGGA | 1637 | UCCAGCUCAUACUCUUUCCGU | [239-259](21/21) |
| 1138 | CUGACUCCGGCAUUUCACUAA | 1638 | UUAGUGAAAUGCCGGAGUCAG | [1138-1158](21/21) |
| 1139 | AGCACAGCAGAAUUCAAUGAU | 1639 | AUCAUUGAAUUCUGCUGUGCU | [1116-1136](21/21) |
| 1140 | UAAAUUCAGAUGCCACAGUCA | 1640 | UGACUGUGGCAUCUGAAUUUA | [925-945](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1141 | CUCAUUAAAUUCAGAUGCCAC | 1641 | GUGGCAUCUGAAUUUAAUGAG | [920-940](21/21) |
| 1142 | ACUGUAGUCCACAUUUUCUUA | 1642 | UAAGAAAAUGUGGACUACAGU | [835-855](21/21) |
| 1143 | UCAAUGGAAAAGAAGUAGGU | 1643 | ACCUACUUCUUUUUCCAUUGA | [813-833](21/21) |
| 1144 | GAGCUAUUAUCCAUUCCUGAG | 1644 | CUCAGGAAUGGAUAAUAGCUC | [681-701](21/21) |
| 1145 | AACAGGACAUUGAGCAAGUUU | 1645 | AAACUUGCUCAAUGUCCUGUU | [655-675](21/21) |
| 1146 | UUAGACGGUAUGCAACAGGAC | 1646 | GUCCUGUUGCAUACCGUCUAA | [642-662](21/21) |
| 1147 | UUUAGACGGUAUGCAACAGGA | 1647 | UCCUGUUGCAUACCGUCUAAA | [641-661](21/21) |
| 1148 | UGAGGUUUCUUCGGCUACGUU | 1648 | AACGUAGCCGAAGAAACCUCA | [512-532](21/21) |
| 1149 | AUGAGGUUUCUUCGGCUACGU | 1649 | ACGUAGCCGAAGAAACCUCAU | [511-531](21/21) |
| 1150 | UGCUUUGUACUUUGAUGACUG | 1650 | CAGUCAUCAAAGUACAAAGCA | [449-469](21/21) |
| 1151 | AGAUGCUUUGUACUUUGAUGA | 1651 | UCAUCAAAGUACAAAGCAUCU | [446-466](21/21) |
| 1152 | CAGCAGGACAUGGAUUUGAUU | 1652 | AAUCAAAUCCAUGUCCUGCUG | [153-173](21/21) |
| 1153 | UUACAACUAGAUGAAGAGACA | 1653 | UGUCUCUUCAUCUAGUUGUAA | [333-353](21/21) |
| 1154 | AGAGCUGGUACUAAUAAGGA | 1654 | UCCUUUAUUAGUACCAGCUCU | [2371-2391](21/21) |
| 1155 | UGACAUCUGGCUAAAAAGAAA | 1655 | UUUCUUUUUAGCCAGAUGUCA | [2244-2264](21/21) |
| 1156 | CUAGUUUCUGUGUAAGUGUAA | 1656 | UUACACUUACACAGAAACUAG | [2156-2176](21/21) |
| 1157 | GGCUAGUUUCUGUGUAAGUGU | 1657 | ACACUUACACAGAAACUAGCC | [2154-2174](21/21) |
| 1158 | UGGGCUAGUUUCUGUGUAAGU | 1658 | ACUUACACAGAAACUAGCCCA | [2152-2172](21/21) |
| 1159 | AAACAAUUUCUUAGGACACCA | 1659 | UGGUGUCCUAAGAAAUUGUUU | [2129-2149](21/21) |
| 1160 | GAGUGUCAGUAUGUUGAAUCA | 1660 | UGAUUCAACAUACUGACACUC | [2089-2109](21/21) |
| 1161 | UACUAAAAGCUCCUACUGUGA | 1661 | UCACAGUAGGAGCUUUUAGUA | [1979-1999](21/21) |
| 1162 | UGCUACGUGAUGAAGAUGGAA | 1662 | UUCCAUCUUCAUCACGUAGCA | [1813-1833](21/21) |
| 1163 | GCACCUUAUAUCUCGAAGUUU | 1663 | AAACUUCGAGAUAUAAGGUGC | [1786-1806](21/21) |
| 1164 | CAGCACCUUAUAUCUCGAAGU | 1664 | ACUUCGAGAUAUAAGGUGCUG | [1784-1804](21/21) |
| 1165 | CACCUACUGAAAAAACAACUC | 1665 | GAGUUGUUUUUUCAGUAGGUG | [1764-1784](21/21) |
| 1166 | AACUAGAGCAAGAUUUAGAUC | 1666 | GAUCUAAAUCUUGCUCUAGUU | [1684-1704](21/21) |
| 1167 | UAGUAGAACUAGAGCAAGAUU | 1667 | AAUCUUGCUCUAGUUCUACUA | [1678-1698](21/21) |
| 1168 | GGGAUAUACGUAGGAGGGGUA | 1668 | UACCCCUCCUACGUAUAUCCC | [1609-1629](21/21) |
| 1169 | UGAGAACACACCAGAGAAAGA | 1669 | UCUUUCUCUGGUGUGUUCUCA | [1379-1399](21/21) |
| 1170 | AAAGAGUAUGAGCUGGAAAAA | 1670 | UUUUUCCAGCUCAUACUCUUU | [243-263](21/21) |
| 1171 | CGGAAAGAGUAUGAGCUGGAA | 1671 | UUCCAGCUCAUACUCUUUCCG | [240-260](21/21) |
| 1172 | UGCCCCUGGAAGUGUCAAACA | 1672 | UGUUUGACACUUCCAGGGGCA | [1262-1282](21/21) |
| 1173 | AUAGUGCCCCUGGAAGUGUCA | 1673 | UGACACUUCCAGGGGCACUAU | [1258-1278](21/21) |
| 1174 | AGCGACGGAAAGAGUAUGAGC | 1674 | GCUCAUACUCUUUCCGUCGCU | [235-255](21/21) |
| 1175 | CAGCGACGGAAAGAGUAUGAG | 1675 | CUCAUACUCUUUCCGUCGCUG | [234-254](21/21) |
| 1176 | GGGCCCAUUGAUGUUUCUGAU | 1676 | AUCAGAAACAUCAAUGGGCCC | [1056-1076](21/21) |
| 1177 | CUGUAGUCCACAUUUUCUUAA | 1677 | UUAAGAAAAUGUGGACUACAG | [836-856](21/21) |
| 1178 | CUCAAUGGAAAAGAAGUAGG | 1678 | CCUACUUCUUUUUCCAUUGAG | [812-832](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1179 | GAUCUUGGAGUAAGUCGAGAA | 1679 | UUCUCGACUUACUCCAAGAUC | [198-218](21/21) |
| 1180 | CUUUGGAGGCAAGAUAUAGAU | 1680 | AUCUAUAUCUUGCCUCCAAAG | [180-200](21/21) |
| 1181 | GACAUUGAGCAAGUUUGGGAG | 1681 | CUCCCAAACUUGCUCAAUGUC | [660-680](21/21) |
| 1182 | GGACAUUGAGCAAGUUUGGGA | 1682 | UCCCAAACUUGCUCAAUGUCC | [659-679](21/21) |
| 1183 | GUCACCUGAAACUUCUGUUGC | 1683 | GCAACAGAAGUUUCAGGUGAC | [602-622](21/21) |
| 1184 | GCCCAGUCUUCAUUGCUACUA | 1684 | UAGUAGCAAUGAAGACUGGGC | [571-591](21/21) |
| 1185 | UCGAGAGCCCAGUCUUCAUUG | 1685 | CAAUGAAGACUGGGCUCUCGA | [565-585](21/21) |
| 1186 | UCGGCUACGUUUCAGUCACUU | 1686 | AAGUGACUGAAACGUAGCCGA | [522-542](21/21) |
| 1187 | GAGGUUUCUUCGGCUACGUUU | 1687 | AAACGUAGCCGAAGAAACCUC | [513-533](21/21) |
| 1188 | UUGUACUUUGAUGACUGCAUG | 1688 | CAUGCAGUCAUCAAAGUACAA | [453-473](21/21) |
| 1189 | AUGCUUUGUACUUUGAUGACU | 1689 | AGUCAUCAAAGUACAAAGCAU | [448-468](21/21) |
| 1190 | GAUGCUUUGUACUUUGAUGAC | 1690 | GUCAUCAAAGUACAAAGCAUC | [447-467](21/21) |
| 1191 | CUAGAUGAAGAGACAGGUGAA | 1691 | UUCACCUGUCUCUUCAUCUAG | [339-359](21/21) |
| 1192 | GUAUGGACAAAAAAUGGCAUU | 1692 | AAUGCCAUUUUUUGUCCAUAC | [2306-2326](21/21) |
| 1193 | UGUAUGGACAAAAAAUGGCAU | 1693 | AUGCCAUUUUUUGUCCAUACA | [2305-2325](21/21) |
| 1194 | ACAAUUUCUUAGGACACCAUU | 1694 | AAUGGUGUCCUAAGAAAUUGU | [2131-2151](21/21) |
| 1195 | UGAUGUGAAAUGCUCAUACUU | 1695 | AAGUAUGAGCAUUUCACAUCA | [1997-2017](21/21) |
| 1196 | UCCUACUGUGAUGUGAAAUGC | 1696 | GCAUUUCACAUCACAGUAGGA | [1989-2009](21/21) |
| 1197 | UCCUAGUGAAUACUCCCUGCA | 1697 | UGCAGGGAGUAUUCACUAGGA | [1844-1864](21/21) |
| 1198 | ACACGGUCCACAGCUCAUCAU | 1698 | AUGAUGAGCUGUGGACCGUGU | [95-115](21/21) |
| 1199 | GAAGUGUCAAACAGAAUGGUC | 1699 | GACCAUUCUGUUUGACACUUC | [1270-1290](21/21) |
| 1200 | UGGAAGUGUCAAACAGAAUGG | 1700 | CCAUUCUGUUUGACACUUCCA | [1268-1288](21/21) |
| 1201 | GUGAUUCUGAAGUGGAAGAGC | 1701 | GCUCUUCCACUUCAGAAUCAC | [1234-1254](21/21) |
| 1202 | GAAAGCACAGCAGAAUUCAAU | 1702 | AUUGAAUUCUGCUGUGCUUUC | [1113-1133](21/21) |
| 1203 | CACAGUCAACACAGAUUUUGG | 1703 | CCAAAAUCUGUGUUGACUGUG | [938-958](21/21) |
| 1204 | CAGAAGCCAAACUGACAGAAG | 1704 | CUUCUGUCAGUUUGGCUUCUG | [760-780](21/21) |
| 1205 | ACCUGAAACUUCUGUUGCUCA | 1705 | UGAGCAACAGAAGUUUCAGGU | [605-625](21/21) |
| 1206 | UUGACAUACUUUGGAGGCAAG | 1706 | CUUGCCUCCAAAGUAUGUCAA | [172-192](21/21) |
| 1207 | UUGAUUGACAUACUUUGGAGG | 1707 | CCUCCAAAGUAUGUCAAUCAA | [168-188](21/21) |
| 1208 | GUCACUUGUUCCUGAUAUUCC | 1708 | GGAAUAUCAGGAACAAGUGAC | [536-556](21/21) |
| 1209 | GCUUUGUACUUUGAUGACUGC | 1709 | GCAGUCAUCAAAGUACAAAGC | [450-470](21/21) |
| 1210 | CAGGACAUGGAUUUGAUUGAC | 1710 | GUCAAUCAAAUCCAUGUCCUG | [156-176](21/21) |
| 1211 | CAGUUACAACUAGAUGAAGAG | 1711 | CUCUUCAUCUAGUUGUAACUG | [330-350](21/21) |
| 1212 | GAUAUGACAUCUGGCUAAAAA | 1712 | UUUUUAGCCAGAUGUCAUAUC | [2240-2260](21/21) |
| 1213 | CAGUAUGUUGAAUCAGUAGUU | 1713 | AACUACUGAUUCAACAUACUG | [2095-2115](21/21) |
| 1214 | AGCAUUGGAGUGUCAGUAUGU | 1714 | ACAUACUGACACUCCAAUGCU | [2082-2102](21/21) |
| 1215 | AAAGCAUUGGAGUGUCAGUAU | 1715 | AUACUGACACUCCAAUGCUUU | [2080-2100](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1216 | CCUACUGUGAUGUGAAAUGCU | 1716 | AGCAUUUCACAUCACAGUAGG | [1990-2010](21/21) |
| 1217 | UGACCUUUUCUGAGCUAGUUU | 1717 | AAACUAGCUCAGAAAAGGUCA | [1945-1965](21/21) |
| 1218 | GAUUUGACCUUUUCUGAGCUA | 1718 | UAGCUCAGAAAAGGUCAAAUC | [1941-1961](21/21) |
| 1219 | CAGCAUGCUACGUGAUGAAGA | 1719 | UCUUCAUCACGUAGCAUGCUG | [1808-1828](21/21) |
| 1220 | CACCUUAUAUCUCGAAGUUUU | 1720 | AAAACUUCGAGAUAUAAGGUG | [1787-1807](21/21) |
| 1221 | UCAGCACCUUAUAUCUCGAAG | 1721 | CUUCGAGAUAUAAGGUGCUGA | [1783-1803](21/21) |
| 1222 | ACUCAGCACCUUAUAUCUCGA | 1722 | UCGAGAUAUAAGGUGCUGAGU | [1781-1801](21/21) |
| 1223 | AUAGUAGAACUAGAGCAAGAU | 1723 | AUCUUGCUCUAGUUCUACUAU | [1677-1697](21/21) |
| 1224 | GGAUAUACGUAGGAGGGGUAA | 1724 | UUACCCCUCCUACGUAUAUCC | [1610-1630](21/21) |
| 1225 | AAAGCUCUCCAUAUCCCAUUC | 1725 | GAAUGGGAUAUGGAGAGCUUU | [1497-1517](21/21) |
| 1226 | GCAAAAGCUCUCCAUAUCCCA | 1726 | UGGGAUAUGGAGAGCUUUUGC | [1494-1514](21/21) |
| 1227 | AGAGAUGAACUUAGGGCAAAA | 1727 | UUUUGCCCUAAGUUCAUCUCU | [1479-1499](21/21) |
| 1228 | CAAGAGAUGAACUUAGGGCAA | 1728 | UUGCCCUAAGUUCAUCUCUUG | [1477-1497](21/21) |
| 1229 | UCACAAGAGAUGAACUUAGGG | 1729 | CCCUAAGUUCAUCUCUUGUGA | [1474-1494](21/21) |
| 1230 | GGAAGUGUCAAACAGAAUGGU | 1730 | ACCAUUCUGUUUGACACUUCC | [1269-1289](21/21) |
| 1231 | CCUGGAAGUGUCAAACAGAAU | 1731 | AUUCUGUUUGACACUUCCAGG | [1266-1286](21/21) |
| 1232 | GAUUCUGAAGUGGAAGAGCUA | 1732 | UAGCUCUUCCACUUCAGAAUC | [1236-1256](21/21) |
| 1233 | GCGACGGAAAGAGUAUGAGCU | 1733 | AGCUCAUACUCUUUCCGUCGC | [236-256](21/21) |
| 1234 | UUCUGAUCUAUCACUUUGCAA | 1734 | UUGCAAAGUGAUAGAUCAGAA | [1070-1090](21/21) |
| 1235 | AUCUUGGAGUAAGUCGAGAAG | 1735 | CUUCUCGACUUACUCCAAGAU | [199-219](21/21) |
| 1236 | CAACAGGACAUUGAGCAAGUU | 1736 | AACUUGCUCAAUGUCCUGUUG | [654-674](21/21) |
| 1237 | UCACCUGAAACUUCUGUUGCU | 1737 | AGCAACAGAAGUUUCAGGUGA | [603-623](21/21) |
| 1238 | AUCGAGAGCCCAGUCUUCAUU | 1738 | AAUGAAGACUGGGCUCUCGAU | [564-584](21/21) |
| 1239 | UACGUUUCAGUCACUUGUUCC | 1739 | GGAACAAGUGACUGAAACGUA | [527-547](21/21) |
| 1240 | GCUACGUUUCAGUCACUUGUU | 1740 | AACAAGUGACUGAAACGUAGC | [525-545](21/21) |
| 1241 | GGCUACGUUUCAGUCACUUGU | 1741 | ACAAGUGACUGAAACGUAGCC | [524-544](21/21) |
| 1242 | CGGCUACGUUUCAGUCACUUG | 1742 | CAAGUGACUGAAACGUAGCCG | [523-543](21/21) |
| 1243 | UUUCUUCGGCUACGUUUCAGU | 1743 | ACUGAAACGUAGCCGAAGAAA | [517-537](21/21) |
| 1244 | GACAUGGAUUUGAUUGACAUA | 1744 | UAUGUCAAUCAAAUCCAUGUC | [159-179](21/21) |
| 1245 | AUAUGACAUCUGGCUAAAAAG | 1745 | CUUUUUAGCCAGAUGUCAUAU | [2241-2261](21/21) |
| 1246 | UUGGGCUAGUUUCUGUGUAAG | 1746 | CUUACACAGAAACUAGCCCAA | [2151-2171](21/21) |
| 1247 | GUCAGUAUGUUGAAUCAGUAG | 1747 | CUACUGAUUCAACAUACUGAC | [2093-2113](21/21) |
| 1248 | UGUCAGUAUGUUGAAUCAGUA | 1748 | UACUGAUUCAACAUACUGACA | [2092-2112](21/21) |
| 1249 | GUGUCAGUAUGUUGAAUCAGU | 1749 | ACUGAUUCAACAUACUGACAC | [2091-2111](21/21) |
| 1250 | UUGGAGUGUCAGUAUGUUGAA | 1750 | UUCAACAUACUGACACUCCAA | [2086-2106](21/21) |
| 1251 | UACUGUGAUGUGAAAUGCUCA | 1751 | UGAGCAUUUCACAUCACAGUA | [1992-2012](21/21) |
| 1252 | ACCUUUUCUGAGCUAGUUUUU | 1752 | AAAAACUAGCUCAGAAAAGGU | [1947-1967](21/21) |
| 1253 | UUUGACCUUUUCUGAGCUAGU | 1753 | ACUAGCUCAGAAAAGGUCAAA | [1943-1963](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1254 | UGCAGCAAACAAGAGAUGGCA | 1754 | UGCCAUCUCUUGUUUGCUGCA | [1861-1881](21/21) |
| 1255 | CUCCUAGUGAAUACUCCCUGC | 1755 | GCAGGGAGUAUUCACUAGGAG | [1843-1863](21/21) |
| 1256 | GCAUGCUACGUGAUGAAGAUG | 1756 | CAUCUUCAUCACGUAGCAUGC | [1810-1830](21/21) |
| 1257 | ACCUUAUAUCUCGAAGUUUUC | 1757 | GAAAACUUCGAGAUAUAAGGU | [1788-1808](21/21) |
| 1258 | UUAAUUCGGGAUAUACGUAGG | 1758 | CCUACGUAUAUCCCGAAUUAA | [1602-1622](21/21) |
| 1259 | CAACGAAAUGAUGUCCAAAGA | 1759 | UCUUUGGACAUCAUUUCGUUG | [1556-1576](21/21) |
| 1260 | AACCUCCCUGUUGUUGACUUC | 1760 | GAAGUCAACAACAGGGAGGUU | [1536-1556](21/21) |
| 1261 | GAGAUGAACUUAGGGCAAAAG | 1761 | CUUUUGCCCUAAGUUCAUCUC | [1480-1500](21/21) |
| 1262 | ACAAGAGAUGAACUUAGGGCA | 1762 | UGCCCUAAGUUCAUCUCUUGU | [1476-1496](21/21) |
| 1263 | AAAGCACAGCAGAAUUCAAUG | 1763 | CAUUGAAUUCUGCUGUGCUUU | [1114-1134](21/21) |
| 1264 | GAUGUUUCUGAUCUAUCACUU | 1764 | AAGUGAUAGAUCAGAAACAUC | [1065-1085](21/21) |
| 1265 | ACAGUCAACACAGAUUUUGGU | 1765 | ACCAAAAUCUGUGUUGACUGU | [939-959](21/21) |
| 1266 | UGAGGAUUCCUUCAGCAGCAU | 1766 | AUGCUGCUGAAGGAAUCCUCA | [863-883](21/21) |
| 1267 | UGACAUACUUUGGAGGCAAGA | 1767 | UCUUGCCUCCAAAGUAUGUCA | [173-193](21/21) |
| 1268 | CAUGGAUUUGAUUGACAUACU | 1768 | AGUAUGUCAAUCAAAUCCAUG | [161-181](21/21) |
| 1269 | GCAGGACAUGGAUUUGAUUGA | 1769 | UCAAUCAAAUCCAUGUCCUGC | [155-175](21/21) |
| 1270 | AUGAAGAGACAGGUGAAUUUC | 1770 | GAAAUUCACCUGUCUCUUCAU | [343-363](21/21) |
| 1271 | AGAUGAAGAGACAGGUGAAUU | 1771 | AAUUCACCUGUCUCUUCAUCU | [341-361](21/21) |
| 1272 | UUGCAAAACUAACCACUAUGU | 1772 | ACAUAGUGGUUAGUUUUGCAA | [2268-2288](21/21) |
| 1273 | AUGACAUCUGGCUAAAAGAA | 1773 | UUCUUUUAGCCAGAUGUCAU | [2243-2263](21/21) |
| 1274 | GGGCUAGUUUCUGUGUAAGUG | 1774 | CACUUACACAGAAACUAGCCC | [2153-2173](21/21) |
| 1275 | UUUGGGCUAGUUUCUGUGUAA | 1775 | UUACACAGAAACUAGCCCAAA | [2150-2170](21/21) |
| 1276 | GGAGUGUCAGUAUGUUGAAUC | 1776 | GAUUCAACAUACUGACACUCC | [2088-2108](21/21) |
| 1277 | UGUGAUGUGAAAUGCUCAUAC | 1777 | GUAUGAGCAUUUCACAUCACA | [1995-2015](21/21) |
| 1278 | CUCAGCACCUUAUAUCUCGAA | 1778 | UUCGAGAUAUAAGGUGCUGAG | [1782-1802](21/21) |
| 1279 | UAAUUCGGGAUAUACGUAGGA | 1779 | UCCUACGUAUAUCCCGAAUUA | [1603-1623](21/21) |
| 1280 | AAAGACAAGAACAACUCCAAA | 1780 | UUUGGAGUUGUUCUUGUCUUU | [283-303](21/21) |
| 1281 | GAAAGACAAGAACAACUCCAA | 1781 | UUGGAGUUGUUCUUGUCUUUC | [282-302](21/21) |
| 1282 | CGAAAUGAUGUCCAAAGAGCA | 1782 | UGCUCUUUGGACAUCAUUUCG | [1559-1579](21/21) |
| 1283 | AACGAAAUGAUGUCCAAAGAG | 1783 | CUCUUUGGACAUCAUUUCGUU | [1557-1577](21/21) |
| 1284 | ACCUCCCUGUUGUUGACUUCA | 1784 | UGAAGUCAACAACAGGGAGGU | [1537-1557](21/21) |
| 1285 | AUCAUUAACCUCCCUGUUGUU | 1785 | AACAACAGGGAGGUUAAUGAU | [1530-1550](21/21) |
| 1286 | UUUCUGAUCUAUCACUUUGCA | 1786 | UGCAAAGUGAUAGAUCAGAAA | [1069-1089](21/21) |
| 1287 | CACUUGUCCUGAUAUUCCCG | 1787 | CGGGAAUAUCAGGAACAAGUG | [538-558](21/21) |
| 1288 | GAUUUGAUUGACAUACUUUGG | 1788 | CCAAAGUAUGUCAAUCAAAUC | [165-185](21/21) |
| 1289 | ACGUUUCAGUCACUUGUUCCU | 1789 | AGGAACAAGUGACUGAAACGU | [528-548](21/21) |
| 1290 | ACAGGUGAAUUUCUCCCAAUU | 1790 | AAUUGGGAGAAAUUCACCUGU | [351-371](21/21) |

TABLE B-continued

21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1291 | GAGCUGGUACUAAUAAAGGAU | 1791 | AUCCUUUAUUAGUACCAGCUC | [2372-2392](21/21) |
| 1292 | CUGUGAUGUGAAAUGCUCAUA | 1792 | UAUGAGCAUUUCACAUCACAG | [1994-2014](21/21) |
| 1293 | GAAAAACUAGAUUUAGGAGGA | 1793 | UCCUCCUAAAUCUAGUUUUUC | [1922-1942](21/21) |
| 1294 | GCUCAAAGAAAAGGAGAAAA | 1794 | UUUUCUCCUUUUUCUUUGAGC | [1730-1750](21/21) |
| 1295 | AGACAAGAACAACUCCAAAAG | 1795 | CUUUUGGAGUUGUUCUUGUCU | [285-305](21/21) |
| 1296 | UUCGGGAUAUACGUAGGAGGG | 1796 | CCCUCCUACGUAUAUCCCGAA | [1606-1626](21/21) |
| 1297 | AUGUCCAAAGAGCAGUUCAAU | 1797 | AUUGAACUGCUCUUUGGACAU | [1566-1586](21/21) |
| 1298 | UGAUGUCCAAAGAGCAGUUCA | 1798 | UGAACUGCUCUUUGGACAUCA | [1564-1584](21/21) |
| 1299 | GAGCUGGAAAAACAGAAAAAA | 1799 | UUUUUUCUGUUUUUCCAGCUC | [252-272](21/21) |
| 1300 | CCGGCAUUUCACUAAACACAA | 1800 | UUGUGUUUAGUGAAAUGCCGG | [1144-1164](21/21) |
| 1301 | UUGAUGUUUCUGAUCUAUCAC | 1801 | GUGAUAGAUCAGAAACAUCAA | [1063-1083](21/21) |
| 1302 | CCAUUGAUGUUUCUGAUCUAU | 1802 | AUAGAUCAGAAACAUCAAUGG | [1060-1080](21/21) |
| 1303 | CCCAUUGAUGUUUCUGAUCUA | 1803 | UAGAUCAGAAACAUCAAUGGG | [1059-1079](21/21) |
| 1304 | GGCCCAUUGAUGUUUCUGAUC | 1804 | GAUCAGAAACAUCAAUGGGCC | [1057-1077](21/21) |
| 1305 | AAGAAGUAGGUAACUGUAGUC | 1805 | GACUACAGUUACCUACUUCUU | [823-843](21/21) |
| 1306 | GACCUUUUCUGAGCUAGUUUU | 1806 | AAAACUAGCUCAGAAAAGGUC | [1946-1966](21/21) |
| 1307 | AUCUCGAAGUUUUCAGCAUGC | 1807 | GCAUGCUGAAAACUUCGAGAU | [1795-1815](21/21) |
| 1308 | AAGACAAGAACAACUCCAAAA | 1808 | UUUUGGAGUUGUUCUUGUCUU | [284-304](21/21) |
| 1309 | GAAAACCCCAUUCACAAAAGA | 1809 | UCUUUUGUGAAUGGGGUUUUC | [1424-1444](21/21) |
| 1310 | GAUAUGGUACAACCCUUGUCA | 1810 | UGACAAGGGUUGUACCAUAUC | [1317-1337](21/21) |
| 1311 | GAAGUGGAAGAGCUAGAUAGU | 1811 | ACUAUCUAGCUCUUCCACUUC | [1242-1262](21/21) |
| 1312 | GUUUCUGAUCUAUCACUUUGC | 1812 | GCAAAGUGAUAGAUCAGAAAC | [1068-1088](21/21) |
| 1313 | GCCCAUUGAUGUUUCUGAUCU | 1813 | AGAUCAGAAACAUCAAUGGGC | [1058-1078](21/21) |
| 1314 | UUGCCCACAUUCCCAAAUCAG | 1814 | CUGAUUUGGGAAUGUGGGCAA | [427-447](21/21) |
| 1315 | GUUGCCCACAUUCCCAAAUCA | 1815 | UGAUUUGGGAAUGUGGGCAAC | [426-446](21/21) |
| 1316 | GCAGCAAACAAGAGAUGGCAA | 1816 | UUGCCAUCUCUUGUUUGCUGC | [1862-1882](21/21) |
| 1317 | UGCUCAAAGAAAAGGAGAAA | 1817 | UUUCUCCUUUUUCUUUGAGCA | [1729-1749](21/21) |
| 1318 | GAAGCUCAACUUGCAUUAAUU | 1818 | AAUUAAUGCAAGUUGAGCUUC | [1587-1607](21/21) |
| 1319 | CAAAGAGCAGUUCAAUGAAGC | 1819 | GCUUCAUUGAACUGCUCUUUG | [1571-1591](21/21) |
| 1320 | GGAAAACCCCAUUCACAAAAG | 1820 | CUUUUGUGAAUGGGGUUUUCC | [1423-1443](21/21) |
| 1321 | UGAGCUGGAAAAACAGAAAAA | 1821 | UUUUUCUGUUUUUCCAGCUCA | [251-271](21/21) |
| 1322 | GCCCAGUAUCAGCAACAGCAU | 1822 | AUGCUGUUGCUGAUACUGGGC | [989-1009](21/21) |
| 1323 | UAGGUAACUGUAGUCCACAUU | 1823 | AAUGUGGACUACAGUUACCUA | [829-849](21/21) |
| 1324 | CAUUCCUGAGUUACAGUGUCU | 1824 | AGACACUGUAACUCAGGAAUG | [692-712](21/21) |
| 1325 | CCGUUUGUAGAUGACAAUGAG | 1825 | CUCAUUGUCAUCUACAAACGG | [495-515](21/21) |
| 1326 | GCUGGUACUAAUAAAGGAUUA | 1826 | UAAUCCUUUAUUAGUACCAGC | [2374-2394](21/21) |
| 1327 | AGGACACCAUUUGGGCUAGUU | 1827 | AACUAGCCCAAAUGGUGUCCU | [2141-2161](21/21) |
| 1328 | GCUCUCCAUAUCCCAUUCCCU | 1828 | AGGGAAUGGGAUAUGGAGAGC | [1500-1520](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1329 | UGGGCCCAUUGAUGUUUCUGA | 1829 | UCAGAAACAUCAAUGGGCCCA | [1055-1075](21/21) |
| 1330 | ACUUUAAGCCAUUCACUCUCU | 1830 | AGAGAGUGAAUGGCUUAAAGU | [1023-1043](21/21) |
| 1331 | CACCUGCUACUUUAAGCCAUU | 1831 | AAUGGCUUAAAGUAGCAGGUG | [1015-1035](21/21) |
| 1332 | CUCACCUGCUACUUUAAGCCA | 1832 | UGGCUUAAAGUAGCAGGUGAG | [1013-1033](21/21) |
| 1333 | UGAAAAUGACAAGCUGGUUGA | 1833 | UCAACCAGCUUGUCAUUUUCA | [719-739](21/21) |
| 1334 | AGCUGGUACUAAUAAGGAUU | 1834 | AAUCCUUUAUUAGUACCAGCU | [2373-2393](21/21) |
| 1335 | AUGCAAAAUCAUAGCCAAAAC | 1835 | GUUUUGGCUAUGAUUUUGCAU | [2031-2051](21/21) |
| 1336 | CAAACAAGAGAUGGCAAUGUU | 1836 | AACAUUGCCAUCUCUUGUUUG | [1866-1886](21/21) |
| 1337 | GAAAAUGACAAAAGCCUUCAC | 1837 | GUGAAGGCUUUUGUCAUUUUC | [1746-1766](21/21) |
| 1338 | AAAACCCCAUUCACAAAAGAC | 1838 | GUCUUUUGUGAAUGGGGUUUU | [1425-1445](21/21) |
| 1339 | AUGAGCUGGAAAAACAGAAAA | 1839 | UUUUCUGUUUUUCCAGCUCAU | [250-270](21/21) |
| 1340 | CUGAAGUGGAAGAGCUAGAUA | 1840 | UAUCUAGCUCUUCCACUUCAG | [1240-1260](21/21) |
| 1341 | ACUCCGGCAUUUCACUAAACA | 1841 | UGUUUAGUGAAAUGCCGGAGU | [1141-1161](21/21) |
| 1342 | CCAUUCACUCUCUGAACUUCU | 1842 | AGAAGUUCAGAGAGUGAAUGG | [1031-1051](21/21) |
| 1343 | AGCCAUUCACUCUCUGAACUU | 1843 | AAGUUCAGAGAGUGAAUGGCU | [1029-1049](21/21) |
| 1344 | CUGCUACUUUAAGCCAUUCAC | 1844 | GUGAAUGGCUUAAAGUAGCAG | [1018-1038](21/21) |
| 1345 | UCACCUGCUACUUUAAGCCAU | 1845 | AUGGCUUAAAGUAGCAGGUGA | [1014-1034](21/21) |
| 1346 | UGCCCUCACCUGCUACUUUAA | 1846 | UUAAAGUAGCAGGUGAGGGCA | [1009-1029](21/21) |
| 1347 | AUGCCCUCACCUGCUACUUUA | 1847 | UAAAGUAGCAGGUGAGGGCAU | [1008-1028](21/21) |
| 1348 | AUGGAAAAGAAGUAGGUAAC | 1848 | GUUACCUACUUCUUUUUCCAU | [816-836](21/21) |
| 1349 | GAAGCCAAACUGACAGAAGUU | 1849 | AACUUCUGUCAGUUUGGCUUC | [762-782](21/21) |
| 1350 | UUAAAAAGCAUUGGAGUGUCA | 1850 | UGACACUCCAAUGCUUUUUAA | [2076-2096](21/21) |
| 1351 | GGCAAUGUUUUCCUUGUUCCC | 1851 | GGGAACAAGGAAAACAUUGCC | [1878-1898](21/21) |
| 1352 | ACAACUCAGCACCUUAUAUCU | 1852 | AGAUAUAAGGUGCUGAGUUGU | [1778-1798](21/21) |
| 1353 | GGCUGCUCAGAAUUGCAGAAA | 1853 | UUUCUGCAAUUCUGAGCAGCC | [1640-1660](21/21) |
| 1354 | AGCUCUCCAUAUCCCAUUCCC | 1854 | GGGAAUGGGAUAUGGAGAGCU | [1499-1519](21/21) |
| 1355 | AAGCUCUCCAUAUCCCAUUCC | 1855 | GGAAUGGGAUAUGGAGAGCUU | [1498-1518](21/21) |
| 1356 | AAGACAAACAUUCAAGCCGCU | 1856 | AGCGGCUUGAAUGUUUGUCUU | [1441-1461](21/21) |
| 1357 | AAACCCCAUUCACAAAAGACA | 1857 | UGUCUUUUGUGAAUGGGGUUU | [1426-1446](21/21) |
| 1358 | CGGCAUUUCACUAAACACAAG | 1858 | CUUGUGUUUAGUGAAAUGCCG | [1145-1165](21/21) |
| 1359 | CCCGUUUGUAGAUGACAAUGA | 1859 | UCAUUGUCAUCUACAAACGGG | [494-514](21/21) |
| 1360 | UCCCGUUUGUAGAUGACAAUG | 1860 | CAUUGUCAUCUACAAACGGGA | [493-513](21/21) |
| 1361 | AUCUGCCAACUACUCCCAGGU | 1861 | ACCUGGGAGUAGUUGGCAGAU | [407-427](21/21) |
| 1362 | GCCAGAUGUUAAGAAAACUA | 1862 | UAGUUUUCUUAACAUCUGGC | [1910-1930](21/21) |
| 1363 | AAAUGACAAAAGCCUUCACCU | 1863 | AGGUGAAGGCUUUUGUCAUUU | [1748-1768](21/21) |
| 1364 | CUGCUCAGAAUUCCAGAAAAA | 1864 | UUUUUCUGCAAUUCUGAGCAG | [1642-1662](21/21) |
| 1365 | AAGCUCAACUUGCAUUAAUUC | 1865 | GAAUUAAUGCAAGUUGAGCUU | [1588-1608](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1366 | GUCAUCGGAAAACCCCAUUCA | 1866 | UGAAUGGGGUUUUCCGAUGAC | [1417-1437](21/21) |
| 1367 | CCCCAACCAGUUGACAGUGAA | 1867 | UUCACUGUCAACUGGUUGGGG | [899-919](21/21) |
| 1368 | GAAAAAGAAGUAGGUAACUGU | 1868 | ACAGUUACCUACUUCUUUUUC | [819-839](21/21) |
| 1369 | UGGAAAAGAAGUAGGUAACU | 1869 | AGUUACCUACUUCUUUUUCCA | [817-837](21/21) |
| 1370 | CAAGUCCAGAAGCCAAACUGA | 1870 | UCAGUUUGGCUUCUGGACUUG | [754-774](21/21) |
| 1371 | UGGGAGGAGCUAUUAUCCAUU | 1871 | AAUGGAUAAUAGCUCCUCCCA | [675-695](21/21) |
| 1372 | UGCAAAACUAACCACUAUGUA | 1872 | UACAUAGUGGUUAGUUUUGCA | [2269-2289](21/21) |
| 1373 | AUGGAAACCUUAUUCUCCUA | 1873 | UAGGAGAAUAAGGUUUUCCAU | [1828-1848](21/21) |
| 1374 | AGCCUUCACCUACUGAAAAA | 1874 | UUUUUUCAGUAGGUGAAGGCU | [1758-1778](21/21) |
| 1375 | AAGGAGAAAAUGACAAAAGCC | 1875 | GGCUUUUGUCAUUUUCUCCUU | [1741-1761](21/21) |
| 1376 | AAAGACAAACAUUCAAGCCGC | 1876 | GCGGCUUGAAUGUUUGUCUUU | [1440-1460](21/21) |
| 1377 | UAAGUCCUGGUCAUCGGAAAA | 1877 | UUUUCCGAUGACCAGGACUUA | [1408-1428](21/21) |
| 1378 | UAUGAGCUGGAAAAACAGAAA | 1878 | UUUCUGUUUUUCCAGCUCAUA | [249-269](21/21) |
| 1379 | ACAACCCUUGUCACCAUCUCA | 1879 | UGAGAUGGUGACAAGGGUUGU | [1325-1345](21/21) |
| 1380 | GUACAACCCUUGUCACCAUCU | 1880 | AGAUGGUGACAAGGGUUGUAC | [1323-1343](21/21) |
| 1381 | GACACACUACUUGGCCUCAGU | 1881 | ACUGAGGCCAAGUAGUGUGUC | [1215-1235](21/21) |
| 1382 | CUGAUCUAUCACUUUGCAAAG | 1882 | CUUUGCAAAGUGAUAGAUCAG | [1072-1092](21/21) |
| 1383 | CCUGCUACUUUAAGCCAUUCA | 1883 | UGAAUGGCUUAAAGUAGCAGG | [1017-1037](21/21) |
| 1384 | CGAGAAGUAUUUGACUUCAGU | 1884 | ACUGAAGUCAAAUACUUCUCG | [213-233](21/21) |
| 1385 | UUCCCGUUUGUAGAUGACAAU | 1885 | AUUGUCAUCUACAAACGGGAA | [492-512](21/21) |
| 1386 | GCGCAGACAUUCCCGUUUGUA | 1886 | UACAAACGGGAAUGUCUGCGC | [483-503](21/21) |
| 1387 | UGGAUCUGCCAACUACUCCCA | 1887 | UGGGAGUAGUUGGCAGAUCCA | [404-424](21/21) |
| 1388 | GCUCAGUUACAACUAGAUGAA | 1888 | UUCAUCUAGUUGUAACUGAGC | [327-347](21/21) |
| 1389 | GCAAAAUCAUAGCCAAAACUA | 1889 | UAGUUUUGGCUAUGAUUUUGC | [2033-2053](21/21) |
| 1390 | CUGAGCUAGUUUUUUUGUACU | 1890 | AGUACAAAAAAACUAGCUCAG | [1954-1974](21/21) |
| 1391 | GGAGGAUUUGACCUUUUCUGA | 1891 | UCAGAAAAGGUCAAAUCCUCC | [1937-1957](21/21) |
| 1392 | UAGGAGGAUUUGACCUUUUCU | 1892 | AGAAAAGGUCAAAUCCUCCUA | [1935-1955](21/21) |
| 1393 | GCUGCUCAGAAUUGCAGAAAA | 1893 | UUUUCUGCAAUUCUGAGCAGC | [1641-1661](21/21) |
| 1394 | GUGGCUGCUCAGAAUUGCAGA | 1894 | UCUGCAAUUCUGAGCAGCCAC | [1638-1658](21/21) |
| 1395 | AAGUGGCUGCUCAGAAUUGCA | 1895 | UGCAAUUCUGAGCAGCCACUU | [1636-1656](21/21) |
| 1396 | UGGUCCUAAAACACCAGUACA | 1896 | UGUACUGGUGUUUUAGGACCA | [1286-1306](21/21) |
| 1397 | GAAUGGUCCUAAAACACCAGU | 1897 | ACUGGUGUUUUAGGACCAUUC | [1283-1303](21/21) |
| 1398 | GGCCUCAGUGAUUCUGAAGUG | 1898 | CACUUCAGAAUCACUGAGGCC | [1227-1247](21/21) |
| 1399 | UCUUCCAGCUAUGGAGACACA | 1899 | UGUGUCUCCAUAGCUGGAAGA | [1200-1220](21/21) |
| 1400 | GGCAUUUCACUAAACACAAGU | 1900 | ACUUGUGUUUAGUGAAAUGCC | [1146-1166](21/21) |
| 1401 | GACUCCGGCAUUUCACUAAAC | 1901 | GUUUAGUGAAAUGCCGGAGUC | [1140-1160](21/21) |
| 1402 | UGCUACUUUAAGCCAUUCACU | 1902 | AGUGAAUGGCUUAAAGUAGCA | [1019-1039](21/21) |
| 1403 | GUAUUUGACUUCAGUCAGCGA | 1903 | UCGCUGACUGAAGUCAAAUAC | [219-239](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1404 | UGAGCCCAGUAUCAGCAACAG | 1904 | CUGUUGCUGAUACUGGGCUCA | [986-1006](21/21) |
| 1405 | GAGAAGUAUUUGACUUCAGUC | 1905 | GACUGAAGUCAAAUACUUCUC | [214-234](21/21) |
| 1406 | UCGAGAAGUAUUUGACUUCAG | 1906 | CUGAAGUCAAAUACUUCUCGA | [212-232](21/21) |
| 1407 | CAGUGAACUCAUUAAAUUCAG | 1907 | CUGAAUUUAAUGAGUUCACUG | [913-933](21/21) |
| 1408 | AGAAGCCAAACUGACAGAAGU | 1908 | ACUUCUGUCAGUUUGGCUUCU | [761-781](21/21) |
| 1409 | GGGAGGAGCUAUUAUCCAUUC | 1909 | GAAUGGAUAAUAGCUCCUCCC | [676-696](21/21) |
| 1410 | UUGGGAGGAGCUAUUAUCCAU | 1910 | AUGGAUAAUAGCUCCUCCCAA | [674-694](21/21) |
| 1411 | GCCCCUGUUGAUUUAGACGGU | 1911 | ACCGUCUAAAUCAACAGGGGC | [630-650](21/21) |
| 1412 | GACAGGUGAAUUUCUCCCAAU | 1912 | AUUGGGAGAAAUUCACCUGUC | [350-370](21/21) |
| 1413 | UGCAAAAUCAUAGCCAAAACU | 1913 | AGUUUUGGCUAUGAUUUUGCA | [2032-2052](21/21) |
| 1414 | UCCCAAAAGUAAGAAGCCAGA | 1914 | UCUGGCUUCUUACUUUUGGGA | [1895-1915](21/21) |
| 1415 | UUGUUCCCAAAAGUAAGAAGC | 1915 | GCUUCUUACUUUUGGGAACAA | [1891-1911](21/21) |
| 1416 | ACAACUCCAAAAGGAGCAAGA | 1916 | UCUUGCUCCUUUUGGAGUUGU | [293-313](21/21) |
| 1417 | UCCCAUUCCCUGUAGAAAAA | 1917 | UUUUUUCUACAGGGAAUGGGA | [1510-1530](21/21) |
| 1418 | UCAUCGGAAAACCCCAUUCAC | 1918 | GUGAAUGGGGUUUUCCGAUGA | [1418-1438](21/21) |
| 1419 | CAGAGAAAGAAUUGCCUGUAA | 1919 | UUACAGGCAAUUCUUUCUCUG | [1390-1410](21/21) |
| 1420 | CAGAGCACUCACGUGCAUGAU | 1920 | AUCAUGCACGUGAGUGCUCUG | [1350-1370](21/21) |
| 1421 | CACCAGUACAUUCUUCUGGGG | 1921 | CCCCAGAAGAAUGUACUGGUG | [1297-1317](21/21) |
| 1422 | UCCGGCAUUUCACUAAACACA | 1922 | UGUGUUUAGUGAAAUGCCGGA | [1143-1163](21/21) |
| 1423 | UGACUCCGGCAUUUCACUAAA | 1923 | UUUAGUGAAAUGCCGGAGUCA | [1139-1159](21/21) |
| 1424 | CCCUCACCUGCUACUUUAAGC | 1924 | GCUUAAAGUAGCAGGUGAGGG | [1011-1031](21/21) |
| 1425 | GUCCAGAAGCCAAACUGACAG | 1925 | CUGUCAGUUUGGCUUCUGGAC | [757-777](21/21) |
| 1426 | GCUGGUUGAGACUACCAUGGU | 1926 | ACCAUGGUAGUCUCAACCAGC | [731-751](21/21) |
| 1427 | UUCCUGAGUUACAGUGUCUUA | 1927 | UAAGACACUGUAACUCAGGAA | [694-714](21/21) |
| 1428 | CCCCUGUUGAUUUAGACCGUA | 1928 | UACCGUCUAAAUCAACAGGGG | [631-651](21/21) |
| 1429 | CCAGUGGAUCUGCCAACUACU | 1929 | AGUAGUUGGCAGAUCCACUGG | [400-420](21/21) |
| 1430 | AGACAGGUGAAUUUCUCCCAA | 1930 | UUGGGAGAAAUUCACCUGUCU | [349-369](21/21) |
| 1431 | UCGCUCAGUUACAACUAGAUG | 1931 | CAUCUAGUUGUAACUGAGCGA | [325-345](21/21) |
| 1432 | CCAGAUGUUAAGAAAAACUAG | 1932 | CUAGUUUUUCUUAACAUCUGG | [1911-1931](21/21) |
| 1433 | AGCCAGAUGUUAAGAAAAACU | 1933 | AGUUUUUCUUAACAUCUGGCU | [1909-1929](21/21) |
| 1434 | AUGGCAAUGUUUUCCUUGUUC | 1934 | GAACAAGGAAAACAUUGCCAU | [1876-1896](21/21) |
| 1435 | AGAGAUGGCAAUGUUUUCCUU | 1935 | AAGGAAAACAUUGCCAUCUCU | [1872-1892](21/21) |
| 1436 | GAACAACUCCAAAAGGAGCAA | 1936 | UUGCUCCUUUUGGAGUUGUUC | [291-311](21/21) |
| 1437 | GGGCAAAGCUCUCCAUAUCC | 1937 | GGAUAUGGAGAGCUUUGCCC | [1492-1512](21/21) |
| 1438 | AUCGGAAAACCCCAUUCACAA | 1938 | UUGUGAAUGGGGUUUUCCGAU | [1420-1440](21/21) |
| 1439 | ACGUGCAUGAUGCCCAAUGUG | 1939 | CACAUUGGGCAUCAUGCACGU | [1360-1380](21/21) |
| 1440 | GGUCCUAAAACACCAGUACAU | 1940 | AUGUACUGGUGUUUUAGGACC | [1287-1307](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1441 | CAGUCAGCGACGGAAAGAGUA | 1941 | UACUCUUUCCGUCGCUGACUG | [230-250](21/21) |
| 1442 | CUCCGGCAUUUCACUAAACAC | 1942 | GUGUUUAGUGAAAUGCCGGAG | [1142-1162](21/21) |
| 1443 | GACUUCAGUCAGCGACGGAAA | 1943 | UUUCCGUCGCUGACUGAAGUC | [225-245](21/21) |
| 1444 | AAGCCAUUCACUCUCUGAACU | 1944 | AGUUCAGAGAGUGAAUGGCUU | [1028-1048](21/21) |
| 1445 | CUGAGCCCAGUAUCAGCAACA | 1945 | UGUUGCUGAUACUGGGCUCAG | [985-1005](21/21) |
| 1446 | GACAGUGAACUCAUUAAAUUC | 1946 | GAAUUUAAUGAGUUCACUGUC | [911-931](21/21) |
| 1447 | GAAGACCCCAACCAGUUGACA | 1947 | UGUCAACUGGUUGGGGUCUUC | [894-914](21/21) |
| 1448 | AGCCAAACUGACAGAAGUUGA | 1948 | UCAACUUCUGUCAGUUUGGCU | [764-784](21/21) |
| 1449 | AAGCUGGUUGAGACUACCAUG | 1949 | CAUGGUAGUCUCAACCAGCUU | [729-749](21/21) |
| 1450 | GAGGAGCUAUUAUCCAUUCCU | 1950 | AGGAAUGGAUAAUAGCUCCUC | [678-698](21/21) |
| 1451 | GGUCCACAGCUCAUCAUGAUG | 1951 | CAUCAUGAUGAGCUGUGGACC | [99-119](21/21) |
| 1452 | GCUACUAAUCAGGCUCAGUCA | 1952 | UGACUGAGCCUGAUUAGUAGC | [585-605](21/21) |
| 1453 | CCCAGUCUUCAUUGCUACUAA | 1953 | UUAGUAGCAAUGAAGACUGGG | [572-592](21/21) |
| 1454 | UGAUGACUGCAUGCAGCUUUU | 1954 | AAAAGCUGCAUGCAGUCAUCA | [461-481](21/21) |
| 1455 | GAGACAGGUGAAUUUCUCCCA | 1955 | UGGGAGAAAUUCACCUGUCUC | [348-368](21/21) |
| 1456 | UUUCGCUCAGUUACAACUAGA | 1956 | UCUAGUUGUAACUGAGCGAAA | [323-343](21/21) |
| 1457 | AUGAUAUGACAUCUGGCUAAA | 1957 | UUUAGCCAGAUGUCAUAUCAU | [2238-2258](21/21) |
| 1458 | GGACACCAUUUGGGCUAGUUU | 1958 | AAACUAGCCCAAAUGGUGUCC | [2142-2162](21/21) |
| 1459 | UCAUAGCCAAAACUAGUAUAG | 1959 | CUAUACUAGUUUUGGCUAUGA | [2039-2059](21/21) |
| 1460 | UCUGAGCUAGUUUUUUUGUAC | 1960 | GUACAAAAAAACUAGCUCAGA | [1953-1973](21/21) |
| 1461 | GAGAUGGCAAUGUUUUCCUUG | 1961 | CAAGGAAAACAUUGCCAUCUC | [1873-1893](21/21) |
| 1462 | GUGAAUACUCCCUGCAGCAAA | 1962 | UUUGCUGCAGGGAGUAUUCAC | [1849-1869](21/21) |
| 1463 | AACCUUAUUCUCCUAGUGAAU | 1963 | AUUCACUAGGAGAAUAAGGUU | [1834-1854](21/21) |
| 1464 | GGAAACCUUAUUCUCCUAGU | 1964 | ACUAGGAGAAUAAGGUUUUCC | [1830-1850](21/21) |
| 1465 | GCCUUCACCUACUGAAAAAAC | 1965 | GUUUUUUCAGUAGGUGAAGGC | [1759-1779](21/21) |
| 1466 | UGCUCAGAAUUGCAGAAAAAG | 1966 | CUUUUUCUGCAAUUCUGAGCA | [1643-1663](21/21) |
| 1467 | GAGUAUGAGCUGGAAAAACAG | 1967 | CUGUUUUCCAGCUCAUACUC | [246-266](21/21) |
| 1468 | AUGGUCCUAAAACACCAGUAC | 1968 | GUACUGGUGUUUUAGGACCAU | [1285-1305](21/21) |
| 1469 | ACACACUACUUGGCCUCAGUG | 1969 | CACUGAGGCCAAGUAGUGUGU | [1216-1236](21/21) |
| 1470 | GAGACACACUACUUGGCCUCA | 1970 | UGAGGCCAAGUAGUGUGUCUC | [1213-1233](21/21) |
| 1471 | AUGGAGACACACUACUUGGCC | 1971 | GGCCAAGUAGUGUGUCUCCAU | [1210-1230](21/21) |
| 1472 | AGCUAUGGAGACACACUACUU | 1972 | AAGUAGUGUGUCUCCAUAGCU | [1206-1226](21/21) |
| 1473 | GCAUUUCACUAAACACAAGUC | 1973 | GACUUGUGUUUAGUGAAAUGC | [1147-1167](21/21) |
| 1474 | UCAGUCAGCGACGGAAAGAGU | 1974 | ACUCUUUCCGUCGCUGACUGA | [229-249](21/21) |
| 1475 | AUUCACUCUCUGAACUUCUAA | 1975 | UUAGAAGUUCAGAGAGUGAAU | [1033-1053](21/21) |
| 1476 | AACACAGAUUUGGUGAUGAA | 1976 | UUCAUCACCAAAUCUGUGUU | [945-965](21/21) |
| 1477 | GUCAACACAGAUUUGGUGAU | 1977 | AUCACCAAAUCUGUGUUGAC | [942-962](21/21) |
| 1478 | GAACUCAUUAAAUUCAGAUGC | 1978 | GCAUCUGAAUUUAAUGAGUUC | [917-937](21/21) |

TABLE B-continued 21-mers siRNAs specific to Nrf2 gene (SEQ ID NOS: 1007-2006)

| SEQ ID NO. | Sense siRNA | SEQ ID NO. | Antisense siRNA | Human 20149575 |
|---|---|---|---|---|
| 1479 | ACCAGUUGACAGUGAACUCAU | 1979 | AUGAGUUCACUGUCAACUGGU | [904-924](21/21) |
| 1480 | AGGUAACUGUAGUCCACAUUU | 1980 | AAAUGUGGACUACAGUUACCU | [830-850](21/21) |
| 1481 | UAUACCCUCAAUGGAAAAGA | 1981 | UCUUUUUCCAUUGAGGGUAUA | [806-826](21/21) |
| 1482 | UCCAUUCCUGAGUUACAGUGU | 1982 | ACACUGUAACUCAGGAAUGGA | [690-710](21/21) |
| 1483 | GGAGCUAUUAUCCAUUCCUGA | 1983 | UCAGGAAUGGAUAAUAGCUCC | [680-700](21/21) |
| 1484 | ACGGUAUGCAACAGGACAUUG | 1984 | CAAUGUCCUGUUGCAUACCGU | [646-666](21/21) |
| 1485 | CCCUGUUGAUUUAGACGGUAU | 1985 | AUACCGUCUAAAUCAACAGGG | [632-652](21/21) |
| 1486 | GUAGCCCCUGUUGAUUUAGAC | 1986 | GUCUAAAUCAACAGGGGCUAC | [627-647](21/21) |
| 1487 | GAAACUUCUGUUGCUCAGGUA | 1987 | UACCUGAGCAACAGAAGUUUC | [609-629](21/21) |
| 1488 | GAGAGCCCAGUCUUCAUUGCU | 1988 | AGCAAUGAAGACUGGGCUCUC | [567-587](21/21) |
| 1489 | AAACCAGUGGAUCUGCCAACU | 1989 | AGUUGGCAGAUCCACUGGUUU | [397-417](21/21) |
| 1490 | UUAGGAGGAUUUGACCUUUUC | 1990 | GAAAAGGUCAAAUCCUCCUAA | [1934-1954](21/21) |
| 1491 | AAGCCAGAUGUUAAGAAAAAC | 1991 | GUUUUUCUUAACAUCUGGCUU | [1908-1928](21/21) |
| 1492 | UUCCCAAAAGUAAGAAGCCAG | 1992 | CUGGCUUCUUACUUUUGGGAA | [1894-1914](21/21) |
| 1493 | GGAGCAAGAGAAAGCCUUUUU | 1993 | AAAAAGGCUUUCUCUUGCUCC | [305-325](21/21) |
| 1494 | GAUGGCAAUGUUUUCCUUGUU | 1994 | AACAAGGAAAACAUUGCCAUC | [1875-1895](21/21) |
| 1495 | AAGGAGCAAGAGAAAGCCUUU | 1995 | AAAGGCUUUCUCUUGCUCCUU | [303-323](21/21) |
| 1496 | AAGCCUUCACCUACUGAAAAA | 1996 | UUUUUCAGUAGGUGAAGGCUU | [1757-1777](21/21) |
| 1497 | UGAAGCUCAACUUGCAUUAAU | 1997 | AUUAAUGCAAGUUGAGCUUCA | [1586-1606](21/21) |
| 1498 | AUGAAGCUCAACUUGCAUUAA | 1998 | UUAAUGCAAGUUGAGCUUCAU | [1585-1605](21/21) |
| 1499 | CCCAUUCCUGUAGAAAAAAU | 1999 | AUUUUUUCUACAGGGAAUGGG | [1511-1531](21/21) |
| 1500 | UUGGAGGCUCAUCUCACAAGA | 2000 | UCUUGUGAGAUGAGCCUCCAA | [1461-1481](21/21) |
| 1501 | AGCUGGAAAAACAGAAAAAC | 2001 | GUUUUUUCUGUUUUUCCAGCU | [253-273](21/21) |
| 1502 | GUGCAUGAUGCCCAAUGUGAG | 2002 | CUCACAUUGGGCAUCAUGCAC | [1362-1382](21/21) |
| 1503 | CACGUGCAUGAUGCCCAAUGU | 2003 | ACAUUGGGCAUCAUGCACGUG | [1359-1379](21/21) |
| 1504 | ACACCAGUACAUUCUUCUGGG | 2004 | CCCAGAAGAAUGUACUGGUGU | [1296-1316](21/21) |
| 1505 | GUCCUAAAACACCAGUACAUU | 2005 | AAUGUACUGGUGUUUUAGGAC | [1288-1308](21/21) |
| 1506 | UGGAGACACACUACUUGGCCU | 2006 | AGGCCAAGUAGUGUGUCUCCA | [1211-1231](21/21) |

Example 2

In Vitro Testing of siRNA Compounds for Nrf2

1. General 1.5-2×10⁵ tested cells (HeLa or 293 cells) were seeded per well in a 6-well plate (70-80% confluent).

24 h subsequently, cells were transfected with siRNA oligos using lipofectamine 2000 reagent (Invitrogene) at a final concentration of 500 μM, 5 nM, 20 nM or 40 W. The cells were incubated at 37° C. in a CO2 incubator for 72 h.

As positive control for cell transfection, PTEN-Cy3 labeled siRNA oligos were used.

As negative control for siRNA activity, GFP siRNA oligos were used.

72 h after transfection cells were harvested and RNA was extracted from cells.

Transfection efficiency was tested by fluorescent microscopy.

Results:

The percent of inhibition of gene expression using specific preferred siRNAs was determined using qPCR analysis of target gene in cells expressing the endogenous gene. The data in Table C demonstrate the percent of knockdown of the expression of the target gene in cells. In general, the siRNAs having specific sequences that were selected for in vitro testing were specific for both human and the rat/rabbit genes. Similar results of reduced expression of specific genes are obtained with other siRNAs, the sequences of which are listed in Tables A and B.

TABLE C

Percent of knockdown of the expression of the target Nrf2 human gene in cells using siRNAs having preferred sequences (results of separate experiments are indicated).

| Active siRNA | Sequence | % knockdown of the human gene |
|---|---|---|
| NFE2L2_10 (Sense SEQ ID NO: 501) having one mismatch (in bold) compared to the human sequence (Antisense SEQ ID NO: 1004) | Sense: CCCUGUCGAAAAAAUCAUU Antisense: AAUGAUUUUUUCGACAGGG | 20 nM in HeLa cells: 91%, 54%, 51% inhibition 5 nM in HeLa cells: 91% inhibition |
| NFE2L2_4 (Sense SEQ ID NO: 119) (Antisense SEQ ID NO: 622) | Sense: CCCAUUCACAAAAGACAAA Antisense: UUUGUCUUUUGUGAAUGGG | 20 nM - 80%, 41% inhibition 5 nM - 73%, 36% inhibition |
| NFE2L2_5 (Sense SEQ ID NO: 195): (Antisense SEQ ID NO: 698) | Sense: CAGCAGGACAUGGAUUUGA Antisense: UCAAAUCCAUGUCCUGCUG | 20 nM - 69%, 17% inhibition 5 nM - 47%, 16% inhibition |
| NFE2L2_9 (Sense SEQ ID NO: 502) (Antsense SEQ ID NO: 1005) | Sense: UCCCUGUCGAAAAAAUCAU Antisense: AUGAUUUUUUCGACAGGGA | 20 nM - 44% inhibition 5 nM - 25% inhibition |
| NFE2L2_11 (Sense SEQ ID NO: 503) (Antisense SEQ ID NO: 1006) | Sense: CCUGUCGAAAAAAUCAUUA Antisense: UAAUGAUUUUUUCGACAGG | 20 nM - 46% inhibition 5 nM - 23% inhibition |
| NFE2L2_1 (Sense SEQ ID NO: 2) (Antisense SEQ ID NO: 505) | Sense: GGAGGGGUAAGAAUAAAGU Antisense: ACUUUAUUCUUACCCCUCC | 20 nM - 55%, 73%, 53% inhibition |
| NFE2L2_2 (Sense SEQ ID NO: 7) (Antisense SEQ ID NO: 510) | Sense: GCCCUCACCUGCUACUUUA Antisense: UAAAGUAGCAGGUGAGGGC | 20 nM - 92%, 49%, 46% inhibition |
| NFE2L2_3 (Sense SEQ ID NO: 10) (Antisense SEQ ID NO: 513) | Sense: UCCCGUUUGUAGAUGACAA Antisense: UUGUCAUCUACAAACGGGA | 20 nM - 96%, 83%, 82% inhibition |
| NFE2L2_12 (Sense SEQ ID NO: 26) (Antisense SEQ ID NO: 529) | Sense: GUAAGAAGCCAGAUGUUAA Antisense: UUAACAUCUGGCUUCUUAC | 20 nM - 95%, 96%, 76% inhibition |

Example 3

The Effect of Nrf2 siRNA Treatment on Tumor Growth In Vivo

Methods:

Tumor Xenografts: A549 cells (5×10⁶) were injected into the hind leg of male athymic nude mice and the tumor was measured weekly. The tumor volumes were measured using the following formula: [length (mm)×width (mm)×width (mm)×0.52]. In the lung metastasis experiments, 2×106 A549-C8-luc cells were injected into SCID-Beige mice (Charles River, Mass.) intravenously.

For the in vivo experiments, all siRNA compounds were chemically synthesized being stabilized by alternating 2-O'-Me modifications. The sequence of siRNA targeting human Nrf2 used for in vivo experiments is 5'-UCCCGUUUGUA-GAUGACAA-3' (sense, SEQ ID NO:10) and 5'-UUGU-CAUCUACAAACGGGA-3' (antisense, SEQ ID NO:513). The sequence of control siRNA targeting GFP is 5'-GGC-UACGUCCAGGAGCGCACC-3' (sense, SEQ ID NO: 2007) and 5'-GGUGCGCUCCUGGACGUAGCC-3' (antisense, SEQ ID NO: 2008).

For in vivo delivery of siRNA into subcutaneous tumors, siRNA duplexes diluted in PBS were injected into the hind leg tumors using insulin syringes at a concentration of 10 µg/mm³. Intraperitoneal injections of carboplatin were given at a dose of 40 mg/kg body weight. Both siRNA and carboplatin were administered twice weekly for 4 weeks.

For lung tumor delivery, female C57B6 mice were injected with Lewis Lung Carcinoma (LLC) cells (0.5×10⁶) intravenously, 24 days prior to the delivery experiment. Upon development of lung metastases, mice were administered with 100 µg/mouse of Cy3-labeled naked chemically stabilized reference siRNA via nebulizer inhalation on 3 consequent days. Mice were euthanized 24 hrs after the last inhalation. Upon termination, lungs were inflated with ice-cold 4% paraformaldehyde, followed by manual sectioning with razor blades. Clearly visible large surface tumors were sectioned separately. Resulting sections were analyzed by Bio-Rad Confocal microscope using a 20× Water objective and 2× zoom combined to give a total of 40× magnification. Control, non-siRNA-treated lungs were used to set up background fluorescence level.

For aerosol delivery of Nrf2 or GFP siRNA into lung tumors, 100 μg of siRNA duplex diluted in PBS was aerosolized using a nebulizer. Mice were given three dose of siRNA (100 μg/dose) every week, for 4 weeks, using a nebulizer. Intraperitoneal injections of carboplatin were given at a dose of 30 mg/kg body weight twice/week.

In Vivo Imaging: Animals inoculated with A549-C8-luc cells, which express a luciferase reporter gene, were anesthetized and injected intraperitoneally with 250 ul of luminescent substrate (15 mg/ml stock) D-Luciferin Firefly (Xenogen Cat# XR-1001). The animals were then imaged and analyzed by using the Xenogen IVIS Optical Imaging Device in the Johns Hopkins Oncology Center.

Statistical Analysis—Statistical comparisons were performed by Student's t-tests. A value of p<0.05 was considered statistically significant. Tumor weights and changes in tumor volume were summarized using descriptive statistics. Differences in tumor measures between treatment groups were examined using linear regression models with generalized estimating equations (GEE). The distributions of both tumor measurements were skewed, so log transformations were used.

Results:

A tumor xenograft experiment with A549 cells which were injected into the hind leg was conducted in order to test the anti-tumor activity of Nrf2 siRNA in vivo. Mice bearing subcutaneous tumors were treated with Nrf2 siRNA (comprising SEQ ID NO: 10) by direct injection into the tumor and by carboplatin twice a week for 4 weeks and tumor weight was measured at the termination of the experiment. Treatment with control non-targeting siRNA (GFP siRNA) did not inhibit tumor growth as compared to control mice treated with PBS alone. The tumor weights were significantly different between GFP siRNA and Nrf2 siRNA treated tumors (P=0.0002). Treatment with Nrf2 siRNA alone reduced mean tumor weight by 53% (±20% SD) compared to the control group. When Nrf2 siRNA was combined with carboplatin, there was an even greater reduction in mean tumor weight in all animals. To explore the effect of radiation exposure in combination with Nrf2 inhibition in vivo, the same A549 cell tumor xenograft model was used. In comparison with control siRNA+ionizing radiation (IR) treated tumors, combination of Nrf2 siRNA+IR (2 fractions of 3Gy irradiation) produced an additive effect on tumor growth inhibition (Tables D1 and D2). Delivery of naked Nrf2 siRNA duplex into tumor inhibited the expression of Nrf2 and its downstream target genes (HO-1 and GCLm), P<0.05 (FIG. 1).

TABLE D1

Mean (SD) of tumor weights and changes in tumor volume in tumor xenograft mice following treatment with Nrf2 siRNA (SEQ ID NO: 10), carboplatin, radiation and combination thereof (Experiment 1).

| Treatment | Mean (SD) change in tumor volume (mm$^3$) | Mean (SD) tumor weight (mg) |
|---|---|---|
| GFP siRNA | 532.94 (260.94) | 426 (187.83) |
| GFP siRNA + radiation | 246.77 (189.39) | 341.25 (275.27) |
| GFP siRNA + carboplatin | 352.34 (170.96) | 212 (66.48) |
| Nrf2 siRNA | 249.17 (111.37) | 238 (64.58) |
| Nrf2 siRNA + radiation | 116.04 (147.9) | 118 (70.85) |
| Nrf2 siRNA + carboplatin | 58.78 (80.06) | 110 (57.62) |

TABLE D2

Mean (SD) of tumor weights and changes in tumor volume in tumor xenograft mice following treatment with Nrf2 siRNA (SEQ ID NO: 10), carboplatin, radiation and combination thereof (Experiment 2).

| Treatment | Mean (SD) change in tumor volume (mm$^3$) | Mean (SD) tumor weight (mg) |
|---|---|---|
| GFP siRNA | 375 (233.7) | 327.5 (201.56) |
| GFP siRNA + carboplatin | 187.33 (76.66) | 185 (67.16) |
| Nrf2 siRNA | 138.67 (128.24) | 143.33 (90.74) |
| Nrf2 siRNA + carboplatin | 45 (33.81) | 58.33 (21.37) |

The delivery of naked siRNA duplexes into orthotopic lung tumors was examined. Mice were injected with Lewis lung carcinoma cells and 24 days later (when the mice developed larger tumors) mice were inhaled for three consecutive days with 100 μg/day/mouse of Cy3 labeled naked chemically stabilized reference siRNA using a nebulizer. Twenty four hours after last siRNA administration, mice were sacrificed; lungs harvested and sectioned. Resulting sections were analyzed by Bio-Rad Confocal microscope using a 20× Water objective and 2× zoom combined to give a total of 40× magnification. Control, non-siRNA-treated lungs were used to set up background fluorescence level. The fluorescence results revealed localization of Cy3 labeled siRNA in a large surface tumor, especially in intraparenchymal tumor. The large surface-protruding tumors showed Cy3 signal but the intensity was several folds lower than that observed in the small intraparenchymal tumors.

Figure 2:
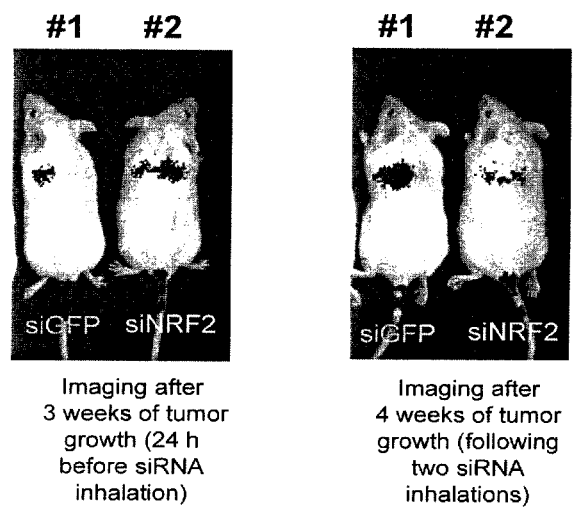
FIG. 2: SCID-Beige mice injected i.v. with ARE-luciferase reporter tumor cells were inhaled with Nrf2 siRNA (sense strand SEQ ID NO: 10) twice during the 4th week of lung tumor growth. Control mice were inhaled with GFP siRNA. Mice were imaged before and after siRNA inhalation.

In the next step, mice with orthotopic growing tumors expressing ARE-Luc Nrf2-dependent reporter were used. The mice with A549 lung tumors were treated with Nrf2 siRNA (SEQ ID NO: 10) intranasally using a nebulizer followed by carboplatin treatment. As demonstrated in FIG. 2, Nrf2 siRNA administered intranasally inhibited Nrf2 reporter activity in vivo, indicating specific inhibition of Nrf2 expression using Nrf2 siRNA following intranasal administration. Mice receiving Nrf2 siRNA together with carboplatin demonstrated higher growth inhibition as compared with control mice receiving GFP siRNA together with carboplatin (Table D3). The mean lung weight at termination and the luminescent flux intensity (evaluated by in vivo imaging) were lowest in mice treated with Nrf2 siRNA+carboplatin. Thus, combination of Nrf2 siRNA with carboplatin/radiation led to a reduction in tumor growth after 4 weeks of treatment compared with either agent alone. This study suggests that Nrf2 siRNA inhibitors may be considered as highly efficient promoters for the antineoplastic potential of platinum drugs such as carboplatin, causing additive/synergistic effects in lung cancer cells.

TABLE D3

Mean (SD) of lung tumor weights following intranasal treatment with Nrf2 siRNA (SEQ ID NO: 10) alone, and in combination with carboplatin.

| Treatment | Mean (SD) tumor weight (mg) |
|---|---|
| GFP siRNA | 710 (167.93) |
| GFP siRNA + carboplatin | 480 (95.13) |
| Nrf2 siRNA | 802 (172.25) |
| Nrf2 siRNA + carboplatin | 370 (62.05) |
| Vehicle siRNA | 760 (98.99) |
| Vehicle siRNA + carboplatin | 495 (49.5) |

The invention claimed is:

1. A double-stranded RNA compound having the structure:

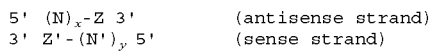

wherein each N and N' is a ribonucleotide which may independently be modified or unmodified in its sugar residue;
wherein each of (N)$_x$ and (N')$_y$ is an oligomer in which each consecutive N or N' is joined to the next N or N' by a covalent bond;
wherein each of x and y is an integer between 19 and 40;
wherein each of Z and Z' may be present or absent, but if present is 1-5 consecutive nucleotides covalently attached at the 3' terminus of the strand in which it is present;
and wherein the sequences of (N)$_x$ and (N')$_y$ are complementary and the sequence of (N)$_x$ comprises SEQ ID NO. 622 and the sequence of (N')$_y$ comprises SEQ ID NO:119.

2. The compound of claim 1, wherein the covalent bond is a phosphodiester bond.

3. The compound of claim 2, wherein x=y=19.

4. The compound of claim 3, wherein Z and Z' are both absent.

5. The compound of claim 3, wherein one of Z or Z' is present.

6. The compound of claim 1, wherein all of the ribonucleotides in (N)$_x$ or (N')$_y$ or both are unmodified in their sugar residues.

7. The compound of claim 1, wherein at least one ribonucleotide in (N)$_x$ or (N')$_y$ comprises a modification in its sugar residue.

8. The compound of claim 7, wherein the modification comprises a modification at the 2' position of the sugar residue.

9. The compound of claim 8, wherein the modification at the 2' position of the sugar residue results in the presence of a moiety selected from the group consisting of amino, fluoro, alkoxy and alkyl groups.

10. A composition comprising a pharmaceutically acceptable carrier and a compound of claim 1.

11. A method of treating a patient suffering from a disorder comprising administering to the patient the compound of claim 1 in a therapeutically effective dose thereby treating the patient.

12. The method of claim 11, wherein the disorder is a cancerous disease selected from the group consisting of lung cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer.

13. The method of claim 12, wherein the cancerous disease is a lung cancer.

14. The method of claim 13, wherein the compound comprises a naked siRNA compound.

15. The method of claim 14, wherein the compound is administered via aerosol directly to the inner lung of the patient.

16. The method of claim 15, further comprising administering to the patient a chemotherapy drug.

17. The compound of claim 9, wherein the modification at the 2' position of the sugar residue comprises the presence of an alkoxy group.

18. The compound of claim 17, wherein the alkoxy group is a methoxy (2'-O-methyl) group.

19. The compound of claim 18, wherein alternating ribonucleotides in the antisense strand or in the sense strand or both strands are modified in their sugar residues.

20. The compound of claim 19, wherein each ribonucleotide at the 5' terminus and at the 3' terminus in the antisense strand is modified in its sugar residue, and each ribonucleotide at the 5' terminus and at the 3' terminus of the sense strand is unmodified in its sugar residue.

21. The compound of claim 20, wherein each of the antisense strand and the sense strand is non-phosphorylated at its 3' terminus and at its 5' terminus.

22. A double-stranded RNA compound having the structure:

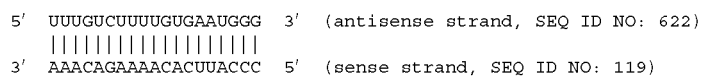

wherein each of A, C, G and U is an unmodified or a 2'O-methyl sugar modified ribonucleotide and each consecutive ribonucleotide is joined to the next ribonucleotide by a covalent bond; and
wherein each vertical line represents base pairing between the ribonucleotides.

23. The compound of claim 20, wherein each of the antisense strand and the sense strand is phosphorylated at its 3' terminus.

24. The compound of claim 23, wherein in the compound the ribonucleotide at the 5' terminus of both the antisense strand and the sense strand is non-phosphorylated.

25. The compound of claim 22, wherein in the compound a 2'-O-methyl group is present on the sugar reside of the first, third, fifth, seventh, ninth, eleventh, thirteenth, fifteenth, seventeenth and nineteenth ribonucleotide of the antisense strand, and wherein a 2'-O-methyl group is present on the sugar residue of the second, fourth, sixth, eight, tenth, twelfth, fourteenth, sixteenth and eighteenth ribonucleotide of the sense strand.

26. The composition of claim 10, wherein the compound is present in an amount effective to down-regulate expression of a human nuclear factor erythroid-2 related factor 2 (Nrf2) gene.

* * * * *